United States Patent
Wu et al.

(10) Patent No.: US 9,181,236 B2
(45) Date of Patent: Nov. 10, 2015

(54) 2-SPIRO-SUBSTITUTED IMINOTHIAZINES AND THEIR MONO-AND DIOXIDES AS BACE INHIBITORS, COMPOSITIONS AND THEIR USE

(75) Inventors: Wen-Lian Wu, Edison, NJ (US); Duane A. Burnett, Wayland, MA (US); Andrew W. Stamford, Chatham, NJ (US); Jared N. Cumming, Garwood, NJ (US); Theodros Asberom, West Orange, NJ (US); Chad Bennett, Metuchen, NJ (US); Thavalakulamgara K. Sasiskumar, Edison, NJ (US); Jack D. Scott, Scotch Plains, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/240,215

(22) PCT Filed: Aug. 21, 2012

(86) PCT No.: PCT/US2012/051687
§ 371 (c)(1),
(2), (4) Date: Feb. 21, 2014

(87) PCT Pub. No.: WO2013/028670
PCT Pub. Date: Feb. 28, 2013

(65) Prior Publication Data
US 2014/0200213 A1 Jul. 17, 2014

Related U.S. Application Data

(60) Provisional application No. 61/526,049, filed on Aug. 22, 2011.

(51) Int. Cl.
| | |
|---|---|
| *C07D 417/14* | (2006.01) |
| *C07D 417/12* | (2006.01) |
| *C07D 513/04* | (2006.01) |
| *C07D 513/10* | (2006.01) |
| *A61K 45/06* | (2006.01) |
| *C07D 417/04* | (2006.01) |
| *C07D 417/10* | (2006.01) |
| *C07D 279/34* | (2006.01) |
| *C07D 519/00* | (2006.01) |

(52) U.S. Cl.
CPC .............. *C07D 417/14* (2013.01); *A61K 45/06* (2013.01); *C07D 279/34* (2013.01); *C07D 417/04* (2013.01); *C07D 417/10* (2013.01); *C07D 417/12* (2013.01); *C07D 513/04* (2013.01); *C07D 513/10* (2013.01); *C07D 519/00* (2013.01)

(58) Field of Classification Search
CPC .. C07D 417/14; C07D 513/04; C07D 513/10; C07D 417/12
USPC ...................... 514/228.5, 227.8, 228.2; 544/6
See application file for complete search history.

(56) References Cited

U.S. PATENT DOCUMENTS

| | | |
|---|---|---|
| 5,534,520 A | 7/1996 | Fischer et al. |
| 6,191,127 B1 | 2/2001 | Holscher et al. |
| 6,683,091 B2 | 1/2004 | Asberom et al. |
| 7,648,983 B2 | 1/2010 | Audia et al. |
| 7,994,167 B2 | 8/2011 | Frank et al. |
| 8,338,413 B1 | 12/2012 | Rueeger |
| 8,557,826 B2 | 10/2013 | Stamford et al. |
| 8,563,543 B2 | 10/2013 | Scott et al. |
| 8,569,310 B2 | 10/2013 | Iserloh |
| 8,729,071 B2 | 5/2014 | Scott et al. |
| 8,940,748 B2 | 1/2015 | Scott et al. |

(Continued)

FOREIGN PATENT DOCUMENTS

| | | |
|---|---|---|
| EP | 1942105 | 7/2008 |
| JP | 2012250933 | 12/2012 |

(Continued)

OTHER PUBLICATIONS

International Search Report and Written Opinion for PCT/US2012/051687 dated Oct. 10, 2012.
Abramov, et al., Amyloid- as a positive endogenous regulator of release probability at hippocampal synapses, Nature Neuroscience 12, 1567-1576 (2009) Published online: Nov. 22, 2009 |doi:10.1038/nn.2433.
Barton, et al., on the Structure of Some Substituted 4, 6-Pyrimidinones, Department of Organic Chemistry, College of Medicine, Jagiellonian University, Ingardena 3, 30-060-Krakow, Poland, Polish J. Chem., 69, 235-245 (1995), revised manuscript Oct. 25, 1994.

(Continued)

*Primary Examiner* — Kahsay Habte
(74) *Attorney, Agent, or Firm* — Keith D. MacMillan; John C. Todaro

(57) ABSTRACT

In its many embodiments, the present invention provides certain iminothiazine dioxide compounds, including compounds Formula (I):

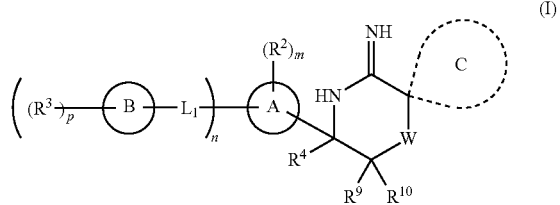

and tautomers and stereoisomers thereof, and pharmaceutically acceptable salts of said compounds, said tautomeros and said stereoisomers, wherein each of the variables shown in the formula are as defined herein. The novel compounds of the invention are useful as BACE inhibitors and/or for the treatment and prevention of various pathologies related thereto. Pharmaceutical compositions comprising one or more such compounds (alone and in combination with one or more other active agents), and methods for their preparation and use, including Alzheimer's disease, are also disclosed.

15 Claims, No Drawings

(56) References Cited

U.S. PATENT DOCUMENTS

| | | |
|---|---|---|
| 9,029,362 B2 | 5/2015 | Scott et al. |
| 2006/0034848 A1 | 2/2006 | Kinoshita et al. |
| 2006/0280854 A1 | 12/2006 | De Roos et al. |
| 2006/0281730 A1 | 12/2006 | Zhu et al. |
| 2007/0072925 A1 | 3/2007 | Malamas et al. |
| 2007/0112190 A1 | 5/2007 | Naidu |
| 2007/0287692 A1 | 12/2007 | Wu et al. |
| 2007/0299087 A1 | 12/2007 | Berg et al. |
| 2008/0200445 A1 | 8/2008 | Zhu et al. |
| 2009/0023762 A1 | 1/2009 | Berg et al. |
| 2009/0062282 A1 | 3/2009 | Albert et al. |
| 2009/0209755 A1 | 8/2009 | Suzuki et al. |
| 2010/0075957 A1 | 3/2010 | Tamura et al. |
| 2010/0292203 A1 | 11/2010 | Zhu et al. |
| 2010/0317850 A1 | 12/2010 | Suzuki et al. |
| 2011/0009395 A1 | 1/2011 | Audia et al. |
| 2011/0046122 A1 | 2/2011 | Andreini et al. |
| 2011/0152253 A1 | 6/2011 | Motoki et al. |
| 2012/0035195 A1 | 2/2012 | Banner et al. |
| 2012/0184540 A1 | 7/2012 | Andreini et al. |
| 2012/0189642 A1 | 7/2012 | Scott et al. |
| 2012/0195881 A1 | 8/2012 | Iserloh et al. |
| 2012/0196863 A1 | 8/2012 | Andreini et al. |
| 2012/0258961 A1 | 10/2012 | Suzuki et al. |
| 2012/0258962 A1 | 10/2012 | Hilpert et al. |
| 2012/0302549 A1 | 11/2012 | Narquizian et al. |
| 2014/0023668 A1 | 1/2014 | Cumming et al. |
| 2014/0128382 A1 | 5/2014 | Wu et al. |
| 2014/0200213 A1 | 7/2014 | Wu et al. |

FOREIGN PATENT DOCUMENTS

| | | |
|---|---|---|
| WO | WO9004917 | 5/1990 |
| WO | WO9304047 | 3/1993 |
| WO | WO9614844 | 5/1996 |
| WO | WO0051992 | 9/2000 |
| WO | WO2005058311 | 6/2005 |
| WO | WO2006009653 | 1/2006 |
| WO | WO2006009655 | 1/2006 |
| WO | WO2006041404 | 4/2006 |
| WO | WO2006041405 | 4/2006 |
| WO | WO2006044497 | 4/2006 |
| WO | WO2006060109 | 6/2006 |
| WO | WO2006065277 | 6/2006 |
| WO | WO2006076284 | 7/2006 |
| WO | WO2006138192 | 12/2006 |
| WO | WO2006138195 | 12/2006 |
| WO | WO2006138217 | 12/2006 |
| WO | WO2006138264 | 12/2006 |
| WO | WO2006138265 | 12/2006 |
| WO | WO2006138266 | 12/2006 |
| WO | WO2007005366 | 1/2007 |
| WO | WO2007005404 | 1/2007 |
| WO | WO2007011810 | 1/2007 |
| WO | WO2007016012 | 2/2007 |
| WO | WO2007038271 | 4/2007 |
| WO | WO2007078813 | 4/2007 |
| WO | WO2007049532 | 5/2007 |
| WO | WO2007050721 | 5/2007 |
| WO | WO2007053506 | 5/2007 |
| WO | WO2007058580 | 5/2007 |
| WO | WO2007058581 | 5/2007 |
| WO | WO2007058583 | 5/2007 |
| WO | WO2007058601 | 5/2007 |
| WO | WO2007058602 | 5/2007 |
| WO | WO2007073284 | 6/2007 |
| WO | WO2007100536 | 9/2007 |
| WO | WO2007114771 | 10/2007 |
| WO | WO2007145568 | 12/2007 |
| WO | WO2007145569 | 12/2007 |
| WO | WO2007145570 | 12/2007 |
| WO | WO2007145571 | 12/2007 |
| WO | WO2007146225 | 12/2007 |
| WO | WO2008022024 | 2/2008 |
| WO | WO2008063114 | 5/2008 |
| WO | WO2008073365 | 6/2008 |
| WO | WO2008073370 | 6/2008 |
| WO | WO2008076043 | 6/2008 |
| WO | WO2008076044 | 6/2008 |
| WO | WO2008076045 | 6/2008 |
| WO | WO2008076046 | 6/2008 |
| WO | WO2008133273 | 6/2008 |
| WO | WO2008133274 | 6/2008 |
| WO | WO2008103351 | 8/2008 |
| WO | WO2008115552 | 9/2008 |
| WO | WO2008118379 | 10/2008 |
| WO | WO2011009897 | 1/2009 |
| WO | WO2009020580 | 2/2009 |
| WO | WO2009091016 | 7/2009 |
| WO | WO2009108550 | 9/2009 |
| WO | WO2009131974 | 10/2009 |
| WO | WO2009131975 | 10/2009 |
| WO | WO2009134617 | 11/2009 |
| WO | WO2009136350 | 11/2009 |
| WO | WO2009151098 | 12/2009 |
| WO | WO2010013302 | 2/2010 |
| WO | WO2010013794 | 2/2010 |
| WO | WO2010021680 | 2/2010 |
| WO | WO2010030954 | 3/2010 |
| WO | WO2010038686 | 4/2010 |
| WO | WO2010047372 | 4/2010 |
| WO | WO2010128058 | 11/2010 |
| WO | WO2011005738 | 1/2011 |
| WO | WO2011009898 | 1/2011 |
| WO | WO2011009943 | 1/2011 |
| WO | WO2011020806 | 2/2011 |
| WO | WO2011029803 | 3/2011 |
| WO | WO2011044181 | 4/2011 |
| WO | WO2011044184 | 4/2011 |
| WO | WO2011044185 | 4/2011 |
| WO | WO2011044187 | 4/2011 |
| WO | WO2011058763 | 5/2011 |
| WO | WO2011069934 | 6/2011 |
| WO | WO2011070029 | 6/2011 |
| WO | WO2011070781 | 6/2011 |
| WO | WO2011071057 | 6/2011 |
| WO | WO2011071109 | 6/2011 |
| WO | WO2011071135 | 6/2011 |
| WO | WO2011072064 | 6/2011 |
| WO | WO2011077726 | 6/2011 |
| WO | WO2011080176 | 7/2011 |
| WO | WO2011106414 | 9/2011 |
| WO | WO2011115928 | 9/2011 |
| WO | WO2011115938 | 9/2011 |
| WO | WO2011123674 | 10/2011 |
| WO | WO2011130347 | 10/2011 |
| WO | WO2011130741 | 10/2011 |
| WO | WO2011138293 | 11/2011 |
| WO | WO2011154374 | 12/2011 |
| WO | WO2011154431 | 12/2011 |
| WO | WO2012006953 | 1/2012 |
| WO | WO2012040641 | 3/2012 |
| WO | WO2012057247 | 5/2012 |
| WO | WO2012057248 | 5/2012 |
| WO | WO2012071279 | 5/2012 |
| WO | WO2012071458 | 5/2012 |

OTHER PUBLICATIONS

Bayden, et al., Web application for studying the free energy of binding and protonation states of protein-ligand complexes based on HINT, J Comput Aided Mol Des (2009) 23:621-632.

Chiriano, et al., Sequential Virtual Screening Approach to the Identification of Small Organic Molecules as Potential BACE-1 Inhibitors, Chem Biol Drug Des 2011; 77: 268-271.

Cho, et al, S-Nitrosylation of Drp1 Mediates β-Amyloid-Related Mitochondrial Fission and Neuronal Injury, Science Apr. 3, 2009: vol. 324 No. 5923 pp. 102-105.

Cole, et al., Review: the Alzheimer's disease B-secretase enzyme, BACEI, Molecular Neurodegeneration 2007, 2:22, Published Nov. 15, 2007.

(56) References Cited

OTHER PUBLICATIONS

Cumming JN, et al. Piperazine sulfonamide BACE1 inhibitors: Design, synthesis, and in vivo characterization. Bioorg Med Chem Lett. 2010;20:2837-42.

Cumming JN, et al. Rational design of novel, potent piperazinone and imidazolidinone BACE1 inhibitors. Bioorg Med Chem Lett. 2008;18:3236-41.

Cumming JN, et al. Structure based design of iminohydantoin BACE1 inhibitors: identification of an orally available, centrally active BACE1 inhibitor. Bioorg Med Chem Lett. Apr. 1, 2012;22(7):2444-9. doi: 10.1016/j.bmcl.2012.02.013.

Cumming, et al., Design and development of cyclic amine BACE1 inhibitors, Current Opinion in Drug Discovery and Development, 2004, 7(4), 536-556.

Edwards, et al., Application of Fragment-Based Lead Generation to the Discovery of Novel, Cyclic Amidine p-Secretase Inhibitors with Nanomolar Potency, Cellular Activity, and High Ligand Efficiency, 1. Med. Chenl. 2007,50, 5912-5925.

Evin, et al., BACE Inhibitors as Potential Drugs for the Treatment of Alzheimer's Disease: Focus on Bioactivity, Recent Patents on CNS Drug Discovery, 2011, 6, 91-106.

Farah, et al., Reduced BACE1 Activity Enhances Clearance of Myelin Debris and Regeneration of Axons in the Injured Peripheral Nervous System, The Journal of Neuroscience, Apr. 13, 2011 • 31(15):5744-5754.

Getchell, et al., 3-Nitrotyrosine immunoreactivity in olfactory receptor neurons of patients with Alzheimer's disease: implications for impaired odor sensitivity, Neurobiology of Aging 24 (2003) 663-673., accepted Oct. 8, 2002, pp. 663-673.

Ginman, et al., "Core refinement toward permeable B-Secretase (BACE-1) Inhibitors with low hERG Activity", Journal of Medicinal Chemistry, Rec'd Aug. 12, 2012.

Gravenfors, et al., "New Aminimidazoles as B-Secretase (BACE-1) inhibitors Showing amylod-B (AB) lowering in the brain", Journal of Medicinal Chemistry, 2012, 55, 9297-9311.

Guo, et al., Targeting Amyloid-B in Glaucoma Treatment, pp. 13444-13449, PNAS, Aug. 14, 2007, vol. 104, No. 33.

Hilpert, et al., "B-Secretase (BACE1) Inhibitors with high in vivo efficacy suitable for clinical evaluation of Alzheimer's disease", Journal of Medicinal Chemistry, 2013, 56, 3980-3995.

Huang, et al., "Structure- and Property-Based Design of Aminooxazoline Xanthines as selective, orally efficacious, and CNS Penetrable BACE inhibitors for the treatment of Alzheimer's disease", Journal of Medicinal Chemistry, Special Issue: Alzheimer's Disease, 2012, 55, 9156-9169.

Huang, et al., Pharmacophore Model Construction of , 8-Secretase Inhibitors, Acta Chimica Sinica, vol. 66, No. 16, 2008, pp. 1889-1897. (English Abstract).

Hunt, et al., "Spirocyclic B-Site Amyloid Precursor Protein Cleaving Enzyme 1 (BACE1) Inhibitors: From hit to Lowering of Cerebralspinal fluid (CSF) Amyloid-B in a higher species", Journal of Medicinal Chemistry 2013, 56, 3379-3403.

Iserloh U, et al. Discovery of an orally efficacious 4-phenoxypyrrolidine-based BACE-1 inhibitor. Bioorg Med Chem Lett. 2008;18:418-22.

Iserloh U, et al. Potent pyrrolidine- and piperidine-based BACE-1 inhibitors. Bioorg Med Chem Lett. 2008;18:414-7.

Jin, et al., Evidence for dimeric BACE-mediated APP processing, Biochemical and Biophysical Research Communications 393 (2010) 21-27.

Loane, et al., Amyloid Precursor Protein Secretases as Therapeutic Targets for Traumatic Brain Injury, Nature Medicine, Advance Online Publication, Received Aug. 27, 2008; accepted Feb. 18, 2009; published online Mar. 15, 2009; doi:10.1038/nm.1940, pp. 1-3.

Luo, et al., mice deficient in BACE1, the Alzheimer's B-secretase, have normal phenotype and abolished B-amyloid, Nature Neuroscience, vol. 4, No. 3, Mar. 2001.

Malamas, et al., Aminoimidazoles as potent and selective human B-secretase (BACE1) inhibitors, J. Med. Chem., 2009, 52, 6314-6323.

Malamas, et al., Design and Synthesis of 5,50-Disubstituted Aminohydantoins as Potent and Selective Human β-Secretase (BACE1) Inhibitors, J. Med. Chem. 2010, 53, 1146-1158 (Published on Web Dec. 7, 2009).

Malamas, et al., Design and synthesis of aminohydantoins as potent and selective human b-secretase (BACE1) inhibitors with enhanced brain permeability, Bioorganic & Medicinal Chemistry Letters 20 (2010) 6597-6605.

Malamas, et al., Di-substituted pyridinyl aminohydantoins as potent and highly selective human b-secretase (BACE1) inhibitors, Bioorganic & Medicinal Chemistry 18 (2010) 630-639.

Malamas, et al., New pyrazolyl and thienyl aminohydantoins as potent BACE1 inhibitors: Exploring the S20 region, Bioorganic & Medicinal Chemistry Letters 21 (2011) 5164-5170.

Malamas, et al., Novel pyrrolyl 2-aminopyridines as potent and selective human b-secretase (BACE1) inhibitors, Bioorganic & Medicinal Chemistry Letters 20 (2010) 2068-2073 (Available online Feb. 23, 2010).

Mandal M, et al., Design and validation of bicyclic iminopyrimidinones as beta amyloid cleaving enzyme-1 (BACE1) inhibitors: conformational constraint to favor a bioactive conformation. J Med Chem. Nov. 8, 2012;55(21):9331-45. doi: 10.1021/jm301039c.

May, et al., Robust Central Reduction of B Amyloid in Humans with an Orally Available, Non-Peptidic B-Secretase Inhibitor, The Journal of Neuroscience, Nov. 16, 2011 • 31(46):16507-16516 • 16507.

McConlogue, et al., Partial reduction of BACE1 as dramatic effects on Alzheimer's plaque and synaptic pathology in APP transgenic mice, J. Biological Chem., vol. 282, No. 36, pp. 26326-26334, Sep. 7, 2007.

Nowak, et al., Discovery and initial optimization of 5,50-disubstituted aminohydantoins as potent b-secretase (BACE1) inhibitors, Bioorganic & Medicinal Chemistry Letters 20 (2010) 632-635. (Available online Nov. 20, 2009).

Ohno, et al., BACE1 deficiency rescues memory deficits and Cholinergic function in a mouse model of Alzheimer's disease, Neuron, vol. 41, 27-33, Jan. 8, 2004.

Ohno, et al. BACE1 gene deletion prevents neuron loss and memory deficits in 5XFAD APP/PS1 transgenic mice, Neurobiology of disease 26 (2006), pp. 134-145.

Osherovich, L. AB's Dry (AMD) Humor, SciBX 4(26); doi:10.1038/scibx.2011.727, Published online Jun. 30, 2011.

Probst, et al., Small-molecule BACE1 inhibitors: a patent literature review, Expert Opinion on Therapeutic Patents, (2006-2011), 2012, 22(5):511-540.

Roberds, et al., BACE knockout mice are healthy despite lacking the primary B-secretase activity in the brain: implications for Alzheimer's disease therapeutics, Human Mol. Genetics, vol. 10, No. 12, pp. 1317-1324. Apr. 3, 2004.

Salloway, et al., A randomized, double-blind, placebo-controlled clinical trial of intravenous bapineuzumab in patients with mild-to-moderate Alzheimer's disease who are alipoprotein E4 non-carriers, European Federation of Neurological Societies, Stockholm, Sweden, Sep. 12, 2012.

Scott, et al., "Novel Imino Pyrimidinone B-Secretase (BACE1) Inhibitors. P1 Thiophenes", Poster presentation, American Chemical Society, Sprint 2011.

Southan, BACE2 as a New Diabetes Target: a patent review 2010-2012, Expert Opinion on Therapeutic Patents, 2013, lnforma UK, Ltd., ISSN 1354-3776, e-1744-7674.

Sperling, et al., A randomized, double-blind, placebo-controlled clinical trial of intravenous bapineuzumab in patients with mild-to-moderate Alzheimer's disease who are alipoprotein E4 non-carriers, European Federation of Neurological Societies, Stockholm, Sweden, Sep. 11, 2012.

Stachel, et al., Structure-Based Design of Potent and Selective Cell-Permeable Inhibitors of Human Beta-Secretase (BACE-1), J. Med. Chem., 2004, vol. 47, pp. 6447-6450.

Stamford, et al., "Fragment-based discovery of BACE1 inhibitors, Potential disease-modifying agents for the treatment of Alzheimer's disease", Slide Presentation R. Bryan Miller Symposium, UC Davis, Mar. 7-8, 2013.

(56) References Cited

OTHER PUBLICATIONS

Stamford, et al., Discovery of an Orally Available, Brain Penetrant BACE1 Inhibitor That Affords Robust CNS Aβ Reduction, ACS Med. Chem. Lett. Jul. 12, 2012, 3, 897-902.

Stamford, et al., Inhibitors of BACE for treating Alzheimer's disease: a fragment-based drug discovery story, Current Opinion in Chemical Biology; v:17 i:3 p. 320-328; Jun. 2013 Elsevier.

Statchel, et al., Conformationally biased P3 amide replacements of b-secretase inhibitors, S. J. Stachel et al./Bioorg. Med. Chem. Lett. 16.(2006) 641-644.

Statchel, et al., Discovery of aminoheterocycles as a novel b-secretase inhibitor class: pH dependence on binding activity part 1, Bioorganic & Medicinal Chemistry Letters 19 (2009) 2977-2980.

Swahn, et al., "Aminimidazoles as BACE-1 inhibitors: The challenge to achieve in vivo brain efficacy", Bioorganic and Medicinal Chemistry Letters, 22 (2012) 1854-1859.

Swahn, et al., "Design and synthesis of beta-site amyloid precursor protein cleaving enzyme (BACE1) inhibitors with in vivo brain reduction of B-amyloid peptides", Journal of Medicinal Chemistry, 2012, 55, 9346-9361.

Tresadern, et al., Rational design and synthesis of aminopiperazinones as b-secretase (BACE) inhibitors, Bioorganic & Medicinal Chemistry Letters 21 (2011) 7255-7260.

Wang YS, et al., Application of fragment-based NMR screening, X-ray crystallography, structure-based design, and focused chemical library design to identify novel microM leads for the development of nM BACE-1 (beta-site APP cleaving enzyme 1) inhibitors. J Med Chem. 2010;53:942-50.

Weiner, Further insights into Alzheimer disease pathogenesis, Weiner, M.W. Nat. Rev. Neurol. 9, 65-66 (2013); published online Jan. 22, 2013.

Welch, J.T., et al., The synthesis and biological activity of pentafluorosulfanyl analogs of fluoxetine, fenfluramine, and norfenfluramine, Bioorganic & Medicinal Chemistry; v:15 i:21 p. 6659-6666; Nov. 1, 2007.

Wyss DF, et al., Combining NMR and X-ray crystallography in fragment-based drug discovery: discovery of highly potent and selective BACE-1 inhibitors. Top Curr Chem. 2012;317:83-114. doi: 10.1007/128_2011_183.

Zhi, et al., Self-organizing molecular field analysis on human b-secretase nonpeptide inhibitors: 5, 5-disubstituted aminohydantoins, European Journal of Medicinal Chemistry 46 (2011) 58-64.

Zhou, et al., An efficient synthesis of 2-amino-4-(4-fluoro-3-(2-fluoropyridin-3-yl)phenyl)-4-(4-methoxy-3-methylphenyl)-1-methyl-1H-imidazol-5(4H)-one, a potent BACE1 inhibitor, ARKIVOC 2010 (vi) 84-88.

Zhou, et al., Pyridinyl aminohydantoins as small molecule BACE1 inhibitors, Bioorganic & Medicinal Chemistry Letters 20 (2010) 2326-2329 (Available online Feb. 12, 2010).

Zhu, et al., Discovery of Cyclic Acylguanidines as Highly Potent and Selective β-Site Amyloid Cleaving Enzyme (BACE) Inhibitors: Part I;Inhibitor Design and Validation),1, J. Med. Chem. 2010, 53, 951-965.

2-SPIRO-SUBSTITUTED IMINOTHIAZINES AND THEIR MONO- AND DIOXIDES AS BACE INHIBITORS, COMPOSITIONS AND THEIR USE

CROSS-REFERENCE TO RELATED APPLICATIONS

This application is a U.S. National Stage Application under 35 U.S.C. 371 of PCT Application No. PCT/US2012/051687, filed Aug. 21, 2012, which claims the benefit of U.S. Provisional Application No. US 61/526,049, filed Aug. 22, 2011.

FIELD OF THE INVENTION

This invention provides certain imino thiazine compounds and mono- and dioxides thereof, and compositions comprising these compounds, which are useful as inhibitors of BACE, and for treating or preventing pathologies related thereto.

BACKGROUND

Amyloid beta peptide ("Aβ") is a primary component of β amyloid fibrils and plaques, which are regarded as having a role in an increasing number of pathologies. Examples of such pathologies include, but are not limited to, Alzheimer's disease, Down's syndrome, Parkinson's disease, memory loss (including memory loss associated with Alzheimer's disease and Parkinson's disease), attention deficit symptoms (including attention deficit symptoms associated with Alzheimer's disease ("AD"), Parkinson's disease, and Down's syndrome), dementia (including pre-senile dementia, senile dementia, dementia associated with Alzheimer's disease, Parkinson's disease, and Down's syndrome), progressive supranuclear palsy, cortical basal degeneration, neurodegeneration, olfactory impairment (including olfactory impairment associated with Alzheimer's disease, Parkinson's disease, and Down's syndrome), β-amyloid angiopathy (including cerebral amyloid angiopathy), hereditary cerebral hemorrhage, mild cognitive impairment ("MCI"), glaucoma, amyloidosis, type II diabetes, hemodialysis (β2 microglobulins and complications arising therefrom), neurodegenerative diseases such as scrapie, bovine spongiform encephalitis, Creutzfeld-Jakob disease, traumatic brain injury and the like.

Aβ peptides are short peptides which are made from the proteolytic break-down of the transmembrane protein called amyloid precursor protein ("APP"). Aβ peptides are made from the cleavage of APP by β-secretase activity at a position near the N-terminus of Aβ, and by gamma-secretase activity at a position near the C-terminus of Aβ. (APP is also cleaved by α-secretase activity, resulting in the secreted, non-amyloidogenic fragment known as soluble APPα.) Beta site APP Cleaving Enzyme ("BACE-1") is regarded as the primary aspartyl protease responsible for the production of Aβ by β-secretase activity. The inhibition of BACE-1 has been shown to inhibit the production of Aβ.

AD is estimated to afflict more than 20 million people worldwide and is believed to be the most common cause of dementia. AD is a disease characterized by degeneration and loss of neurons and also by the formation of senile plaques and neurofibrillary tangles. Presently, treatment of Alzheimer's disease is limited to the treatment of its symptoms rather than the underlying causes. Symptom-improving agents approved for this purpose include, for example, N-methyl-D-aspartate receptor antagonists such as memantine (Namenda®, Forrest Pharmaceuticals, Inc.), cholinesterase inhibitors such as donepezil (Aricept®, Pfizer), rivastigmine (Exelon®, Novartis), galantamine (Razadyne Reminyl®), and tacrine (Cognex®).

In AD, Aβ peptides, formed through β-secretase and gamma-secretase activity, can form tertiary structures that aggregate to form amyloid fibrils. Aβ peptides have also been shown to form Aβ oligomers (sometimes referred to as "Aβ aggregates" or "Abeta oligomers"). Aβ oligomers are small multimeric structures composed of 2 to 12 Aβ peptides that are structurally distinct from Aβ fibrils. Amyloid fibrils can deposit outside neurons in dense formations known as senile plaques, neuritic plaques, or diffuse plaques in regions of the brain important to memory and cognition. Aβ oligomers are cytotoxic when injected in the brains of rats or in cell culture. This Aβ plaque formation and deposition and/or Aβ oligomer formation, and the resultant neuronal death and cognitive impairment, are among the hallmarks of AD pathophysiology. Other hallmarks of AD pathophysiology include intracellular neurofibrillary tangles comprised of abnormally phosphorylated tau protein, and neuroinflammation.

Evidence suggests that Aβ, Aβ fibrils, aggregates, oligomers, and/or plaque play a causal role in AD pathophysiology. (Ohno et al., Neurobiology of Disease, No. 26 (2007), 134-145). Mutations in the genes for APP and presenilins 1/2 (PS1/2) are known to cause familial AD and an increase in the production of the 42-amino acid form of Aβ is regarded as causative. Aβ has been shown to be neurotoxic in culture and in vivo. For example, when injected into the brains of aged primates, fibrillar Aβ causes neuronal cell death around the injection site. Other direct and circumstantial evidence of the role of Aβ in Alzheimer etiology has also been published.

BACE-1 has become an accepted therapeutic target for the treatment of Alzheimer's disease. For example, McConlogue et al., J. Bio. Chem., Vol. 282, No. 36 (September 2007), have shown that partial reductions of BACE-1 enzyme activity and concomitant reductions of Aβ levels lead to a dramatic inhibition of Aβ-driven AD-like pathology, making β-secretase a target for therapeutic intervention in AD. Ohno et al. Neurobiology of Disease, No. 26 (2007), 134-145, report that genetic deletion of BACE-1 in 5XFAD mice abrogates Aβ generation, blocks amyloid deposition, prevents neuron loss found in the cerebral cortex and subiculum (brain regions manifesting the most severe amyloidosis in 5XFAD mice), and rescues memory deficits in 5XFAD mice. The group also reports that Aβ is ultimately responsible for neuron death in AD and concludes that BACE-1 inhibition has been validated as an approach for the treatment of AD. Roberds et al., Human Mol. Genetics, 2001, Vol. 10, No. 12, 1317-1324, established that inhibition or loss of β-secretase activity produces no profound phenotypic defects while inducing a concomitant reduction in Aβ. Luo et al., Nature Neuroscience, Vol. 4, No. 3, March 2001, report that mice deficient in BACE-1 have normal phenotype and abolished β-amyloid generation.

More recently, Jonsson, et al. have reported in Nature, Vol. 488, pp. 96-99 (August 2012), that a coding mutation (A673T) in the APP gene protects against Alzheimer's disease and cognitive decline in the elderly without Alzheimer's disease. More specifically, the A allele of rs63750847, a single nucleotide polymorphism (SNP), results in an alanine to threonine substitution at position 673 in APP (A673T). This SNP was found to be significantly more common in a healthy elderly control group than in an Alzheimer's disease group. The A673T substitution is adjacent to the aspartyl protease beta-site in APP, and results in an approximately 40% reduction in the formation of amyloidogenic peptides in a heterologous cell expression system in vitro. Jonsson, et al. report that an APP-derived peptide substrate containing the A673T mutation is processed 50% less efficiently by purified human BACE1 enzyme when compared to a wild-type peptide. Jonsson et al. indicate that the strong protective effect of the APP-A673T substitution against Alzheimer's disease provides proof of principle for the hypothesis that reducing the beta-cleavage of APP may protect against the disease.

BACE-1 has also been identified or implicated as a therapeutic target for a number of other diverse pathologies in which Aβ or Aβ fragments have been identified to play a causative role. One such example is in the treatment of AD-type symptoms of patients with Down's syndrome. The gene encoding APP is found on chromosome 21, which is also the chromosome found as an extra copy in Down's syndrome. Down's syndrome patients tend to acquire AD at an early age, with almost all those over 40 years of age showing Alzheimer's-type pathology. This is thought to be due to the extra copy of the APP gene found in these patients, which leads to overexpression of APP and therefore to increased levels of Aβ causing the prevalence of AD seen in this population. Furthermore, Down's patients who have a duplication of a small region of chromosome 21 that does not include the APP gene do not develop AD pathology. Thus, it is thought that inhibitors of BACE-1 could be useful in reducing Alzheimer's type pathology in Down's syndrome patients.

Another example is in the treatment of glaucoma (Guo et al., PNAS, Vol. 104, No. 33, Aug. 14, 2007). Glaucoma is a retinal disease of the eye and a major cause of irreversible blindness worldwide. Guo et al. report that Aβ colocalizes with apoptotic retinal ganglion cells (RGCs) in experimental glaucoma and induces significant RGC cell loss in vivo in a dose- and time-dependent manner. The group report having demonstrated that targeting different components of the Aβ formation and aggregation pathway, including inhibition of β-secretase alone and together with other approaches, can effectively reduce glaucomatous RGC apoptosis in vivo. Thus, the reduction of Aβ production by the inhibition of BACE-1 could be useful, alone or in combination with other approaches, for the treatment of glaucoma.

Another example is in the treatment of olfactory impairment. Getchell et al., Neurobiology of Aging, 24 (2003), 663-673, have observed that the olfactory epithelium, a neuroepithelium that lines the posterior-dorsal region of the nasal cavity, exhibits many of the same pathological changes found in the brains of AD patients, including deposits of Aβ, the presence of hyperphosphorylated tau protein, and dystrophic neurites among others. Other evidence in this connection has been reported by Bacon A W, et al., Ann NY Acad Sci 2002; 855:723-31; Crino P B, Martin J A, Hill W D, et al., Ann Otol Rhinol Laryngol, 1995; 104:655-61; Davies D C, et al., Neurobiol Aging, 1993; 14:353-7; Devanand D P, et al., Am J Psychiatr, 2000; 157:1399-405; and Doty R L, et al., Brain Res Bull, 1987; 18:597-600. It is reasonable to suggest that addressing such changes by reduction of Aβ by inhibition of BACE-1 could help to restore olfactory sensitivity in patients with AD.

For compounds which are inhibitors of BACE-2, another example is in the treatment of type-II diabetes, including diabetes associated with amyloidogenesis. BACE-2 is expressed in the pancreas. BACE-2 immunoreactivity has been reported in secretory granules of beta cells, co-stored with insulin and IAPP, but lacking in the other endocrine and exocrine cell types. Stoffel et al., WO2010/063718, disclose the use of BACE-2 inhibitors in the treatment of metabolic diseases such as Type-II diabetes. The presence of BACE-2 in secretory granules of beta cells suggests that it may play a role in diabetes-associated amyloidogenesis. (Finzi, G. Franzi, et al., Ultrastruct Pathol. 2008 November-December; 32(6):246-51.)

Other diverse pathologies characterized by the formation and deposition of Aβ or fragments thereof, and/or by the presence of amyloid fibrils, oligomers, and/or plaques, include neurodegenerative diseases such as scrapie, bovine spongiform encephalitis, traumatic brain injury ("TBI"), Creutzfeld-Jakob disease and the like, type II diabetes (which is characterized by the localized accumulation of cytotoxic amyloid fibrils in the insulin producing cells of the pancreas), and amyloid angiopathy. In this regard reference can be made to the patent literature. For example, Kong et al., US2008/0015180, disclose methods and compositions for treating amyloidosis with agents that inhibit Aβ peptide formation. As another example, Loane, et al. report the targeting of amyloid precursor protein secretases as therapeutic targets for traumatic brain injury. (Loane et al., "Amyloid precursor protein secretases as therapeutic targets for traumatic brain injury", Nature Medicine, Advance Online Publication, published online Mar. 15, 2009.) Still other diverse pathologies characterized by the inappropriate formation and deposition of Aβ or fragments thereof, and/or by the presence of amyloid fibrils, and/or for which inhibitor(s) of BACE-1 is expected to be of therapeutic value are discussed further hereinbelow.

The therapeutic potential of inhibiting the deposition of Aβ has motivated many groups to characterize BACE-1 and to identify inhibitors of BACE-1 and of other secretase enzyme inhibitors. Examples from the patent literature are growing and include WO2006009653, WO2007005404, WO2007005366, WO2007038271, WO2007016012, US2005/0282826, US2007072925, WO2007149033, WO2007145568, WO2007145569, WO2007145570, WO2007145571, WO2007114771, US20070299087, WO2005/016876, WO2005/014540, WO2005/058311, WO2006/065277, WO2006/014762, WO2006/014944, WO2006/138195, WO2006/138264, WO2006/138192, WO2006/138217, WO2007/050721, WO2007/053506, WO2007/146225, WO2006/138230, WO2006/138265, WO2006/138266, WO2007/053506, WO2007/146225, WO2008/073365, WO2008/073370, WO2008/103351, US2009/041201, US2009/041202, and WO2010/047372.

SUMMARY OF THE INVENTION

The present invention provides certain imino thiazine compounds and mono- and dioxides thereof, which are collectively or individually referred to herein as "compound(s) of the invention", as described herein. The compounds of the invention are useful as inhibitors of BACE-1 and/or BACE-2.

In one embodiment, the compounds of the invention have the structural Formula (I):

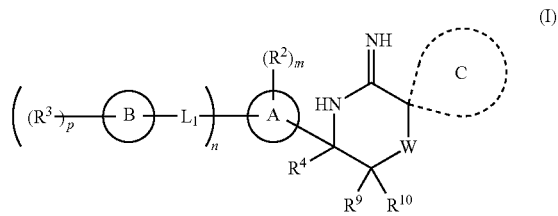

or a tautomer thereof having the structural Formula (I'):

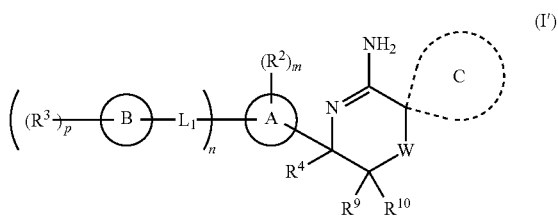

or pharmaceutically acceptable salt thereof, wherein:

W is selected from the group consisting of S, S(O), and $S(O)_2$;

ring C is selected from the group consisting of:

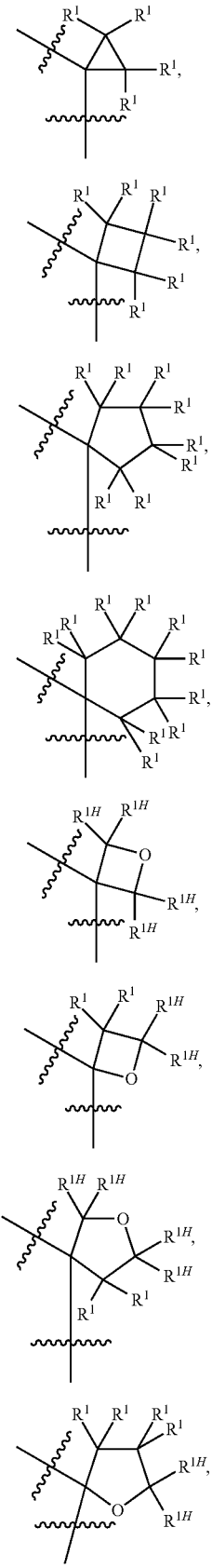

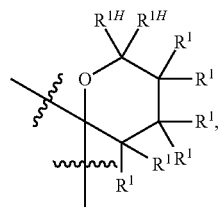

(C9)

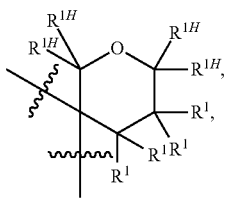

(C10)

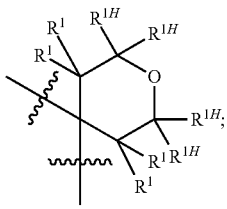

(C11)

ring A is selected from the group consisting of aryl, monocyclic heteroaryl, monocyclic cycloalkyl, monocyclic cycloalkenyl, monocyclic heterocycloalkyl, monocyclic heterocycloalkenyl, and a multicyclic group;

ring B (when present) is independently selected from the group consisting of aryl, monocyclic heteroaryl, monocyclic cycloalkyl, monocyclic cycloalkenyl, monocyclic heterocycloalkyl, monocyclic heterocycloalkenyl, and a multicyclic group;

-$L_1$- (when present) independently represents a bond or a divalent moiety selected from the group consisting -alkyl-, -haloalkyl-, -heteroalkyl-, -alkenyl-, -alkynyl-, —N($R^6$)—, —O—, —NHC(O)—, —C(O)NH—, NHS(O)$_2$—, —S(O)$_2$NH—, —O—CH$_2$—, —CH$_2$—O—, —NHCH$_2$—, —CH$_2$NH—, and —CH(CF$_3$)NH—, —NHCH(CF$_3$)—;

m, n, and p are each independently selected integers, wherein:
  m is 0 or more;
  n is 0 or 1; and
  p is 0 or more,
  wherein the maximum value of m is the maximum number of available substitutable hydrogen atoms on ring A, and wherein the maximum value of p is the maximum number of available substitutable hydrogen atoms on ring B;

each $R^1$ (when present) is independently selected from the group consisting of: H, halogen, —OH, alkyl, alkoxy, -alkyl-OH, haloalkyl, haloalkoxy, heteroalkyl, haloheteroalkyl, cycloalkyl, -alkyl-cycloalkyl, —O-cycloalkyl, —O-alkyl-cycloalkyl, heterocycloalkyl, -alkyl-heterocycloalkyl, —O-heterocycloalkyl, and —O-alkyl-heterocycloalkyl,
  wherein said cycloalkyl, -alkyl-cycloalkyl, —O-cycloalkyl, —O-alkyl-cycloalkyl, heterocycloalkyl, -alkyl-heterocycloalkyl, —O-heterocycloalkyl, and —O-alkyl-heterocycloalkyl is optionally substituted with halogen, alkyl, alkoxy, haloalkyl, haloalkoxy, heteroalkyl, haloheteroalkyl;

each $R^{1H}$ is independently selected from the group consisting of: H, alkyl, -alkyl-OH, haloalkyl, heteroalkyl, haloheteroalkyl, cycloalkyl, -alkyl-cycloalkyl, heterocycloalkyl, -alkyl-heterocycloalkyl, wherein said cycloalkyl, -alkyl-cycloalkyl, heterocycloalkyl, and
-alkyl-heterocycloalkyl is optionally substituted with halogen, alkyl, alkoxy, haloalkyl, haloalkoxy, heteroalkyl, haloheteroalkyl;

each $R^2$ (when present) is independently selected from the group consisting of: halogen, —OH, —CN, —SF$_5$, —OSF$_5$, —NO$_2$, —Si(R$^5$)$_3$, —P(O)(OR$^5$)$_2$, —P(O)(OR$^5$)(R$^5$), —N(R$^6$)$_2$, —NR$^7$C(O)R$^6$, —NR$^7$S(O)$_2$R$^6$, —NR$^7$S(O)$_2$N(R$^6$)$_2$, —NR$^7$C(O)N(R$^6$)$_2$, —NR$^7$C(O)OR$^6$, —C(O)R$^6$, —C(O)$_2$R$^6$, —C(O)N(R$^6$)$_2$, —S(O)R$^6$, —S(O)$_2$R$^6$, —S(O)$_2$N(R$^6$)$_2$, —OR$^6$, —SR$^6$, alkyl, haloalkyl, heteroalkyl, alkenyl, alkynyl, cycloalkyl, -alkyl-cycloalkyl, aryl, -alkyl-aryl, heteroaryl, -alkyl-heteroaryl, heterocycloalkyl, and -alkyl-heterocycloalkyl, wherein said alkyl, haloalkyl, heteroalkyl, alkenyl, alkynyl, cycloalkyl, -alkyl-cycloalkyl, aryl, -alkyl-aryl, heteroaryl, -alkyl-heteroaryl, heterocycloalkyl, and -alkyl-heterocycloalkyl of $R^2$ are each optionally unsubstituted or substituted with one or more groups independently selected from $R^8$;

each $R^3$ (when present) is independently selected from the group consisting of: halogen, —OH, —CN, —SF$_5$, —OSF$_5$, —NO$_2$, —Si(R$^5$)$_3$, —P(O)(OR$^5$)$_2$, —P(O)(OR$^5$)(R$^5$), —N(R$^6$)$_2$, —NR$^7$C(O)R$^6$, —NR$^7$S(O)$_2$R$^6$, —NR$^7$S(O)$_2$N(R$^6$)$_2$, —NR$^7$C(O)N(R$^6$)$_2$, —NR$^7$C(O)OR$^6$, —C(O)R$^6$, —C(O)$_2$R$^6$, —C(O)N(R$^6$)$_2$, —S(O)R$^6$, —S(O)$_2$R$^6$, —S(O)$_2$N(R$^6$)$_2$, —OR$^6$, —SR$^6$, alkyl, haloalkyl, heteroalkyl, alkenyl, alkynyl, cycloalkyl, -alkyl-cycloalkyl, aryl, -alkyl-aryl, heteroaryl, -alkyl-heteroaryl, heterocycloalkyl, and -alkyl-heterocycloalkyl, wherein said alkyl, haloalkyl, heteroalkyl, alkenyl, alkynyl, cycloalkyl, -alkyl-cycloalkyl, aryl, -alkyl-aryl, heteroaryl, -alkyl-heteroaryl, and heterocycloalkyl of $R^3$ are each optionally unsubstituted or substituted with one or more groups independently selected from $R^8$;

$R^4$ is selected from the group consisting of H, alkyl, haloalkyl, heteroalkyl, alkenyl, alkynyl, aryl, -alkyl-aryl, heteroaryl, -alkyl-heteroaryl, cycloalkyl, -alkyl-cycloalkyl, cycloalkenyl, -alkyl-cycloalkenyl, heterocycloalkyl, -alkyl-heterocycloalkyl, heterocycloalkenyl, and -alkyl-heterocycloalkenyl, wherein each of said alkyl, haloalkyl, heteroalkyl, aryl, -alkyl-aryl, heteroaryl, -alkyl-heteroaryl, cycloalkyl, -alkyl-cycloalkyl, cycloalkenyl, -alkyl-cycloalkenyl, heterocycloalkyl, -alkyl-heterocycloalkyl, heterocycloalkenyl, and -alkyl-heterocycloalkenyl of $R^4$ is unsubstituted or substituted with one or more independently selected $R^{11}$ groups;

each $R^5$ (when present) is independently selected from the group consisting of alkyl, heteroalkyl, haloalkyl, cycloalkyl, -alkyl-cycloalkyl, aryl, -alkyl-aryl, heteroaryl, and -alkyl-heteroaryl, wherein each said aryl, -alkyl-aryl, heteroaryl, and -alkyl-heteroaryl of $R^5$ is unsubstituted or substituted with one or more groups independently selected from halogen, alkyl, cycloalkyl, heteroalkyl, haloalkyl, alkoxy, —O-heteroalkyl, and haloalkoxy;

each $R^6$ (when present) is independently selected from the group consisting of H, alkyl, -alkyl-OH, alkenyl, alkynyl, heteroalkyl, -heteroalkyl-OH, haloalkyl, -haloalkyl-OH, cycloalkyl, lower alkyl-substituted cycloalkyl, lower alkyl-substituted -alkyl-cycloalkyl, heterocycloalkyl, -alkyl-heterocycloalkyl, aryl, -alkyl-aryl, heteroaryl, and -alkyl-heteroaryl, wherein each said heterocycloalkyl, -alkyl-heterocycloalkyl, aryl, -alkyl-aryl, heteroaryl, and said -alkyl-heteroaryl of $R^6$ is unsubstituted or substituted with one or more groups independently selected from halogen, —CN, alkyl, cycloalkyl, heteroalkyl, haloalkyl, alkoxy, —O-heteroalkyl, and haloalkoxy;

each $R^7$ (when present) is independently selected from the group consisting of H, alkyl, heteroalkyl, haloalkyl, cycloalkyl, -alkyl-cycloalkyl, aryl, -alkyl-aryl, heteroaryl, and -alkyl-heteroaryl, wherein each said aryl, -alkyl-aryl, heteroaryl, and -alkyl-heteroaryl of $R^7$ is unsubstituted or substituted with one or more groups independently selected from halogen, alkyl, cycloalkyl, heteroalkyl, haloalkyl, alkoxy, —O-heteroalkyl, and haloalkoxy;

each $R^8$ (when present) is independently selected from the group consisting of halogen, —OH, —CN, —SF$_5$, —OSF$_5$, alkyl, alkoxy, haloalkyl, haloalkoxy, cycloalkyl, -alkyl-cycloalkyl, —O-cycloalkyl, —O-alkyl-cycloalkyl, heteroalkyl, —O-heteroalkyl, and -alkyl-OH;

$R^9$ and $R^{10}$ are each independently selected from the group consisting of H, halogen, —CN, —P(O)(OR$^5$)$_2$, —P(O)(OR$^5$)(R$^5$), —NR$^7$C(O)R$^6$, —NR$^7$S(O)$_2$R$^6$, —NR$^7$C(O)N(R$^6$)$_2$, —NR$^7$C(O)OR$^6$, —C(O)R$^6$, —C(O)$_2$R$^6$, —C(O)N(R$^6$)$_2$, —S(O)R$^6$, —S(O)$_2$R$^6$, —S(O)$_2$N(R$^6$)$_2$, —OR$^6$, —SR$^6$, alkyl, haloalkyl, heteroalkyl, alkenyl and alkynyl, wherein each of said alkyl, haloalkyl, heteroalkyl, alkenyl and alkynyl of $R^9$ and $R^{10}$ is unsubstituted or substituted with one or more independently selected $R^{12}$ groups;

each $R^{11}$ (when present) is independently selected from the group consisting of halogen, —OH, —CN, —SF$_5$, —OSF$_5$, —P(O)(OR$^5$)$_2$, —P(O)(OR$^5$)(R$^5$), —N(R$^6$)$_2$, —NR$^7$C(O)R$^6$, —NR$^7$S(O)$_2$R$^6$, —NR$^7$S(O)$_2$N(R$^6$)$_2$, —NR$^7$C(O)N(R$^6$)$_2$, —NR$^7$C(O)OR$^6$, —C(O)R$^6$, —C(O)$_2$R$^6$, —C(O)N(R$^6$)$_2$, —S(O)R$^6$, —S(O)$_2$R$^6$, —S(O)$_2$N(R$^6$)$_2$, —OR$^6$, —SR$^6$, alkyl, haloalkyl, haloalkoxy, heteroalkyl, -alkyl-OH, cycloalkyl, -alkyl-cycloalkyl;

each $R^{12}$ (when present) is independently selected from the group consisting of halogen, —OH, —CN, —SF$_5$, —OSF$_5$, —P(O)(OR$^{13}$)$_2$, —P(O)(OR$^{13}$)(R$^{13}$), —N(R$^{14}$)$_2$, —NR$^{14}$C(O)R$^{14}$, —NR$^{14}$S(O)$_2$R$^{14}$, —NR$^{14}$S(O)$_2$N(R$^{14}$)$_2$, —NR$^{14}$C(O)N(R$^{14}$)$_2$, —NR$^{14}$C(O)OR$^{14}$, —C(O)R$^{14}$, —C(O)$_2$R$^{14}$, —C(O)N(R$^{14}$)$_2$, —S(O)R$^{14}$, —S(O)$_2$R$^{14}$, —S(O)$_2$N(R$^{14}$)$_2$, —OR$^{14}$, —SR$^{14}$, alkyl, haloalkyl, haloalkoxy, heteroalkyl, -alkyl-OH;

each $R^{13}$ (when present) is independently selected from the group consisting of alkyl, -alkyl-OH, alkenyl, alkynyl, heteroalkyl, -heteroalkyl-OH, haloalkyl, -haloalkyl-OH; and each $R^{14}$ (when present) is independently selected from the group consisting of H, alkyl, -alkyl-OH, alkenyl, alkynyl, heteroalkyl, -heteroalkyl-OH, haloalkyl, -haloalkyl-OH.

In other embodiments, the invention provides compositions, including pharmaceutical compositions, comprising one or more compounds of the invention (e.g., one compound of the invention), or a tautomer thereof, or a pharmaceutically acceptable salt or solvate of said compound(s) and/or said tautomer(s), optionally together with one or more additional therapeutic agents, optionally in an acceptable (e.g., pharmaceutically acceptable) carrier or diluent.

In other embodiments, the invention provides various methods of treating, preventing, ameliorating, and/or delaying the onset of an Aβ pathology and/or a symptom or symptoms thereof, comprising administering a composition comprising an effective amount of one or more compounds of the invention, or a tautomer thereof, or pharmaceutically acceptable salt or solvate of said compound(s) and/or said tautomer(s), to a patient in need thereof. Such methods optionally additionally comprise administering an effective amount of one or more additional therapeutic agents suitable for treating the patient being treated.

These and other embodiments of the invention, which are described in detail below or will become readily apparent to those of ordinary skill in the art, are included within the scope of the invention.

DETAILED DESCRIPTION

In one embodiment, the compounds of the invention have the structural Formula (I) as described above.

In one embodiment, the compounds of the invention have the structural Formula (IA):

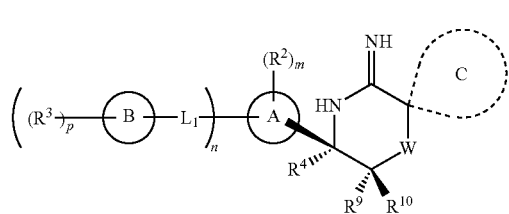

(IA)

or a tautomer thereof having the structural Formula (IA'):

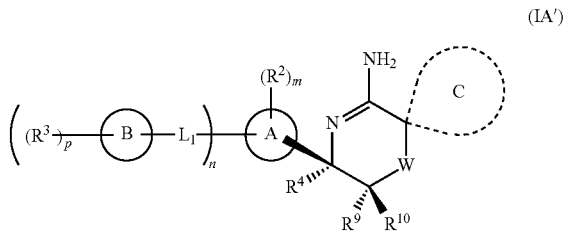

(IA')

or pharmaceutically acceptable salt thereof, wherein each variable is as described in Formula (I).

In one embodiment, the compounds of the invention have the structural Formula (IB):

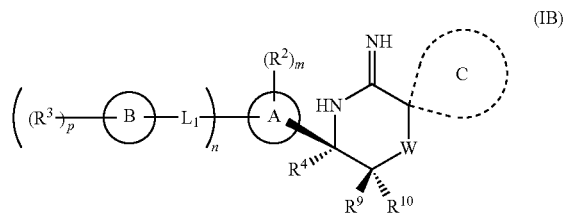

(IB)

or a tautomer thereof having the structural Formula (IB'):

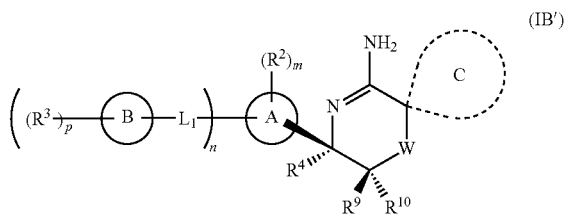

(IB')

or pharmaceutically acceptable salt thereof, wherein each variable is as described in Formula (I).

In one embodiment, in each of Formulas (I), (IA), (IA'), (IB), and (IB'), $R^9$ is selected from the group consisting of H, halo, alkyl, haloalkyl, and heteroalkyl.

In one embodiment, in each of Formulas (I), (IA), (IA'), (IB), and (IB'), $R^9$ is selected from the group consisting of H, halo, lower alkyl, lower haloalkyl, and lower alkyl ether.

In one embodiment, in each of Formulas (I), (IA), (IA'), (IB), and (IB'), $R^9$ is H.

In one embodiment, in each of Formulas (I), (IA), (IA'), (IB), and (IB'), $R^{10}$ is selected from the group consisting of H, halo, alkyl, haloalkyl, and heteroalkyl.

In one embodiment, in each of Formulas (I), (IA), (IA'), (IB), and (IB'), $R^{10}$ is selected from the group consisting of H, halo, lower alkyl, lower haloalkyl, and lower alkyl ether.

In one embodiment, in each of Formulas (I), (IA), (IA'), (IB), and (IB'), $R_{10}$ is H.

In one embodiment, in each of Formulas (I), (IA), (IA'), (IB), and (IB'), one of $R^9$ and $R^{10}$ is H and the other is selected from the group consisting of H, halogen, alkyl, haloalkyl, and heteroalkyl.

In one embodiment, in each of Formulas (I), (IA), (IA'), (IB), and (IB'), one of $R^9$ and $R^{10}$ is H and the other is selected from the group consisting of H, halo, lower alkyl, lower haloalkyl, and lower alkyl ether; and $R^{10}$ is H.

In one embodiment, in each of Formulas (I), (IA), (IA'), (IB), and (IB'), $R^9$ is H and $R^{10}$ is H.

In one embodiment, in each of Formulas (I), (IA), (IA'), (IB), and (IB'), $R^4$ is selected from the group consisting of lower alkyl and lower haloalkyl.

In one embodiment, in each of Formulas (I), (IA), (IA'), (IB), and (IB'), $R^4$ is selected from the group consisting of —CH$_3$, —CH$_2$F, —CHF$_2$, and —CF$_3$.

In one embodiment, in each of Formulas (I), (IA), (IA'), (IB), and (IB'), $R^4$ is selected from the group consisting of —CH$_3$, and —CHF$_2$.

In one embodiment, in each of Formulas (I), (IA), (IA'), (IB), and (IB'):

$R^4$ is selected from the group consisting of —CH$_3$ and —CHF$_2$;

one of $R^9$ and $R^{10}$ is H and the other is selected from the group consisting of H, halogen, alkyl, haloalkyl, and heteroalkyl.

In one embodiment, in each of Formulas (I), (IA), (IA'), (IB), and (IB'):

$R^4$ is selected from the group consisting of —CH$_3$ and —CHF$_2$; and one of $R^9$ and $R^{10}$ is H and the other is selected from the group consisting of H, lower alkyl, lower haloalkyl, and lower alkyl ether.

In one embodiment, in each of Formulas (I), (IA), (IA'), (IB), and (IB'):

$R^4$ is selected from the group consisting of —CH$_3$ and —CHF$_2$;

$R^9$ is H; and $R^{10}$ is H.

In one embodiment, the compounds of the invention have the structural Formula (II):

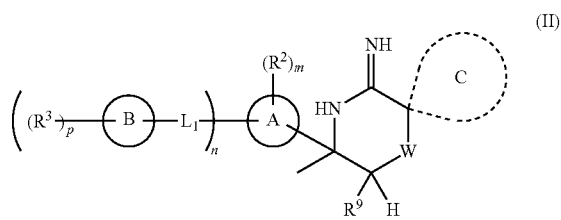

(II)

or a tautomer thereof having the structural Formula (II'):

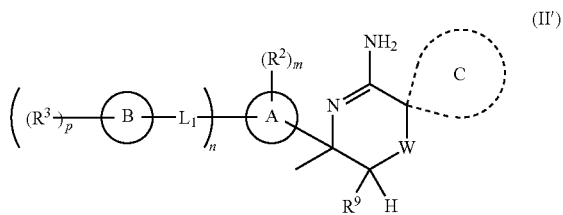

(II')

or pharmaceutically acceptable salt thereof, wherein each variable is as described in Formula (I).

In one embodiment, the compounds of the invention have the structural Formula (IIA):

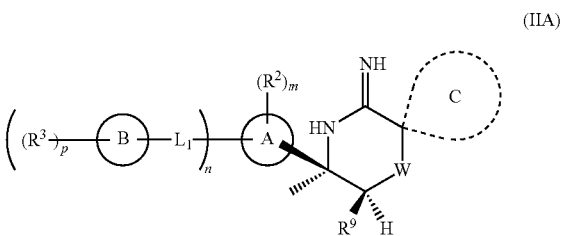

(IIA)

or a tautomer thereof having the structural Formula (IIA'):

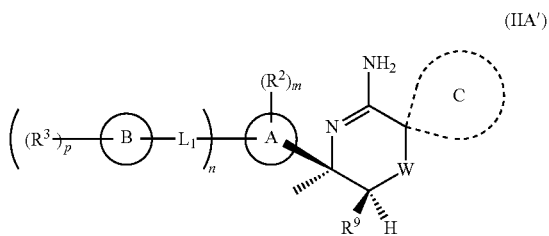

(IIA')

or pharmaceutically acceptable salt thereof, wherein each variable is as described in Formula (I).

In one embodiment, the compounds of the invention have the structural Formula (IIB):

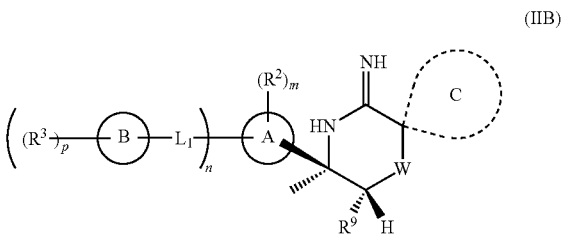

(IIB)

or a tautomer thereof having the structural Formula (IIA'):

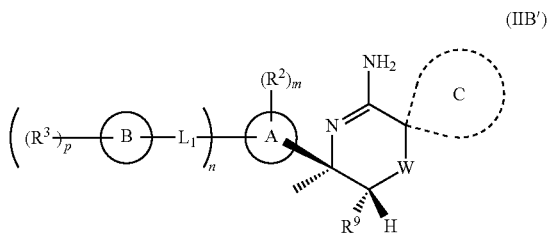

(IIB')

or pharmaceutically acceptable salt thereof, wherein each variable is as described in Formula (I).

In one embodiment, in each of Formulas (II), (IIA), (IIA'), (IIB), and (IIB'), $R^9$ is selected from the group consisting of H, halo, alkyl, haloalkyl, and heteroalkyl.

In one embodiment, in each of Formulas (II), (IIA), (IIA'), (IIB), and (IIB'), $R^9$ is selected from the group consisting of H, halo, lower alkyl, lower haloalkyl, and lower alkyl ether.

In one embodiment, in each of Formulas (II), (IIA), (IIA'), (IIB), and (IIB'), $R^9$ is H.

In one embodiment, in each of Formulas (I), (IA), (IA'), (IB), (IB'), (II), (II'), (IIA), (IIA'), (IIB), and (IIB'): W is S.

In one embodiment, in each of Formulas (I), (IA), (IA'), (IB), (IB'), (II), (II'), (IIA), (IIA'), (IIB), and (IIB'): W is S(O).

In one embodiment, in each of Formulas (I), (IA), (IA'), (IB), (IB'), (II), (II'), (IIA), (IIA'), (IIB), and (IIB'): W is $S(O)_2$.

In one embodiment, in each of Formulas (I), (IA), (IA'), (IB), (IB'), (II), (II'), (IIA), (IIA'), (IIB), and (IIB'):
each $R^1$ is independently selected from the group consisting of H, fluoro, methyl, ethyl, cyclopropyl, —$OCH_3$, —$OCH_2CH_3$, —O-cyclopropyl, —$OCH_2$-cyclopropyl, —$OCHF_2$, —$OCF_3$, —$CH_2$-cyclopropyl, —$CH_2OH$, —$CH_2OCH_3$, —$CH_2OCH_2CH_3$, trifluoromethyl, —$CH_2F$, —$CHF_2$.

In one embodiment, in each of Formulas (I), (IA), (IA'), (IB), (IB'), (II), (II'), (IIA), (IIA'), (IIB), and (IIB'):
Ring C is selected from the group consisting of (C1), (C2), (C3), (C4), (C5), (C7), and (C11); and
each $R^1$ is independently selected from the group consisting of H, fluoro, methyl, ethyl, cyclopropyl, —$OCH_3$, —$OCH_2CH_3$, —O-cyclopropyl, —$OCH_2$-cyclopropyl, —$OCHF_2$, —$OCF_3$, —$CH_2$-cyclopropyl, —$CH_2OH$, —$CH_2OCH_3$, —$CH_2OCH_2CH_3$, trifluoromethyl, —$CH_2F$, —$CHF_2$.

In another embodiment, in each of Formulas (I), (I'), (IA), and (IA'), (IB), (IB'), (II), (II'), (IIA), (IIA'), (IIB), and (IIB'):
each $R^{1H}$ is independently selected from the group consisting of H, methyl, ethyl, cyclopropyl, —$CH_2$-cyclopropyl, —$CH_2OCH_3$, —$CH_2OCH_2CH_3$, trifluoromethyl, —$CH_2F$, —$CHF_2$.

In one embodiment, in each of Formulas (I), (IA), (IA'), (IB), (IB'), (II), (II'), (IIA), (IIA'), (IIB), and (IIB'):
Ring C is selected from the group consisting of (C1), (C2), (C3), (C4), (C5), (C7), and (C11); and
each $R^{1H}$ is independently selected from the group consisting of H, methyl, ethyl, cyclopropyl, —$CH_2$-cyclopropyl, —$CH_2OCH_3$, —$CH_2OCH_2CH_3$, trifluoromethyl, —$CH_2F$, —$CHF_2$.

In one embodiment, in each of Formulas (I), (IA), (IA'), (IB), (IB'), (II), (II'), (IIA), (IIA'), (IIB), and (IIB'):
each $R^1$ is independently selected from the group consisting of H, fluoro, methyl, cyclopropyl, —$OCH_3$, —$OCF_3$, —$CH_2OCH_3$, —$CF_3$, and —$CHF_2$; and
each $R^{1H}$ is independently selected from the group consisting of H, methyl, cyclopropyl, —$CH_2OCH_3$, —$CF_3$, and —$CHF_2$.

In one embodiment, in each of Formulas (I), (IA), (IA'), (IB), (IB'), (II), (II'), (IIA), (IIA'), (IIB), and (IIB'):
Ring C is selected from the group consisting of (C1), (C2), (C3), (C4), (C5), (C7), and (C11); and
each $R^1$ is independently selected from the group consisting of H, fluoro, methyl, cyclopropyl, —$OCH_3$, —$OCF_3$, —$CH_2OCH_3$, —$CF_3$, and —$CHF_2$; and
each $R^{1H}$ is independently selected from the group consisting of H, methyl, cyclopropyl, —$CH_2OCH_3$, —$CF_3$, and —$CHF_2$.

In one embodiment, in each of Formulas (I), (IA), (IA'), (IB), (IB'), (II), (II'), (IIA), (IIA'), (IIB), and (IIB):
$R^1$ and $R^{1H}$ are each H.

In one embodiment, in each of Formulas (I), (IA), (IA'), (IB), (IB'), (II), (II'), (IIA), (IIA'), (IIB), and (IIB):
Ring C is selected from the group consisting of (C1), (C2), (C3), (C4), (C5), (C7), and (C11); and $R^1$ and $R^{1H}$ are each independently selected from the group consisting of H and OH.

In one embodiment, in each of Formulas (I), (IA), (IA'), (IB), (IB'), (II), (II'), (IIA), (IIA'), (IIB), and (IIB'):
$R^1$ and $R^{1H}$ are each independently H.

In one embodiment, in each of Formulas (I), (IA), (IA'), (IB), (IB'), (II), (II'), (IIA), (IIA'), (IIB), and (IIB'):
Ring C is selected from the group consisting of (C1), (C2), (C3), (C4), (C5), (C7), and (C11); and
$R^1$ and $R^{1H}$ are each H.

In an alternative of each of the embodiments described herein, in each of Formulas (I), (IA), (IA'), (IB), (IB'), (II), (II'), (IIA), (IIA'), (IIB), and (IIB'), Ring C is (C1).

In an alternative of each of the embodiments described herein, in each of Formulas (I), (IA), (IA'), (IB), (IB'), (II), (II'), (IIA), (IIA'), (IIB), and (IIB'), Ring C is (C2).

In an alternative of each of the embodiments described herein, in each of Formulas (I), (IA), (IA'), (IB), (IB'), (II), (II'), (IIA), (IIA'), (IIB), and (IIB'), Ring C is (C3).

In an alternative of each of the embodiments described herein, in each of Formulas (I), (IA), (IA'), (IB), (IB'), (II), (II'), (IIA), (IIA'), (IIB), and (IIB'), Ring C is (C4).

In an alternative of each of the embodiments described herein, in each of Formulas (I), (IA), (IA'), (IB), (IB'), (II), (II'), (IIA), (IIA'), (IIB), and (IIB'), Ring C is (C5).

In an alternative of each of the embodiments described herein, in each of Formulas (I), (IA), (IA'), (IB), (IB'), (II), (II'), (IIA), (IIA'), (IIB), and (IIB'), Ring C is (C6).

In an alternative of each of the embodiments described herein, in each of Formulas (I), (IA), (IA'), (IB), (IB'), (II), (II'), (IIA), (IIA'), (IIB), and (IIB'), Ring C is (C7).

In an alternative of each of the embodiments described herein, in each of Formulas (I), (IA), (IA'), (IB), (IB'), (II), (II'), (IIA), (IIA'), (IIB), and (IIB'), Ring C is (C8).

In an alternative of each of the embodiments described herein, in each of Formulas (I), (IA), (IA'), (IB), (IB'), (II), (II'), (IIA), (IIA'), (IIB), and (IIB'), Ring C is (C9).

In an alternative of each of the embodiments described herein, in each of Formulas (I), (IA), (IA'), (IB), (IB'), (II), (II'), (IIA), (IIA'), (IIB), and (IIB'), Ring C is (C10).

In an alternative of each of the embodiments described herein, in each of Formulas (I), (IA), (IA'), (IB), (IB'), (II), (II'), (IIA), (IIA'), (IIB), and (IIB'), Ring C is (C11).

In some embodiments, in each of Formulas (I), (IA), (IA'), (IB), (IB'), (II), (II'), (IIA), (IIA'), (IIB), and (IIB):
n is 1. In these embodiments, the moiety:

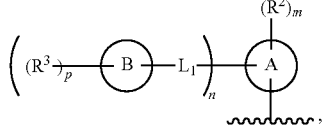

has the form:

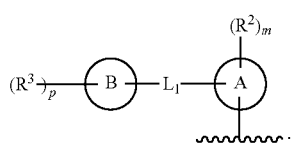

In another embodiment, in each of Formulas (I), (IA), (IA'), (IB), (IB'), (II), (II'), (IIA), (IIA'), (IIB), and (IIB'):
n is 1;
m is 0 or more; and
ring A is selected from the group consisting of phenyl, pyridyl, pyrazinyl, furanyl, thienyl, pyrimidinyl, pyridazinyl, thiazolyl, oxazolyl, imidazolyl, pyrazolyl, quinazolinyl, benzofuranyl, benzimidazolyl, benzoxazolyl, benzothiazolyl, benzothienyl, naphthyl, quinolyl, isoquinolyl, indazolyl, indolyl, thienopyridyl, and thienopyrazolyl.

In another embodiment, in each of Formulas (I), (IA), (IA'), (IB), (IB'), (II), (II'), (IIA), (IIA'), (IIB), and (IIB'):
n is 1;
m is 0 or more; and
ring A is selected from the group consisting of phenyl, pyridyl, thienyl, thiazolyl, naphthyl, isoquinolyl, benzothienyl, benzimidazolyl, indazolyl, indolyl, thienopyridyl, and thienopyrazolyl.

In another embodiment, in each of Formulas (I), (IA), (IA'), (IB), (IB'), (II), (II'), (IIA), (IIA'), (IIB), and (IIB'):
n is 1;
m is 0 or more; and
ring A is selected from the group consisting of phenyl, thienyl, and pyridyl.

In another embodiment, in each of Formulas (I), (IA), (IA'), (IB), (IB'), (II), (II'), (IIA), (IIA'), (IIB), and (IIB'):
n is 1;
m is 0 or more; and
each $R^2$ (when present) is independently selected from the group consisting of halogen, —CN, —SF$_5$, —OSF$_5$, —NO$_2$, —NH$_2$, —N(alkyl)$_2$, —NH(alkyl), —NHC(O)R$^6$, —NHS(O)$_2$R$^6$, —NHC(O)N(R$^6$)$_2$, —NHC(O)OR$^6$, —C(O)R$^6$, —C(O)$_2$R$^6$, —C(O)N(R$^6$)$_2$, —S(O)R$^6$, —S(O)$_2$R$^6$, —S(O)$_2$N(R$^6$)$_2$, —OR$^6$, —SR$^6$, lower alkyl, lower haloalkyl, lower heteroalkyl, lower alkenyl, lower alkynyl, phenyl, benzyl, lower cycloalkyl, —CH$_2$-(lower cycloalkyl), monocyclic heteroaryl, and —CH$_2$-(monocyclic heteroaryl),
wherein said phenyl, benzyl, lower cycloalkyl, —CH$_2$-(lower cycloalkyl), monocyclic heteroaryl, and —CH$_2$-(monocyclic heteroaryl) of $R^2$ is unsubstituted or substituted with one or more groups independently selected from the group consisting of halogen, alkyl, heteroalkyl, haloalkyl, alkoxy, —O-cyclopropyl, —O-heteroalkyl, haloalkoxy, —CN, —SF$_5$, and —OSF$_5$.

In one such embodiment, each $R^6$ (when present) is independently selected from the group consisting of H, lower alkyl, lower cycloalkyl, lower haloalkyl, and lower heteroalkyl.

In another embodiment, in each of Formulas (I), (IA), (IA'), (IB), (IB'), (II), (II'), (IIA), (IIA'), (IIB), and (IIB'):
each $R^3$ group (when present) is independently selected from the group consisting of halogen, —CN, —SF$_5$, —NH$_2$, —NH(alkyl), —N(alkyl)$_2$, —OH, —O-alkyl, —SH, —S(alkyl), methyl, ethyl, propyl, haloalkyl, —C≡C—CH$_3$, cyclopropyl, —CH$_2$-cyclopropyl, —C(O)OH, —C(O)O-alkyl, —O-haloalkyl, optionally substituted phenyl, and optionally substituted monocyclic heteroaryl, wherein each said optional substituent is, independently, as defined in Formula (I).

In another embodiment, in each of Formulas (I), (IA), (IA'), (IB), (IB'), (II), (II'), (IIA), (IIA'), (IIB), and (IIB'):
n is 1;
m is 0 or more; and
each $R^2$ group (when present) is independently selected from the group consisting of halogen, —CN, —SF$_5$, —NHCH$_3$, —N(CH$_3$)$_2$, —OCH$_3$, —OCH$_2$CH$_3$, —O-cyclopropyl, —S(CH$_3$), methyl, ethyl, propyl, cyclopropyl, —CH$_2$-cyclopropyl, —C≡C—CH$_3$, —CF$_3$, —CHF$_2$, —C(O)OH, —C(O)OCH$_3$, —C(O)OCH$_2$CH$_3$, —OCF$_3$, and —OCHF$_2$.

In another embodiment, in each of Formulas (I), (IA), (IA'), (IB), (IB'), (II), (II'), (IIA), (IIA'), (IIB), and (IIB'):
n is 1;
m is 0, 1, or 2; and
each $R^2$ group (when present) is independently selected from F, Cl, Br, —CN, —$CF_3$, —$CHF_2$, cyclopropyl, —$OCF_3$, and —$OCHF_2$.

In another embodiment, in each of Formulas (I), (IA), (IA'), (IB), (IB'), (II), (II'), (IIA), (IIA'), (IIB), and (IIB'):
n is 1;
ring A is selected from the group consisting of phenyl, thienyl, and pyridyl;
m is 0, 1, or 2; and
each $R^2$ group (when present) is independently selected from the group consisting F, Cl, Br, —CN, —$CF_3$, —$CHF_2$, cyclopropyl, —$OCF_3$, and —$OCHF_2$.

In another embodiment, in each of Formulas (I), (IA), (IA'), (IB), (IB'), (II), (II'), (IIA), (IIA'), (IIB), and (IIB'):
n is 1; and
-$L_1$- represents a bond or a divalent moiety selected from the group consisting of —NHC(O), —C(O)NH—, —NHS(O)$_2$—, —S(O)$_2$NH—, —O—$CH_2$—, —$CH_2$—O—, —NH$CH_2$—, —$CH_2$NH—, —NHCH($CF_3$)—, and —CH($CF_3$)NH—.

In another embodiment, in each of Formulas (I), (IA), (IA'), (IB), (IB'), (II), (II'), (IIA), (IIA'), (IIB), and (IIB'):
n is 1; and
-$L_1$- represents a bond or a divalent moiety selected from the group consisting of —NHC(O)— and —C(O)NH—.

In another embodiment, in each of Formulas (I), (IA), (IA'), (IB), (IB'), (II), (II'), (IIA), (IIA'), (IIB), and (IIB'):
n is 1; and
-$L_1$- represents a bond.

In another embodiment, in each of Formulas (I), (IA), (IA'), (IB), (IB'), (II), (II'), (IIA), (IIA'), (IIB), and (IIB):
n is 1; and
-$L_1$- represents a divalent moiety selected from the group consisting of —NHC(O)— and —C(O)NH—.

In another embodiment, in each of Formulas (I), (IA), (IA'), (IB), (IB'), (II), (II'), (IIA), (IIA'), (IIB), and (IIB'):
n is 1;
p is 0 or more; and
ring B is selected from the group consisting of phenyl, monocyclic heterocycloalkyl, monocyclic heteroaryl, and a multicyclic group.

In another embodiment, in each of Formulas (I), (IA), (IA'), (IB), (IB'), (II), (II'), (IIA), (IIA'), (IIB), and (IIB'):
n is 1;
p is 0 or more; and
ring B is selected from the group consisting of phenyl, pyridyl, pyrimidinyl, pyrrolyl, oxazolyl, isoxazolyl, pyrazinyl, thienyl, pyrazolyl, furanyl, thiazolyl, pyridazinyl, isothiazolyl, isoxazolyl, isothiazolyl, indolyl, pyrrolopyridinyl, and pyrrolopyrimidinyl.

In another embodiment, in each of Formulas (I), (IA), (IA'), (IB), (IB'), (II), (II'), (IIA), (IIA'), (IIB), and (IIB'):
n is 1;
p is 0 or more; and
ring B is selected from the group consisting of phenyl, pyridinyl, pyrimidinyl, pyrazinyl, oxazolyl, pyrrolyl, indolyl, pyrrolopyridinyl, and pyrrolopyrimidinyl.

In another embodiment, in each of Formulas (I), (IA), (IA'), (IB), (IB'), (II), (II'), (IIA), (IIA'), (IIB), and (IIB'):
n is 1;
p is 0 or more; and
ring B is selected from the group consisting of benzimidazolyl, benzofuranyl, benzoisothiazole, benzoisoxazole, benzothiazole, benzothiophenyl, benzoxazole, furanyl, cyclobutyl, cyclohexyl, cyclopentyl, cyclopropyl, imidazopyridyl, imidazothiazoyl, imidazothiadiazolyl, imidazolyl, indazolyl, indolyl, isothiazoyl, isoxazolopyridyl, isoxazolyl, morpholinoyl, oxadiazolyl, oxazolyl, oxetanyl, phenyl, pyrazinyl, pyrazolyl, pyridazinyl, pyridyl, pyrimidinyl, pyrrolyl, pyrrolopyridinyl, pyrrolopyrimidinyl, pyrazolopyridinyl, tetrahydrofuranyl, tetrahydropyranyl, thiadiazolyl, thiazolyl, thienyl, triazolyl.

In another embodiment, in each of Formulas (I), (IA), (IA'), (IB), (IB'), (II), (II'), (IIA), (IIA'), (IIB), and (IIB'):
n is 1;
p is 0 or more; and
ring B is selected from the group consisting of benzimidazolyl, benzofuranyl, cyclobutyl, cyclopentyl, cyclopropyl, imidazopyridyl, imidazothiazoyl, imidazothiadiazolyl, imidazolyl, indazolyl, indolyl, isothiazoyl, isoxazolopyridyl, isoxazolyl, morpholinoyl, oxadiazolyl, oxazolyl, oxetanyl, phenyl, pyrazinyl, pyrazolyl, pyridazinyl, pyridyl, pyrimidinyl, pyrrolyl, pyrrolopyridinyl, pyrrolopyrimidinyl, pyrazolopyridinyl, tetrahydrofuranyl, tetrahydropyranyl, thiadiazolyl, thiazolyl, triazolyl.

In another embodiment, in each of Formulas (I), (IA), (IA'), (IB), (IB'), (II), (II'), (IIA), (IIA'), (IIB), and (IIB'):
n is 1;
p is 0 or more; and
each $R^3$ (when present) is independently selected from the group consisting of halogen, —CN, —$SF_5$, —$OSF_5$, —$NO_2$, —$NH_2$, —N(alkyl)$_2$, —NH(alkyl), —NHC(O)$R^6$, —NHS(O)$_2R^6$, —NHC(O)N($R^6$)$_2$, —NHC(O)O$R^6$, —C(O)$R^6$, —C(O)$_2R^6$, —C(O)N($R^6$)$_2$, —S(O)$R^6$, —S(O)$_2R^6$, —S(O)$_2$N($R^6$)$_2$, —O$R^6$, —S$R^6$, lower alkyl, lower haloalkyl, lower heteroalkyl, lower alkenyl, lower alkynyl, phenyl, benzyl, lower cycloalkyl, —$CH_2$-(lower cycloalkyl), monocyclic heteroaryl, and —$CH_2$-(monocyclic heteroaryl), wherein said phenyl, benzyl, lower cycloalkyl, —$CH_2$-(lower cycloalkyl), monocyclic heteroaryl, and —$CH_2$-(monocyclic heteroaryl) of $R^3$ is unsubstituted or substituted with one or more groups independently selected from the group consisting of halogen, alkyl, heteroalkyl, haloalkyl, alkoxy, —O-cyclopropyl, —O-heteroalkyl, haloalkoxy, —CN, —$SF_5$, and —$OSF_5$.

In one such embodiment, each $R^6$ (when present) is independently selected from the group consisting of H, lower alkyl, lower cycloalkyl, lower haloalkyl, and lower heteroalkyl.

In another embodiment, in each of Formulas (I), (IA), (IA'), (IB), (IB'), (II), (II'), (IIA), (IIA'), (IIB), and (IIB'):
n is 1;
p is 0 or more; and
each $R^3$ group (when present) is independently selected from the group consisting of halogen, —OH, —CN, —$SF_5$, —$NH_2$, —NH($CH_3$), —N($CH_3$)$_2$, —O$CH_3$, —O$CH_2CH_3$, —O-cyclopropyl, —S($CH_3$), methyl, ethyl, propyl, cyclopropyl, —$CH_2$-cyclopropyl, —C≡C—$CH_3$, —$CF_3$, —$CHF_2$, —C(O)OH, —C(O)O$CH_3$, —C(O)O$CH_2CH_3$, —O$CF_3$, —O$CH_2CF_3$, and —$OCHF_2$.

In another embodiment, in each of Formulas (I), (IA), (IA'), (IB), (IB'), (II), (II'), (IIA), (IIA'), (IIB), and (IIB'):
n is 1;
ring A is selected from the group consisting of phenyl, thienyl, and pyridyl;
m is 0 or 1;
each $R^2$ group (when present) is independently selected from the group consisting of halogen, —CN, —$SF_5$, —NH$CH_3$, —N($CH_3$)$_2$, —O$CH_3$, —O$CH_2CH_3$, —O-cyclopropyl, —S($CH_3$), methyl, ethyl, propyl, cyclopropyl, —CH$_2$-cyclopropyl, —C≡C—CH$_3$, —CF$_3$, —CHF$_2$, —C(O)OH, —C(O)OCH$_3$, —C(O)OCH$_2$CH$_3$, —OCF$_3$, and —OCHF$_2$.

-L$_1$- is a bond or a divalent moiety selected from the group consisting of —NHC(O)— and —C(O)NH—;

ring B is selected from the group consisting of phenyl, monocyclic heterocycloalkyl, and monocyclic heteroaryl;

p is 0 or more; and each R$^3$ group (when present) is independently selected from the group consisting of halogen, —OH, —CN, —SF$_5$, —NH$_2$, —NH(CH$_3$), —N(CH$_3$)$_2$, —OCH$_3$, —OCH$_2$CH$_3$, —O-cyclopropyl, —S(CH$_3$), methyl, ethyl, propyl, cyclopropyl, —CH$_2$-cyclopropyl, —C≡C—CH$_3$, —CF$_3$, —CHF$_2$, —C(O)OH, —C(O)OCH$_3$, —C(O)OCH$_2$CH$_3$, —OCF$_3$, —OCH$_2$CF$_3$, and —OCHF$_2$.

In another embodiment, in each of Formulas (I), (IA), (IA'), (IB), (IB'), (II), (II'), (IIA), (IIA'), (IIB), and (IIB'):

n is 1; ring A is phenyl or pyridyl; and the moiety

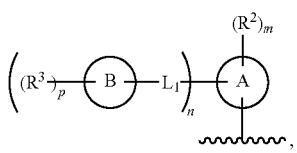

has the form:

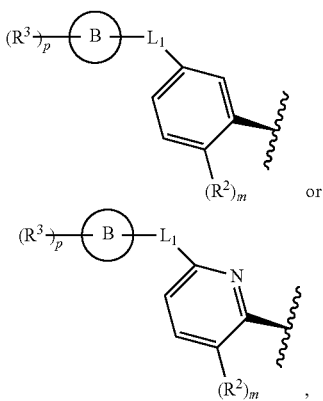

wherein:

m is 0 or 1;

each R$^2$ group (when present) is independently selected from the group consisting of halogen, —CN, —SF$_5$, —NHCH$_3$, —N(CH$_3$)$_2$, —OCH$_3$, —OCH$_2$CH$_3$, —O-cyclopropyl, —S(CH$_3$), methyl, ethyl, propyl, cyclopropyl, —CH$_2$-cyclopropyl, —C≡C—CH$_3$, —CF$_3$, —CHF$_2$, —C(O)OH, —C(O)OCH$_3$, —C(O)OCH$_2$CH$_3$, —OCF$_3$, and —OCHF$_2$;

-L$_1$- is a bond or a divalent moiety selected from the group consisting of —NHC(O)— and —C(O)NH—;

ring B is selected from the group consisting of benzimidazolyl, benzofuranyl, benzoisothiazole, benzoisoxazole, benzothiazole, benzothiophenyl, benzoxazole, furanyl, cyclobutyl, cyclohexyl, cyclopentyl, cyclopropyl, imidazopyridyl, imidazothiazoyl, imidazothiadiazolyl, imidazolyl, indazolyl, indolyl, isothiazoyl, isoxazolopyridyl, isoxazolyl, morpholinoyl, oxadiazolyl, oxazolyl, oxetanyl, phenyl, pyrazinyl, pyrazolyl, pyridazinyl, pyridyl, pyrimidinyl, pyrrolyl, pyrrolopyridinyl, pyrrolopyrimidinyl, pyrazolopyridinyl, tetrahydrofuranyl, tetrahydropyranyl, thiadiazolyl, thiazolyl, thienyl, triazolyl;

p is 0 or more; and each R$^3$ group (when present) is independently selected from the group consisting of halogen, —OH, —CN, —SF$_5$, —NH$_2$, —NH(CH$_3$), —N(CH$_3$)$_2$, —OCH$_3$, —OCH$_2$CH$_3$, —O-cyclopropyl, —S(CH$_3$), methyl, ethyl, propyl, cyclopropyl, —CH$_2$-cyclopropyl, —C≡C—CH$_3$, —CF$_3$, —CHF$_2$, —C(O)OH, —C(O)OCH$_3$, —C(O)OCH$_2$CH$_3$, —OCF$_3$, —OCH$_2$CF$_3$, and —OCHF$_2$.

In an alternative of the immediately preceeding embodiment, R$^9$ is H.

In an another alternative of the immediately preceeding embodiment, ring B is selected from the group consisting of benzimidazolyl, benzofuranyl, cyclobutyl, cyclopentyl, cyclopropyl, imidazopyridyl, imidazothiazoyl, imidazothiadiazolyl, imidazolyl, indazolyl, indolyl, isothiazoyl, isoxazolopyridyl, isoxazolyl, morpholinoyl, oxadiazolyl, oxazolyl, oxetanyl, phenyl, pyrazinyl, pyrazolyl, pyridazinyl, pyridyl, pyrimidinyl, pyrrolyl, pyrrolopyridinyl, pyrrolopyrimidinyl, pyrazolopyridinyl, tetrahydrofuranyl, tetrahydropyranyl, thiadiazolyl, thiazolyl, and triazolyl.

In an another alternative of the immediately preceeding embodiment, ring B is selected from the group consisting of phenyl, cyclopropyl, cyclobutyl, cyclopentyl, cyclohexyl, pyridinyl, pyrimidinyl, pyrazinyl, oxazolyl, pyrrolyl, indolyl, pyrrolopyidinyl, pyrrolopyrimidinyl, triazolyl, thiadiazolyl, oxadiazolyl, morpholinoyl, benzofuranyl, oxetanyl, tetrahydrofuranyl, and tetrahydropyranyl.

In another embodiment, in each of Formulas (I), (IA), (IA'), (IB), (IB'), (II), (II'), (IIA), (IIA'), (IIB), and (IIB'):

n is 1; ring A is thienyl; and the moiety

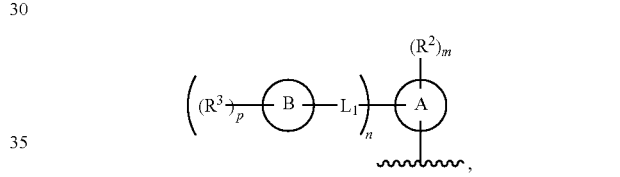

has the form:

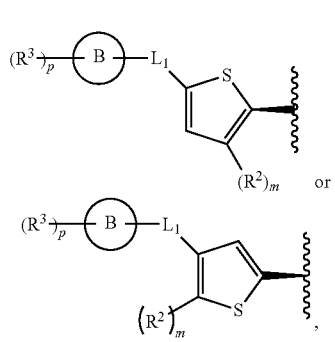

wherein:

m is 0 or 1;

each R$^2$ group (when present) is independently selected from the group consisting of halogen, —CN, —SF$_5$, —NHCH$_3$, —N(CH$_3$)$_2$, —OCH$_3$, —OCH$_2$CH$_3$, —O-cyclopropyl, —S(CH$_3$), methyl, ethyl, propyl, cyclopropyl, —CH$_2$-cyclopropyl, —C≡C—CH$_3$, —CF$_3$, —CHF$_2$, —C(O)OH, —C(O)OCH$_3$, —C(O)OCH$_2$CH$_3$, —OCF$_3$, and —OCHF$_2$.

-L$_1$- is a bond or a divalent moiety selected from the group consisting of —NHC(O)— and —C(O)NH—;

ring B is selected from the group consisting of benzimidazolyl, benzofuranyl, benzoisothiazole, benzoisoxazole, benzothiazole, benzothiophenyl, benzoxazole, furanyl, cyclobutyl, cyclohexyl, cyclopentyl, cyclopropyl, imidazopyridyl, imidazothiazoyl, imidazothiadiazolyl, imidazolyl, indazolyl, indolyl, isothiazoyl, isoxazolopyridyl, isoxazolyl, morpholinoyl, oxadiazolyl, oxazolyl, oxetanyl, phenyl, pyrazinyl, pyrazolyl, pyridazinyl, pyridyl, pyrimidinyl, pyrrolyl, pyrrolopyridinyl, pyrrolopyrimidinyl, pyrazolopyridinyl, tetrahydrofuranyl, tetrahydropyranyl, thiadiazolyl, thiazolyl, thienyl, triazolyl;

p is 0 or more; and each $R^3$ group (when present) is independently selected from the group consisting of halogen, —OH, —CN, —SF$_5$, —NH$_2$, —NH(CH$_3$), —N(CH$_3$)$_2$, —OCH$_3$, —OCH$_2$CH$_3$, O-cyclopropyl, —S(CH$_3$), methyl, ethyl, propyl, cyclopropyl, —CH$_2$-cyclopropyl, —C≡C—CH$_3$, —CF$_3$, —CHF$_2$, —C(O)OH, —C(O)OCH$_3$, —C(O)OCH$_2$CH$_3$, —OCF$_3$, —OCH$_2$CF$_3$, and —OCHF$_2$.

In an alternative of the immediately preceeding embodiment, $R^9$ is H.

In an another alternative of the immediately preceeding embodiment, ring B is selected from the group consisting of benzimidazolyl, benzofuranyl, cyclobutyl, cyclopentyl, cyclopropyl, imidazopyridyl, imidazothiazoyl, imidazothiadiazolyl, imidazolyl, indazolyl, indolyl, isothiazoyl, isoxazolopyridyl, isoxazolyl, morpholinoyl, oxadiazolyl, oxazolyl, oxetanyl, phenyl, pyrazinyl, pyrazolyl, pyridazinyl, pyridyl, pyrimidinyl, pyrrolyl, pyrrolopyridinyl, pyrrolopyrimidinyl, pyrazolopyridinyl, tetrahydrofuranyl, tetrahydropyranyl, thiadiazolyl, thiazolyl, and triazolyl.

In an another alternative of the immediately preceeding embodiment, ring B is selected from the group consisting of phenyl, pyridyl, pyrimidinyl, pyrrolyl, oxazolyl, isoxazolyl, prazinyl, thienyl, pyrazolyl, furanyl, thiazolyl, pyridazinyl, isothiazolyl, isoxazolyl, isothiazolyl, indolyl, pyrrolopyridinyl, and pyrrolopyrimidinyl.

In another embodiment, in each of Formulas (I), (IA), (IA'), (IB), (IB'), (II), (II'), (IIA), (IIA'), (IIB), and (IIB'), n is 1, and the moiety

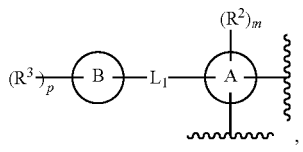

is as shown in the corresponding moiety of the compounds in the tables of examples below.

In another embodiment, in each of Formulas (I), (IA), (IA'), (IB), (IB'), (II), (II'), (IIA), (IIA'), (IIB), and (IIB'), n is 1, the moiety n is 1 and the moiety

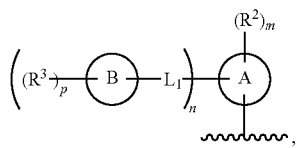

has the form:

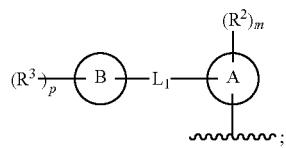

-L$_1$- is selected from the group consisting of -alkynyl-, —NHC(O)— and —C(O)NH—;

ring A is selected from the group consisting of phenyl, pyridyl, pyrazinyl, furanyl, thienyl, pyrimidinyl, pyridazinyl, thiazolyl, oxazolyl, imidazolyl, pyrazolyl, quinazolinyl, benzofuranyl, benzimidazolyl, benzoxazolyl, benzothiazolyl, benzothienyl, naphthyl, quinolyl, isoquinolyl, indazolyl, indolyl, thienopyridyl, and thienopyrazolyl;

m is 0, 1, 2, or 3;

each $R^2$ (when present) is independently selected from the group consisting of halogen, —CN, —SF$_5$, —OSF$_5$, —NO$_2$, —NH$_2$, —N(alkyl)$_2$, —NH(alkyl), —NHC(O)R$^6$, —NHS(O)$_2$R$^6$, —NHC(O)N(R$^6$)$_2$, —NHC(O)OR$^6$, —C(O)R$^6$, —C(O)$_2$R$^6$, —C(O)N(R$^6$)$_2$, —S(O)R$^6$, —S(O)$_2$R$^6$, —S(O)$_2$N(R$^6$)$_2$, —OR$^6$, —SR$^6$, lower alkyl, lower haloalkyl, lower heteroalkyl, lower alkenyl, lower alkynyl, phenyl, benzyl, lower cycloalkyl, —CH$_2$-(lower cycloalkyl), monocyclic heteroaryl, and —CH$_2$-(monocyclic heteroaryl), wherein said phenyl, benzyl, lower cycloalkyl, —CH$_2$-(lower cycloalkyl), monocyclic heteroaryl, and —CH$_2$-(monocyclic heteroaryl) of $R^2$ is unsubstituted or substituted with one or more groups independently selected from the group consisting of halogen, alkyl, heteroalkyl, haloalkyl, alkoxy, —O-cyclopropyl, —O-heteroalkyl, haloalkoxy, —CN, —SF$_5$, and —OSF$_5$;

ring B is selected from the group consisting of benzimidazolyl, benzofuranyl, benzoisothiazole, benzoisoxazole, benzothiazole, benzothiophenyl, benzoxazole, furanyl, cyclobutyl, cyclohexyl, cyclopentyl, cyclopropyl, imidazopyridyl, imidazothiazoyl, imidazothiadiazolyl, imidazolyl, indazolyl, indolyl, isothiazoyl, isoxazolopyridyl, isoxazolyl, morpholinoyl, oxadiazolyl, oxazolyl, oxetanyl, phenyl, pyrazinyl, pyrazolyl, pyridazinyl, pyridyl, pyrimidinyl, pyrrolyl, pyrrolopyridinyl, pyrrolopyrimidinyl, pyrazolopyridinyl, tetrahydrofuranyl, tetrahydropyranyl, thiadiazolyl, thiazolyl, thienyl, triazolyl;

p is 0, 1, 2, or 3;

and each $R^3$ (when present) is independently selected from the group consisting of halogen, —CN, —SF$_5$, —OSF$_5$, —NO$_2$, —NH$_2$, —N(alkyl)$_2$, —NH(alkyl), —NHC(O)R$^6$, —NHS(O)$_2$R$^6$, —NHC(O)N(R$^6$)$_2$, —NHC(O)OR$^6$, —C(O)R$^6$, —C(O)$_2$R$^6$, —C(O)N(R$^6$)$_2$, —S(O)R$^6$, —S(O)$_2$R$^6$, —S(O)$_2$N(R$^6$)$_2$, —OR$^6$, —SR$^6$, lower alkyl, lower haloalkyl, lower heteroalkyl, lower alkenyl, lower alkynyl, phenyl, benzyl, lower cycloalkyl, —CH$_2$-(lower cycloalkyl), monocyclic heteroaryl, and —CH$_2$-(monocyclic heteroaryl), wherein said phenyl, benzyl, lower cycloalkyl, —CH$_2$-(lower cycloalkyl), monocyclic heteroaryl, and —CH$_2$-(monocyclic heteroaryl) of $R^3$ is unsubstituted or substituted with one or more groups independently selected from the group consisting of halogen, alkyl, heteroalkyl, haloalkyl, alkoxy, —O-cyclopropyl, —O-heteroalkyl, haloalkoxy, —CN, —SF$_5$, and —OSF$_5$.

In an alternative of the immediately preceeding embodiment, -L$_1$- is selected from the group consisting of —NHC(O)— and —C(O)NH—.

In an alternative of the immediately preceeding embodiment, -L$_1$- is -alkynyl-.

Non-limiting examples of the immediately preceeding embodiment of the moiety

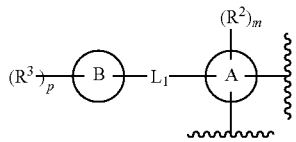

when n is 1 and -L₁- is —NHC(O)— or —C(O)NH— include:
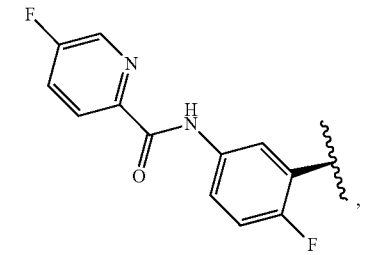,
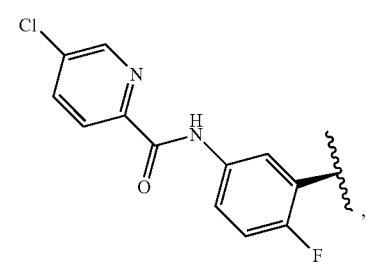,
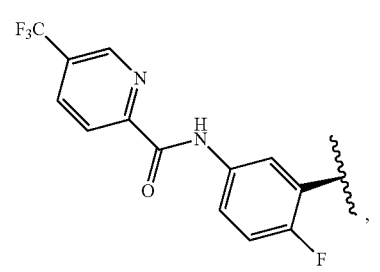,
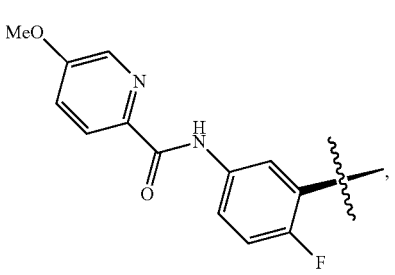,
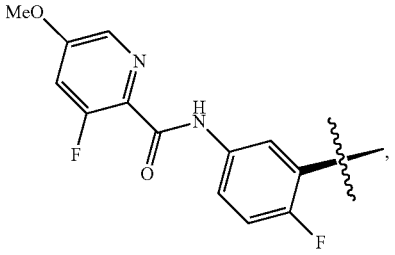,
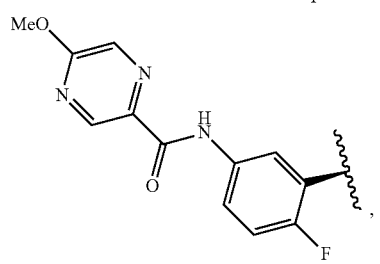,
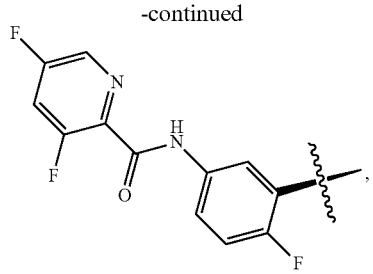,
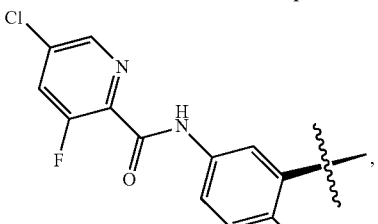,
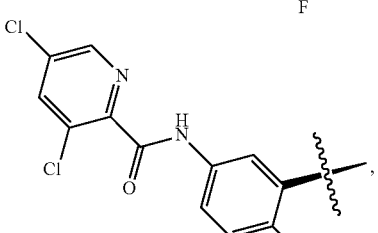,
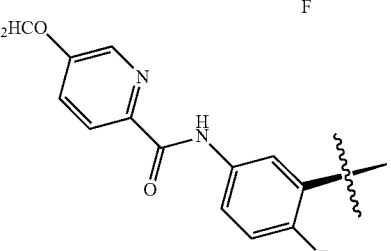,
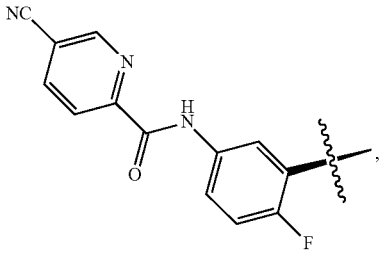,
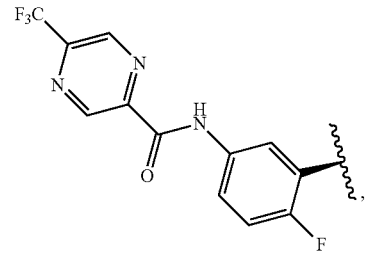,
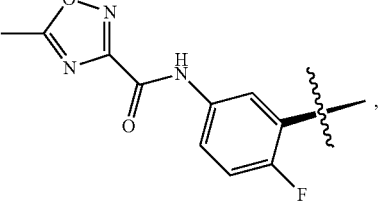,

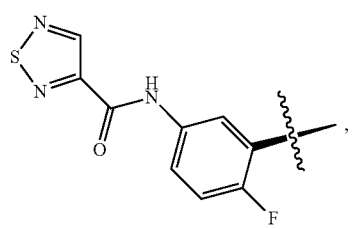
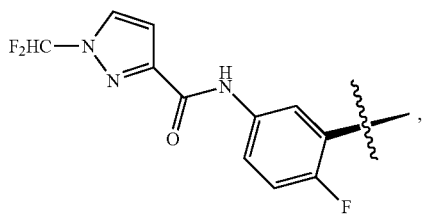
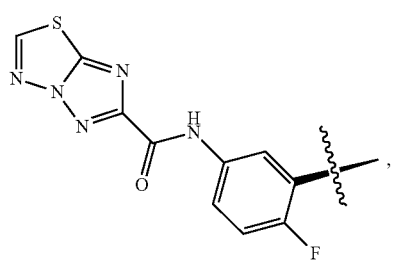
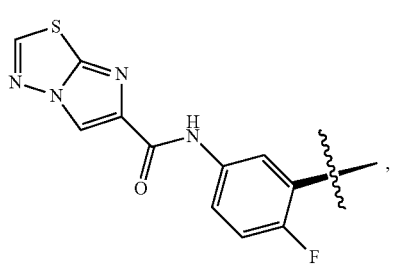
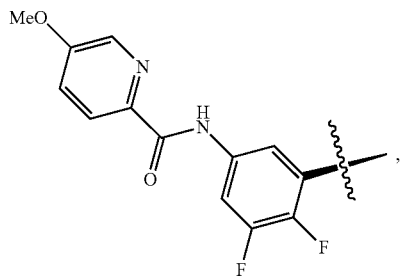
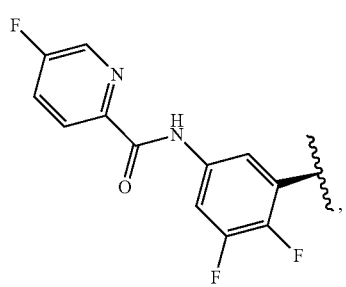
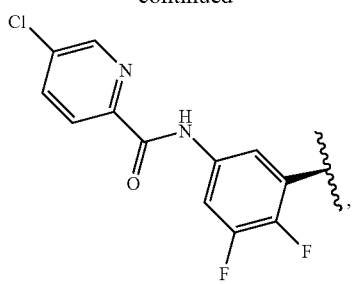
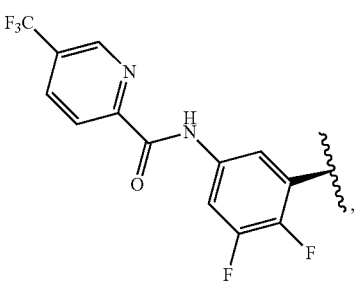
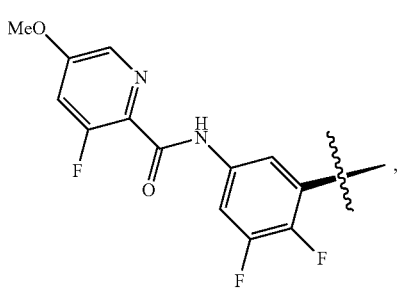
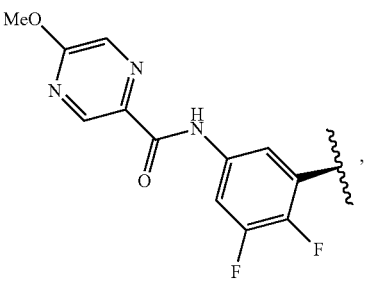
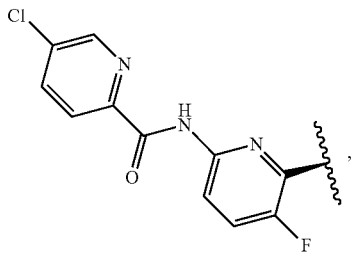
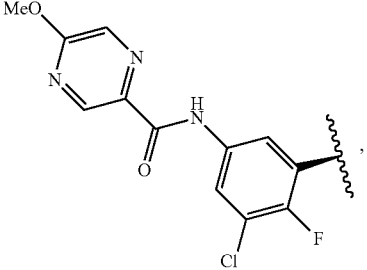

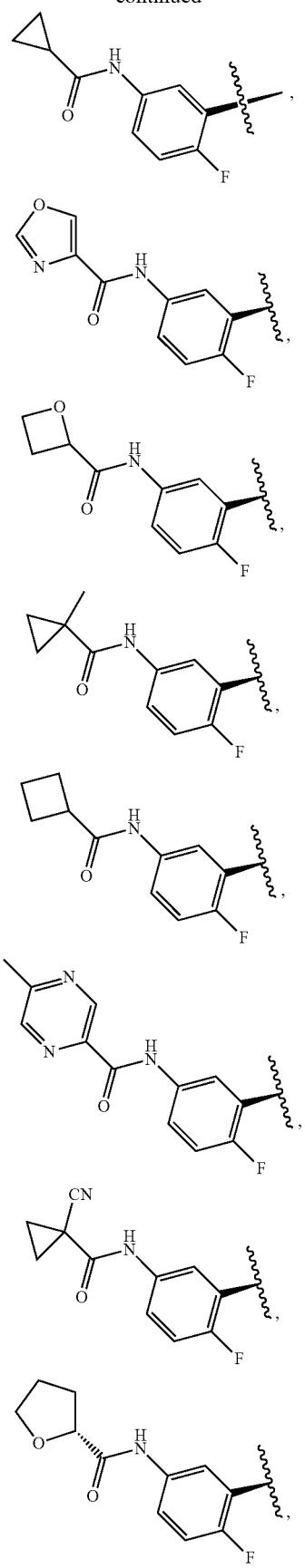
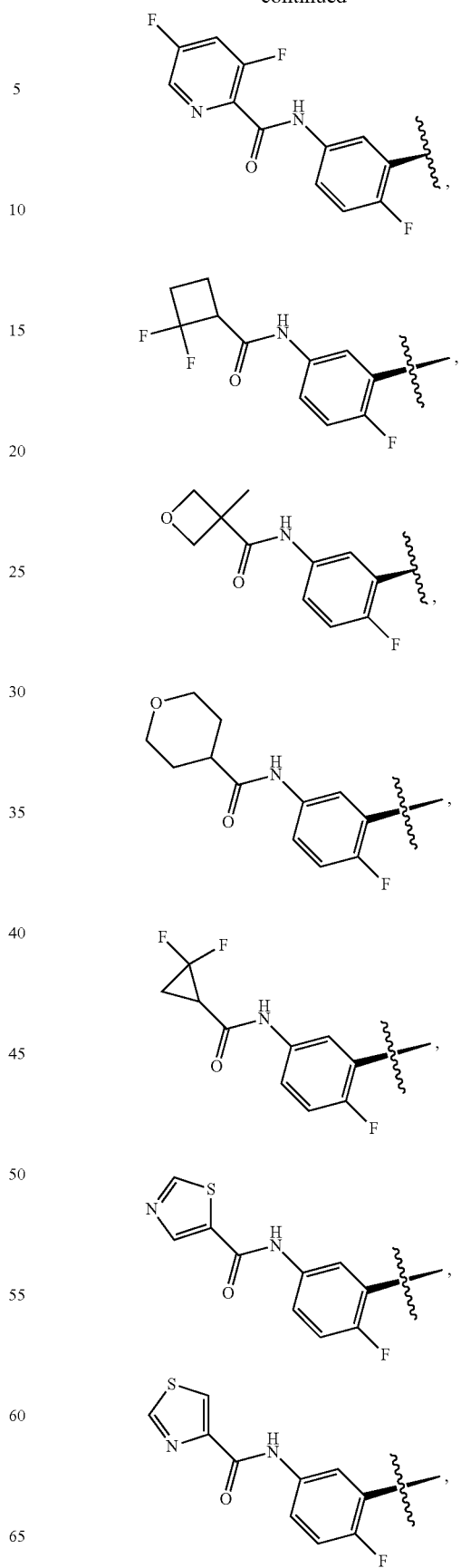

-continued
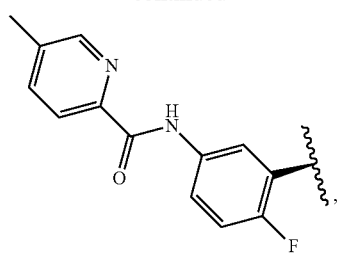
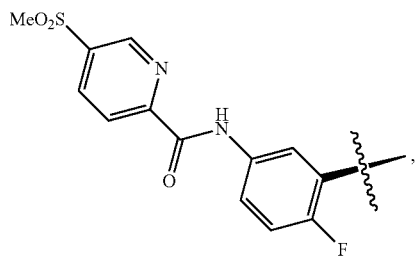
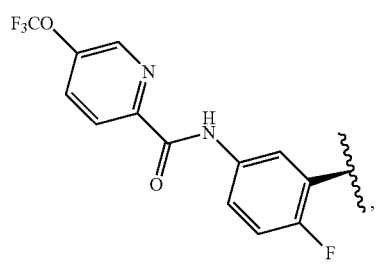
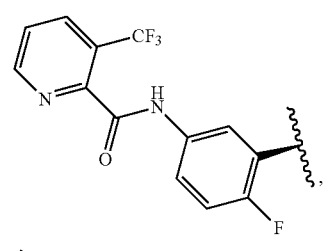
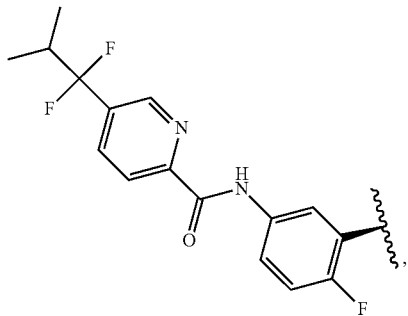
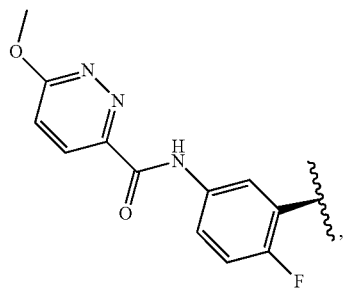
-continued
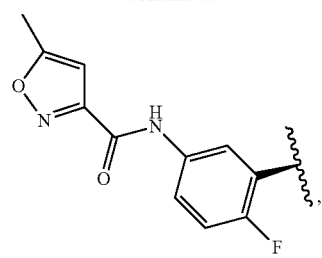
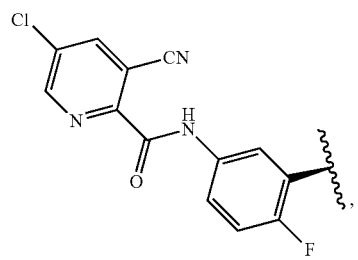
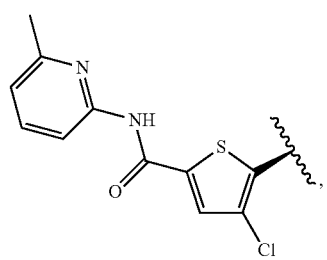
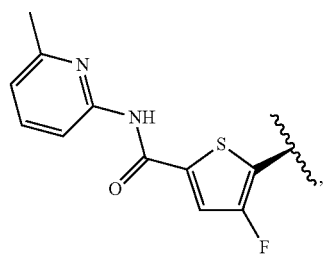
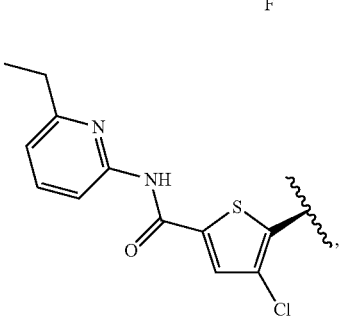
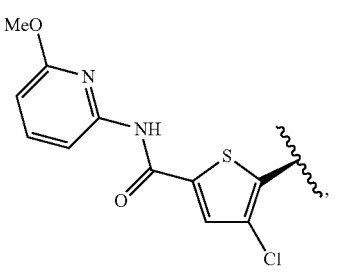

-continued

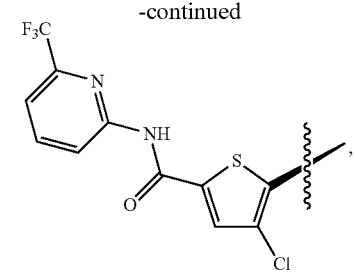

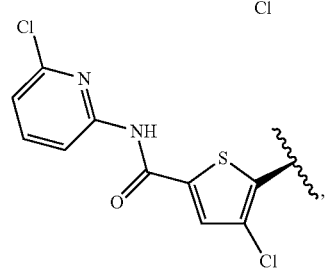

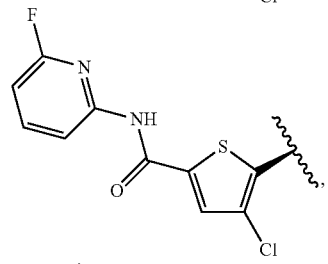

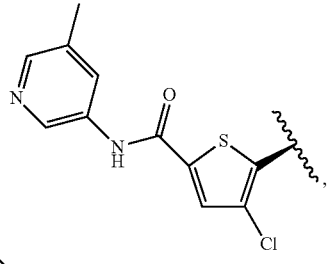

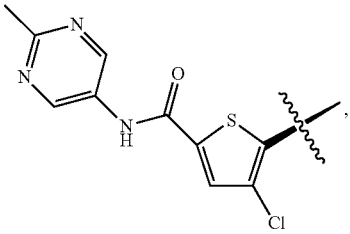

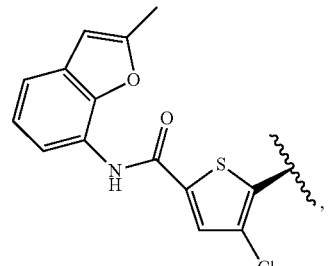

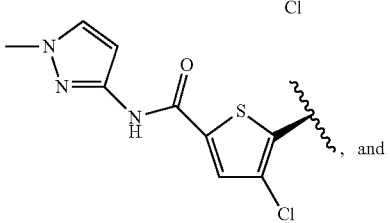, and

-continued

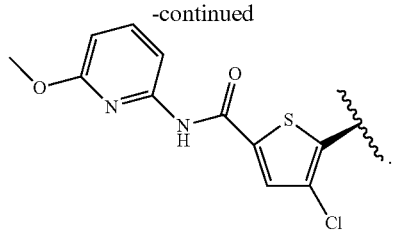.

Non-limiting examples of the immediately preceeding embodiment of the moiety

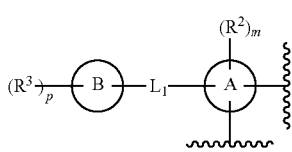

when n is 1 and -L$_1$- is -alkynyl- include:

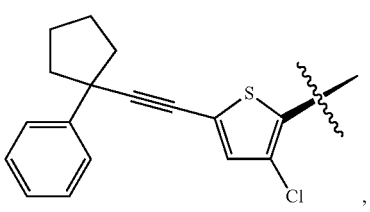,

,

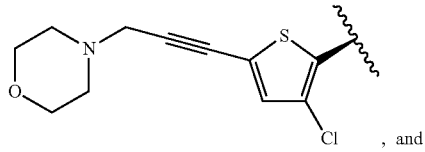, and

.

In another embodiment, in each of Formulas (I), (IA), (IA'), (IB), (IB'), (II), (II'), (IIA), (IIA'), (IIB), and (IIB'):
n is 1;
-L$_1$- is a bond;
ring A is selected from the group consisting of phenyl, pyridyl, pyrazinyl, furanyl, thienyl, pyrimidinyl, pyridazinyl, thiazolyl, oxazolyl, imidazolyl, pyrazolyl, quinazolinyl, benzofuranyl, benzimidazolyl, benzoxazolyl, benzothiazolyl, benzothienyl, naphthyl, quinolyl, isoquinolyl, indazolyl, indolyl, thienopyridyl, and thienopyrazolyl.
m is 0 or more;

each R² group (when present) is independently selected from the group consisting of halogen, —CN, —SF₅, —NHCH₃, —N(CH₃)₂, —OCH₃, —OCH₂CH₃, —O-cyclopropyl, —S(CH₃), methyl, ethyl, propyl, cyclopropyl, —CH₂-cyclopropyl, —C≡C—CH₃, —CF₃, —CHF₂, —C(O)OH, —C(O)OCH₃, —C(O)OCH₂CH₃, —OCF₃, and —OCHF₂;

ring B is selected from the group consisting of phenyl, cyclopropyl, cyclobutyl, cyclopentyl, cyclohexyl, pyridyl, pyrimidinyl, pyrrolyl, oxazolyl, isoxazolyl, pyrazinyl, thienyl, pyrazolyl, furanyl, thiazolyl, triazolyl, thiadiazolyl, oxadiazolyl, pyridazinyl, isothiazolyl, indolyl, pyrrolopyridinyl, pyrrolopyrimidinyl, morpholinoyl, benzofuranyl, oxetanyl, tetrahydrafuranyl, and tetrahydropyranyl;

p is 1; and R³ is selected from the group consisting of cycloalkyl, -alkyl-cycloalkyl, aryl, -alkyl-aryl, heteroaryl, -alkyl-heteroaryl, heterocycloalkyl, and -alkyl-heterocycloalkyl, wherein said cycloalkyl, -alkyl-cycloalkyl, aryl, -alkyl-aryl, heteroaryl, -alkyl-heteroaryl, heterocycloalkyl, and -alkyl-heterocycloalkyl of R³ are each optionally unsubstituted or substituted with one or more groups independently selected from R⁸.

Non-limiting examples of the immediately preceeding embodiment include:

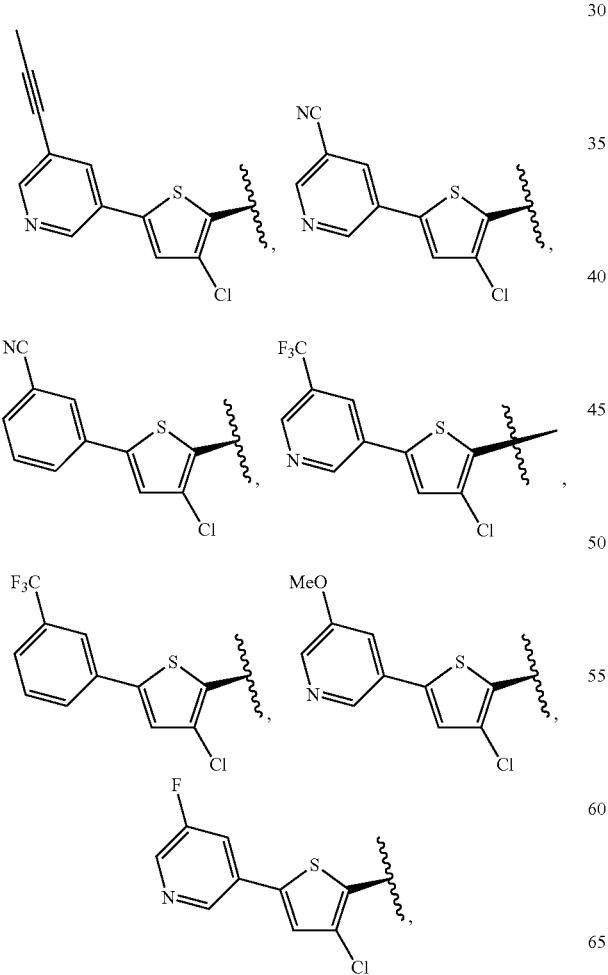

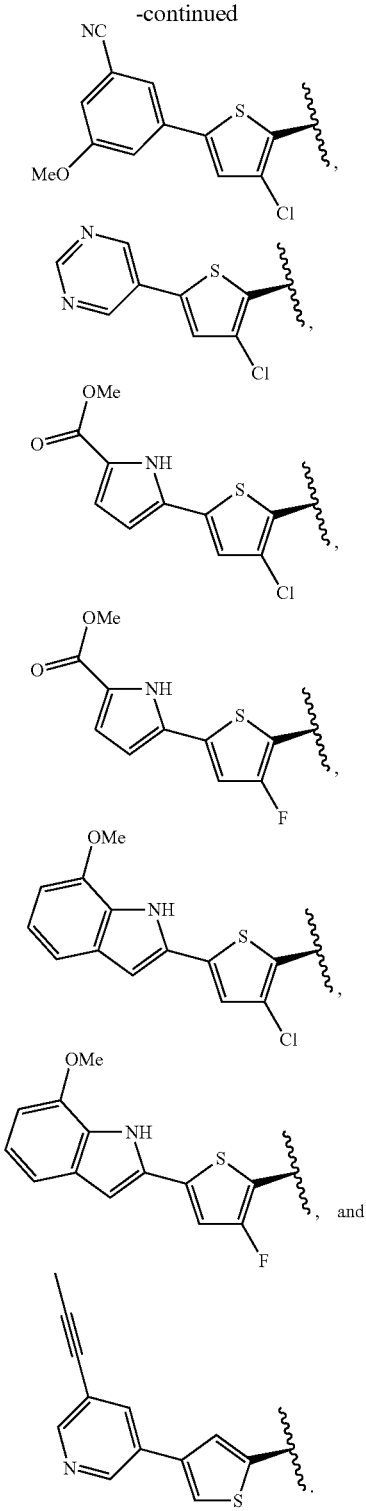

In another embodiment, in each of Formulas (I), (IA), (IA'), (IB), (IB'), (II), (II'), (IIA), (IIA'), (IIB), and (IIB'):

n is 1;

-L₁- is a bond;

ring A is selected from the group consisting of phenyl, pyridyl, pyrazinyl, furanyl, thienyl, pyrimidinyl, pyridazinyl, thiazolyl, oxazolyl, imidazolyl, pyrazolyl, quinazolinyl, benzofuranyl, benzimidazolyl, benzoxazolyl, benzothiazolyl, benzothienyl, naphthyl, quinolyl, isoquinolyl, indazolyl, indolyl, thienopyridyl, and thienopyrazolyl;

ring B is selected from the group consisting of cyclopropyl, cyclobutyl, cyclopentyl, cyclohexyl, phenyl, furanyl, thienyl, pyridyl, pyrimidinyl, pyrazinyl, pyridazinyl, pyrrolyl, imidazolyl, pyrazolyl, triazoyl, isothiazolyl, thiazolyl, thiadiazolyl, oxazolyl, isoxazolyl, oxadiazolyl, morpholinoyl, pyrrolidinyl, piperidinyl, piperazinyltetrahydrafuranyl, and tetrahydropyranyl p is 1; and $R^3$ is selected from the group consisting of cyclopropyl, cyclobutyl, cyclopentyl, cyclohexyl, phenyl, furanyl, thienyl, pyridyl, pyrazinyl, pyrimidinyl, pyridazinyl, thiadiazoyl, thiazolyl, isothiazoyl, oxadiazoyl, oxazolyl, isoxazolyl, pyrrolyl, imidazolyl, pyrazolyl, triazoyl, tetrazolyl, morpholinoyl, azetidinyl, pyrrolidinyl, piperidinyl, piperazinyl, oxetanyl, tetrahydrafuranyl, and tetrahydropyranyl; wherein said $R^3$ group is optionally unsubstituted or substituted with one or more groups independently selected from $R^8$.

In another embodiment, in each of Formulas (I), (IA), (IA'), (IB), (IB'), (II), (II'), (IIA), (IIA'), (IIB), and (IIB'):

n is 1 and the moiety

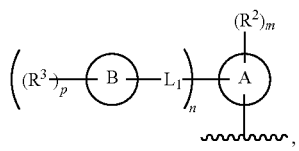

has the form:

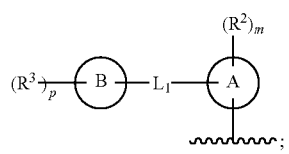

-$L_1$- is a bond;

ring A is selected from the group consisting of phenyl, pyridyl, pyrazinyl, furanyl, thienyl, pyrimidinyl, pyridazinyl, thiazolyl, oxazolyl, imidazolyl, pyrazolyl, quinazolinyl, benzofuranyl, benzimidazolyl, benzoxazolyl, benzothiazolyl, benzothienyl, naphthyl, quinolyl, isoquinolyl, indazolyl, indolyl, thienopyridyl, and thienopyrazolyl;

m is 0, 1, 2, or 3;

each $R^2$ (when present) is independently selected from the group consisting of halogen, —CN, —SF$_5$, —OSF$_5$, —NO$_2$, —NH$_2$, —N(alkyl)$_2$, —NH(alkyl), —NHC(O)R$^6$, —NHS(O)$_2$R$^6$, —NHC(O)N(R$^6$)$_2$, —NHC(O)OR$^6$, —C(O)R$^6$, —C(O)$_2$R$^6$, —C(O)N(R$^6$)$_2$, —S(O)R$^6$, —S(O)$_2$R$^6$, —S(O)$_2$N(R$^6$)$_2$, —OR$^6$, —SR$^6$, lower alkyl, lower haloalkyl, lower heteroalkyl, lower alkenyl, lower alkynyl, phenyl, benzyl, lower cycloalkyl, —CH$_2$-(lower cycloalkyl), monocyclic heteroaryl, and —CH$_2$-(monocyclic heteroaryl), wherein said phenyl, benzyl, lower cycloalkyl, —CH$_2$-(lower cycloalkyl), monocyclic heteroaryl, and —CH$_2$-(monocyclic heteroaryl) of $R^2$ is unsubstituted or substituted with one or more groups independently selected from the group consisting of halogen, alkyl, heteroalkyl, haloalkyl, alkoxy, —O-cyclopropyl, —O-heteroalkyl, haloalkoxy, —CN, —SF$_5$, and —OSF$_5$;

ring B is selected from the group consisting of cyclopropyl, cyclobutyl, cyclopentyl, cyclohexyl, phenyl, furanyl, thienyl, pyridyl, pyrimidinyl, pyrazinyl, pyridazinyl, pyrrolyl, imidazolyl, pyrazolyl, triazoyl, isothiazolyl, thiazolyl, thiadiazolyl, oxazolyl, isoxazolyl, oxadiazolyl, morpholinoyl, pyrrolidinyl, piperidinyl, piperazinyltetrahydrafuranyl, and tetrahydropyranyl;

p is 1; and $R^3$ is selected from the group consisting of cyclopropyl, cyclobutyl, cyclopentyl, cyclohexyl, phenyl, furanyl, thienyl, pyridyl, pyrazinyl, pyrimidinyl, pyridazinyl, thiadiazoyl, thiazolyl, isothiazoyl, oxadiazoyl, oxazolyl, isoxazolyl, pyrrolyl, imidazolyl, pyrazolyl, triazoyl, tetrazolyl, morpholinoyl, azetidinyl, pyrrolidinyl, piperidinyl, piperazinyl, oxetanyl, tetrahydrafuranyl, and tetrahydropyranyl; wherein said $R^3$ group is optionally unsubstituted or substituted with one or more groups independently selected from $R^8$.

Non-limiting examples of the immediately preceeding embodiment include:

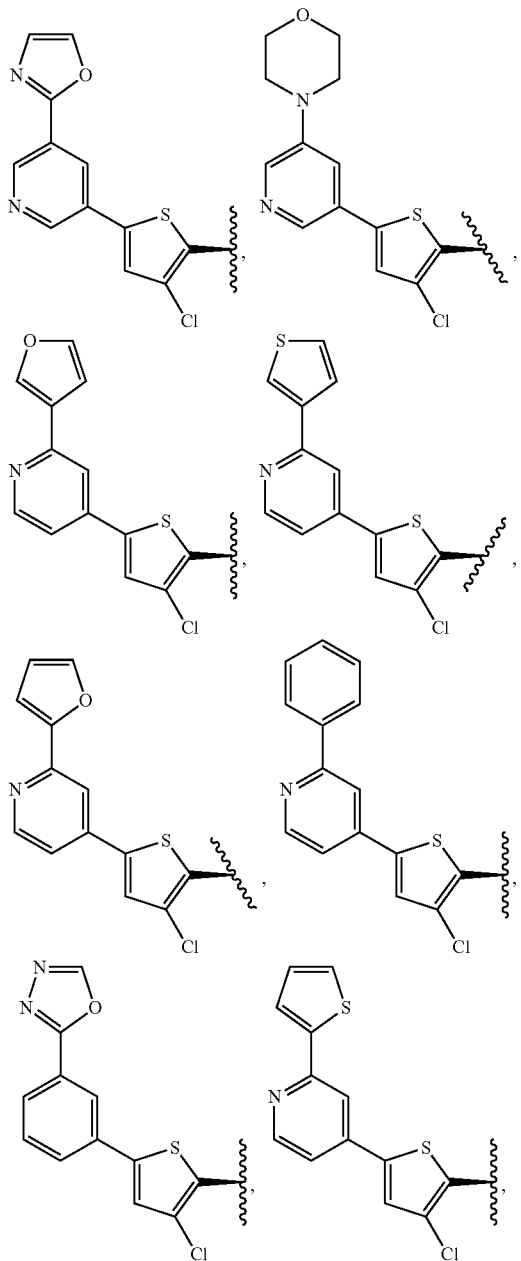

-continued

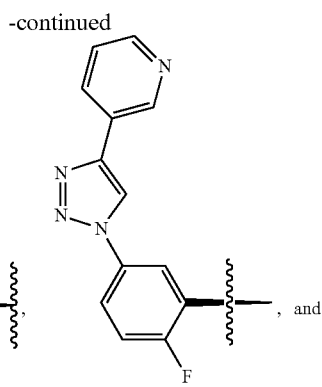

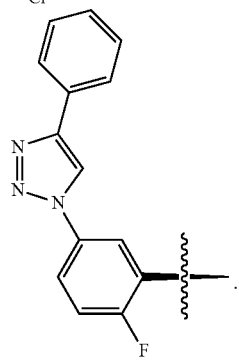

In another embodiment, in each of Formulas (I), (IA), (IA'), (IB), (IB'), (II), (II'), (IIA), (IIA'), (IIB), and (IIB'), n is 1; -L₁- is -alkynyl-;
ring A is selected from the group consisting of phenyl, pyridyl, and thienyl;
m is 0, 1, 2, or 3;
each R² is In some embodiments, in each of Formulas (I), (IA), (IA'), (IB), (IB'), (II), (II'), (IIA), (IIA'), (IIB), and (IIB), n is 0. In these embodiments, the moiety:

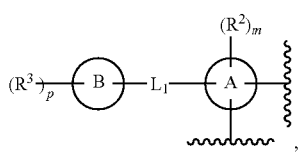

has the form

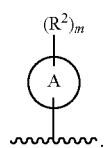

In another embodiment, in each of Formulas (I), (IA), (IA'), (IB), (IB'), (II), (II'), (IIA), (IIA'), (IIB), and (IIB):
n is 0;
ring A is selected from the group consisting of phenyl, pyridyl, pyrazinyl, furanyl, thienyl, pyrimidinyl, pyridazinyl, thiazolyl, oxazolyl, imidazolyl, pyrazolyl, quinazolinyl, benzofuranyl, benzimidazolyl, benzoxazolyl, benzothiazolyl, benzothienyl, naphthyl, quinolyl, isoquinolyl, indazolyl, indolyl, thienopyridyl, and thienopyrazolyl; and
R² and m are each as defined in Formula (I).

In another embodiment, in each of Formulas (I), (IA), (IA'), (IB), (IB'), (II), (II'), (IIA), (IIA'), (IIB), and (IIB'):
n is 0;
ring A is selected from the group consisting of phenyl, pyridyl, pyrazinyl, furanyl, thienyl, pyrimidinyl, pyridazinyl, thiazolyl, and oxazolyl; and
R² and m are each as defined in Formula (I).

In another embodiment, in each of Formulas (I), (IA), (IA'), (IB), (IB'), (II), (II'), (IIA), (IIA'), (IIB), and (IIB'):
n is 0;
ring A is selected from the group consisting of phenyl, pyridyl, pyrazinyl, furanyl, thienyl, pyrimidinyl, pyridazinyl, thiazolyl, and oxazolyl, thienopyridyl, and benzothienyl;
m is 0 to 5; and
each R² (when present) is independently selected from the group consisting of halogen, —OH, —CN, —SF₅, —OSF₅, —NO₂, —N(R⁶)₂, —NR⁷C(O)R⁶, —NR⁷S(O)₂R⁶, —NR⁷C(O)N(R⁶)₂, —NR⁷C(O)OR⁶, —C(O)R⁶, —C(O)₂R⁶, —C(O)N(R⁶)₂, —S(O)R⁶, —S(O)₂R⁶, —S(O)₂N(R₆)₂, —OR⁶, —SR⁶, lower alkyl, -(lower alkyl)-OH, lower haloalkyl, lower heteroalkyl, lower alkenyl, lower alkynyl, lower alkynyl which is substituted with from 1 to 3 independently selected R⁸ groups, phenyl, benzyl, lower cycloalkyl, —CH₂-(lower cycloalkyl), monocyclic heteroaryl, and —CH₂-(monocyclic heteroaryl),
wherein said phenyl, benzyl, lower cycloalkyl, —CH₂-(lower cycloalkyl), monocyclic heteroaryl, and —CH₂-(monocyclic heteroaryl) of R² is unsubstituted or substituted with one or more groups independently selected from the group consisting of halogen, alkyl, heteroalkyl, haloalkyl, alkoxy, —O-cyclopropyl, —O-heteroalkyl, haloalkoxy, —CN, —SF₅, and —OSF₅.

In one such embodiment,
each R⁶ (when present) is independently selected from the group consisting of H, lower alkyl, lower haloalkyl, and lower heteroalkyl, and
and R⁷ (when present) is selected from the group consisting of H, lower alkyl.

In another embodiment, in each of Formulas (I), (IA), (IA'), (IB), (IB'), (II), (II'), (IIA), (IIA'), (IIB), and (IIB'):
n is 0;
ring A is selected from the group consisting of phenyl, pyridyl, and thienyl; and
R² and m are each as defined in Formula (I).

In another embodiment, in each of Formulas (I), (IA), (IA'), (IB), (IB'), (II), (II'), (IIA), (IIA'), (IIB), and (IIB'):
n is 0;
ring A is phenyl and
R² and m are each as defined in Formula (I).

In another embodiment, in each of Formulas (I), (IA), (IA'), (IB), (IB'), (II), (II'), (IIA), (IIA'), (IIB), and (IIB'):
n is 0;
ring A is phenyl;
m is 0 to 5; and
each R² (when present) is independently selected from the group consisting of halogen, —CN, —SF₅, —OSF₅, —NO₂, —NH₂, —N(alkyl)₂, —NH(alkyl), —NHC(O)R⁶, —NHS(O)₂R⁶, —NHC(O)N(R⁶)₂, —NHC(O)OR⁶, —C(O)R⁶, —C(O)₂R⁶, —C(O)N(R⁶)₂, —S(O)R⁶, —S(O)₂R⁶, —S(O)₂N(R⁶)₂, —OR⁶, —SR⁶, lower alkyl, lower haloalkyl, lower heteroalkyl, lower alkenyl, lower alkynyl, phenyl, benzyl, lower cycloalkyl, —CH₂-(lower cycloalkyl), monocyclic heteroaryl, and —CH₂-(monocyclic heteroaryl),
wherein said phenyl, benzyl, lower cycloalkyl, —CH₂-(lower cycloalkyl), monocyclic heteroaryl, and —CH₂-(monocyclic heteroaryl) of R² is unsubstituted or substituted with one or more groups independently selected from the group consisting of halogen, alkyl, heteroalkyl, haloalkyl, alkoxy, —O-cyclopropyl, —O-heteroalkyl, haloalkoxy, —CN, —SF$_5$, and —OSF$_5$.

In one such embodiment, each R$^6$ (when present) is independently selected from the group consisting of H, lower alkyl, lower haloalkyl, lower cycloalkyl, and lower heteroalkyl.

In another embodiment, in each of Formulas (I), (IA), (IA'), (IB), (IB'), (II), (II'), (IIA), (IIA'), (IIB), and (IIB'):
n is 0;
ring A is phenyl;
m is 0 to 4; and
each R$^2$ group (when present) is independently selected from the group consisting of halogen, —CN, —SF$_5$, —NH$_2$, —NHCH$_3$, —N(CH$_3$)$_2$, —OCH$_3$, —OCH$_2$CH$_3$, —O-cyclopropyl, —S(CH$_3$), methyl, ethyl, propyl, cyclopropyl, —CH$_2$-cyclopropyl, —C≡C—(C$_1$-C$_6$alkyl), —C≡C—CH$_2$CH$_2$NHSO$_2$CH$_3$, —CF$_3$, —CHF$_2$, —C(O)OH, —C(O)OCH$_3$, —C(O)OCH$_2$CH$_3$, —OCF$_3$, and —OCHF$_2$.

In another embodiment, in each of Formulas (I), (IA), (IA'), (IB), (IB'), (II), (II'), (IIA), (IIA'), (IIB), and (IIB'):
n is 0;
ring A is phenyl;
m is 0 to 4; and
each R$^2$ group (when present) is independently selected from the group consisting of halogen, haloalkyl, cyclopropyl, and —CN.

In another embodiment, in each of Formulas (I), (IA), (IA'), (IB), (IB'), (II), (II'), (IIA), (IIA'), (IIB), and (IIB'):
n is 0;
ring A is phenyl;
m is 0 to 4; and
each R$^2$ group (when present) is independently selected from the group consisting of fluorine, chlorine, bromo, cyclopropyl, —CF$_3$, and —CN.

Non-limiting examples, in each of Formulas (I), (IA), (IA'), (IB), (IB'), (II), (II'), (IIA), (IIA'), (IIB), and (IIB'), when n is 0, of the moiety

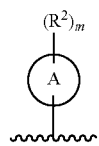

include:

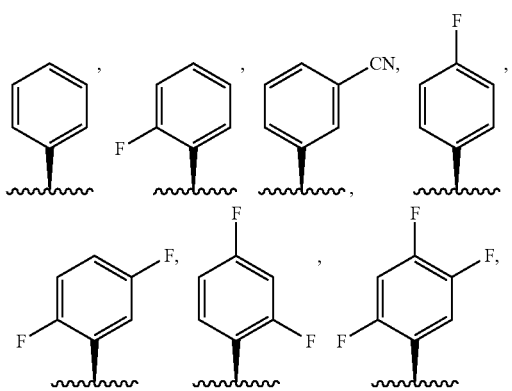

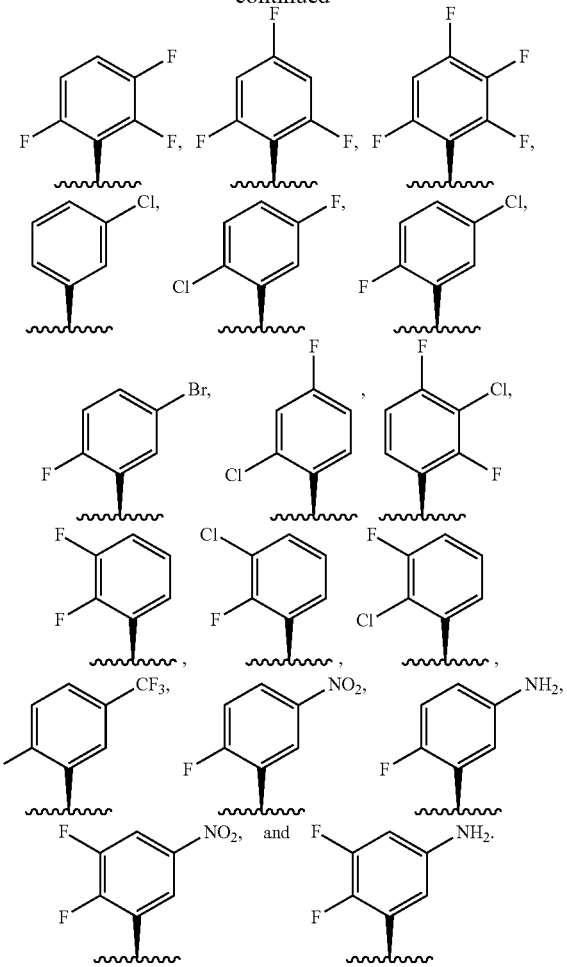

Additional non-limiting examples, in each of Formulas (I), (IA), (IA'), (IB), (IB'), (II), (II'), (IIA), (IIA'), (IIB), and (IIB'), when n is 0, of the moiety

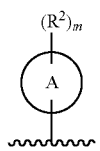

include:

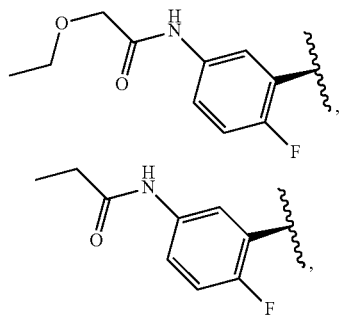

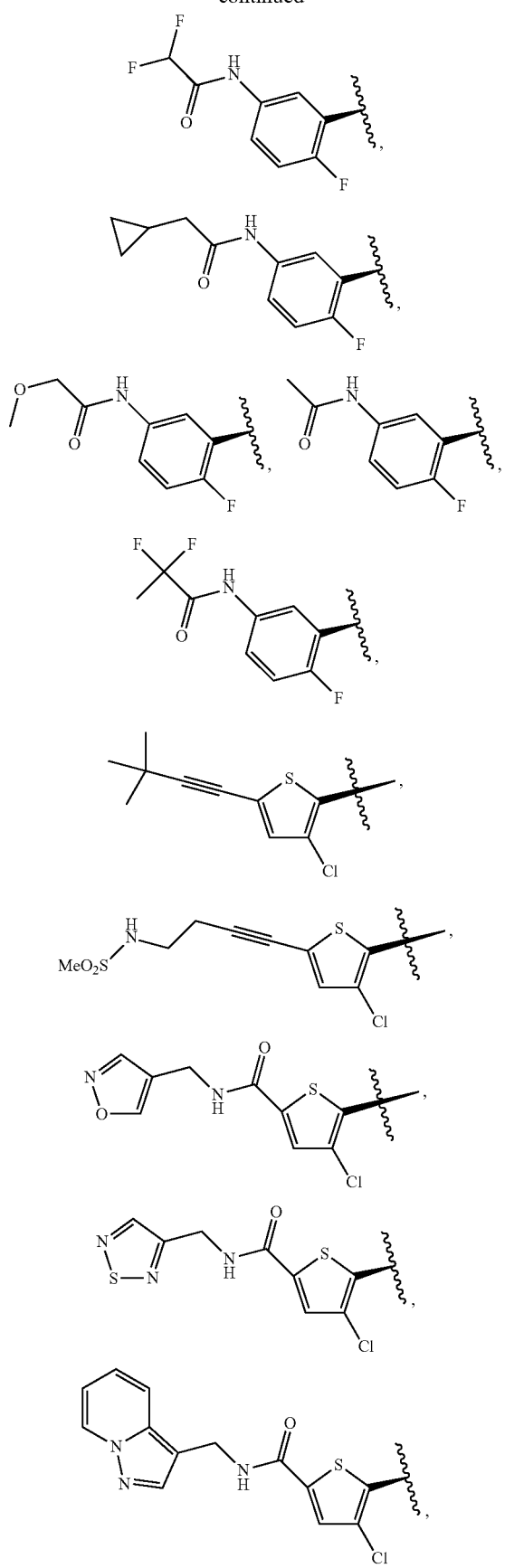
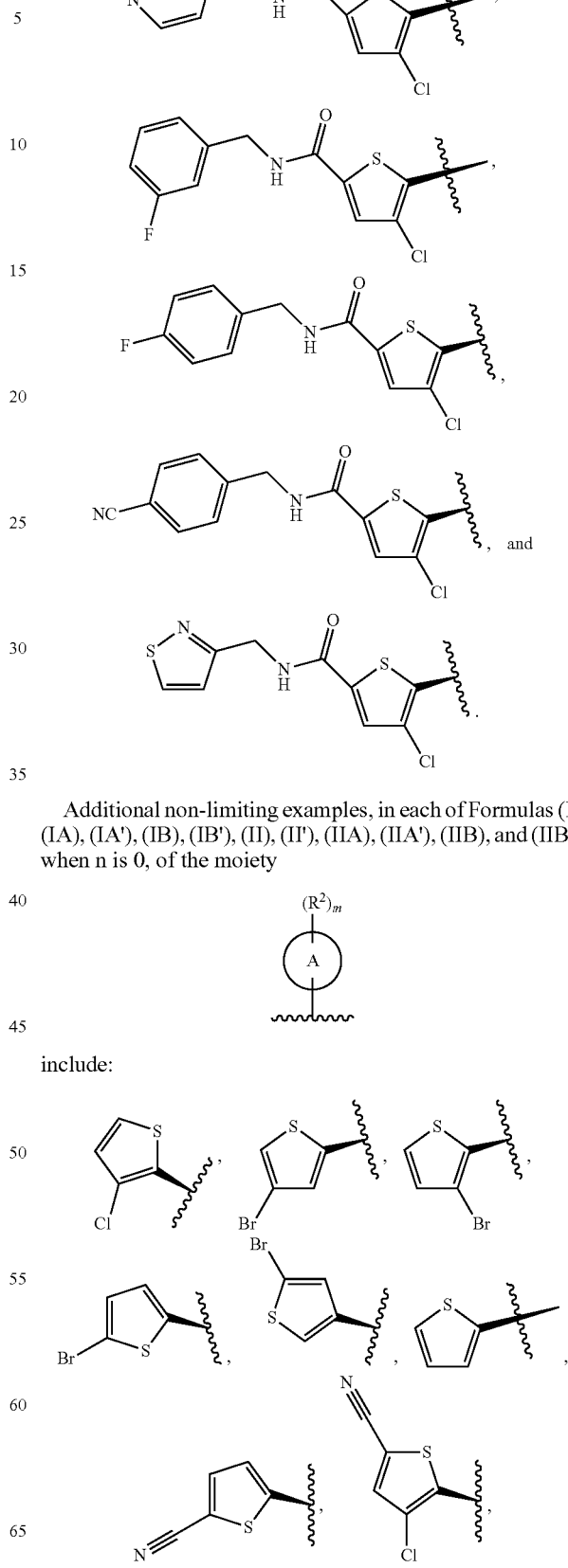
Additional non-limiting examples, in each of Formulas (I), (IA), (IA'), (IB), (IB'), (II), (II'), (IIA), (IIA'), (IIB), and (IIB'), when n is 0, of the moiety
include:

-continued

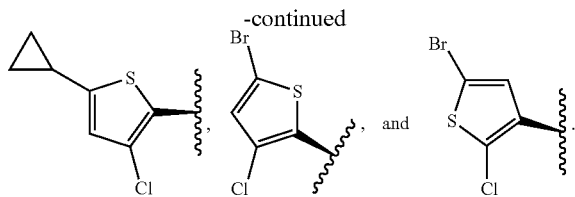

Specific non-limiting examples of compounds of the invention are shown in the table of examples below. While only one tautomeric form of each compound is shown in the tables, it shall be understood that all tautomeric forms of the compounds are contemplated as being within the scope of the non-limiting examples.

In another embodiment, 1 to 3 carbon atoms of the compounds of the invention may be replaced with 1 to 3 silicon atoms so long as all valency requirements are satisfied.

In another embodiment, there is provided a composition comprising a compound of the invention and a pharmaceutically acceptable carrier or diluent.

Another embodiment provides a composition comprising a compound of the invention, either as the sole active agent, or optionally in combination with one or more additional therapeutic agents, and a pharmaceutically acceptable carrier or diluent. Non-limiting examples of additional therapeutic agents for use in combination with the compounds of the invention include those selected from the group consisting of: (a) drugs useful for the treatment of Alzheimer's disease and/or drugs useful for treating one or more symptoms of Alzheimer's disease, (b) drugs useful for inhibiting the synthesis Aβ, (c) drugs useful for treating neurodegenerative diseases, and (d) drugs useful for the treatment of type II diabetes and/or one or more symptoms or associated pathologies thereof.

Additional non-limiting examples of additional therapeutic agents for use in combination with the compounds of the invention include drugs useful for the treatment, prevention, delay of onset, amelioration of any pathology associated with Aβ and/or a symptom thereof. Non-limiting examples of pathologies associated with Aβ include: Alzheimer's Disease, Down's syndrome, Parkinson's disease, memory loss, memory loss associated with Alzheimer's disease, memory loss associated with Parkinson's disease, attention deficit symptoms, attention deficit symptoms associated with Alzheimer's disease ("AD"), Parkinson's disease, and/or Down's syndrome, dementia, stroke, microgliosis and brain inflammation, pre-senile dementia, senile dementia, dementia associated with Alzheimer's disease, Parkinson's disease, and/or Down's syndrome, progressive supranuclear palsy, cortical basal degeneration, neurodegeneration, olfactory impairment, olfactory impairment associated with Alzheimer's disease, Parkinson's disease, and/or Down's syndrome, β-amyloid angiopathy, cerebral amyloid angiopathy, hereditary cerebral hemorrhage, mild cognitive impairment ("MCI"), glaucoma, amyloidosis, type II diabetes, hemodialysis complications (from $\beta_2$ microglobulins and complications arising therefrom in hemodialysis patients), scrapie, bovine spongiform encephalitis, and Creutzfeld-Jakob disease, comprising administering to said patient at least one compound of the invention, or a tautomer or isomer thereof, or pharmaceutically acceptable salt or solvate of said compound or said tautomer, in an amount effective to inhibit or treat said pathology or pathologies.

Additional non-limiting examples of additional therapeutic agents for use in combination with compounds of the invention include: muscarinic antagonists (e.g., $m_1$ agonists (such as acetylcholine, oxotremorine, carbachol, or McNa343), or $m_2$ antagonists (such as atropine, dicycloverine, tolterodine, oxybutynin, ipratropium, methoctramine, tripitamine, or gallamine)); cholinesterase inhibitors (e.g., acetyl- and/or butyrylchlolinesterase inhibitors such as donepezil (Aricept®, (±)-2,3-dihydro-5,6-dimethoxy-2-[[1-(phenylmethyl)-4-piperidinyl]methyl]-1H -inden-1-one hydrochloride), galantamine (Razadyne®), and rivastigimine (Exelon®); N-methyl-D-aspartate receptor antagonists (e.g., Namenda® (memantine HCl, available from Forrest Pharmaceuticals, Inc.); combinations of cholinesterase inhibitors and N-methyl-D-aspartate receptor antagonists; gamma secretase modulators; gamma secretase inhibitors; non-steroidal anti-inflammatory agents; anti-inflammatory agents that can reduce neuroinflammation; anti-amyloid antibodies (such as bapineuzemab, Wyeth/Elan); vitamin E; nicotinic acetylcholine receptor agonists; CB1 receptor inverse agonists or CB1 receptor antagonists; antibiotics; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors; Tau kinase inhibitors (e.g., GSK3beta inhibitors, cdk5 inhibitors, or ERK inhibitors); Tau aggregation inhibitors (e.g., Rember®); RAGE inhibitors (e.g., TTP 488 (PF-4494700)); anti-Abeta vaccine; APP ligands; agents that upregulate insulin, cholesterol lowering agents such as HMG-CoA reductase inhibitors (for example, statins such as Atorvastatin, Fluvastatin, Lovastatin, Mevastatin, Pitavastatin, Pravastatin, Rosuvastatin, Simvastatin) and/or cholesterol absorption inhibitors (such as Ezetimibe), or combinations of HMG-CoA reductase inhibitors and cholesterol absorption inhibitors (such as, for example, Vytorin®); fibrates (such as, for example, clofibrate, Clofibride, Etofibrate, and Aluminium Clofibrate); combinations of fibrates and cholesterol lowering agents and/or cholesterol absorption inhibitors; nicotinic receptor agonists; niacin; combinations of niacin and cholesterol absorption inhibitors and/or cholesterol lowering agents (e.g., Simcor® (niacin/simvastatin, available from Abbott Laboratories, Inc.); LXR agonists; LRP mimics; H3 receptor antagonists; histone deacetylase inhibitors; hsp90 inhibitors; 5-HT4 agonists (e.g., PRX-03140 (Epix Pharmaceuticals)); 5-HT6 receptor antagonists; mGluR1 receptor modulators or antagonists; mGluR5 receptor modulators or antagonists; mGluR2/3 antagonists; Prostaglandin EP2 receptor antagonists; PAI-1 inhibitors; agents that can induce Abeta efflux such as gelsolin; Metal-protein attenuating compound (e.g, PBT2); and GPR3 modulators; and antihistamines such as Dimebolin (e.g., Dimebon®, Pfizer).

Another embodiment provides a method of preparing a pharmaceutical composition comprising the step of admixing at least one compound of the invention, or a tautomer or stereoisomer thereof, or pharmaceutically acceptable salt or solvate of said compound, said stereoisomer, or said tautomer, and a pharmaceutically acceptable carrier or diluent.

Another embodiment provides a method of inhibiting β-secretase (BACE-1 and/or BACE-2) comprising exposing a population of cells expressing β-secretase to at least one compound of the invention, or a tautomer or stereoisomer thereof, or pharmaceutically acceptable salt or solvate of said compound, said stereoisomer, or said tautomer, in an amount effective to inhibit β-secretase. In one such embodiment, said population of cells is in vivo. In another such embodiment, said population of cells is ex vivo. In another such embodiment, said population of cells is in vitro.

Another embodiment provides a method of inhibiting β-secretase in a patient in need thereof. Another embodiment provides a method of inhibiting the formation of Aβ from APP in a patient in need thereof. Another embodiment, the invention provides a method of inhibiting the formation of Aβ plaque and/or Aβ fibrils and/or Aβ oligomers and/or senile plaques and/or neurofibrillary tangles and/or inhibiting the deposition of amyloid protein (e.g., amyloid beta protein) in, on or around neurological tissue (e.g., the brain), in a patient in need thereof. Each such embodiment comprises administering at least one compound of the invention, or a tautomer or stereoisomer thereof, or pharmaceutically acceptable salt or solvate of said compound, said stereoisomer, or said tautomer, in a therapeutically effective amount to inhibit said pathology or condition in said patient.

In another embodiment, the invention provides a method of treating, preventing, and/or delaying the onset of one or more pathologies associated with Aβ and/or one or more symptoms of one or more pathologies associated with Aβ. Non-limiting examples of pathologies associated with Aβ include: Alzheimer's Disease, Down's syndrome, Parkinson's disease, memory loss, memory loss associated with Alzheimer's disease, memory loss associated with Parkinson's disease, attention deficit symptoms, attention deficit symptoms associated with Alzheimer's disease ("AD"), Parkinson's disease, and/or Down's syndrome, dementia, stroke, microgliosis and brain inflammation, pre-senile dementia, senile dementia, dementia associated with Alzheimer's disease, Parkinson's disease, and/or Down's syndrome, progressive supranuclear palsy, cortical basal degeneration, neurodegeneration, olfactory impairment, olfactory impairment associated with Alzheimer's disease, Parkinson's disease, and/or Down's syndrome, β-amyloid angiopathy, cerebral amyloid angiopathy, hereditary cerebral hemorrhage, mild cognitive impairment ("MCI"), glaucoma, amyloidosis, type II diabetes, hemodialysis complications (from $\beta_2$ microglobulins and complications arising therefrom in hemodialysis patients), scrapie, bovine spongiform encephalitis, and Creutzfeld-Jakob disease, comprising administering to said patient at least one compound of the invention, or a tautomer or stereoisomer thereof, or pharmaceutically acceptable salt or solvate of said compound, said stereoisomer, or said tautomer, in an amount effective to inhibit said pathology or pathologies.

In one embodiment, the invention provides a method of treating Alzheimer's disease, comprising administering an effective (i.e., therapeutically effective) amount of one or more compounds of the invention (or a tautomer or stereoisomer thereof, or pharmaceutically acceptable salt or solvate of said compound, said stereoisomer, or said tautomer), optionally in further combination with one or more additional therapeutic agents effective to treat Alzheimer's disease or a disease or condition associated therewith, to a patient in need of treatment. In embodiments wherein one or more additional therapeutic agents are administered, such agents may be administered sequentially or together. Non-limiting examples of associated diseases or conditions, and non-limiting examples of suitable additional therapeutically active agents, are as described above.

In one embodiment, the invention provides a method of treating mild cognitive impairment ("MCI"), comprising administering an effective (i.e., therapeutically effective) amount of one or more compounds of the invention (or a tautomer or stereoisomer thereof, or pharmaceutically acceptable salt or solvate of said compound, said stereoisomer, or said tautomer) to a patient in need of treatment. In one such embodiment, treatment can begin prior to the onset of symptoms.

In one embodiment, the invention provides a method of preventing, or alternatively of delaying the onset, of mild cognitive impairment or, in a related embodiment, of preventing or alternatively of delaying the onset of Alzheimer's disease. In such embodiments, treatment can be initiated prior to the onset of symptoms, in some embodiments significantly before (e.g., from several months to several years before) the onset of symptoms to a patient at risk for developing MCI or Alzheimer's disease. Thus, such methods comprise administering, prior to the onset of symptoms or clinical or biological evidence of MCI or Alzheimer's disease (e.g., from several months to several yards before, an effective (i.e., therapeutically effective), and over a period of time and at a frequency of dose sufficient for the substantial inhibition of the BACE enzyme over the period of treatment, an amount of one or more compounds of the invention (or a tautomer or stereoisomer thereof, or pharmaceutically acceptable salt or solvate of said compound, said stereoisomer, or said tautomer) to a patient in need of treatment.

In one embodiment, the invention provides a method of treating Down's syndrome, comprising administering an effective (i.e., therapeutically effective) amount of one or more compounds of the invention (or a tautomer or stereoisomer thereof, or pharmaceutically acceptable salt or solvate of said compound, said stereoisomer, or said tautomer) to a patient in need of treatment.

In one embodiment, the invention provides a kit comprising, in separate containers, in a single package, pharmaceutical compositions for use in combination, wherein one container comprises an effective amount of a compound of the invention (or a tautomer or stereoisomer thereof, or pharmaceutically acceptable salt or solvate of said compound, said stereoisomer, or said tautomer) in a pharmaceutically acceptable carrier, and another container (i.e., a second container) comprises an effective amount of another pharmaceutically active ingredient, the combined quantities of the compound of the invention and the other pharmaceutically active ingredient being effective to: (a) treat Alzheimer's disease, or (b) inhibit the deposition of amyloid protein in, on or around neurological tissue (e.g., the brain), or (c) treat neurodegenerative diseases, or (d) inhibit the activity of BACE-1.

In various embodiments, the compositions and methods disclosed above and below wherein the compound(s) of the invention is a compound or compounds selected from the group consisting of the exemplary compounds of the invention described below.

In another embodiment, the invention provides for the use of a compound of the invention, or a tautomer or stereoisomer thereof, or pharmaceutically acceptable salt or solvate of said compound, said stereoisomer, or said tautomer, in the manufacture of a medicament for use in the treatment, the delay of onset, and/or the prevention of one or more Aβ pathologies and/or in the treatment, the delay of onset, and/or the prevention of one or more symptoms of one or more Aβ pathologies.

DEFINITIONS

The terms used herein have their ordinary meaning and the meaning of such terms is independent at each occurrence thereof. That notwithstanding and except where stated otherwise, the following definitions apply throughout the specification and claims. Chemical names, common names and chemical structures may be used interchangeably to describe that same structure. These definitions apply regardless of whether a term is used by itself or in combination with other terms, unless otherwise indicated. Hence the definition of "alkyl" applies to "alkyl" as well as the "alkyl" portion of "hydroxyalkyl", "haloalkyl", arylalkyl-, alkylaryl-, "alkoxy" etc.

It shall be understood that, in the various embodiments of the invention described herein, any variable not explicitly defined in the context of the embodiment is as defined in Formula (I). All valences not explicitly filled are assumed to be filled by hydrogen.

In the various embodiments described herein, each variable is selected independently of the others unless otherwise indicated.

As described herein, variables of the formulas presented herein, such as ring A and ring B may be unsubstituted or substituted with "one or more" groups. For example, ring A may be unsubstituted or substituted with one or more $R^2$ groups; ring B may be unsubstituted or substituted with one or more $R^3$ groups. It shall be understood that the upper limit of the number of substituents (referred to in the phrase "one or more substituents") is the number of available hydrogen atoms on the relevant moiety (e.g., ring A or ring B) that are available for replacement by a substituent which will result in a chemically stable and chemically neutral moiety. Thus, for example, in the various Formulas of the compounds of the invention, e.g., in Formula (I), m, n, and p are each independently selected integers, wherein:

m is 0 or more,
n is 0 or 1, and
p is 0 or more, wherein the maximum value of m is the maximum number of available substitutable hydrogen atoms on ring A, and wherein the maximum value of p is the maximum number of available substitutable hydrogen atoms on ring B. By way of non-limiting illustration, when ring A is a

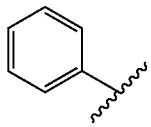 [SMILES: *c1ccccc1]

group, the maximum value of m is 5. When ring A is a

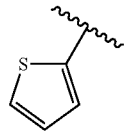 [SMILES: *c1cccs1]

group, the maximum value of m is 3. When ring A is a

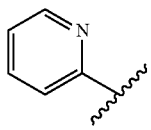 [SMILES: *c1ccccn1]

group, the maximum value of m is 4.

"Patient" includes both human and non-human animals. Non-human animals include those research animals and companion animals such as mice, primates, monkeys, great apes, canine (e.g., dogs), and feline (e.g., house cats).

"Pharmaceutical composition" (or "pharmaceutically acceptable composition") means a composition suitable for administration to a patient. Such compositions may contain the neat compound (or compounds) of the invention or mixtures thereof, or salts, solvates, prodrugs, isomers, or tautomers thereof, or they may contain one or more pharmaceutically acceptable carriers or diluents. The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the aforesaid "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the aforesaid bulk composition and individual dosage units.

"Halogen" (or "halo") means fluorine, chlorine, bromine, or iodine. Preferred are fluorine, chlorine and bromine.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. Non-limiting examples of suitable alkyl groups include methyl, ethyl, n-propyl, isopropyl and t-butyl.

"Haloalkyl" means an alkyl as defined above wherein one or more hydrogen atoms on the alkyl is replaced by a halo group defined above.

"Heteroalkyl" means an alkyl moiety as defined above, having one or more carbon atoms, for example one, two or three carbon atoms, replaced with one or more heteroatoms, which may be the same or different, where the point of attachment to the remainder of the molecule is through a carbon atom of the heteroalkyl radical. Suitable such heteroatoms include O, S, S(O), $S(O)_2$, and —NH—, —N(alkyl)-. Non-limiting examples include ethers, thioethers, amines, and the like.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene. More generally, the suffix "ene" on alkyl, aryl, hetercycloalkyl, etc. indicates a divalent moiety, e.g., —$CH_2CH_2$— is ethylene, and

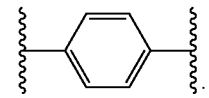

is para-phenylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butyryl and 3-methylbutynyl.

"Alkenylene" means a difunctional group obtained by removal of a hydrogen from an alkenyl group that is defined above. Non-limiting examples of alkenylene include —CH=CH—, —C(CH₃)=CH—, and —CH=CHCH₂—.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl. "Monocyclic aryl" means phenyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more substituents, which may be the same or different, as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl (which alternatively may be referred to as thiophenyl), pyrimidinyl, pyridone (including N-substituted pyridones), isoxazolyl, isothiazolyl, oxazolyl, oxadiazolyl, thiazolyl, thiadiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like. The term "monocyclic heteroaryl" refers to monocyclic versions of heteroaryl as described above and includes 4- to 7-membered monocyclic heteroaryl groups comprising from 1 to 4 ring heteroatoms, said ring heteroatoms being independently selected from the group consisting of N, O, and S, and oxides thereof. The point of attachment to the parent moiety is to any available ring carbon or ring heteroatom. Non-limiting examples of monocyclic heteroaryl moities include pyridyl, pyrazinyl, furanyl, thienyl, pyrimidinyl, pyridazinyl, pyridoneyl, thiazolyl, isothiazolyl, oxazolyl, oxadiazolyl, isoxazolyl, pyrazolyl, furazanyl, pyrrolyl, pyrazolyl, triazolyl, thiadiazolyl (e.g., 1,2,4-thiadiazolyl), imidazolyl, and triazinyl (e.g., 1,2,4-triazinyl), and oxides thereof "Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more substituents, which may be the same or different, as described herein. Monocyclic cycloalkyl refers to monocyclic versions of the cycloalkyl moieties described herein. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like. Further non-limiting examples of cycloalkyl include the following:

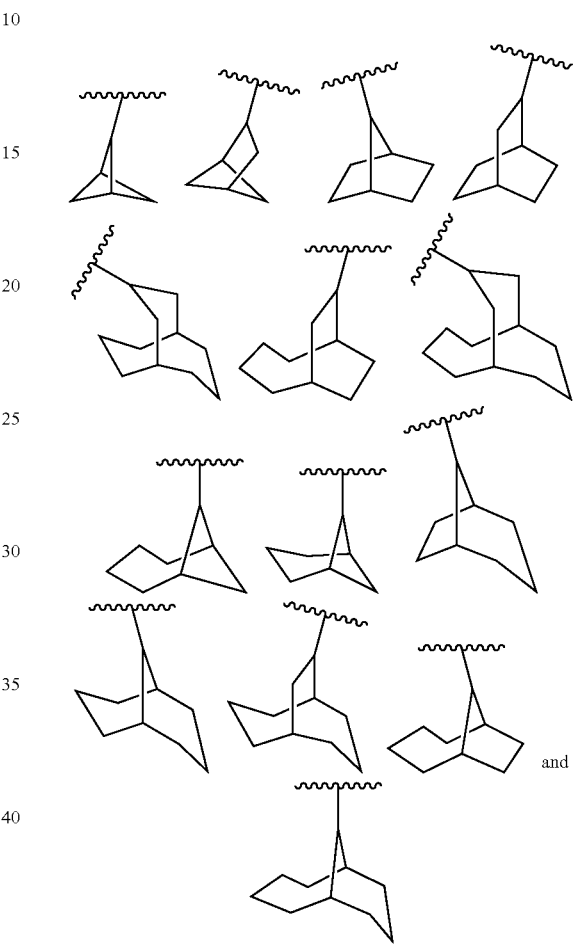

and

"Cycloalkenyl" means a non-aromatic mono or multicyclic ring system comprising about 3 to about 10 carbon atoms, preferably about 5 to about 10 carbon atoms which contain at least one carbon-carbon double bond. Preferred cycloalkenyl rings contain about 5 to about 7 ring atoms. The cycloalkenyl can be optionally substituted with one or more substituents, which may be the same or different, as described herein. The term "monocyclic cycloalkenyl" refers to monocyclic versions of cycloalkenyl groups described herein and includes non-aromatic 3- to 7-membered monocyclic cycloalkyl groups which contains one or more carbon-carbon double bonds. Non-limiting examples include cyclopropenyl, cyclobutenyl, cyclopentenyl, cyclohexenyl, cyclohetpenyl, cyclohepta-1,3-dienyl, and the like. Non-limiting example of a suitable multicyclic cycloalkenyl is norbornylenyl.

"Heterocycloalkyl" (or "heterocyclyl") means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more substituents, which may be the same or different, as described herein. The nitrogen or sulfur atom of the heterocyclyl can be optionally oxidized to the corresponding N-oxide, S-oxide or S,S-dioxide. Thus, the term "oxide," when it appears in a definition of a variable in a general structure described herein, refers to the corresponding N-oxide, S-oxide, or S,S-dioxide. "Heterocyclyl" also includes rings wherein =O replaces two available hydrogens on the same carbon atom (i.e., heterocyclyl includes rings having a carbonyl group in the ring). Such =O groups may be referred to herein as "oxo." An example of such a moiety is pyrrolidinone (or pyrrolidone):

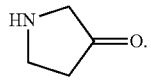

As used herein, the term "monocyclic heterocycloalkyl" refers monocyclic versions of the heterocycloalkyl moieties described herein and include a 4- to 7-membered monocyclic heterocycloalkyl groups comprising from 1 to 4 ring heteroatoms, said ring heteroatoms being independently selected from the group consisting of N, N-oxide, O, S, S-oxide, S(O), and S(O)$_2$. The point of attachment to the parent moiety is to any available ring carbon or ring heteroatom. Non-limiting examples of monocyclic heterocycloalkyl groups include piperidyl, oxetanyl, pyrrolyl, piperazinyl, morpholinyl, thiomorpholinyl, thiazolidinyl, 1,4-dioxanyl, tetrahydrofuranyl, tetrahydrothiophenyl, beta lactam, gamma lactam, delta lactam, beta lactone, gamma lactone, delta lactone, and pyrrolidinone, and oxides thereof. Non-limiting examples of lower alkyl-substituted oxetanyl include the moiety:

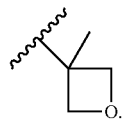

"Heterocycloalkenyl" (or "heterocyclenyl") means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more substituents, which may be the same or different, as described herein. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" also includes rings wherein =O replaces two available hydrogens on the same carbon atom (i.e., heterocyclyl includes rings having a carbonyl group in the ring). Example of such moiety is pyrrolidenone (or pyrrolone):

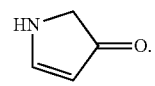

As used herein, the term "monocyclic heterocycloalkenyl" refers to monocyclic versions of the heterocycloalkenyl moities described herein and include 4- to 7-membered monocyclic heterocycloalkenyl groups comprising from 1 to 4 ring heteroatoms, said ring heteroatoms being independently selected from the group consisting of N, N-oxide, O, S, S-oxide, S(O), and S(O)$_2$. The point of attachment to the parent moiety is to any available ring carbon or ring heteroatom. Non-limiting examples of monocyclic heterocyloalkenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, dihydrothiophenyl, and dihydrothiopyranyl, and oxides thereof It should be noted that in hetero-atom containing ring systems of this invention, there are no hydroxyl groups on carbon atoms adjacent to a N, O or S, as well as there are no N or S groups on carbon adjacent to another heteroatom.

there is no —OH attached directly to carbons marked 2 and 5.

As used herein, the term "multicyclic group" refers to a fused ring system comprising two (bicyclic), three (tricyclic), or more fused rings, wherein each ring of the fused ring system is independently selected from the group consisting of phenyl, monocyclic heteroaryl, monocyclic cycloalkyl, monocyclic cycloalkenyl, monocyclic heterocycloalkyl, and monocyclic heterocycloalkenyl, as defined above. The point of attachment to the parent moiety is to any available ring carbon or (if present) ring heteroatom on any of the fused rings. It shall be understood that each of the following multicyclic groups pictured may be unsubstituted or substituted, as described herein. Only the point of attachment to the parent moiety is shown by the wavy line.

The term multicyclic groups includes bicyclic aromatic groups. Non-limiting examples of multicyclic groups which are bicyclic aromatic groups include:

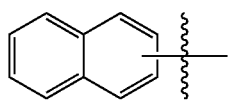

The term multicyclic group thus includes bicyclic heteroaromatic groups comprising from 1 to 3 ring heteroatoms, each said ring heteroatom being independently selected from the group consisting of N, O, and S, S(O), S(O)$_2$, and oxides of N, O, and S, and oxides thereof.

The term multicyclic group includes saturated bicyclic cycloalkyl groups. Non-limiting examples of multicyclic groups which are saturated bicyclic cycloalkyl groups include the following:

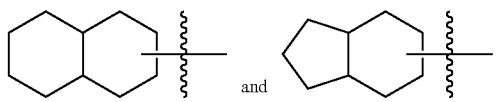

The term multicyclic group includes partially unsaturated bicyclic cycloalkyl groups. Non-limiting examples of multicyclic groups which comprise partially unsaturated bicyclic cycloalkyl groups include the following:

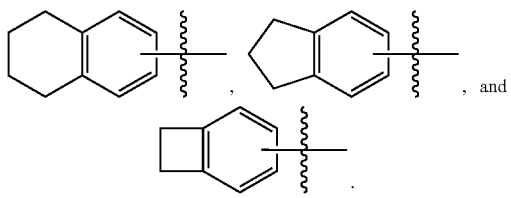

The term multicyclic groups includes partially or fully saturated bicyclic groups comprising from 1 to 3 ring heteroatoms, each said ring heteroatom is independently selected from the group consisting of N, O, and S, S(O), S(O)$_2$, and oxides of N, O, and S.

The term multicyclic group includes aromatic tricyclic groups, cycloalkyl tricyclic groups, as well as heteroaromatic and partially and fully saturated tricyclic groups. For tricyclic groups comprising ring heteroatoms, said tricyclic groups comprise one or more (e.g., from 1 to 5) ring heteroatoms, wherein each said ring heteroatom is independently selected from N, O, and S, S(O), S(O)$_2$, and oxides of N, O, and S:

"Arylalkyl" (or "aralkyl") means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl. The term (and similar terms) may be written as "arylalkyl-" (or as "-alkyl-aryl") to indicate the point of attachment to the parent moiety. Similarly, "heteroarylalkyl", "cycloalkylalkyl", "cycloalkenylalkyl", "heterocycloalkylalkyl", "heterocycloalkenylalkyl", etc., mean a heteroaryl, cycloalkyl, cycloalkenyl, heterocycloalkyl, heterocycloalkenyl, etc. as described herein bound to a parent moiety through an alkyl group. Preferred groups contain a lower alkyl group. Such alkyl groups may be straight or branched, unsubstituted and/or substituted as described herein.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkylether" means a non-aromatic ring of 3 to 7 members comprising an oxygen atom and 2 to 7 carbon atoms. Ring carbon atoms can be substituted, provided that substituents adjacent to the ring oxygen do not include halo or substituents joined to the ring through an oxygen, nitrogen or sulfur atom.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl, adamantylpropyl, and the like.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclylalkyl" (or "heterocycloalkylalkyl") means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenylalkyl" means a heterocyclenyl moiety as defined above linked via an alkyl moiety (defined above) to a parent core.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Cyanoalkyl" means a NC-alkyl- group in which alkyl is as previously defined. Preferred cyanoalkyls contain lower alkyl. Non-limiting examples of suitable cyanoalkyl groups include cyanomethyl and 2-cyanoethyl.

"Alkoxy" means an alkyl-O-group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Alkyoxyalkyl" means a group derived from an alkoxy and alkyl as defined herein. The bond to the parent moiety is through the alkyl.

"Spirocycloalkyl" means a cycloalkyl group attached to a parent moiety at a single carbon atom. Non-limiting examples of spirocycloalkyl wherein the parent moiety is a cycloalkyl include spiro[2.5]octane, spiro[2.4]heptane, etc. Non-limiting examples of spriocycloalkyl wherein the parent moiety is an The alkyl moiety linking fused ring systems (such as the alkyl moiety in heteroarylfused heteroarylalkyl-) may optionally be substituted with spirocycloalkyl or other groups as described herein. Non-limiting spirocycloalkyl groups include spirocyclopropyl, spriorcyclobutyl, spirocycloheptyl, and spirocyclohexyl.

"Spiroheterocycloalkyl" means a heterocycloalkyl group, as defined herein, attached to a parent moiety at a single carbon atom.

Any of the foregoing functional groups may be unsubstituted or substituted as described herein. The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

Substitution on a cycloalkylalkyl, heterocycloalkylalkyl, arylalkyl, heteroarylalkyl, arylfused cycloalkylalkyl- moiety or the like includes substitution on any ring portion and/or on the alkyl portion of the group.

When a variable appears more than once in a group, e.g., $R^8$ in $-N(R^6)_2$, or a variable appears more than once in a structure presented herein, the variables can be the same or different.

The line —, as a bond generally indicates a mixture of, or either of, the possible isomers, e.g., containing (R)- and (S)-stereochemistry. For example:

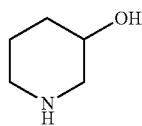

means containing both

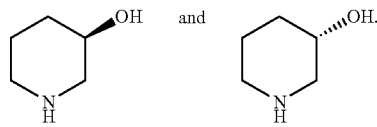

The wavy line ～, as used herein, indicates a point of attachment to the rest of the compound. Lines drawn into the ring systems, such as, for example:

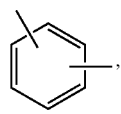

indicate that the indicated line (bond) may be attached to any of the substitutable ring carbon atoms.

"Oxo" is defined as a oxygen atom that is double bonded to a ring carbon in a cycloalkyl, cycloalkenyl, heterocyclyl, heterocyclenyl, or other ring described herein, e.g.,

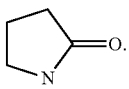

In this specification, where there are multiple oxygen and/or sulfur atoms in a ring system, there cannot be any adjacent oxygen and/or sulfur present in said ring system.

As well known in the art, a bond drawn from a particular atom wherein no moiety is depicted at the terminal end of the bond indicates a methyl group bound through that bond to the atom, unless stated otherwise. For example:

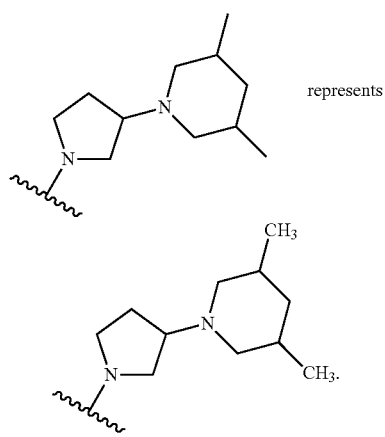

represents

In another embodiment, the compounds of the invention, and/or compositions comprising them, are present in isolated and/or purified form. The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound (or a tautomer or stereoisomer thereof, or pharmaceutically acceptable salt or solvate of said compound, said stereoisomer, or said tautomer) after being obtained from a purification process or processes described herein or well known to the skilled artisan (e.g., chromatography, recrystallization and the like), in sufficient purity to be suitable for in vivo or medicinal use and/or characterizable by standard analytical techniques described herein or well known to the skilled artisan.

It shall be understood that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

Another embodiment provides prodrugs and/or solvates of the compounds of the invention. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of the invention or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of the invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

Another embodiment provides pharmaceutically acceptable salts of the compounds of the invention. Thus, reference to a compound of the invention herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of the invention contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the invention may be formed, for example, by reacting a compound of the invention with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Another embodiment provides pharmaceutically acceptable esters of the compounds of the invention. Such esters include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

As mentioned herein, another embodiment provides tautomers of the compounds of the invention. It shall be understood that all tautomeric forms of such compounds are within the scope of the compounds of the invention. For example, all keto-enol and imine-enamine forms of the compounds, when present, are included in the invention.

The compounds of the invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric and positional isomers. For example, if a compound of the invention incorporates a double bond or a fused ring, both the cis- and trans-forms, as well as mixtures, are embraced within the scope of the invention.

Another embodiment provides for diastereomeric mixtures and individual enantiomers of the compounds of the invention. Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of chiral HPLC column.

All stereoisomers (for example, geometric isomers, optical isomers and the like) of the compounds of the invention (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated as embodiments within the scope of this invention, as are positional isomers (such as, for example, 4-pyridyl and 3-pyridyl). (For example, if a compound of the invention incorporates a double bond or a fused ring, both the cis- and trans-forms, as well as mixtures, are embraced within the scope of the invention. Also, for example, all keto-enol and imine-enamine forms of the compounds are included in the invention.).

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

Another embodiment provides isotopically-labelled compounds of the invention. Such compounds are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^{1}H$) and deuterium ($^{2}H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of the invention can be prepared without undue experimentation by conventional techniques well known to those skilled in the art or by processes analogous to those described in the schemes and examples herein using appropriate isotopically-enriched reagents and/or intermediates.

Polymorphic forms of the compounds of the invention, and of the salts, solvates, esters and prodrugs of the compounds of the invention, are intended to be included in the present invention.

Another embodiment provides suitable dosages and dosage forms of the compounds of the invention. Suitable doses for administering compounds of the invention to patients may readily be determined by those skilled in the art, e.g., by an attending physician, pharmacist, or other skilled worker, and may vary according to patient health, age, weight, frequency of administration, use with other active ingredients, and/or indication for which the compounds are administered. Doses may range from about 0.001 to 500 mg/kg of body weight/day of the compound of the invention. In one embodiment, the dosage is from about 0.01 to about 25 mg/kg of body weight/day of a compound of the invention, or a pharmaceutically acceptable salt or solvate of said compound. In another embodiment, the quantity of active compound in a unit dose of preparation may be varied or adjusted from about 1 mg to about 100 mg, preferably from about 1 mg to about 50 mg, more preferably from about 1 mg to about 25 mg, according to the particular application. In another embodiment, a typical recommended daily dosage regimen for oral administration can range from about 1 mg/day to about 500 mg/day, preferably 1 mg/day to 200 mg/day, in two to four divided doses.

As discussed above, the amount and frequency of administration of the compounds of the invention and/or the pharmaceutically acceptable salts thereof will be regulated according to the judgment of the attending clinician considering such factors as age, condition and size of the patient as well as severity of the symptoms being treated.

When used in combination with one or more additional therapeutic agents, the compounds of this invention may be administered together or sequentially. When administered sequentially, compounds of the invention may be administered before or after the one or more additional therapeutic agents, as determined by those skilled in the art or patient preference.

If formulated as a fixed dose, such combination products employ the compounds of this invention within the dosage range described herein and the other pharmaceutically active agent or treatment within its dosage range.

Accordingly, another embodiment provides combinations comprising an amount of at least one compound of the invention, or a pharmaceutically acceptable salt, solvate, ester or prodrug thereof, and an effective amount of one or more additional agents described above.

The pharmacological properties of the compounds of this invention may be confirmed by a number of pharmacological assays. Certain assays are exemplified elsewhere in this document.

Another embodiment provides for pharmaceutically acceptable compositions comprising a compound of the invention, either as the neat chemical or optionally further comprising additional ingredients. For preparing pharmaceutical compositions from the compounds of the invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

Another embodiment provides for compositions comprising a compound of the invention formulated for transdermal delivery. The transdermal compositions can take the form of creams, lotions, aerosols and/or emulsions and can be included in a transdermal patch of the matrix or reservoir type as are conventional in the art for this purpose.

Another embodiment provides for compositions comprising a compound of the invention formulated for subcutaneous delivery. Another embodiment provides for compositions suitable for oral delivery. In some embodiments, it may be advantageous for the pharmaceutical preparation comprising one or more compounds of the invention be prepared in a unit dosage form. In such forms, the preparation is subdivided into suitably sized unit doses containing appropriate quantities of the active component, e.g., an effective amount to achieve the desired purpose. Each of the foregoing alternatives, together with their corresponding methods of use, are considered as included in the various embodiments of the invention.

PREPARATIVE EXAMPLES

Compounds of the invention can be made using procedures known in the art. The following reaction schemes show typical procedures, but those skilled in the art will recognize that other procedures can also be suitable. Reactions may involve monitoring for consumption of starting material, and there are many methods for said monitoring, including but not limited to thin layer chromatography (TLC) and liquid chromatography mass spectrometry (LCMS), and those skilled in the art will recognize that where one method is specified, other non-limiting methods may be substituted.

Techniques, solvents and reagents may be referred to by their abbreviations as follows:
[1,1'-Bis(diphenylphosphino)ferrocene]-dichloropalladium (II): PdCl₂dppf
1-(3-Dimethylaminopropyl)-3-ethylcarbodiimide hydrochloride: EDCI
1,2-dimethoxyethane: DME
2-(Trimethylsilyl)ethanol: TMSethanol
2-(Trimethylsilyl)ethoxycarbonyl: Teoc
3-Chloroperoxybenzoic acid: mCPBA
Acetonitrile: MeCN
Allyl carbamate: Alloc
Aqueous: aq.
Atmosphere: atm
Benzyl: Bn
Bis(2-oxo-3-oxazolidinyl)phosphinic chloride: BOPCl
n-Butyllithium: n-BuLi
Centimeters: cm
Ceric ammonium nitrate: CAN
Concentrated: conc.
Dichloromethane: DCM
2-Dicyclohexylphosphino-2',4',6'-triisopropylbiphenyl: Xphos
Diisopropylamine: iPr₂NH
Diisopropylethylamine: DIEA or iPr₂NEt
Dimethylacetamide: DMA
Dimethylformamide: DMF
Dimethylsulfoxide: DMSO
Diphenylphosphoryl azide: DPPA
Ether or diethyl ether: Et₂O
Ethyl: Et
Ethyl acetate: AcOEt or EtOAc or EA
Ethyl alcohol: EtOH
Example: Ex. or ex.
Grams: g
High performance liquid chromatography: HPLC
High resolution mass spectrometry: HRMS
Hours: hrs or h
Iron(III) acetylacetonate: Fe(acac)₃
Inhibition: Inh.
Liquid chromatography mass Spectrometry: LCMS
Lithium diisopropylamide: LDA
Methanesulfonyl chloride: MeSO₂Cl
Methanol: MeOH
Methyl magnesium bromide: MeMgBr
Microliters: μl or μL
Milligrams: mg
Milliliters: mL
Millimoles: mmol
N-bromosuccinimide: NBS
n-Butyllithium: nBuLi or n-BuLi
Nuclear magnetic resonance spectroscopy: NMR
Palladium(II) acetate: Pd(OAc)₂
paramethoxy benzyl: PMB
Petroleum ether: PE
Preparative: prep
Retention time: $t_R$
Reverse Phase: RP
Room temperature (ambient, ~25° C.): rt or RT
Supercritical Fluid Chromatography: SFC
tert-Butoxycarbonyl: t-Boc or Boc
Tetrahydrofuran: THF
Thin layer chromatography: TLC
Triethylamine: Et₃N or TEA
Trifluoroacetic acid: TFA
2,4,6-Tripropyl-1,3,5,2,4,6-trioxatriphosphorinane-2,4-6-trioxide (1-propanephosphonic anhydride): T3P

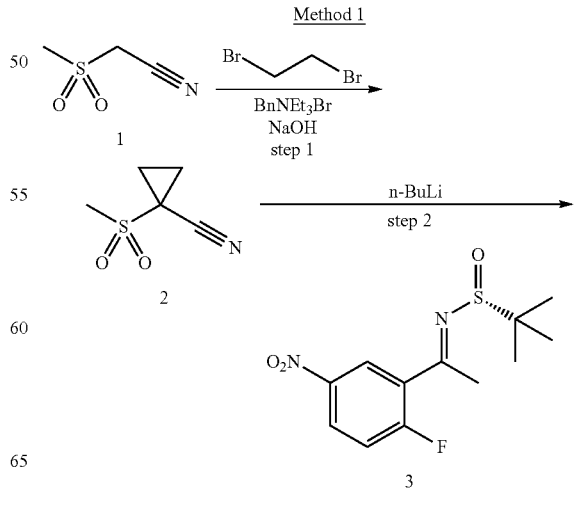

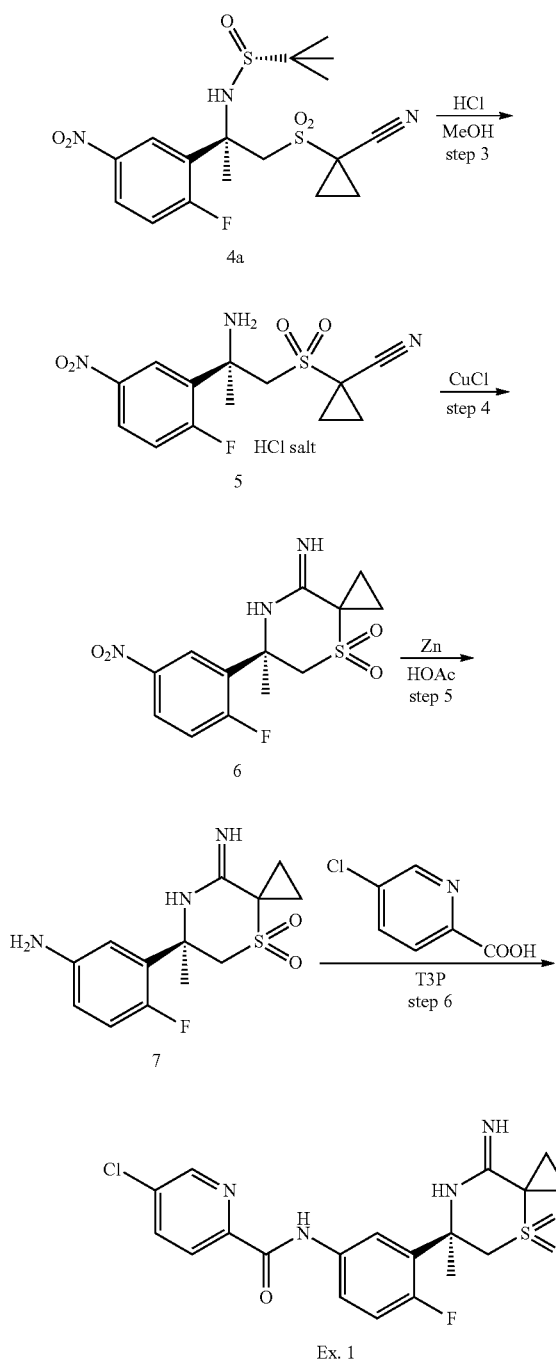

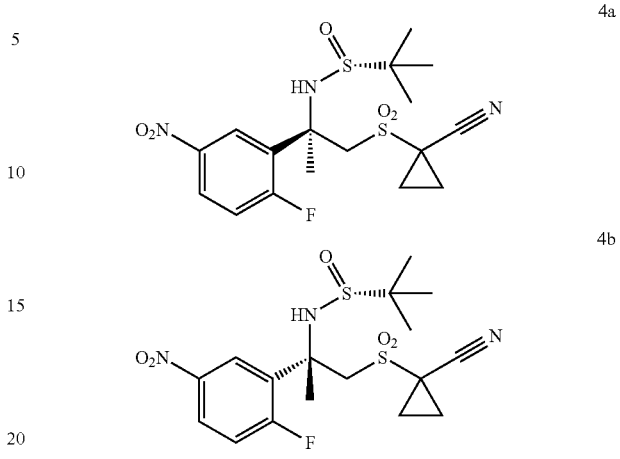

Step 2

To a −78° C. solution of 2.5 M n-butyllithium in hexanes (2.4 mL, 6.00 mmol) in tetrahydrofuran (3 mL) was added a solution of 2 (0.84 g, 5.79 mmol) in tetrahydrofuran (10 mL). The resulting −78° C. solution was stirred for 50 min, and then a solution of 3 (1.66 g, 5.80 mmol) in tetrahydrofuran (10 mL) was added. After being stirred for 2 h at −78° C., the reaction was quenched with saturated aq. NH$_4$Cl. The resulting mixture was diluted with water and then extracted with EtOAc (3×50 mL). The combined organic layers were dried over Na$_2$SO$_4$, filtered, and concentrated. This crude material was dissolved in CH$_2$Cl$_2$ and purified by flash silica gel chromatography (100 g cartridge, 0-100% Ethyl acetate/hexanes gradient) followed by SFC purification (Chiralpak 250×21 mm AD-H column, 20% isopropanol/CO$_2$, 50 g/min on a Thar SFC Prep 80 system) to afford 4a (0.572 g) and a 7:10 mixture of 4a and 4b (0.059 g) Data for 4a: LCMS (conditions A): $t_R$=2.21 min, m/e=432 (M+H). Data for 4b: LCMS (conditions A): $t_R$=2.16 min, m/e=432 (M+H).

Step 3

To a 0° C. solution of 4a (0.57 g, 1.32 mmol) in methanol (13 mL) was added a solution of 4 M HCl in dioxane (3.30 mL, 13.2 mmol). The cooling bath was removed after several minutes. After 1 h, the reaction mixture was concentrated. The resulting material was dissolved in ethanol and then re-concentrated. This crude 5 was used in the next step without purification. LCMS (conditions A): $t_R$=1.68 min, m/e=328 (M+H).

Step 4

A mixture of 5 (0.481 g, 1.32 mmol) and copper(I) chloride (0.137 g, 1.39 mmol) in ethanol (13 mL) was placed in an 80° C. oil bath. After ~2 h the mixture was cooled and stirred with CH$_2$Cl$_2$ and 2 M aq. NaOH, and then the layers were separated. The aq. layer was extracted with CH$_2$Cl$_2$ (2×). The combined organic layers were washed with brine, dried over Na$_2$SO$_4$, filtered, and concentrated. The crude material was purified by flash silica gel chromatography (50 g of SiO$_2$, 0-7.5% methanol/CH$_2$Cl$_2$ gradient with 0.1% NH$_4$OH) to afford 6 (0.345 g, 1.06 mmol). LCMS (conditions A): $t_R$=1.70 min, m/e=328 (M+H).

Step 5

To a 0° C. mixture of 6 (0.34 g, 1.04 mmol) and acetic acid (0.30 mL, 5.24 mmol) in tetrahydrofuran (5.2 mL) and ethanol (1.3 mL) was added zinc dust (0.68 g, 10.4 mmol) in portions over 2.5 min. The reaction mixture was removed from the ice bath after 1-2 min, and then was placed in a 70°

Step 1

To a room temperature mixture of methylsulfonylacetonitrile 1 (1.00 g, 8.39 mmol) and benzyltriethylammonium bromide (0.228 g, 0.839 mmol) in 50% aq. sodium hydroxide (14 mL, 175 mmol) was added 1,2-dibromoethane (0.72 mL, 8.32 mmol). After 2 h, the reaction mixture was diluted with water (25 mL), and then extracted with EtOAc (1×75 mL, 1×25 mL). The combined organic layers were washed with brine, dried over Na$_2$SO$_4$, filtered, and concentrated to afford compound 2 (0.85 g, 5.56 mmol). $^1$H NMR (CDCl$_3$, 500 MHz) δ 3.18 (s, 3H), 1.88-1.86 (m, 2H), 1.76-1.73 (m, 2H).

C. oil bath. After 1 h at 70° C., the reaction mixture was cooled, diluted with methanol, and filtered through a plug of Celite. The Celite plug was washed with methanol, and then the filtrate was concentrated. This crude material was dissolved in methanol/CH$_2$Cl$_2$ and purified by flash silica gel chromatography (50 g of SiO$_2$, 2-10% methanol/CH$_2$Cl$_2$ gradient with 0.1% NH$_4$OH) to afford aniline 7 (0.284 g, 0.956 mmol). LCMS (conditions A): t$_R$=0.55 min, m/e=298 (M+H).

Step 6

To a 0° C. solution of aniline 7 (56 mg, 0.188 mmol) and 5-chloro-2-pyridine carboxylic acid (39 mg, 0.248 mmol) in DMF (1.9 mL) was added T3P (50% in EtOAc, 0.17 mL, 0.285 mmol). After 10 min, the cooling bath was removed. After 1.5 h the reaction solution was diluted with CH$_2$Cl$_2$ (15 mL), washed with saturated aq. NaHCO$_3$ (2×20 mL), washed with brine (20 mL), dried over Na$_2$SO$_4$, filtered, and concentrated. This crude material was dissolved in CH$_2$Cl$_2$ and purified by flash silica gel chromatography (23 g of SiO$_2$, 0-7.5% Methanol/CH$_2$Cl$_2$ gradient with 0.1% NH$_4$OH) to afford Example 1 (57 mg, 0.13 mmol). LCMS (conditions A): t$_R$=1.90 min, m/e=437 (M+H).

The examples in Table 1 were prepared from aniline 7 according to Method 1, Step 6 using the requisite carboxylic acids:

TABLE 1

| Example no. | Example | Expected M + H | Observed M + H | t$_R$ (min) | LCMS method | BACE1 K$_i$ (nM) |
|---|---|---|---|---|---|---|
| 1 | | 437 | 437 | 1.90 | A | 1.6 |
| 2 | | 434 | 434 | 1.84 | A | 4.2 |
| 3 | | 421 | 421 | 1.84 | A | 5.5 |
| 4 | | 439 | 439 | 1.82 | A | 5.0 |
| 5 | | 433 | 433 | 1.89 | A | 3.4 |

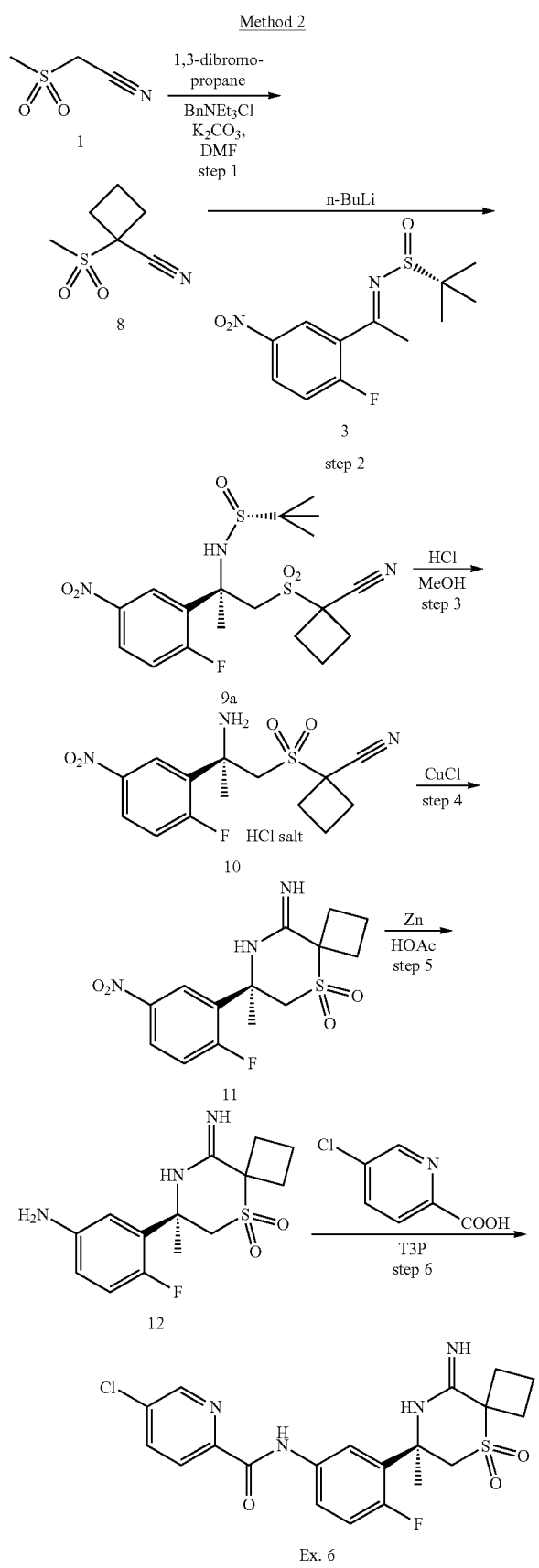

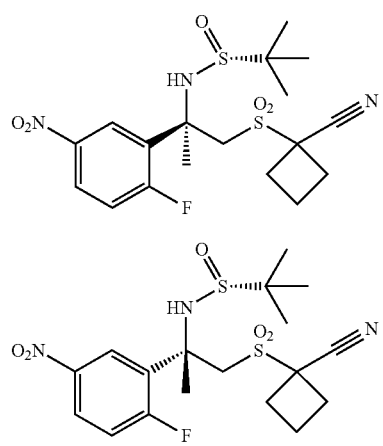

Step 1

To a room temperature mixture of methylsulfonylacetonitrile 1 (5.00 g, 42.0 mmol), benzyltriethylammonium chloride (0.478 g, 2.10 mmol), and potassium carbonate (14.5 g, 105 mmol) in DMF (100 mL) was added 1,3-dibromopropane (4.3 mL, 42 mmol), over ~2 min. After 2 h the reaction mixture was diluted with water (1000 mL), and then extracted with 40% EtOAc/hexanes (4×100 mL). The combined organic layers were washed with water (4×200 mL). The aqueous layers were then combined and further extracted with EtOAc (2×400 mL). These EtOAc washes were combined, washed with water (300 mL), washed with brine (300 mL), dried over MgSO$_4$, filtered, and concentrated to afford 8 (5.27 g, 29.8 mmol) of sufficient purity for use in subsequent reactions. $^1$H NMR (CDCl$_3$, 500 MHz) δ 3.02 (s, 3H), 2.97-2.91 (m, 2H), 2.73-2.68 (m, 2H), 2.39-2.30 (m, 1H), 2.29-2.20 (m, 1H).

Step 2

To a −78° C. solution of 2.5 M n-butyllithium in hexanes (13.8 mL, 34.5 mmol) and THF β2 mL), was added dropwise a solution of sulfone 8 (5.26 g, 33.0 mmol) in THF (50 mL) over 20 min. To the resulting solution at −78° C. was added a solution of imine 3 (9.46 g, 33.0 mmol) in THF (50 mL) dropwise over 30 min. After 2.5 h at −78° C., the reaction was quenched with saturated aq. NH$_4$Cl (25 mL). The cooling bath was removed, and then additional saturated aq. NH$_4$Cl (75 mL) was added. The resulting mixture was diluted with water (100 mL) and then extracted with EtOAc (1×250 mL, 2×100 mL). The combined organic layers were washed with brine (150 mL), dried over Na$_2$SO$_4$, filtered, and concentrated. The crude material was purified by flash silica gel chromatography (330 g cartridge, 0-100% ethyl acetate/hexanes gradient) to afford 9a (3.62 g) as a 45:1 mixture with 9b, as well as 2.51 g of a sample that was a 3.5:1 mixture of 9a to 9b. Data for 9a: LCMS (conditions A): $t_R$=2.27 min, m/e=446 (M+H). Data for 9b: LCMS (conditions A): $t_R$=2.22 min, m/e=446 (M+H).

Step 3

Using the procedure described in step 3 of Method 1, compound 9a was converted to amine 10. LCMS for amine 10 (conditions A): $t_R$=1.84 min, m/e=342 (M+H).

Step 4

Using the procedure described in step 4 of Method 1, amine 10 was converted to cyclic amidine 11. LCMS for cyclic amidine 11 (conditions A): $t_R$=1.80 min, m/e=342 (M+H).

Step 5

Using the procedure described in step 5 of Method 1, cyclic amidine 11 was converted to aniline 12. LCMS for aniline 12 (conditions A): $t_R$=0.87 min, m/e=312 (M+H).

Step 6

Using the procedure described in step 6 of Method 1, aniline 12 was converted to Example 6. LCMS for Example 6 (conditions A): $t_R$=2.04 min, m/e=473 (M+Na).

The examples in Table 2 were prepared from aniline 12 according to Method 1, Step 6 using the requisite carboxylic acids:

TABLE 2

| Ex. no. | Example | Expected M + H (or M + Na if noted) | Observed M + H (or M + Na if noted) | $t_R$ (min) | LCMS method | BACE1 $K_i$ (nM) |
|---|---|---|---|---|---|---|
| 6 | | 473 (M + Na$^+$) | 473 (M + Na$^+$) | 2.04 | A | 8.0 |
| 7 | | 470 (M + Na$^+$) | 470 (M + Na$^+$) | 1.96 | A | 11.7 |
| 8 | | 435 | 435 | 1.97 | A | 17.1 |
| 9 | | 453 | 453 | 1.93 | A | 12.6 |
| 10 | | 469 (M + Na$^+$) | 469 (M + Na$^+$) | 1.98 | A | 10.7 |
| 11 | | 464 (M + Na$^+$) | 464 (M + Na$^+$) | 1.94 | A | 5.4 |

Method 3

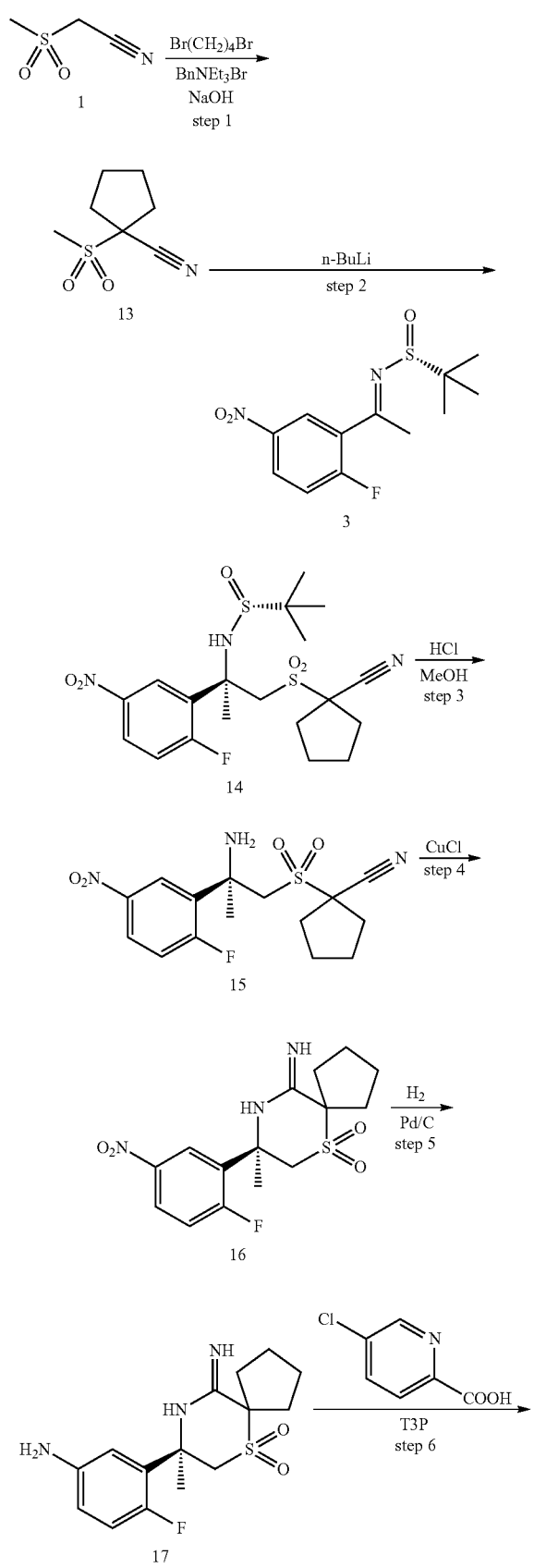

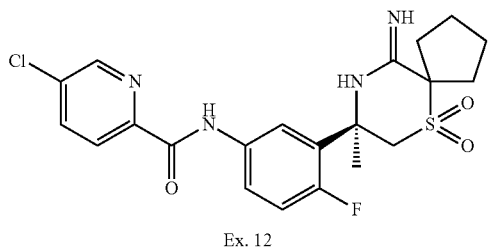

Ex. 12

Step 1

Using an analogous procedure to the one described in step 1 of Method 1 using 1,4-dibromobutane instead of 1,2-dibromoethane, compound 13 was prepared from compound 1. $^1$H NMR (CDCl$_3$, 400 MHz) δ 3.11 (s, 3H), 2.45 (m, 2H), 2.35 (m, 2H), 1.93 (m, 4H).

Step 2

Using the procedure described in step 2 of Method 1, compound 13 was converted to compound 14. LCMS for compound 14 (conditions A): $t_R$=2.40 min, m/e=460 (M+H).

Step 3

Using the procedure described in step 3 of Method 1, compound 14 was converted to amine 15. LCMS for amine 15 (conditions A): $t_R$=1.89 min, m/e=356 (M+H).

Step 4

Using the procedure described in step 4 of Method 1, amine 15 was converted to cyclic amidine 16. LCMS for cyclic amidine 16 (conditions A): $t_R$=1.83 min, m/e=356 (M+H).

Step 5

A solution of cyclic amidine 16 (1.75 g, 4.92 mmol) in methanol (70 mL) was treated with Pd/C (0.175 g, 0.164 mmol) and the mixture was hydrogenated at 1 atm H$_2$ (balloon) at room temperature for 5 hours. The mixture was diluted with MeOH and filtered through Celite. The filtrate was concentrated. The residue was purified by column chromatography on silica gel (50 g of SiO$_2$, eluting with 0 to 10% CH$_2$Cl$_2$/MeOH) to give aniline 17 (0.83 g). LCMS for aniline 17 (conditions A) $t_R$=1.45 min, m/e=326.2 (M+H).

Step 6

Using the procedure described in step 6 of Method 1, compound 17 was coupled with 5-chloropicolinic acid to provide Example 12. LCMS for Ex. 12 (conditions A): $t_R$=2.04 min, m/e=465 (M+H).

The examples in Table 3 were prepared from aniline 17 according to Method 1, Step 6 using the requisite carboxylic acids:

TABLE 3

| Example no. | Example | Expected M + H | Observed M + H | $t_R$ (min) | LCMS method | BACE1 $K_i$ (nM) |
|---|---|---|---|---|---|---|
| 12 | | 465 | 465 | 2.04 | A | 1.3 |
| 13 | | 449 | 449 | 1.80 | A | 3.1 |
| 14 | | 499 | 499 | 2.08 | A | 2.2 |
| 15 | | 461 | 461 | 1.99 | A | 5.2 |
| 16 | | 500 | 500 | 2.05 | A | 13 |
| 17 | | 462 | 462 | 1.97 | A | 3.6 |
| 18 | | 499 | 499 | 2.05 | A | 2.7 |

TABLE 3-continued
| Example no. | Example | Expected M + H | Observed M + H | $t_R$ (min) | LCMS method | BACE1 $K_i$ (nM) |
|---|---|---|---|---|---|---|
| 19 | 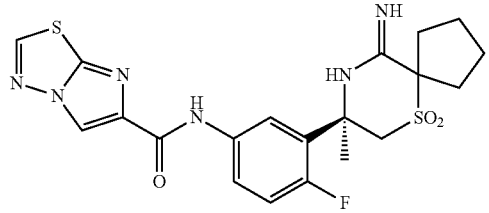 [SMILES: C[C@@]1(c2cc(NC(=O)c3cn4ncsc4n3)ccc2F)CS(=O)(=O)C2(CCCC2)C(=N)N1] | 477 | 477 | 1.91 | A | 18.4 |
| 20 | 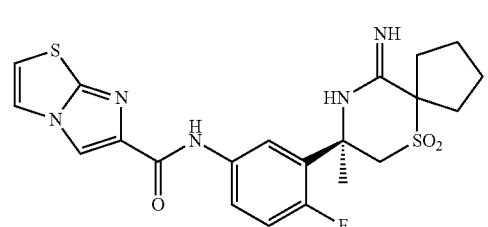 | 476 | 476 | 1.94 | A | 82 |
| 21 | 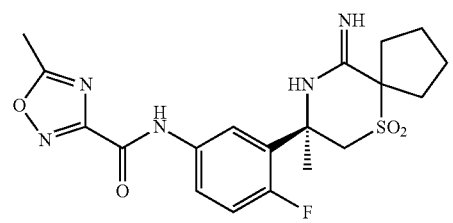 [SMILES: Cc1nc(C(=O)Nc2ccc(F)c([C@]3(C)CS(=O)(=O)C4(CCCC4)C(=N)N3)c2)no1] | 436 | 436 | 1.85 | A | 13.9 |
| 22 | 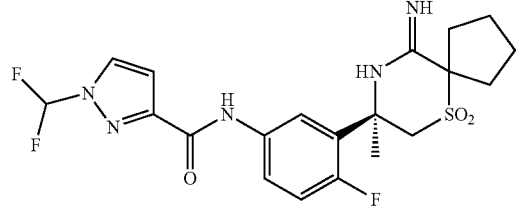 [SMILES: C[C@@]1(c2cc(NC(=O)c3ccn(C(F)F)n3)ccc2F)CS(=O)(=O)C2(CCCC2)C(=N)N1] | 470 | 470 | 1.98 | A | 12.7 |
| 23 | 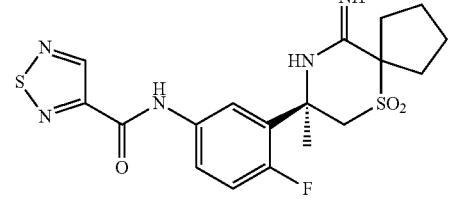 | 438 | 438 | 1.92 | A | 108 |

Method 4

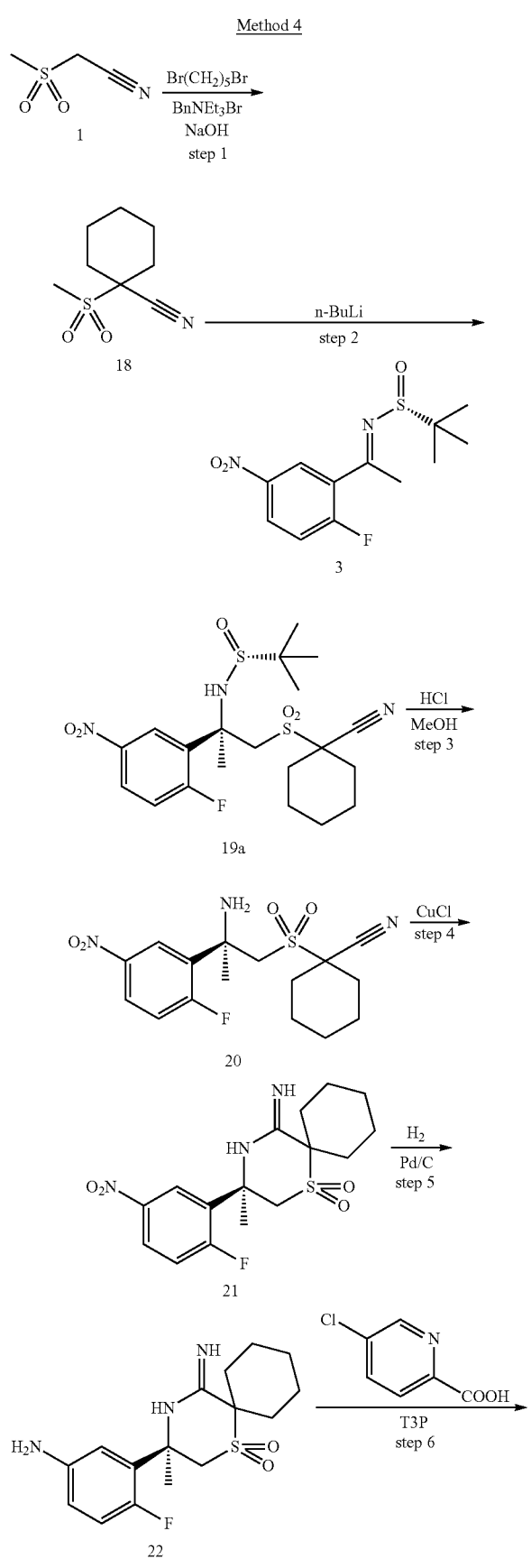

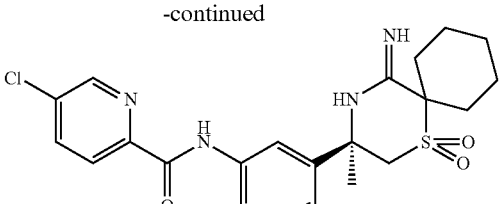

Ex. 24

Step 1
Using an analogous procedure to that described in step 1 of Method 1 and using 1,5-dibromopentane instead of 1,2-dibromoethane, compound 18 was prepared from compound 1. $^{1}$H NMR (CDCl$_3$, 400 MHz) δ 3.06 (s, 3H), 2.27 (m, 2H), 1.83 (m, 5H), 1.57 (m, 2H), 1.23 (m, 1H).

Step 2

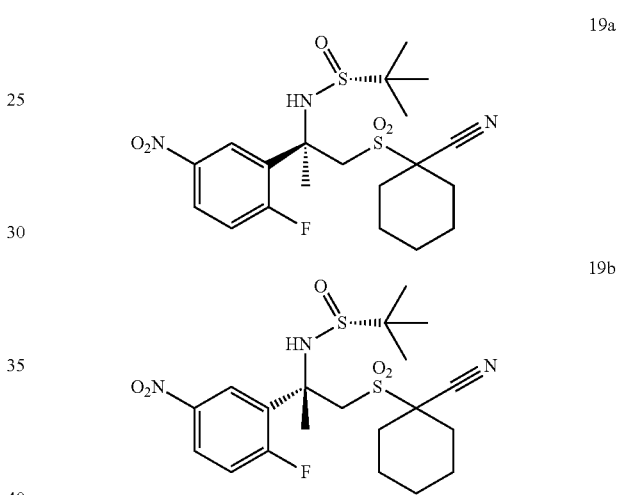

Using the procedure described in step 2 of Method 1, compound 18 was converted to compounds 19a and 19b. LCMS for compound 19a (conditions A): $t_R$=2.36 min, m/e=474 (M+H). LCMS for compound 19b (conditions A): $t_R$=2.18 min, m/e=474 (M+H).

Step 3
Using the procedure described in step 3 of Method 1, compound 19a was converted to amine 20. LCMS for amine 20 (conditions A): $t_R$=1.95 min, m/e=370 (M+H).

Step 4
Using the procedure described in step 4 of Method 1, amine 20 was converted to cyclic amidine 21. LCMS for cyclic amidine 21 (conditions A): $t_R$=1.94 min, m/e=370 (M+H).

Step 5
Using the procedure described in step 5 of Method 3, cyclic amidine 21 was converted to aniline 22. LCMS for aniline 22 (conditions A): $t_R$=1.69 min, m/e=340 (M+H).

Step 6
Using the procedure described in step 6 of Method 1, aniline 22 was coupled with 5-chloropicolinic acid to provide Example 24. LCMS for Ex. 24 (conditions A): $t_R$=2.10 min, m/e=479 (M+H).

The examples in Table 4 were made from aniline 22 following the procedure described in Method 1, Step 6, using the appropriate carboxylic acids:

TABLE 4

| Example no. | Example | Expected M + H | Observed M + H | $t_R$ (min) | LCMS method | BACE1 $K_i$ (nM) |
|---|---|---|---|---|---|---|
| 24 | | 479 | 479 | 2.10 | A | 8.4 |
| 25 | | 463 | 463 | 2.05 | A | 32 |
| 26 | | 475 | 475 | 2.06 | A | 37 |
| 27 | | 476 | 476 | 2.03 | A | 36 |
| 28 | | 470 | 470 | 1.77 | A | 10.6 |
| 29 | | 513 | 513 | 1.90 | A | 23.3 |

Step 1

Sodium metal (524 mg, 22.8 mmol) was added in portions to anhydrous methanol (15 mL) at room temperature. After the sodium was consumed, the mixture was cooled down in an ice bath for 5 minutes. To this solution was added compound 1 (1.0 g, 8.23 mmol) in 8 mL of DMF. After stirring the reaction in the cold bath for 15 minutes, 2-chloroethyl ether (1.26 mL, 10.69 mmol) was added. The mixture was stirred at room temperature under nitrogen overnight and then at 70° C. for additional 4.5 hrs. The reaction mixture was cooled to room temperature, diluted with water and extracted twice with EtOAc. The combined organic extracts were washed with brine and concentrated in vacuo to give compound 23 (1.5 g). $^1$H NMR (CDCl$_3$, 500 MHz) δ 3.78 (m, 2H), 3.61 (m, 2H), 3.58 (m, 2H), 3.39 (s, 3H).

Step 2

Using the procedure described in step 2 of Method 1, compound 23 was converted to compound 24. LCMS for compound 24 (conditions A): $t_R$=2.22 min, m/e=498 (M+H).

Step 3

Using the procedure described in step 3 of Method 1, compound 24 was converted to amine 25. LCMS for amine 25 (conditions A): $t_R$=1.77 min, m/e=372 (M+H).

Step 4

Using the procedure described in step 4 of Method 1, amine 25 was converted to cyclic amidine 26. LCMS for cyclic amidine 26 (conditions A): $t_R$=1.75 min, m/e=372 (M+H).

Step 5

Using the procedure described in step 5 of Method 3, cyclic amidine 26 was converted to aniline 27. LCMS for aniline 27 (conditions A): $t_R$=0.91 min, m/e=342 (M+H).

Step 6

Using the procedure described in step 6 of Method 1, aniline 27 was coupled with 5-fluoropicolinic acid to provide Example 30. LCMS for Ex. 30 (conditions A): $t_R$=1.47 min, m/e=465 (M+H).

The examples in Table 5 were made from aniline 27 following the procedure described in Method 1, step 6, using the appropriate carboxylic acids:

TABLE 5

| Example no. | Example | Expected M + H | Observed M + H | $t_R$ (min) | LCMS method | BACE1 $K_i$ (nM) |
|---|---|---|---|---|---|---|
| 30 | | 465 | 465 | 1.47 | A | 10.9 |
| 31 | | 515 | 515 | 1.98 | A | 4.1 |
| 32 | | 478 | 478 | 1.47 | A | 16.3 |
| 33 | | 481 | 481 | 1.72 | A | 6.1 |
| 34 | | 515 | 515 | 1.78 | A | 19.8 |
| 35 | | 477 | 477 | 1.66 | A | 16.4 |
| 35a | | 499 | 499 | 1.96 | A | 6.5 |

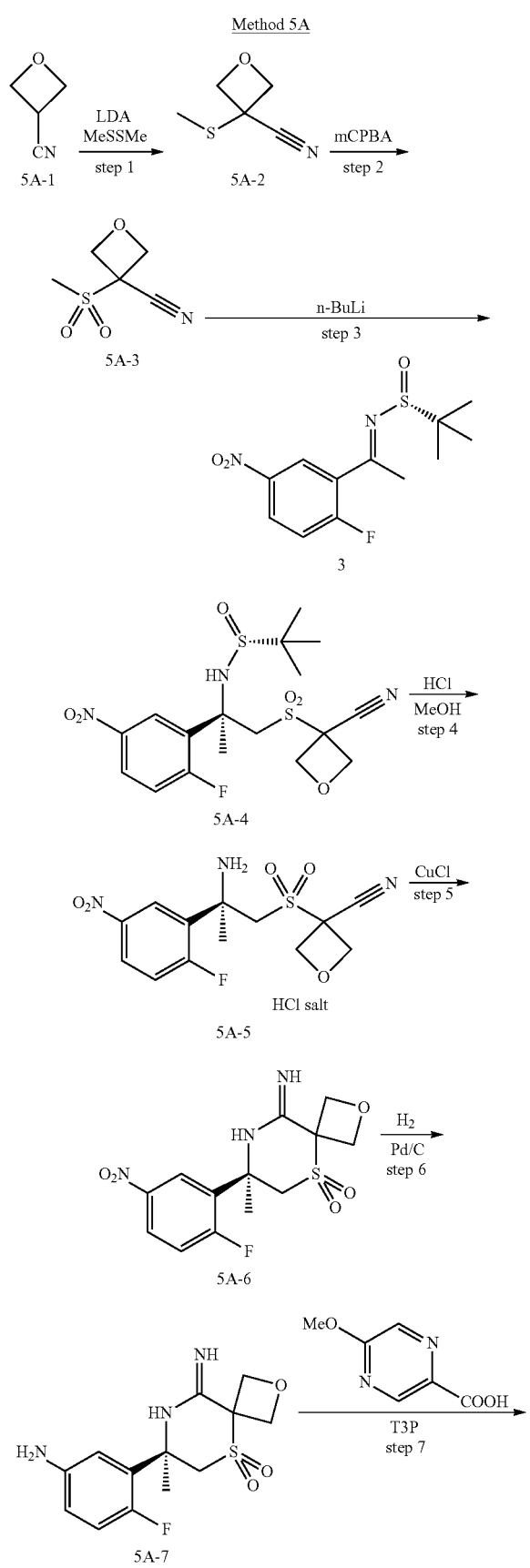

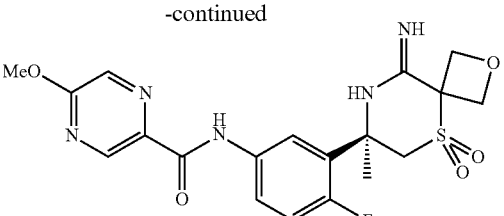

Ex. 35b

Step 1

To a solution of diisopropylamine (3.57 mL, 25.3 mmol) in THF (50 mL) at 0° C. was added n-butyllithium (9.63 ml, 24.07 mmol) dropwise, and the mixture was stirred at 0° C. for 30 minutes. The resulting LDA solution was cooled to −78° C. and a solution of compound 5A-1 (1.0 g, 12.04 mmol) in 2 mL THF was added at −78° C. and stirred for 30 minutes at that temperature. A solution of MeSSMe (2.18 mL, 24.07 mmol) in 1 mL of THF was added and the mixture was stirred at −78° C. for 3 hours. The reaction was quenched by addition of saturated aq. NH$_4$Cl and extracted with ethyl acetate. The combined organic extracts were concentrated; the residue was purified by flash chromatography (40 g of SiO$_2$) eluting with 0-100% ethyl acetate/hexane to give compound 5A-2 (161 mg). $^1$H NMR (CDCl$_3$, 500 MHz) δ 5.08 (m, 2H), 4.78 (m, 2H), 2.22 (s, 3H).

Step 2

To a solution of compound 5A-2 (0.16 g, 1.239 mmol) in DCM was added mCPBA (0.611 g, 2.477 mmol) at 0° C. The reaction mixture was stirred at 0° C. for 3 hours, diluted with water, and extracted with DCM. The combined organic extracts were washed with 5% aq. NaHCO$_3$ and then brine. The solvent was then removed in vacuo to give 150 mg of product 5A-3. $^1$H NMR (CDCl$_3$, 500 MHz) δ 5.10 (m, 4H), 3.14 (s, 3H).

Step 3

Using the procedure described in step 2 of Method 1, compound 5A-3 was converted to compound 5A-4. LCMS for compound 5A-4 (conditions A): t$_R$=2.22 min, m/e=470 (M+Na).

Step 4

Using the procedure described in step 3 of Method 1, compound 5A-4 was converted to amine 5A-5. LCMS for amine 5A-5 (conditions A): t$_R$=1.74 min, m/e=344 (M+H).

Step 5

Using the procedure described in step 4 of Method 1, compound 5A-5 was converted to compound 5A-6. LCMS for amine 5A-6 (conditions A): t$_R$=1.73 min, m/e=344 (M+H).

Step 6

Using the procedure described in step 5 of Method 3, compound 5A-6 was converted to amine 5A-7. LCMS for amine 5A-7 (conditions A): t$_R$=0.62 min, m/e=314 (M+H).

Step 7

Using the procedure described in step 6 of Method 1, compound 5A-7 was converted to Example 35b using 5-methoxypyrazine-2-carboxylic acid. LCMS for Example 35b (conditions A): t$_R$=1.95 min, m/e=450 (M+H). BACE1 K$_i$ for Example 35b=24.1 nM.

Method 6

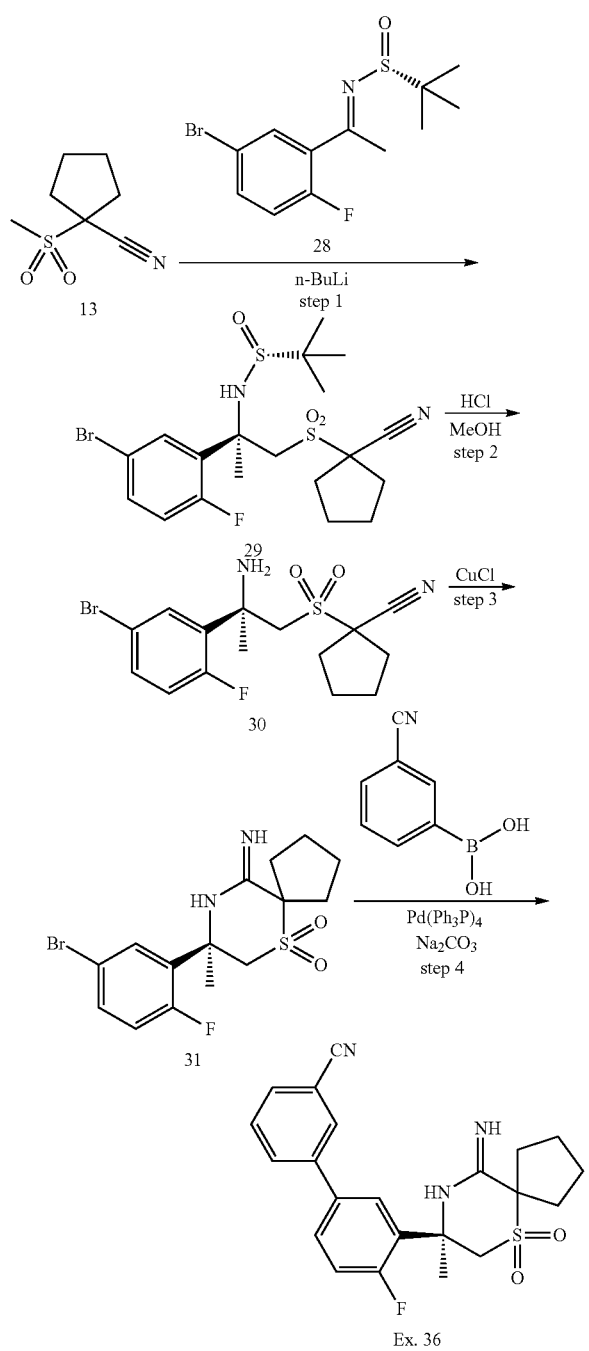

Ex. 36

Step 1

To a solution of 13 (5.19 g, 30.0 mmol) in THF (60 mL) at −78° C. was added n-BuLi (12 mL, 30.0 mmol). After stirring for 30 min, a solution of 28 (4.8 g, 14.99 mmol) in THF (23 mL) was added, and the mixture was stirred for 3 hours. The mixture was poured into 40 mL of saturated aq. $NH_4Cl$ and 160 mL of water. After separating the layers, the aqueous phase was extracted with EtOAc (3×). The combined organic layers were washed with brine, dried over $Na_2SO_4$, filtered and concentrated. The residue was purified by silica gel column chromatography, eluting with EtOAc/hexane 0 to 100% gradient to give 4.81 g of compound 29. LCMS (conditions A) $t_R$=2.40 min, m/e=495 (M+H).

Step 2

To a solution of 29 (4.1 g, 8.31 mmol) in MeOH (100 mL) at 0° C. was added 4N HCl in dioxane (34 mL). The mixture was stirred at 0° C. for 2 h, and then concentrated in vacuo to give 2.84 g of amine 30. LCMS (conditions A) $t_R$=1.94 min, m/e=391 (M+H).

Step 3

To a suspension of amine 30 (389.5 mg, 1.00 mmol) in EtOH (7.0 mL) was added CuCl (178 mg, 1.32 mmol). The reaction tube was sealed and the mixture was heated at 80° C. for 4 hours. After cooling to room temperature the mixture was diluted with $CH_2Cl_2$ and filtered through Celite. The Celite was washed with $CH_2Cl_2$ and the filtrate was concentrated in vacuo. The residue was diluted with $CH_2Cl_2$, washed with 1N aq. NaOH, dried ($Na_2SO_4$) and concentrated in vacuo to afford 210 mg of cyclic amidine 31. LCMS (conditions A) $t_R$=1.94 min, m/e=391 (M+H).

Step 4

A mixture of cyclic amidine 31 (100 mg, 0.257 mmol), 3-cyanophenylboronic acid (56.6 mg, 0.385 mmol), tetrakis(triphenylphosphine)palladium(O) (30 mg, 0.026 mmol) in ethanol (2.0 mL) and toluene (2.0 mL) was treated with aqueous $Na_2CO_3$ (0.2 mL, 0.400 mmol, 2M). The reaction tube was sealed and the mixture was heated at 80° C. for 2 h. After cooling to RT, the solvents were removed in vacuo. The residue was purified by silica gel column chromatography, eluting with $CH_2Cl_2$/MeOH/$NH_4OH$ (95/5/1) to give 99.0 mg of Example 36. LCMS (conditions A) $t_R$=2.07 min, m/e=412 (M+H).

The examples in Table 6 were made from cyclic amidine 31 following the procedure described in Method 6, step 4 using the requisite boronic acids or boronate esters.

TABLE 6

| Example no. | Example | Expected M + H | Observed M + H | $t_R$ (min) | LCMS method | BACE1 $K_i$ (nM) |
|---|---|---|---|---|---|---|
| 36 | | 412 | 412 | 2.07 | A | 1292 |

TABLE 6-continued
| Example no. | Example | Expected M + H | Observed M + H | $t_R$ (min) | LCMS method | BACE1 $K_i$ (nM) |
|---|---|---|---|---|---|---|
| 37 | | 422 | 422 | 2.01 | A | 459 |
| 38 | | 413 | 413 | 1.95 | A | 939 |
| 39 | | 556 | 556 | 2.30 | A | 1326 |
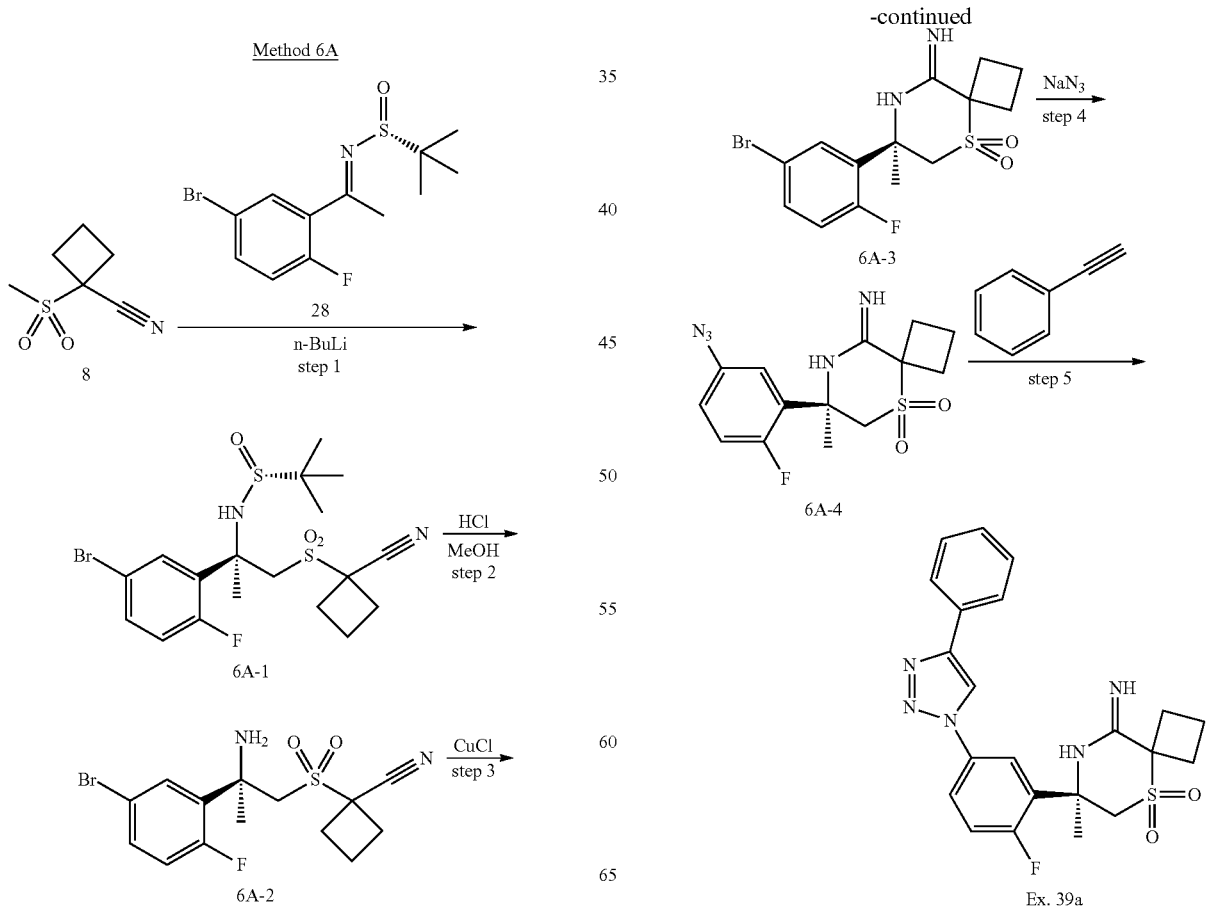

Step 1

Using the procedure described in step 1 of Method 6, compound 8 was converted to compound 6A-1. LCMS for amine 6A-1 (conditions A): $t_R$=2.39 min, m/e=481 (M+H).

Step 2

Using the procedure described in step 2 of Method 6, compound 6A-1 was converted to amine 6A-2. LCMS for amine 6A-2 (conditions A): $t_R$=1.88 min, m/e=375 (M+H).

Step 3

Using the procedure described in step 3 of Method 6, compound 6A-2 was converted to amine 6A-3. LCMS for amine 6A-3 (conditions A): $t_R$=1.88 min, m/e=375 (M+H).

Step 4

To a mixture of compound 6A-3 (800 mg, 2.13 mmol) in EtOH (16 mL) at room temperature and under nitrogen was added trans-N,N'-dimethylcyclohexane-1,2-diamine (0.111 mL, 0.704 mmol), followed by sodium azide (416 mg, 6.40 mmol), sodium ascorbate (1.42 mL, 0.938 mmol), and water (1.6 mL). The mixture was then degassed, evacuated, and filled with nitrogen. Cupric sulfate (74.9 mg, 0.469 mmol) was added and the vessel was equipped with a condenser and heated at 80° C. for 2 h. The reaction was quenched with ice-water, extracted with ethyl acetate. The combined organic extracts were dried over $Na_2SO_4$ and concentrated. The residue was purified by flash chromatography (100 g of $SiO_2$) eluting with 0-10% MeOH in $CH_2Cl_2$ to give compound 6A-4 (158 mg). LCMS for azide 6A-4 (conditions A): $t_R$=1.93 min, m/e=338 (M+H).

Step 5

Compound 6A-4 (25 mg, 0.074 mmol), phenylacetylene (8.14 μL, 0.074 mmol), water (148 μL), and t-BuOH (148 μl) were added to a 4 mL vial followed by a freshly prepared sodium ascorbate solution (22. μl, 0.022 mmol), and then copper sulfate monohydrate (0.40 mg, 2.22 μmol). After 20 h, the reaction mixture was diluted with water, and extracted with EtOAc. The combined organic extracts were dried over $Na_2SO_4$ and concentrated. The residue was purified by flash chromatography (12 g of $SiO_2$) eluting with 0-10% MeOH in $CH_2Cl_2$ to give Example 39a (13 mg). LCMS for Example 39a (conditions A): $t_R$=2.10 min, m/e=440 (M+H).

The examples in Table 6A were made from compound 6A-4 following the procedure described in Method 6A, step 5 using the requisite acetylenes.

TABLE 6A

| Example no. | Example | Expected M + H | Observed M + H | $t_R$ (min) | LCMS method | BACE1 $K_i$ (nM) |
|---|---|---|---|---|---|---|
| 39a | | 440 | 440 | 2.10 | A | 2323 |
| 39b | | 441 | 441 | 2.01 | A | 8557 |

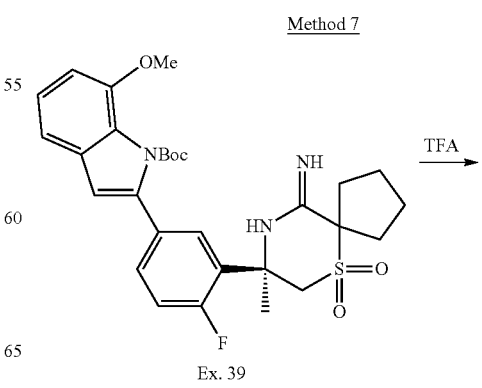

Ex. 39

-continued

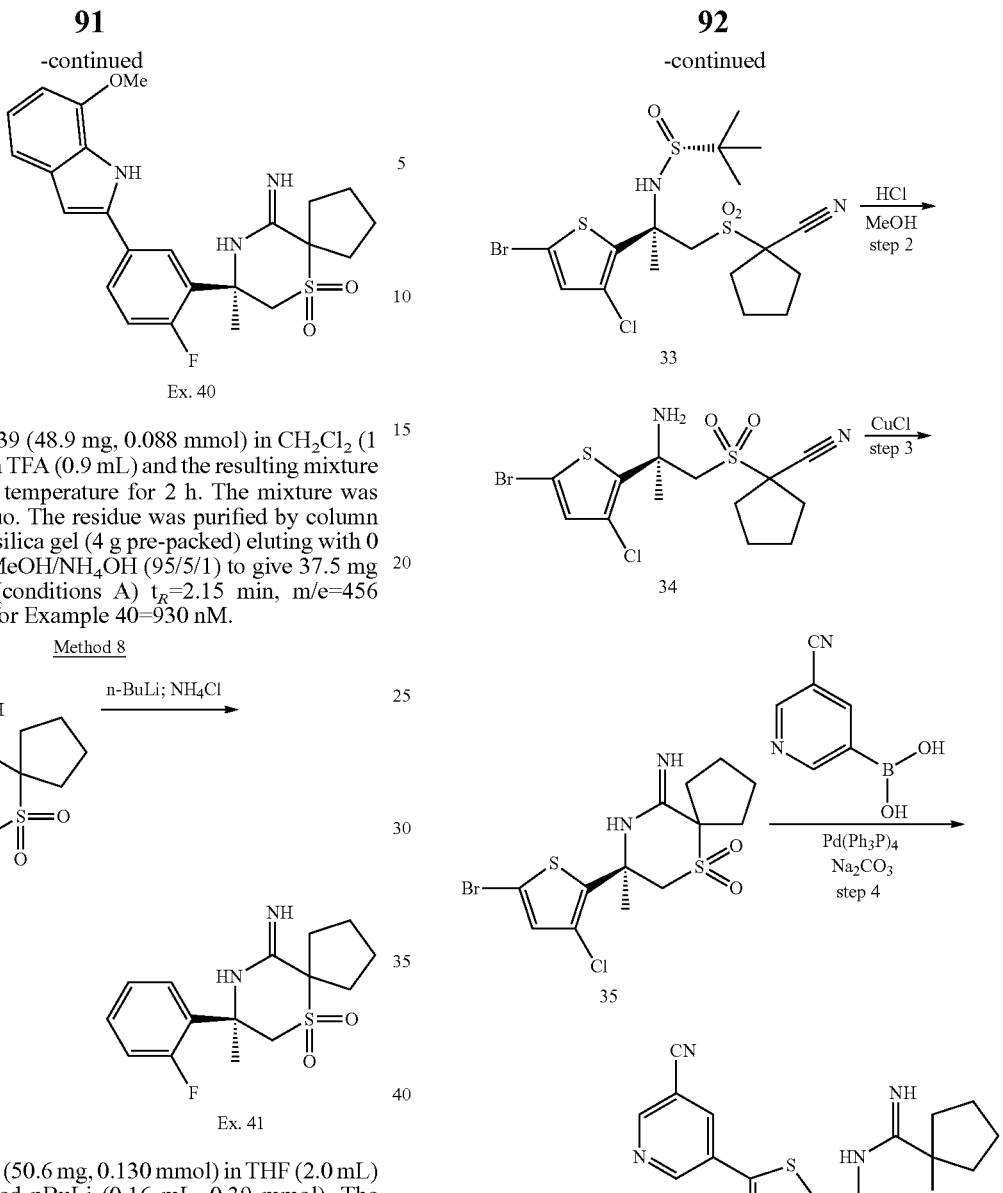

A solution of Ex. 39 (48.9 mg, 0.088 mmol) in CH$_2$Cl$_2$ (1 mL) was treated with TFA (0.9 mL) and the resulting mixture was stirred at room temperature for 2 h. The mixture was concentrated in vacuo. The residue was purified by column chromatography on silica gel (4 g pre-packed) eluting with 0 to 60% of CH$_2$Cl$_2$/MeOH/NH$_4$OH (95/5/1) to give 37.5 mg of Ex. 40 LCMS (conditions A) $t_R$=2.15 min, m/e=456 (M+H). BACE1 $K_i$ for Example 40=930 nM.

Method 8

To a solution of 31 (50.6 mg, 0.130 mmol) in THF (2.0 mL) at −78° C. was added nBuLi (0.16 mL, 0.39 mmol). The mixture was stirred at −78° C. for 30 min. Additional n-BuLi (0.16 mL, 0.39 mmol) was added and reaction was stirred for an additional 1 h. The reaction was quenched with saturated aq. NH$_4$Cl and extracted with EtOAc. The combined organic layers were dried (Na$_2$SO$_4$) and concentrated in vacuo. The residue was purified using prep TLC (1000 μm SiO$_2$) eluting with EtOAc to afford 13.2 mg of Example 41. LCMS (condition A) $t_R$=1.85 min, m/e=311 (M+H). BACE1 $K_i$ for Example 41=727 nM.

Method 9

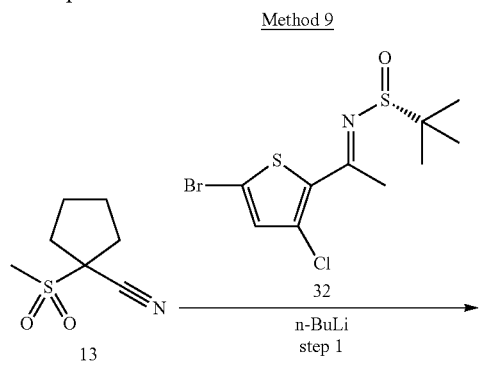

Step 1

To a solution of compound 13 (1.00 g, 5.77 mmol) in THF (130 mL) at −78° C. was slowly added n-BuLi (2.3 mL, 5.75 mmol). After stirring for 30 min, a solution of imine 32 (1.0 g, 2.92 mmol) in THF (10 mL) was added dropwise and the resulting mixture was stirred at −78° C. for 4 h. The reaction was quenched with saturated aq. NH$_4$Cl, extracted with EtOAc (3×), dried (Na$_2$SO$_4$) and concentrated in vacuo. The residue was purified by column chromatography on silica gel (20 g), eluting with EtOAc/Hexanes (0 to 100%) to give 743 mg of compound 33. LCMS (conditions A): $t_R$=2.51 min, m/e=516 (M+).

Step 2

To a solution of 33 (742 mg, 1.44 mmol) in methanol (12 mL) was added 4N HCl in dioxane (0.118 mL, 1.44 mmol).

The mixture was stirred at RT for 30 min, and then concentrated in vacuo to give amine 34 as HCl salt. LCMS (conditions A): $t_R$=2.06 min, m/e=396 (M+H—NH$_3$).

Step 3

To a suspension of amine 34 (640 mg, 1.43 mmol) in ethanol (10 mL) was added CuCl (256 mg, 1.90 mmol). The reaction flask was sealed, and the mixture was heated at 80° C. for 4 h. After cooling to room temperature, the mixture was diluted with CH$_2$Cl$_2$ and then filtered through Celite. The Celite was washed with CH$_2$Cl$_2$ and the filtrate was concentrated in vacuo. The residue was taken up in CH$_2$Cl$_2$, washed with 1N aq. NaOH, dried (Na$_2$SO$_4$), filtered and concentrated in vacuo to give 460 mg of cyclic amidine 35. LCMS (conditions A): $t_R$=1.99 min, m/e=413 (M+H).

Step 4

To a mixture of cyclic amidine 35 (107 mg, 0.260 mmol), 3-cyanopyridine boronic acid (89.7 mg, 0.390 mmol), tetrakis(triphenylphosphine)palladium(O) (30 mg, 0.026 mmol) in toluene/EtOH (2 mL/2 mL) was added 2M aq. Na$_2$CO$_3$ (0.2 mL, 0.40 mmol). The reaction tube was sealed and heated at 70° C. for 3 h. After cooling to room temperature, the volatiles were removed in vacuo. The residue was purified by preparative TLC (2000 µm SiO$_2$), eluting with DCM/MeOH/NH$_4$OH (95/5/1), to give Example 42. LCMS (conditions A): $t_R$=1.98 min, m/e=435 (M+H).

The examples in Table 7 were made from compound 35 following the procedure described in Method 9, step 4 using the requisite boronic acids or boronate esters.

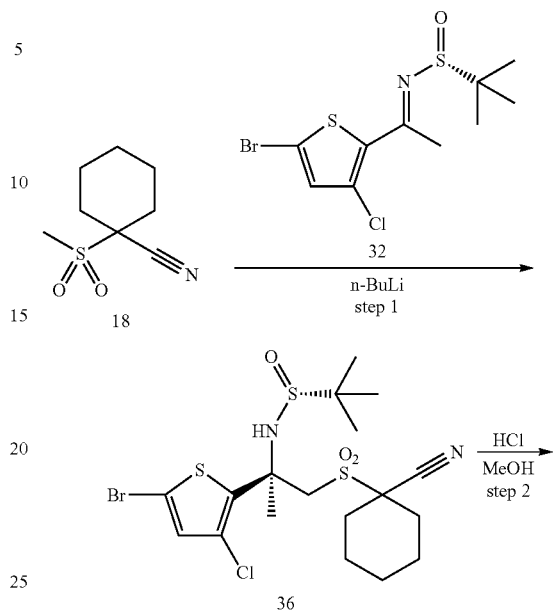

Method 10

TABLE 7

| Example no. | Example | Expected M + H | Observed M + H | $t_R$ (min) | LCMS method | BACE1 $K_i$ (nM) |
|---|---|---|---|---|---|---|
| 42 | (structure with CN-pyridine) | 435 | 435 | 1.98 | A | 18.3 |
| 43 | (structure with pyrimidine) | 411 | 411 | 1.75 | A | 73.1 |
| 43a | (structure with oxadiazole-phenyl) | 477 | 477 | 2.02 | A | 37.0 |

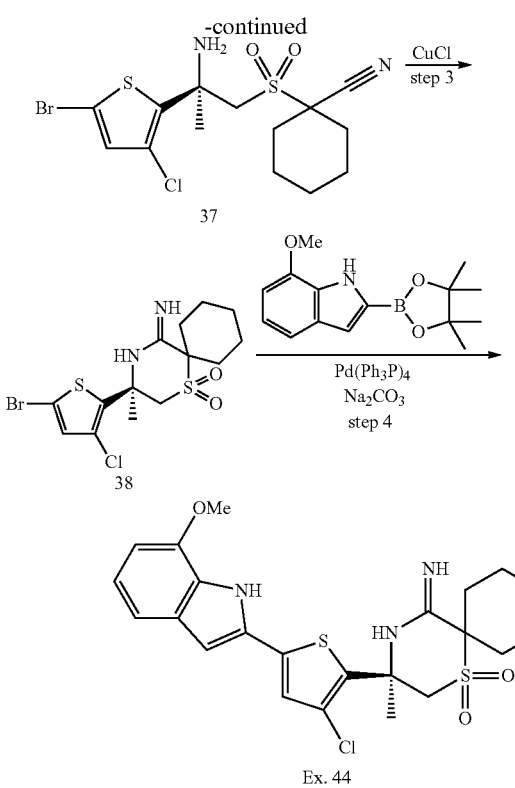

Step 1

Using the procedure described in step 1 of Method 9, sulfone 18 was converted to compound 36. LCMS for compound 36 (conditions A): $t_R$=2.56 min, m/e=531 (M+H).

Step 2

Using the procedure described in step 2 of Method 9, compound 36 was converted to amine 37. LCMS for amine 37 (conditions A): $t_R$=2.14 min, m/e=449 (M+Na$^+$).

Step 3

Using the procedure described in step 3 of Method 9, amine 37 was converted to cyclic amidine 38. LCMS for cyclic amidine 38 (conditions A): $t_R$=1.81 min, m/e=427 (M+H).

Step 4

To a solution of cyclic amidine 38 (0.1 g, 0.235 mmol) in toluene/ethanol (3 mL/3 mL) was added 7-methoxy-1H-indole-2-boronic acid pinacol ester (0.083 g, 0.305 mmol) at room temperature followed by aq. Na$_2$CO$_3$ solution (2M, 0.24 mL), and the mixture was stirred for 30 seconds under nitrogen. Tetrakis(triphenylphosphine)palladium(O) (0.041 g, 0.035 mmol) was added, and the mixture was degassed for 30 seconds and then heated at 110° C. in a microwave reactor for 40 minutes. After cooling, the reaction mixture was diluted with ethyl acetate and passed through a short pad of Celite. The filtrate was concentrated; the residue was purified by preparative TLC eluting with 3% 7N NH$_3$-MeOH/CH$_2$Cl$_2$ followed by silica gel column chromatography using 0-50% ethyl acetate/hexane as eluent to give 47 mg of Example 44. LCMS (conditions A): $t_R$=2.20 min, m/e=492 (M+H)

The examples in Table 8 were made from compound 38 following the procedure described in Method 10, step 4 using the requisite boronic acids or boronate esters.

TABLE 8

| Example no. | Example | Expected M + H | Observed M + H | $t_R$ (min) | LCMS method | BACE1 $K_i$ (nM) |
|---|---|---|---|---|---|---|
| 44 | [structure with OMe-indole, thiophene-Cl, cyclic amidine, sulfone] | 492 | 492 | 2.20 | A | 20.2 |
| 45 | [structure with CN-phenyl, thiophene-Cl, cyclic amidine, sulfone] | 448 | 448 | 1.92 | A | 48 |
| 46 | [structure with CN-pyridine, thiophene-Cl, cyclic amidine, sulfone] | 449 | 449 | 2.01 | A | 114 |

TABLE 8-continued

| Example no. | Example | Expected M + H | Observed M + H | $t_R$ (min) | LCMS method | BACE1 $K_i$ (nM) |
|---|---|---|---|---|---|---|
| 47 | | 425 | 425 | 1.91 | A | 545 |
| 47a | | 491 | 491 | 2.07 | A | 35.9 |

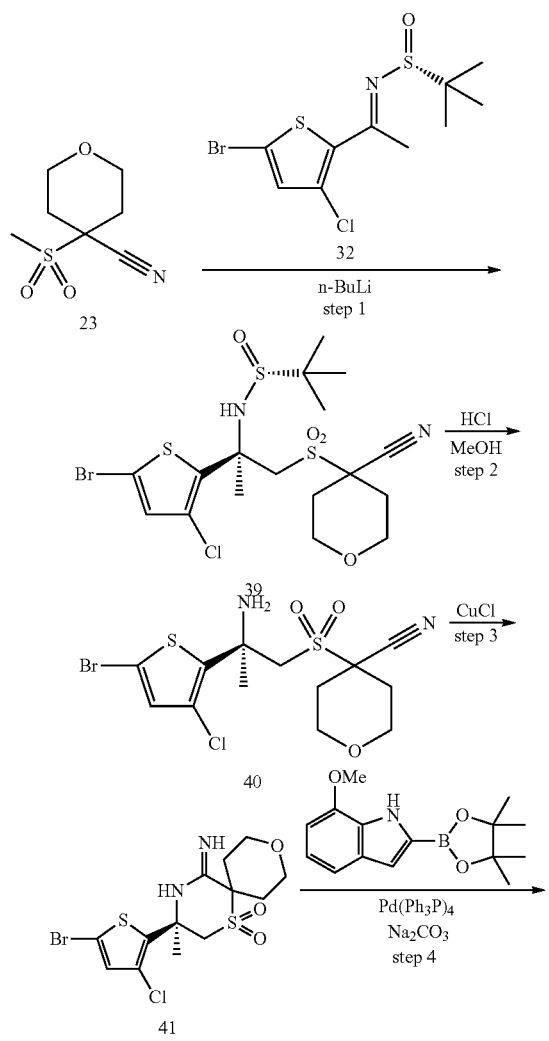

Step 1

Using the procedure described in step 1 of Method 9, sulfone 23 was converted to compound 39. LCMS for compound 39 (conditions A): $t_R$=2.44 min, m/e=553 (M+H).

Step 2

Using the procedure described in step 2 of Method 9, compound 39 was converted to amine 40. LCMS for amine 40 (conditions A): $t_R$=1.79 min, m/e=449 (M+Na$^+$).

Step 3

Using the procedure described in step 3 of Method 9, amine 40 was converted to cyclic amidine 41. LCMS for cyclic amidine 41 (conditions A): $t_R$=1.69 min, m/e=429 (M+H).

Step 4

To a solution of cyclic amidine 41 (0.095 g, 0.222 mmol) in toluene/ethanol (3 mL/3 mL) was added 7-methoxy-1H-indole-2-boronic acid pinacol ester (0.055 g, 0.289 mmol) at room temperature followed by Na$_2$CO$_3$ solution (2M, 0.22 mL) and the resulting mixture was stirred for 30 seconds under nitrogen. Tetrakis(triphenylphosphine)palladium(O) (0.038 g, 0.033 mmol) was added and the mixture was heated at 110° C. in a microwave reactor for 35 minutes. After cooling, the reaction mixture was diluted with ethyl acetate and passed through a short pad of Celite. The filtrate was concentrated; the residue was purified by silica gel prep TLC eluting with 4% 7N NH₃-MeOH/CH₂Cl₂ to get 50 mg of compound Example 48. LCMS (conditions A): $t_R$=2.10 min, m/e=494 (M+H).

The examples in Table 9 were made from compound 41 following the procedure described in Method 11, step 4 using the requisite boronic acids or boronic esters.

TABLE 9

| Example no. | Example | Expected M + H | Observed M + H | $t_R$ (min) | LCMS method | BACE1 $K_i$ (nM) |
|---|---|---|---|---|---|---|
| 48 | | 494 | 494 | 2.10 | A | 19.8 |
| 49 | | 450 | 450 | 1.72 | A | 113 |
| 50 | | 451 | 451 | 1.92 | A | 130 |
| 51 | | 427 | 427 | 1.52 | A | 688 |
| 52 | | 493 | 493 | 1.97 | A | 147 |
| 53 | | 456 | 456 | 1.58 | A | 555 |

TABLE 9-continued

| Example no. | Example | Expected M + H | Observed M + H | $t_R$ (min) | LCMS method | BACE1 $K_i$ (nM) |
|---|---|---|---|---|---|---|
| 54 | | 494 | 494 | 2.03 | A | 157 |
| 55 | | 444 | 444 | 1.93 | A | 260 |
| 56 | | 494 | 494 | 2.17 | A | 5743 |
| 57 | | 480 | 480 | 1.85 | A | 161 |
| 57a | | 493 | 493 | 1.73 | C | 34.9 |

Method 12

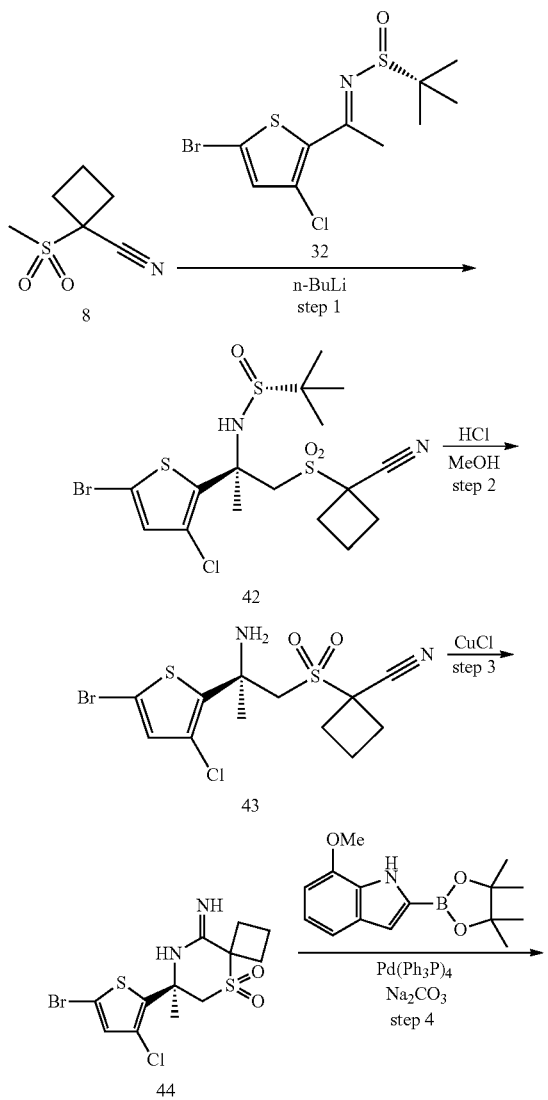

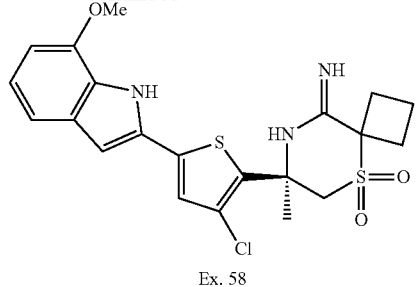

Ex. 58

Step 1

Using the procedure described in step 1 of Method 9, sulfone 8 was converted to compound 42. LCMS for compound 42 (conditions A): $t_R$=2.84 min, m/e=503 (M+H).

Step 2

Using the procedure described in step 2 of Method 9, compound 42 was converted to amine 43. LCMS for amine 43 (conditions A): $t_R$=1.99 min, m/e=382 (M+H—NH$_3$).

Step 3

Using the procedure described in step 3 of Method 9, amine 43 was converted to cyclic amidine 44. LCMS for cyclic amidine 44 (conditions A): $t_R$=1.96 min, m/e=399 (M+H).

Step 4

A mixture of cyclic amidine 44 (0.200 g, 0.503 mmol), 7-methoxy-1H-indole-2-boronic acid pinacol ester (0.179 g, 0.654 mmol), and 1,1'-bis(diphenylphosphino)ferrocene-palladium(II)dichloride dichloromethane complex (0.041 g, 0.050 mmol) in toluene (1.25 mL), ethanol (1.25 mL), and 2 M sodium carbonate in water (0.503 mL, 1.01 mmol) was degassed by bubbling nitrogen through the mixture for several minutes. This degassed mixture was then sealed. After sitting overnight at rt, the reaction mixture was heated in the microwave reactor at 120° C. for 30 min. The reaction mixture was absorbed onto silica gel and purified by flash silica gel chromatography (50 g cartridge, 0-10% Methanol/0-1% NH$_4$OH/CH$_2$Cl$_2$ gradient) to afford a sample that was further purified by flash silica gel chromatography (23 g cartridge, 0-100% ethyl acetate/hexanes gradient) to afford Example 58 (13.8 mg, 0.028 mmol). LCMS (conditions A): $t_R$=2.12 min, m/e=464 (M+H)

The examples in Table 10 were made from compound 44 following the procedure described in Method 12, step 4 using the requisite boronic acids or boronic esters.

TABLE 10

| Example no. | Example | Expected M + H | Observed M + H | $t_R$ (min) | LCMS method | BACE1 $K_i$ (nM) |
|---|---|---|---|---|---|---|
| 58 | 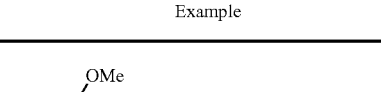 | 464 | 464 | 2.12 | A | 7.7 |

TABLE 10-continued

| Example no. | Example | Expected M + H | Observed M + H | $t_R$ (min) | LCMS method | BACE1 $K_i$ (nM) |
|---|---|---|---|---|---|---|
| 59 | | 421 | 421 | 1.91 | A | 56 |
| 60 | | 397 | 397 | 1.82 | A | 374 |
| 61 | | 420 | 420 | 2.05 | A | 35.6 |
| 61a | | 463 | 463 | 1.97 | A | 18.6 |

Method 13

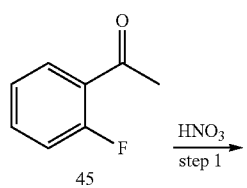

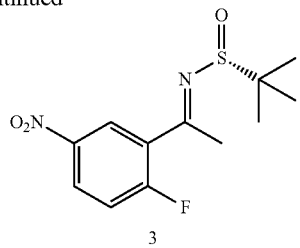

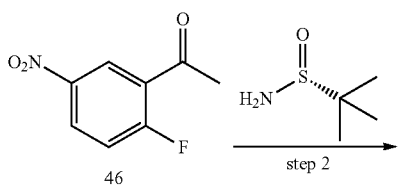

Step 1

To a mechanically stirred slurry of conc. $H_2SO_4$ (93-98%, 360 mL) at –42° C. were added dropwise 2'-fluoro-acetophenone 45 (90.0 g, 652 mmol) and a solution of fuming nitric acid (53.1 mL) in conc. $H_2SO_4$ (129 mL). The slurry was stirred for 30 min at –42° C. The mixture was slowly poured onto 1.3 kg of ice. To the mixture was added water (1 L). The product precipitated out of solution. After all of the ice melted, the product was collected via filtration. The solid was dissolved with EtOAc. The organic layer was washed with 5% Na₂CO₃ (2×300 mL), water (300 mL), and brine (300 mL), and dried over Na₂SO₄. It was filtered, the filtrate was concentrated to give compound 46 (115 g) as a solid.

Step 2

To a solution of compound 46 (115 g, 628 mmol) in THF (900 mL) was added (R)-2-methylpropane-2-sulfinamide (87.7 g, 691 mmol) and Ti(OEt)₄ (315 g, 1.38 mole). The solution was heated at reflux for 20 h, cooled to RT, and poured onto ice (3 kg). The mixture was stirred for 20 min and then filtered. The organic layer was washed with brine, and dried over Na₂SO₄, filtered, and the filtrate was concentrated. The residue was purified by flash chromatography (SiO₂, 15% EtOAc in hexanes) to give compound 3 (154 g). LCMS for 3 (conditions A): $t_R$=2.26 min, m/e=287 (M+H).

The ketimines in Table 11 were prepared from the requisite ketones according to the procedures outlined in Method 13, step 2:

TABLE 11

| Entry | Ketone | Ketimine |
|---|---|---|
| 1 | 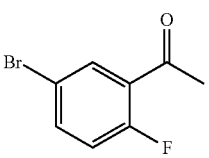 | 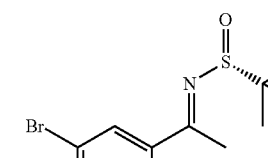 |
| 2 | 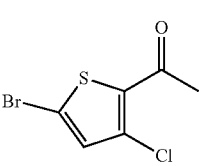 | 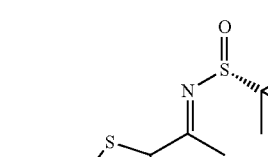 |

1-(5-Bromo-3-chlorothiophen-2-yl)ethanone (ketone in Table 11, entry 2) was prepared as follows: To a solution of methyl 3-chlorothiophene-2-carboxylate (50 g, 0.28 mol) in MeOH (100 mL) was added a solution of aq. NaOH (2M) (400 mL) dropwise at 0° C. The resulting mixture was stirred at RT for 2 h. After removing MeOH, the aqueous was washed with ether and acidified with 2 N HCl. The solid formed was collected by filtration and dried to give 45 g of 3-chlorothiophene-2-carboxylic acid. MS (M+H): 163.

To a solution of DIPA (26.3 g, 0.26 mol) in 400 mL of dry THF was added a solution of n-BuLi (104 mL, 0.26 mol, 2.5M in n-hexane) at −78° C. under nitrogen. After the addition was completed, the mixture was stirring for 1 h and then warmed to 0° C. and stirred for 30 min. To above LDA solution was added a solution of 3-chlorothiophene-2-carboxylic acid (21 g, 0.13 mol) in THF (50 mL) at −78° C. After stirring for 1 h, a solution of 1,2-dibromo-ethane (48.9 g, 0.26 mmol) in THF (50 mL) was added at −78° C. The mixture was stirred at −78° C. for 1.5 h and slowly warm to RT. The mixture was poured into aq. HCl solution, and then extracted with EtOAc. The combined extracts were dried over Na₂SO₄, concentrated to give 25 g of 5-bromo-3-chlorothiophene-2-carboxylic acid. MS (M+H): 241, 243. ¹H NMR (400 MHz, DMSO-d6): δ 7.50 (s, 1H).

To a solution of compound 3 (50 g, 0.21 mol) in pyridine (500 mL) was added N,O-dimethylhydroxylamine hydrochloride (40.4 g, 0.42 mol) and EDCI (87 g, 0.42 mol) at 0° C. The mixture was stirred at RT overnight, concentrated and purified by silica gel chromatography to give 35 g of compound 4 in 60% yield. MS (M+H): 284, 286. ¹H NMR (400 MHz, CDCl₃): δ 6.98 (s, 1H), 3.70 (s, 3H), 3.31 (s, 3H).

To a stirred solution of 5-bromo-3-chloro-N-methoxy-N-methylthiophene-2-carboxamide (1 g, 3.5 mmol) in THF (10 mL) was added MeMgBr (1.1 mL, 3.5 mmol) under N₂ at RT. The mixture was stirred at RT for 0.5 h and quenched by aqueous NH₄Cl. The resulting solution was extracted with EtOAc. The organic layers were dried over Na₂SO₄, concentrated and purified by column to give 0.6 g of 1-(5-bromo-3-chlorothiophen-2-yl)ethanone. MS (M+H): 239, 241. ¹H NMR (400 MHz, CDCl₃): δ 6.95 (s, 1H), 2.57 (s, 3H).

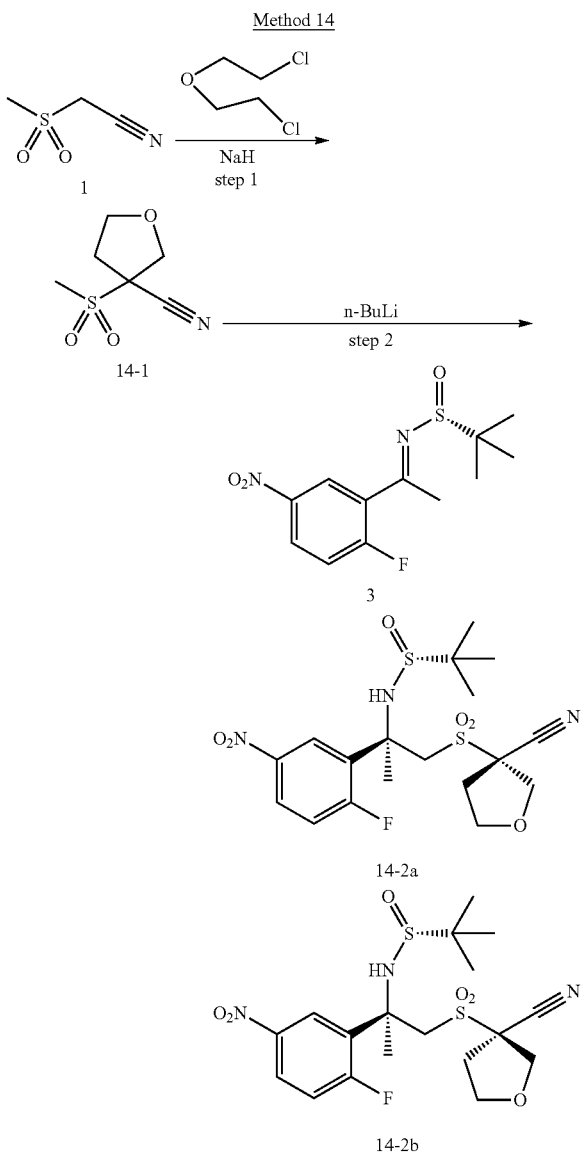

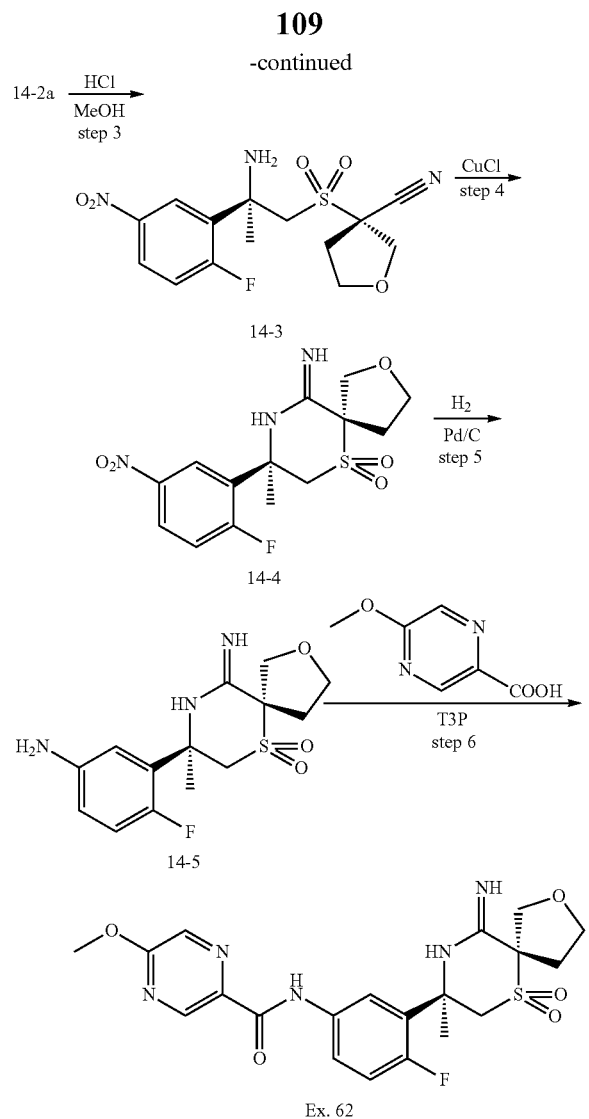

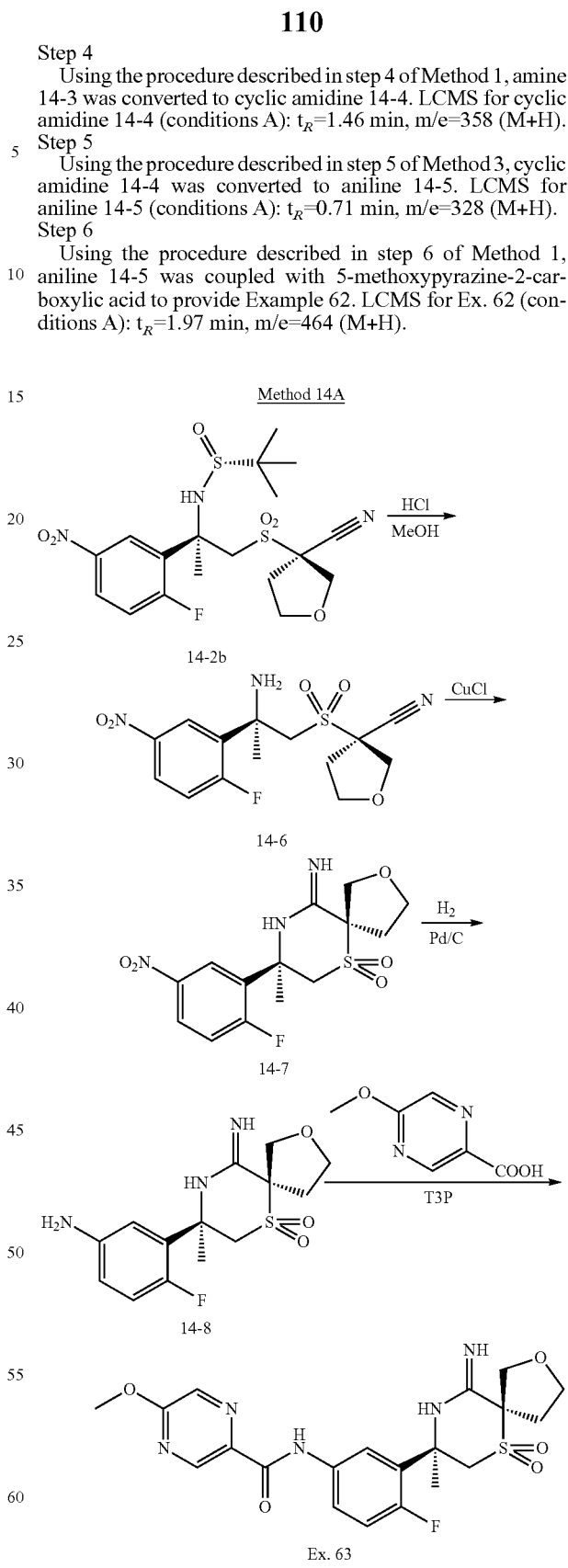

Step 4

Using the procedure described in step 4 of Method 1, amine 14-3 was converted to cyclic amidine 14-4. LCMS for cyclic amidine 14-4 (conditions A): $t_R$=1.46 min, m/e=358 (M+H).

Step 5

Using the procedure described in step 5 of Method 3, cyclic amidine 14-4 was converted to aniline 14-5. LCMS for aniline 14-5 (conditions A): $t_R$=0.71 min, m/e=328 (M+H).

Step 6

Using the procedure described in step 6 of Method 1, aniline 14-5 was coupled with 5-methoxypyrazine-2-carboxylic acid to provide Example 62. LCMS for Ex. 62 (conditions A): $t_R$=1.97 min, m/e=464 (M+H).

Step 1

NaH (6.04 g, 60% in oil, 151 mmol) was washed with hexane, suspended in THF (45 mL), and cooled to −20° C. Compound 1 was added portion-wise and stirred at −20° C. for 10 minutes. 1-Chloro-2-(chloromethoxy)ethane (7.44 g, 55.4 mmol) was added slowly at −20° C., and the reaction mixture was slowly warmed to room temperature, stirred at room temperature for 2 hours, and then quenched by addition of water. The mixture was extracted with 50% ethyl acetate/hexanes, and the organic layer was washed with brine and concentrated in vacuo to give compound 14-1 (8.86 g). $^1$HNMR (CDCl$_3$, 500 MHz) δ 4.05 (m, 2H), 3.87 (m, 2H), 3.67 (m, 2H), 3.34 (s, 3H).

Step 2

Using the procedure described in step 2 of Method 1, compound 14-1 was converted a mixture of compounds 14-2a and 14-2b. SFC purification (Chiralpak 250×21 mm AD-H column, 20% isopropanol/CO$_2$, 50 g/min on a Thar SFC Prep 80 system) afforded 14-2a and 14-2b. Data for 14-2a: LCMS (conditions A): $t_R$=2.06 min, m/e=462 (M+H). Data for 14-2b: LCMS (conditions A): $t_R$=2.06 min, m/e=462 (M+H).

Step 3

Using the procedure described in step 3 of Method 1, compound 14-2a was converted to amine 14-3. LCMS for amine 14-3 (conditions A): $t_R$=1.547 min, m/e=358 (M+H).

Using the procedures described in Method 14, steps 3-6, compound 14-2b was converted to Example 63. LCMS for Ex. 63 (conditions A): $t_R$=1.97 min, m/e=464 (M+H).

The Examples in Table 12 were made from compounds 14-2a or 14-2b as appropriate according to the procedures described in Method 14, steps 3-6 using the requisite carboxylic acids in step 6.

TABLE 12

| Example no. | Example | Expected M + H | Observed M + H | $t_R$ (min) | LCMS method | BACE1 $K_i$ (nM) |
| --- | --- | --- | --- | --- | --- | --- |
| 62 | | 464 | 464 | 1.97 | A | 25.4 |
| 62a | | 463 | 463 | 2.00 | A | 30.3 |
| 62b | | 451 | 451 | 1.97 | A | 24.0 |
| 62c | | 467 | 467 | 2.04 | A | 8.1 |
| 62d | | 501 | 501 | 2.10 | A | 17.0 |
| 62e | | 458 | 458 | 1.95 | A | 6.1 |

TABLE 12-continued

| Example no. | Example | Expected M + H | Observed M + H | $t_R$ (min) | LCMS method | BACE1 $K_i$ (nM) |
| --- | --- | --- | --- | --- | --- | --- |
| 63 | | 464 | 464 | 1.97 | A | 41 |
| 63a | | 463 | 463 | 2.24 | A | 24.2 |
| 63b | | 451 | 451 | 1.46 | B | 18.7 |
| 63c | | 467 | 467 | 2.00 | A | 5.9 |
| 63d | | 458 | 458 | 1.95 | A | 5.2 |

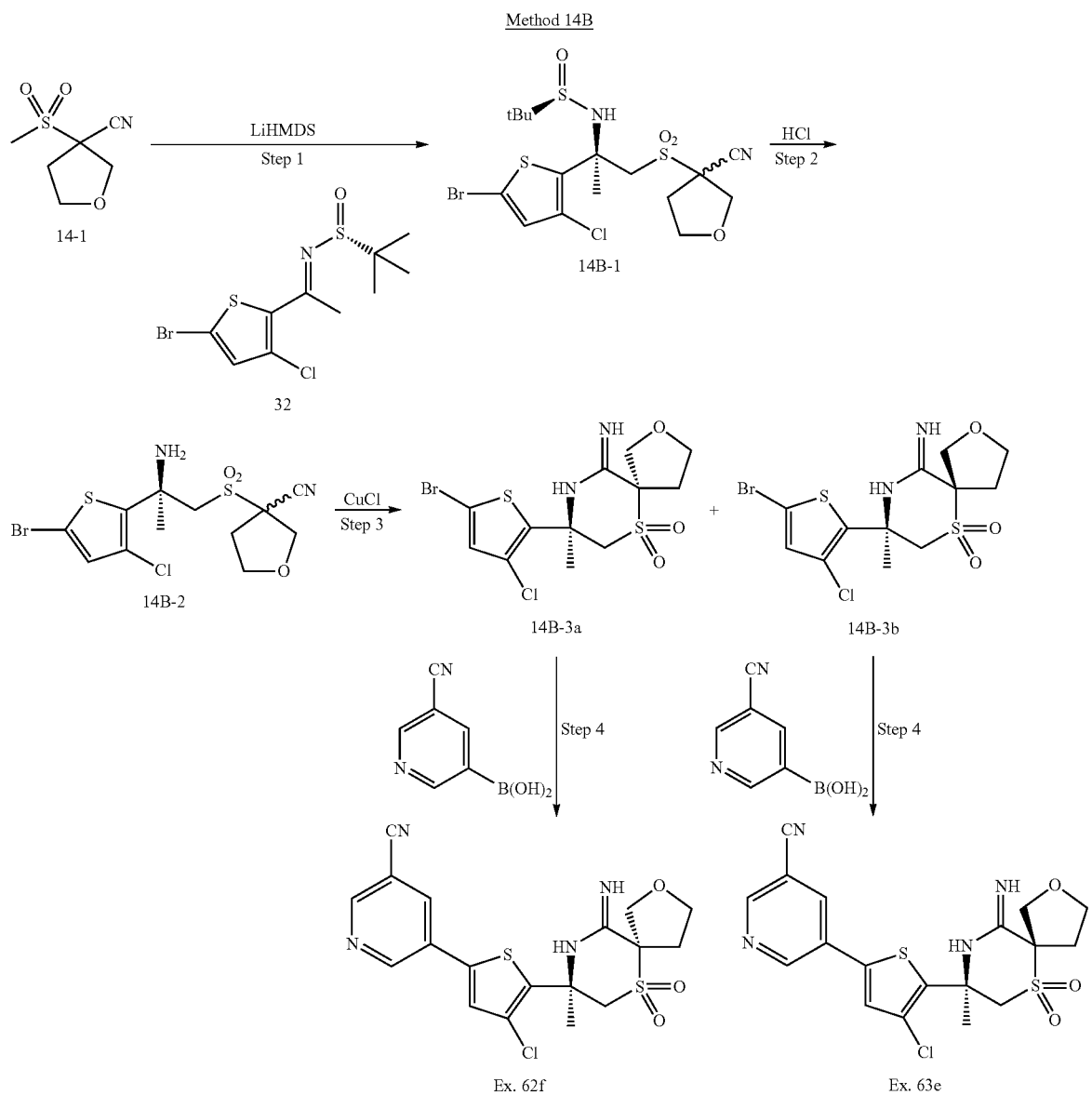

Step 1

A solution of compound 14-1 (6.62 g, 37.8 mmol) in 30 mL of toluene/THF (1:1) was immersed in a −78° C. bath for 5 minutes. LiHMDS (1.0 M in hexane, 36.8 mL, 36.8 mmol) solution was then added slowly. After stirring for 60 min at −78° C., a solution of sulfinimine 32 (7.0 g, 20.4 mmol) in 30 mL of toluene/THF (1:1) was added. The resulting solution was stirred at −78° C. under nitrogen for 4.5 hrs, quenched with 60 mL of saturated aq. NH$_4$Cl solution and diluted with 100 mL of water. The phases were separated and the aqueous was extracted twice with EtOAc. The combined organic extracts were concentrated in vacuo; the residue was purified by flash chromatography (180 g of SiO$_2$, 0-50% EtOAc/hexane) to give compound 14B-1 (1.7 g) as a mixture of two diastereoisomers. LCMS for compound 14B-1 (conditions A): $t_R$=2.47 min, m/e=519 (M+1).

Step 2

To a solution of compound 14B-1 (1.68 g, 3.24 mmol) in 16 mL of DCM was added 10 mL of 4 N HCl in 1,4-dioxane. The mixture was stirred at room temperature under nitrogen for 3 hrs and concentrated in vacuo. The residue was stirred with ether and the resulting solid was collected by filtration to give compound 14B-2 as HCl salt (1.82 g). LCMS for compound 14B-2 (conditions A): $t_R$=2.23 min, m/e=398 (M+H−NH$_3$).

Step 3

Compound 14B-2 (1.82 g, 4.40 mmol) was combined with CuCl (871 mg, 8.80 mmol) in 20 mL of ethanol and heated at 85° C. under nitrogen for 4.5 hrs. The mixture was concentrated in vacuo and the residue was partitioned between 1N NaOH and DCM. The aqueous layer was extracted with DCM twice. The combined organic extracts were washed with brine, dried with MgSO$_4$, filtered, and the filtrate was concentrated in vacuo. The residue was purified by flash chromatography (80 g of SiO$_2$) eluting with 0-5% MeOH in DCM to give a mixture of compound 14B-3a and compound 14B-3b (1.24 g). The mixture was separated by SFC. Compound 14B-3a (465 mg), LCMS (conditions A): $t_R$=1.95 min, m/e=415 (M+1). Compound 14B-3b (417 mg), LCMS (conditions B): $t_R$=1.46 min, m/e=415 (M+1).

Step 4

Using the procedure described in step 4 of Method 9, compounds 14B-3a and 14B-3b were separately converted to Example 62f and Example 63e, respectively. LCMS for Example 62f (conditions A): $t_R$=2.15 min, m/e=437 (M+H).

LCMS for Example 63e (conditions A): $t_R$=1.43 min, m/e=437 (M+H).

The examples in Table 12A were made from either compound 14B-3a or 14B-3b as appropriate following the procedure described in Method 9, step 4 using the requisite boronic acids or boronate esters.

TABLE 12A

| Example no. | Example | Exptected M + H | Observed M + H | $t_R$ (min) | LCMS method | BACE1 $K_i$ (nM) |
|---|---|---|---|---|---|---|
| 62f | ![structure] | 437 | 437 | 2.15 | A | 67.1 |
| 62g | ![structure] | 480 | 480 | 2.33 | A | 6.3 |
| 62h | ![structure] | 479 | 479 | 1.92 | A | 56.7 |
| 62i | ![structure] | 497 | 497 | 1.76 | A | 1662 |

TABLE 12A-continued

| Example no. | Example | Exptected M + H | Observed M + H | $t_R$ (min) | LCMS method | BACE1 $K_i$ (nM) |
|---|---|---|---|---|---|---|
| 62j | | 478 | 478 | 1.86 | A | 295.6 |
| 62k | | 494 | 494 | 2.04 | A | 305.3 |
| 62l | | 478 | 478 | 1.89 | A | 45.3 |
| 62m | | 470 | 470 | 1.73 | A | 2422 |

TABLE 12A-continued

| Example no. | Example | Exptected M + H | Observed M + H | $t_R$ (min) | LCMS method | BACE1 $K_i$ (nM) |
|---|---|---|---|---|---|---|
| 62n | | 488 | 488 | 1.92 | A | 312.8 |
| 63e | | 437 | 437 | 1.43 | A | 192 |
| 63f | | 480 | 480 | 1.68 | A | 14.2 |
| 63g | | 479 | 479 | 1.56 | A | 20.2 |
| 63h | | 479 | 479 | 1.92 | A | 106.6 |

TABLE 12A-continued
| Example no. | Example | Exptected M + H | Observed M + H | $t_R$ (min) | LCMS method | BACE1 $K_i$ (nM) |
| --- | --- | --- | --- | --- | --- | --- |
| 63i | 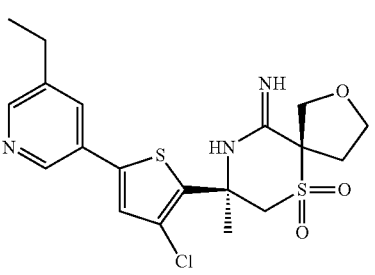 [SMILES: CCc1cncc(-c2cc(Cl)c([C@]3(C)CS(=O)(=O)[C@@]4(CCOC4)C(=N)N3)s2)c1] | 440 | 440 | 1.71 | A | 1776 |
| 63j | 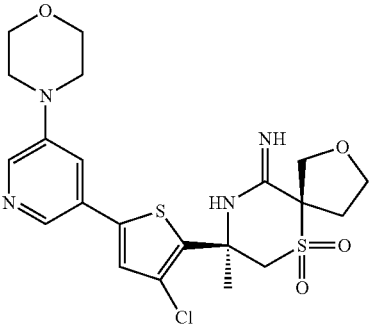 [SMILES: C[C@@]1(c2sc(-c3cncc(N4CCOCC4)c3)cc2Cl)CS(=O)(=O)[C@@]2(CCOC2)C(=N)N1] | 497 | 497 | 1.75 | A | 3689 |
| 63k | 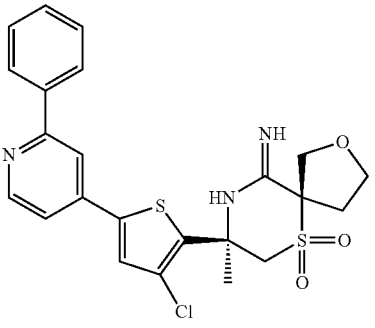 [SMILES: C[C@@]1(c2sc(-c3ccnc(-c4ccccc4)c3)cc2Cl)CS(=O)(=O)[C@@]2(CCOC2)C(=N)N1] | 488 | 488 | 1.92 | A | 849 |
| 63l | 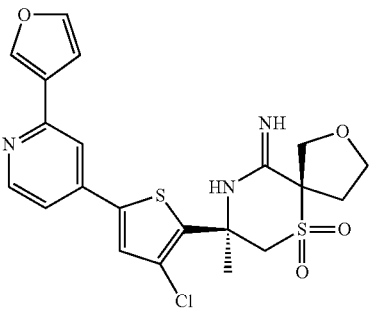 | 478 | 478 | 1.85 | A | 673.8 |

TABLE 12A-continued

| Example no. | Example | Exptected M + H | Observed M + H | $t_R$ (min) | LCMS method | BACE1 $K_i$ (nM) |
|---|---|---|---|---|---|---|
| 63m | | 494 | 494 | 1.89 | A | 986.4 |
| 63n | | 494 | 494 | 2.04 | A | 428.2 |

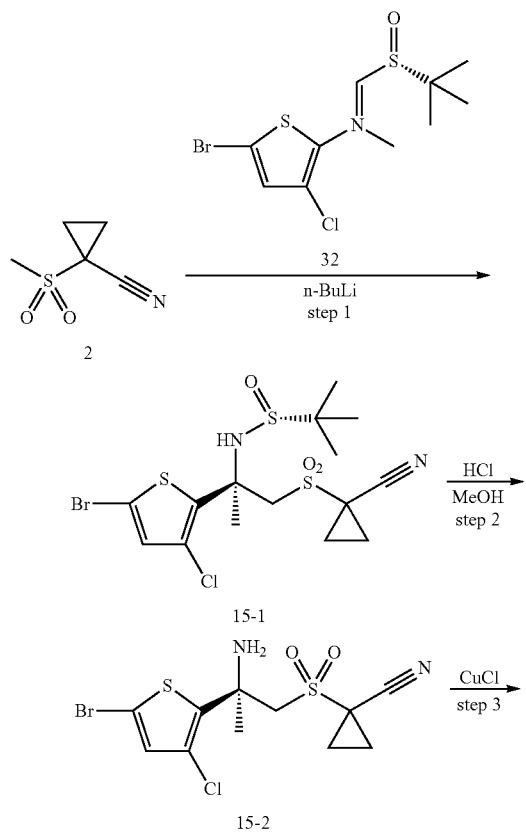

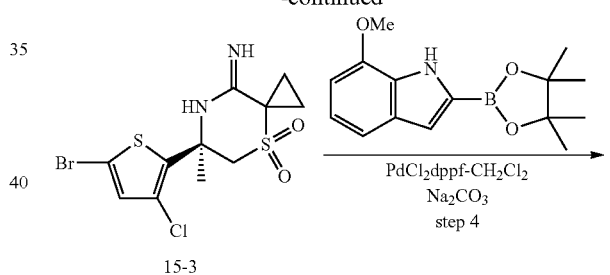

Step 1

Using the procedure described in step 1 of Method 9, sulfone 2 was converted to compound 15-1. LCMS for compound 15-1 (conditions A): $t_R$=2.44 min, m/e=489 (M+H).

Step 2

Using the procedure described in step 2 of Method 9, compound 15-1 was converted to amine 15-2. LCMS for amine 15-2 (conditions A): $t_R$=1.95 min, m/e=368 (M+H—NH$_3$).

Step 3

Using the procedure described in step 3 of Method 9, amine 15-2 was converted to cyclic amidine 15-3. LCMS for cyclic amidine 15-3 (conditions A): $t_R$=1.40 min, m/e=385 (M+H).

Step 4

A mixture of 15-3 (0.100 g, 0.261 mmol), 7-methoxy-1H-indole-2-boronic acid pinacol ester (0.107 g, 0.391 mmol), and 1,1'-bis(diphenylphosphino)ferrocene-palladium(II) dichloride-dichloromethane complex (0.021 g, 0.026 mmol) in toluene (0.65 mL), ethanol (0.65 mL), and 2 M sodium carbonate in water (0.261 mL, 0.521 mmol) was degassed by bubbling nitrogen through the mixture for several minutes. This flask was then sealed and immediately heated in a microwave reactor at 120° C. for 30 min. The reaction mixture was diluted with $CH_2Cl_2$, filtered through a fritted cartridge, and absorbed onto silica gel. The resulting sample was subjected to flash silica gel chromatography (40 g $SiO_2$, 0-100% Ethyl acetate/hexanes gradient) followed by additional flash silica gel chromatography (24 g $SiO_2$, 0-70% of 10% methanol/1% $NH_4OH/CH_2Cl_2+CH_2Cl_2$ gradient) to afford Example 64 (0.013 g). LCMS (conditions A): $t_R$=2.14 min, m/e=450 (M+H)

The examples in Table 13 were made from compound 15-3 following the procedure described in Method 15, step 4 or Method 9, step 4 using the requisite boronic pinacol esters.

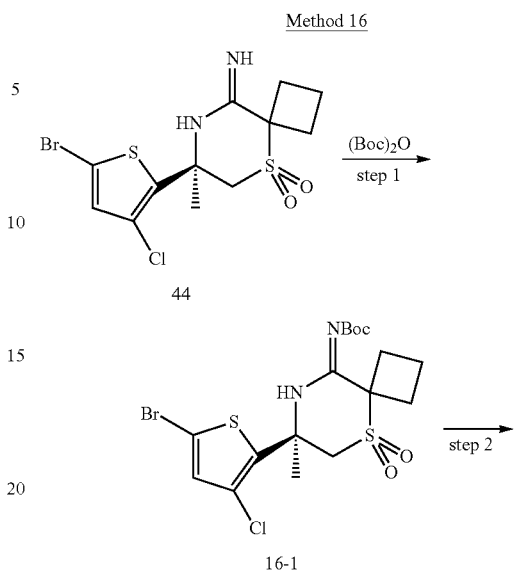

Method 16

TABLE 13

| Example no. | Example | Expected M + H | Observed M + H | $t_R$ (min) | LCMS method | BACE1 $K_i$ (nM) |
|---|---|---|---|---|---|---|
| 64 | | 450 | 450 | 2.14 | A | 10 |
| 65 | | 407 | 407 | 1.89 | A | 108 |
| 65a | | 449 | 449 | 1.94 | A | 11.0 |

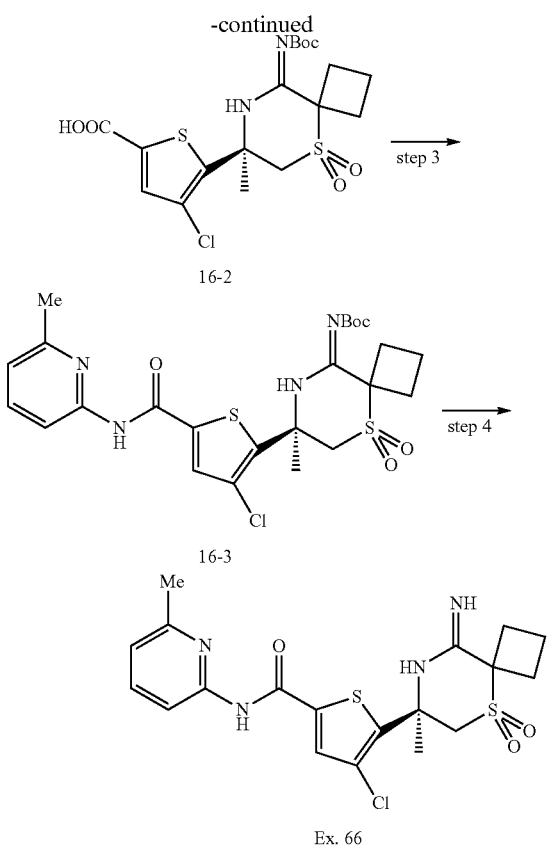

ture for 3 h, and the solvent was then removed under reduced pressure. The residue was purified by silica gel chromatography eluting with PE/EA (5:1) to afford 16-1 (1.1 g). $^1$H NMR (CDCl$_3$, 400 MHz) δ 6.89 (s, 1H), 3.90 (d, J=14.8 Hz, 1H), 3.43 (d, J=14.8 Hz, 1H), 3.02-3.10 (m, 1H), 2.63-2.80 (m, 3H), 2.10-2.18 (m, 2H), 1.96 (s, 3H), 1.52 (s, 9H).

Step 2

To a solution of compound 16-1 in THF at 0° C. is added methyl magnesium bromide. The reaction is stirred at 0° C. for 30 minutes and then cooled to −78° C. A hexane solution of n-butyllithium is added over 10 minutes and the reaction is stirred for an additional hour at −78° C. CO$_2$ gas is then bubbled through the reaction for 5 minutes at which time the cold bath is removed. After warming to room temperature, 1N HCl and ethyl acetate are added to the mixture. The mixture is extracted with ethyl acetate. The combined organic layers are washed with water and brine, dried (MgSO$_4$), filtered, and concentrated in vacuo. The residue is purified by silica gel chromatography to provide 16-2.

Step 3

Using the procedure described in step 6 of Method 1, compound 16-2 is coupled with 2-amino-6-methylpyridine to provide 16-3.

Step 4

A solution of compound 16-3 in TFA: dichloromethane (1:1) is stirred at RT for 3 h, and concentrated. The residue is purified to give Ex. 66.

Following the procedures described in Method 16 steps 3 and 4, the examples shown in Table 14 are prepared from compound 16-2 using the appropriate anilines in step 3. Alternatively, compound 16-2 was prepared as described in Method 18, and the Examples in Table 14 can be prepared from 16-2 using methods analogous to those described in Method 24.

Step 1

To a solution of 44 (1.0 g, 2.51 mmol) in DCM (10 mL) were added TEA (0.38 g, 3.75 mmol) and (Boc)$_2$O (0.62 g, 3.0 mmol). The reaction mixture was stirred at room tempera-

TABLE 14

| Aniline | Example Number | Example |
|---|---|---|
|  | 66 |  |
|  | 67 |  |

TABLE 14-continued
| Aniline | Example Number | Example |
|---|---|---|
| | 68 | |
| | 69 | |
| | 70 | |
| | 71 | |
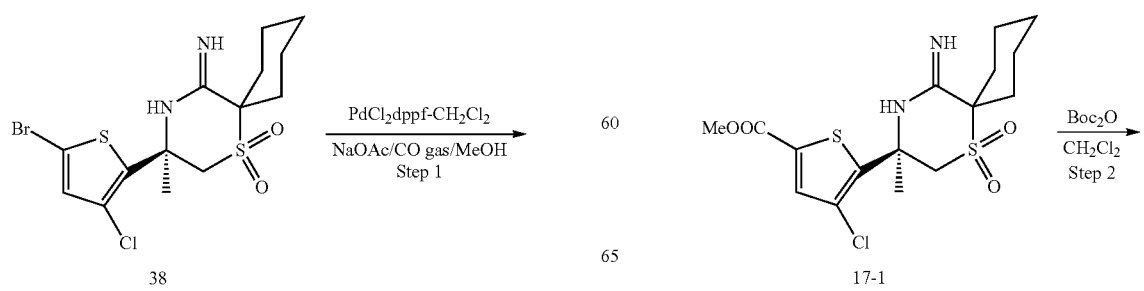

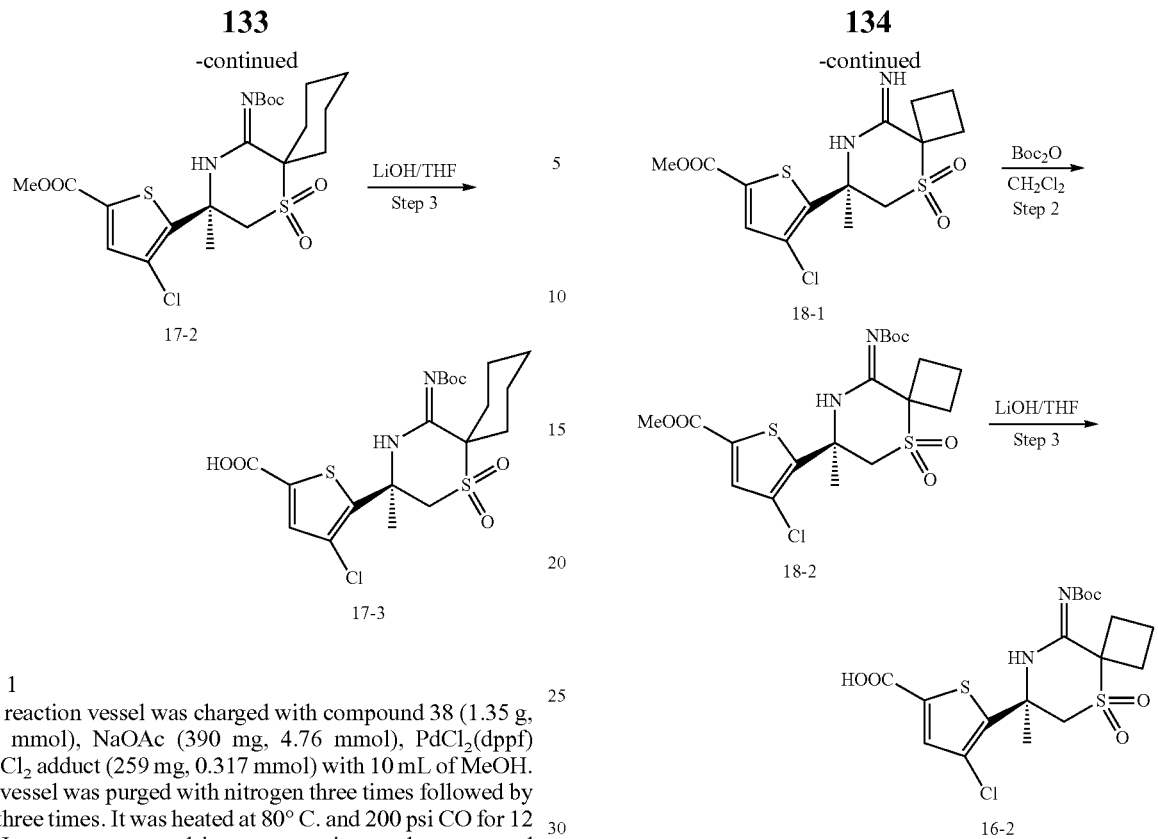

Step 1

A reaction vessel was charged with compound 38 (1.35 g, 3.17 mmol), NaOAc (390 mg, 4.76 mmol), PdCl$_2$(dppf) CH$_2$Cl$_2$ adduct (259 mg, 0.317 mmol) with 10 mL of MeOH. The vessel was purged with nitrogen three times followed by CO three times. It was heated at 80° C. and 200 psi CO for 12 hrs. It was concentrated in vacuo to give crude compound 17-1 (2.17 g). LCMS for compound 17-1 (conditions D): $t_R$=0.72 min, m/e=405 (M+H).

Step 2

Compound 17-1 (crude, 2.17 g) was put in 20 mL of DCM. TEA (0.75 mL, 5.36 mmol) was added followed by Boc$_2$O (1.75 g, 8.04 mmol). The reaction mixture was stirred at room temperature under nitrogen overnight. It was concentrated in vacuo; the residue was purified by preparative TLC eluting with 2% MeOH/DCM to afford compound 17-2 (1.43 g). LCMS for compound 17-2 (conditions D): $t_R$=1.37 min, m/e=449 (M+H-tBu).

Step 3

To a solution of compound 17-2 (1.42 g, 2.81 mmol) in 15 mL of THF was added LiOH solution (2 M, 8.4 mL, 16.9 mmol). The reaction mixture was stirred at room temperature overnight, and quenched with saturated aq. NH$_4$Cl. It was extracted with EtOAc (70 mL×3); the combined organic extracts were washed with 0.1 N HCl followed by brine, and dried with MgSO$_4$. It was filtered; the filtrate was concentrated in vacuo to give compound 17-3 (1.28 g). LCMS for compound 17-3 (conditions D): $t_R$=1.25 min, m/e=435 (M+H-tBu).

Step 1

Using the procedure described in step 1 of Method 17, compound 44 was converted to 18-1. LCMS for compound 18-1 (conditions D): $t_R$=0.62 min, m/e=377 (M+1).

Step 2

Using the procedure described in step 2 of Method 17, compound 18-1 was converted to 18-2. LCMS for compound 18-2 (conditions D): $t_R$=1.25 min, m/e=421 (M+1).

Step 3

Using the procedure described in step 3 of Method 17, compound 18-2 was converted to 16-2. LCMS for compound 16-2 (conditions D): $t_R$=1.13 min, m/e=407 (M−56).

Method 19

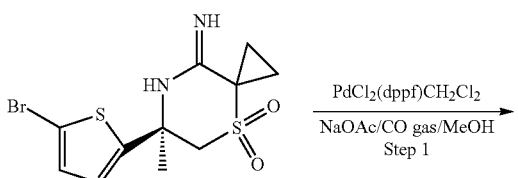

Method 18

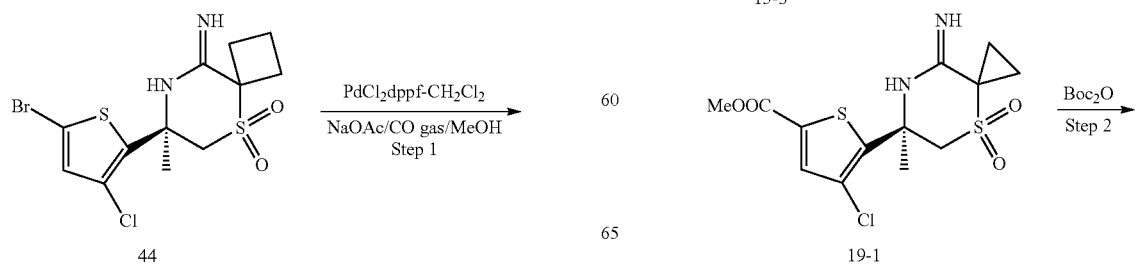

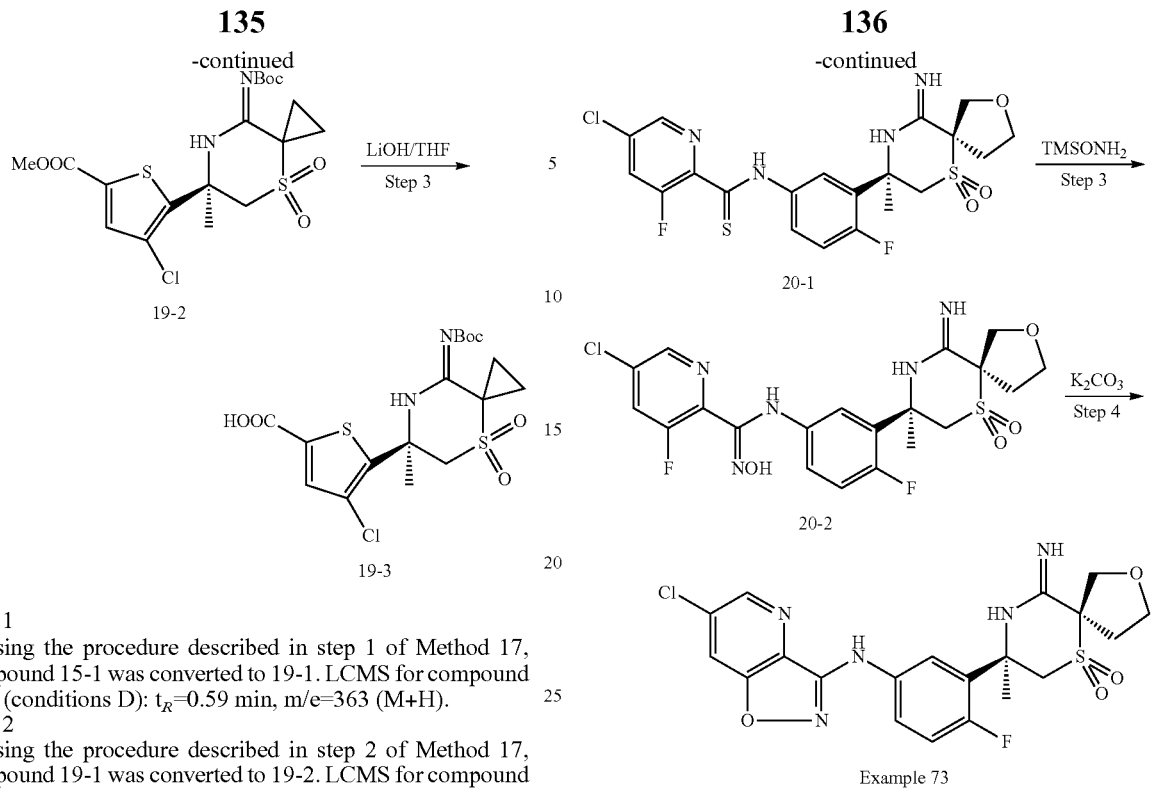

Step 1
Using the procedure described in step 1 of Method 17, compound 15-1 was converted to 19-1. LCMS for compound 19-1 (conditions D): $t_R$=0.59 min, m/e=363 (M+H).

Step 2
Using the procedure described in step 2 of Method 17, compound 19-1 was converted to 19-2. LCMS for compound 19-2 (conditions D): $t_R$=1.20 min, m/e=407 (M-56).

Step 3
Using the procedure described in step 1 of Method 17, compound 19-2 was converted to 19-3. LCMS for compound 19-3 (conditions D): $t_R$=1.07 min, m/e=393 (M-56).

Method 20

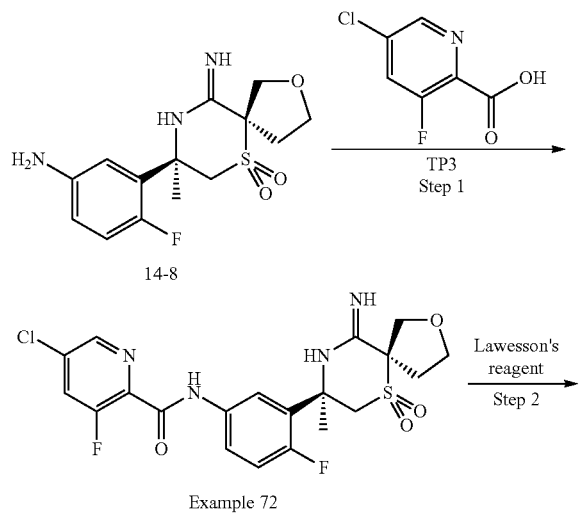

Step 1
Using the procedure described in step 6 of Method 14, compound 14-8 was converted to Example 72 LCMS for Example 72 (conditions D): $t_R$=0.67 min, m/e=485 (M+1).

Step 2
A suspension of 1.15 g (2.37 mmol) of Example 72 and 0.96 g (2.37 mmol) of Lawesson's reagent in 15 mL of toluene was stirred at reflux for 7 h, and cooled to room temperature. The mixture was concentrated; the residue was purified by flash chromatography (120 g of $SiO_2$: 0-5% MeOH in $CH_2Cl_2$ plus 1% $NH_4OH$) to give compound 20-1 (0.61 g). LCMS for compound 20-1 (conditions D): $t_R$=0.73 min, m/e=501 (M+1).

Step 3
A solution of 0.61 g (1.22 mmol) of thioamide 20-1 and 0.40 g (3.42 mmol) of $TMSONH_2$ in 15 mL of MeCN was stirred at 80° C. for 1.5 h and concentrated. The residue was purified by preparative silica gel TLC eluting with 7% MeOH in DCM to give compound 20-2 (0.21 g). LCMS for compound 20-2 (conditions D): $t_R$=0.60 min, m/e=500 (M+1).

Step 4
To a solution of compound 20-2 (0.21 g, 0.42 mmol) in 4 mL of DMF was added 0.116 g (0.84 mmol) of $K_2CO_3$. The mixture was stirred at 80° C. for 1 h, and concentrated. The residue was purified by preparative silica gel TLC eluting with 5% MeOH in methylene chloride to give Example 73 (0.17 g). LCMS for Example 73 (conditions D): $t_R$=0.76 min, m/e=480 (M+1). BACE1 $K_i$ for Example 73=5.1 nM.

Method 21

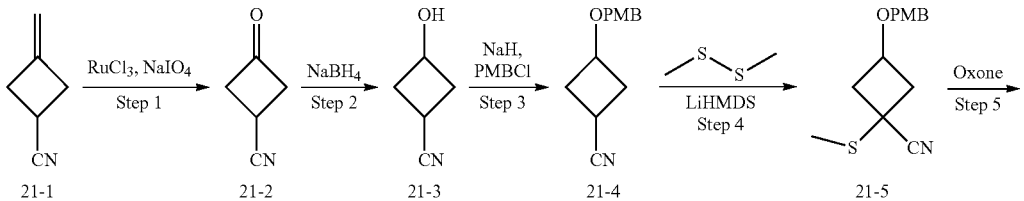

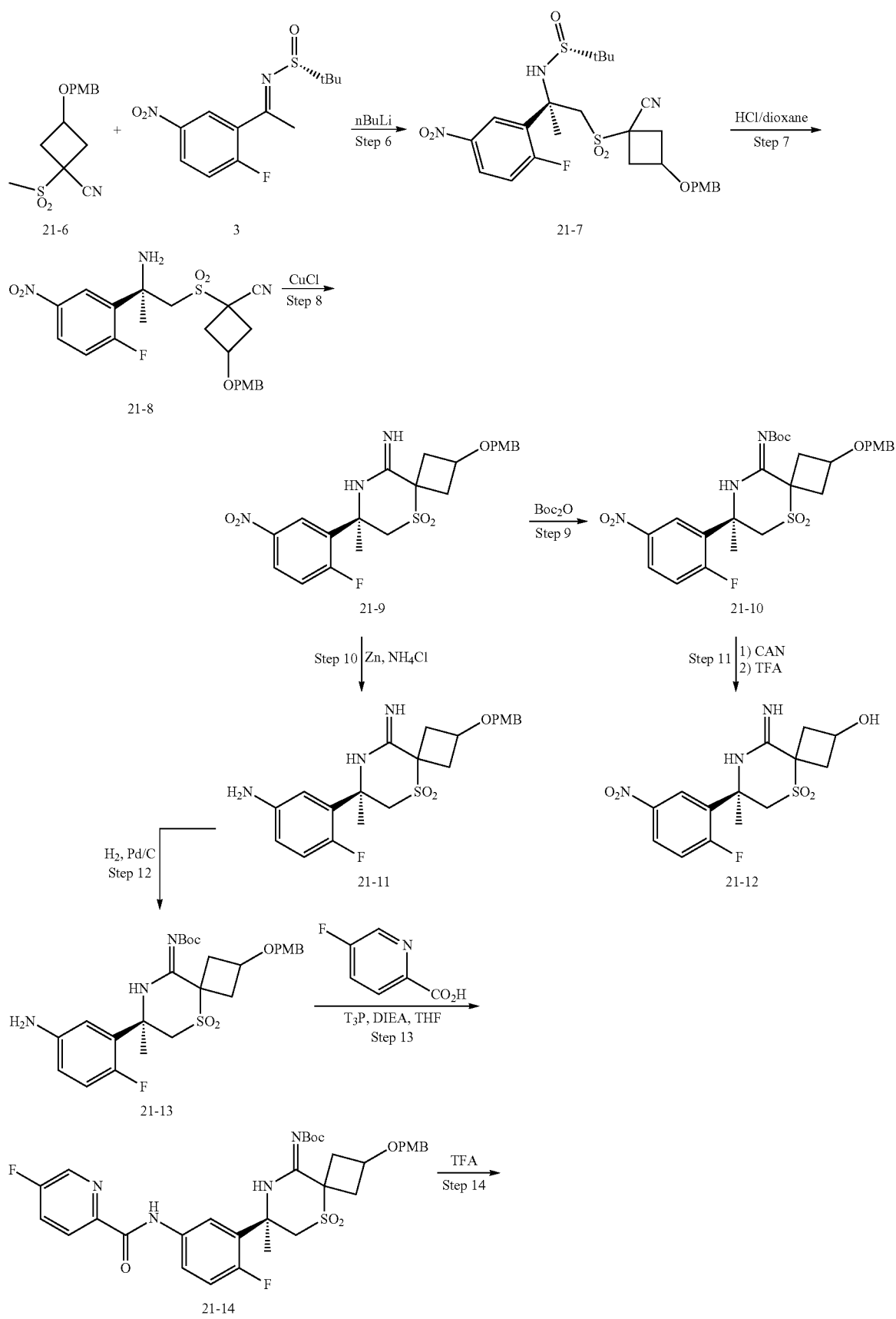

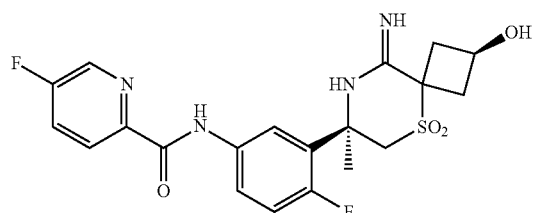

Example 74

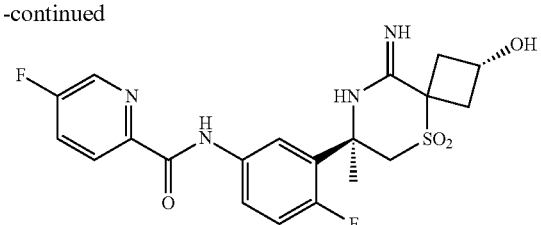

Example 75

Step 1

To a solution of compound 21-1 (5 g, 62 mmol) and RuCl₃ (0.25 g, 1.4 mmol) in CH₃CN/DCM/H₂O (100 mL/100 mL/150 mL) at 0° C. was added NaIO₄ (47.3 g, 250 mmol). The mixture was stirred at RT overnight, quenched with water, and extracted with DCM. The combined extracts were washed with brine, dried over Na₂SO₄, concentrated and purified by silica gel chromatography (PE: EA=5:1) to give 4.5 g of compound 21-2. ¹H NMR (400 MHz, CDCl₃): δ 3.53-3.55 (m, 4H), 3.23-3.29 (m, 1H).

Step 2

To a solution of compound 21-2 (5 g, 53 mmol) in 50 mL of MeOH was added NaBH₄ (3 g, 79 mmol) at 0° C., and the mixture was stirred at room temperature for 2 h. The solvent was removed from the reaction mixture in vacuo, and EtOAc (150 mL) and water (100 mL) were added to the residue. The organic layer was separated, washed with water and brine, dried over MgSO₄, filtered, and concentrated to give 4.8 g of compound 21-3. ¹H NMR (400 MHz, CDCl₃): δ 4.18-4.22 (m, 1H), 2.69-2.73 (m, 3H), 2.53-2.58 (m, 1H), 2.23-2.34 (m, 2H).

Step 3

To a suspension of NaH (2.7 g, 68 mmol) in DMF (60 mL) at 0° C. was added compound 21-3 (5 g, 52 mmol). The mixture was stirred for 30 min, and then PMBCl (9.7 g, 62 mmol) in DMF (10 mL) was added slowly. The reaction mixture was stirred at 0° C. for 2 h and then quenched with water. The aqueous layer was separated and extracted with EtOAc. The combined organic layers were washed with brine, dried over Na₂SO₄ and filtered. The filtrate was concentrated and purified by silica gel chromatography (PE: EA=10:1) to give 10 g of compound 21-4. ¹H NMR (400 MHz, CDCl₃): δ 7.23 (d, J=8.0 Hz, 2H), 6.85 (d, J=8.0 Hz, 2H), 4.33 (s, 2H), 3.90-3.94 (m, 1H), 3.78 (s, 3H), 2.56-2.62 (m, 3H), 2.31-2.35 (m, 2H).

Step 4

To a solution of compound 21-4 (5 g, 23 mmol) in THF (50 mL) at −78° C. was added LiHMDS (35 mL, 35 mmol, 1M solution in THF) and stirred at −78° C. for 1 h. Then 1,2-dimethyldisulfide (2.6 g, 28 mmol) in THF (10 mL) was added, and this mixture was stirred at −78° C. for 3 h. The mixture was quenched with aq. NH₄Cl solution and extracted with EtOAc. The combined extracts were washed with water and brine, dried with Na₂SO₄, concentrated. The residue was purified by silica gel chromatography (PE: EA=5:1) to give 5 g of compound 21-5. ¹H NMR (400 MHz, CDCl₃): δ 7.23 (d, J=8.0 Hz, 2H), 6.86 (d, J=8.0 Hz, 2H), 4.36 (s, 2H), 4.21-4.27 (m, 1H), 3.78 (s, 3H), 2.31-2.99 (m, 4H), 2.11 (m, 3H).

Step 5

To a solution of oxone (5.8 g, 9.5 mmol) in H₂O (40 mL) at 0° C. was added a solution of compound 21-5 (2.5 g, 9.5 mmol) in MeOH (40 mL) dropwise. The mixture was stirred at RT overnight, quenched with water, and extracted with EtOAc. The combined extracts were washed with brine, dried over Na₂SO₄, concentrated and purified by silica gel chromatography (PE: EA=5:1) to give 2 g of compound 21-6. ¹H NMR (400 MHz, CDCl₃): δ 7.23 (d, J=8.0 Hz, 2H), 6.88 (d, J=8.0 Hz, 2H), 4.39 (s, 2H), 4.28-4.31 (m, 1H), 3.81 (s, 3H), 3.00-3.09 (m, 5H), 2.71-2.80 (m, 2H).

Step 6

To a solution of compound 21-6 (296 mg, 1.0 mmol) in THF (10 mL) at −78° C. was added n-BuLi (0.45 mL, 2.5 M in hexane) dropwise. The mixture was stirred for 60 min, and then a solution of compound 3 (286 mg, 1.0 mmol) in THF (1 mL) was added, and the reaction mixture was stirred for an additional 4 h. The reaction was quenched with water, the phases separated and the aqueous layer was extracted with EtOAc. The combined organic extracts were washed with water and brine, dried over Na₂SO₄, filtered, and concentrated. The residue was purified by silica gel chromatography (PE: EA=5:1) to give 300 mg of compound 21-7. LCMS (conditions F5): m/e=582 (M+H), $t_R$=1.32 min. ¹H NMR (400 MHz, CDCl₃): δ 8.49-8.51 (m, 1H), 8.23-8.25 (m, 1H), 7.18-7.24 (m, 3H), 6.83-6.85 (m, 2H), 4.14-4.36 (m, 4H), 3.78 (s, 3H), 3.38-3.42 (m, 1H), 2.66-2.85 (m, 4H), 1.95 (s, 3H), 1.38 (s, 9H).

Step 7

To a solution of compound 21-7 (2 g, 3.4 mmol) in DCM (20 mL) at 0° C. was added 4 N HCl in dioxane (6 mL). The mixture was stirred for 1 h and then concentrated. The residue was diluted with aq. NaHCO₃, extracted with DCM. The combined organic extracts were dried over Na₂SO₄ and concentrated to give 1 g of compound 21-8. LCMS (conditions F5): m/e=478 (M+H), $t_R$=1.06 min.

Step 8

A suspension of compound 21-8 (200 mg, 0.42 mmol) and CuCl (69 mg, 0.69 mmol) in EtOH (10 mL) was refluxed under N₂ for 24 h. The reaction mixture was diluted with water and extracted with EtOAc. The combined extracts were washed with water and brine, dried over Na₂SO₄, and concentrated. The residue was purified by prep RP-HPLC (column 150×20 mm, 5 μm; mobile phases A=water with 0.075% v/v TFA, B=MeCN; gradient 19-49% B, 10 min, 25 mL/min) to give 100 mg of compound 21-9. LCMS (conditions F5): m/e=478 (M+H), $t_R$=1.04 min. ¹H NMR (400 MHz, CDCl₃): δ 8.24-8.35 (m, 2H), 7.23-7.49 (m, 3H), 6.85-6.89 (m, 2H), 4.00-4.45 (m, 4H), 3.77 (s, 3H), 2.68-3.15 (m, 5H), 2.05 (s, 3H).

Step 9

To a solution of compound 21-9 (1.5 g, 3.14 mmol) and DIEA (1.62 g, 12.56 mmol) in MeOH (15 mL) was added Boc₂O (1.36 g, 6.28 mmol) at 0° C. The mixture was stirred at RT for 6 h and concentrated. The residue was purified by silica gel chromatography (PE: EA=5:1) to give 839 mg of compound 21-10. LCMS (conditions F5): m/e=578 (M+H), $t_R$=0.94 min.

Step 10

To a solution of compound 21-9 (400 mg, 0.84 mmol) in EtOH (10 mL) at 0° C. were added NH₄Cl (221 mg, 4.18 mmol) and zinc power (544 mg, 8.37 mmol). The mixture was stirred at 80° C. for 16 h and filtered. The filtrate was concentrated, and the residue purified by silica gel chromatography (DCM: MeOH=10:1) to afford 160 mg of 21-11. LCMS (conditions F1): m/e=448 (M+H), $t_R$=3.39 min. ¹H NMR (400 MHz, CD₃OD): δ 7.30-7.32 (m, 2H), 7.11-7.16 (m, 1H), 7.01-7.04 (m, 2H), 6.91-6.95 (m, 2H), 4.15 (d, J=15.6 Hz, 1H), 3.96 (d, J=15.6 Hz, 1H), 3.32 (s, 3H), 3.13-3.18 (m, 2H), 2.98-3.03 (m, 1H), 2.70 (q, 1H), 2.00 (s, 3H).

Step 11

To a solution of compound 21-10 (2 g, 3.4 mmol) in CH₃CN (20 mL) at 0° C. was added CAN (3.75 g, 6.8 mmol). The mixture was stirred at 25° C. for 5 h, quenched with water, and then extracted with EtOAc. The combined extracts were washed with water and brine, dried over Na₂SO₄, concentrated to give 500 mg of alcohol intermediate. To a solution of this alcohol (100 mg, 0.22 mmol) in DCM (5 mL) was added TFA (0.5 mL) at 0° C. The mixture was stirred at 25° C. for 1 h and concentrated. The residue was purified by prep RP-HPLC (column 150×30 mm, 5 μm; mobile phases A=water with 0.075% v/v TFA, B=MeCN; gradient 0-28% B, 10 min, 35 mL/min) to give 21-12. LCMS (conditions F2): m/e=358 (M+H), $t_R$=1.91 min. ¹H NMR (400 MHz, CD₃OD): δ 8.30-8.42 (m, 2H), 7.50-7.55 (m, 1H), 4.54-4.58 (m, 1H), 4.04-4.28 (m, 2H), 3.22-3.29 (m, 2H), 2.71-2.91 (m, 2H), 2.07 (s, 3H).

Step 12

To a solution of compound 21-11 (500 mg, 0.87 mmol) in EtOH (10 mL) was added Pd/C (100 mg). The mixture was stirred under H₂ atmosphere (45 psi) at 45° C. for 10 h and was then filtered. The filtrate was concentrated to afford 450 mg of compound 21-13. LCMS (conditions F5): m/e=548 (M+H), $t_R$=1.10 min.

Step 13

To a solution of compound 21-13 (450 mg, 0.86 mmol), 5-fluoropyridine-2-carboxylic acid (182 mg, 1.29 mmol) and DIEA (665 mg, 5.15 mmol) in THF (10 mL) at 0° C. was added T3P (820 mg, 2.58 mmol, 50% in EtOAc) dropwise. The mixture was stirred at 0° C. for 0.5 h and then RT overnight. It was diluted with water, and then extracted with EtOAc. The combined extracts were washed with brine, dried over anhydrous Na₂SO₄, and concentrated. The residue was purified by silica gel chromatography (PE: EA=10:1) to give 450 mg of compound 21-14. LCMS (conditions F5): m/e=671 (M+H), $t_R$=1.37 min.

Step 14

To a solution of compound 21-14 (400 mg, 0.62 mmol) in DCM (10 mL) at 0° C. was added TFA (2 mL). The mixture was stirred at RT for 4 h and concentrated. The residue was purified by prep RP-HPLC (column 150×30 mm, 5 μm; mobile phases A=water with 0.075% v/v TFA, B=MeCN; gradient 5-35% B, 10 min, 35 mL/min) to give Examples 74 and 75.

Example 74: ¹H NMR (400 MHz, CD₃OD): δ 8.62 (d, J=2.4 Hz, 1H), 8.29 (q, J=4.4 Hz, 1H), 8.06-8.09 (m, 1H), 7.82-7.85 (m, 2H), 7.24-7.30 (m, 1H), 4.53-4.57 (m, 1H), 4.00-4.09 (m, 2H), 2.85-3.03 (m, 4H), 2.05 (s, 3H). LCMS (conditions F2): $t_R$=2.21 min, m/e=451 (M+H).

Example 75: ¹H NMR (400 MHz, CD₃OD) δ 8.61 (d, J=2.8 Hz, 1H), 8.29 (q, J=4.8 Hz, 1H), 8.08-8.10 (m, 1H), 7.82-7.86 (m, 2H), 7.28 (q, J=8.8 Hz, 2H), 4.18 (d, J=16 Hz, 1H), 4.00 (d, J=15.2 Hz, 1H), 3.19-3.24 (m, 2H), 2.89-2.94 (m, 1H), 2.66-2.69 (m, 1H), 2.06 (s, 3H). LCMS (conditions F2): $t_R$=2.24 min, m/e=451 (M+H).

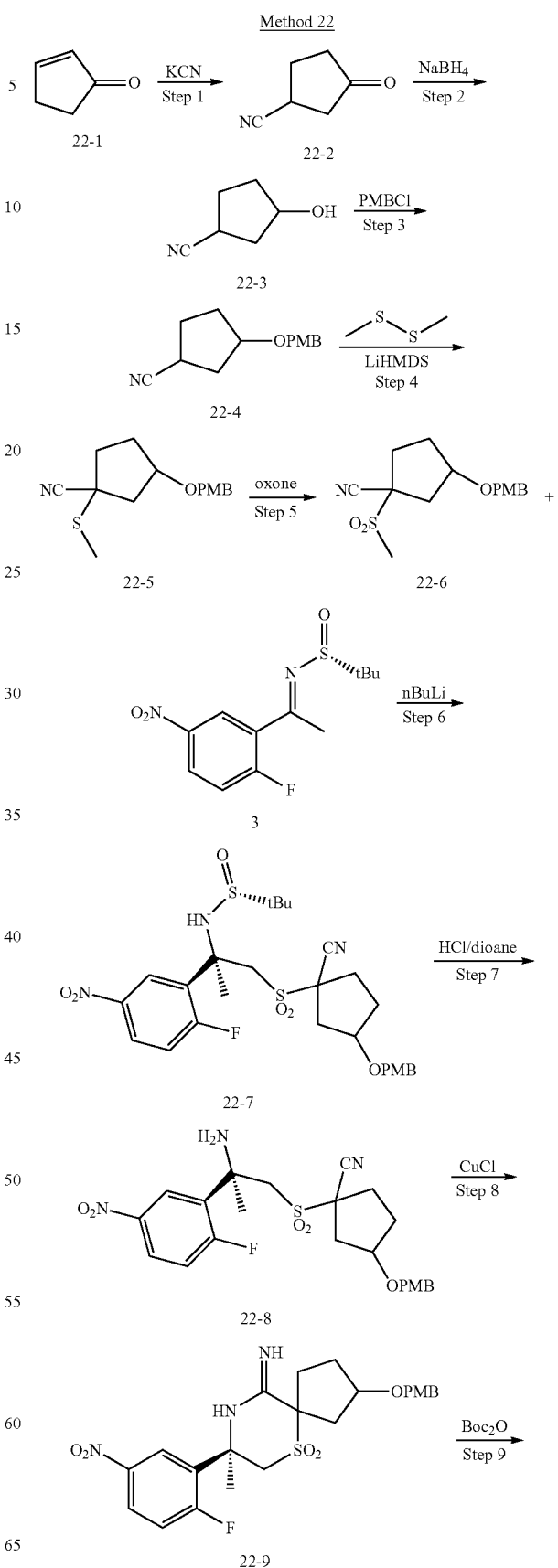

Method 22

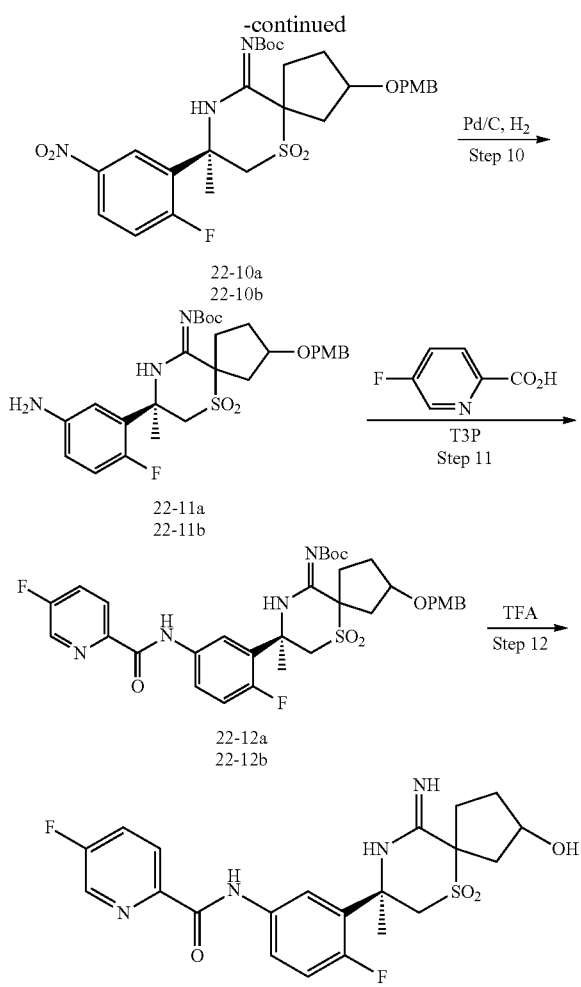

Example 76A (Isomeric sample 1)
Example 76B (Isomeric sample 2)

Step 1

A solution of compound 22-1 (10 g, 122 mmol), KCN (9.5 g, 146 mmol) and Et₃N.HCl (25 g, 83 mmol) in MeOH (150 mL) was stirred at rt for 4 h. The mixture was concentrated; the residue was re-dissolved in EtOAc. The solution was washed with water and brine, dried over Na₂SO₄, concentrated. The residue was purified by silica gel chromatography (PE: EA=5:1) to give 7.5 g of compound 22-2. ¹H NMR (400 MHz, CDCl₃): δ 3.13-3.51 (m, 1H), 2.56-2.63 (m, 1H), 2.16-2.48 (m, 5H).

Step 2

To a solution of compound 22-2 (8 g, 73 mmol) in MeOH (100 mL) at 0° C. was added NaBH₄ (4 g, 88 mmol) in portions. The solution was stirred at 0° C. for 30 min, then at rt for 2 h. The mixture was concentrated, and the residue was re-dissolved in EtOAc. The solution was washed with water and brine, dried over Na₂SO₄, and concentrated. The residue was purified by silica gel chromatography (PE: EA=3:1) to give 5.3 g of compound 22-3. ¹H NMR (400 MHz, CD₃OD): δ 2.88-3.09 (m, 1H), 2.22-2.30 (m, 1H), 1.83-2.11 (m, 5H).

Step 3

To a suspension of NaH (1.7 g, 39.6 mmol) in DMF (50 mL) at 0° C. was added dropwise compound 22-3 (4 g, 36 mmol) under N₂. After 30 min, PMBCl (8.5 g, 54 mmol) was added dropwise. The solution was stirred at 0° C. for 2 h, and then quenched with water and extracted with EtOAc. The combined extracts were washed with water and brine, dried over Na₂SO₄, and concentrated. The residue was purified by silica gel chromatography (PE: EA=5:1) to give 6 g of compound 22-4. ¹H NMR (400 MHz, CDCl₃): δ 7.22 (d, J=8.4 Hz, 2H), 6.87 (d, J=8.4 Hz, 2H), 4.36 (s, 2H), 3.79 (s, 3H), 2.92-3.00 (m, 1H), 2.20-2.24 (m, 2H), 1.83-1.96 (m, 4H).

Step 4

To a solution of compound 22-4 (0.47 g, 2 mmol) in THF (10 mL) at −78° C. was added LiHMDS (3 mL, 3 mmol, 1M in THF) dropwise under N₂. After 30 min, 1,2-dimethyldisulfide (0.23 g, 2.4 mmol) in THF (2 mL) was added dropwise. The mixture was stirred at −78° C. for 2 h, quenched with H₂O, and then extracted with EtOAc. The combined organic extracts were washed with brine, dried over Na₂SO₄, and concentrated. The residue was purified by silica gel chromatography (PE: EA=5:1) to give 0.5 g of compound 22-5. ¹H NMR (400 MHz, CDCl₃): δ 7.23-7.27 (m, 2H), 6.88 (d, J=8.4 Hz, 2H), 4.41 (d, J=4.8 Hz, 2H), 3.79 (s, 3H), 2.47-2.69 (m, 2H), 2.27-2.32 (m, 3H), 1.83-2.18 (m, 4H).

Step 5

To a solution of compound 22-5 (0.5 g, 1.8 mmol) in MeOH (5 mL) and H₂O (5 mL) at 0° C. was added oxone (1.1 g, 7.2 mmol) in portions. The solution was stirred at rt for 4 h and then diluted with EtOAc. The layers were separated; the aqueous layer was extracted with EtOAc. The combined extracts were washed with water and brine, dried over Na₂SO₄, and concentrated. The residue was purified by silica gel chromatography (PE: EA=3:1) to give 0.48 g of compound 22-6. ¹H NMR (400 MHz, CDCl₃): δ 7.21-7.27 (m, 2H), 6.85-6.88 (m, 2H), 4.38-4.49 (m, 2H), 3.78 (s, 3H), 3.09-3.11 (m, 3H), 1.83-2.64 (m, 6H).

Step 6

To a solution of compound 22-6 (300 mg, 1.0 mmol) in THF (10 mL) at −78° C. was added n-BuLi (0.4 mL, 1.0 mmol, 2.5 M in hexane) under N₂ and the resulting mixture was stirred at −78° C. for 1 h. A solution of compound 3 (290 mg, 1 mmol) in THF (5 mL) was added and the mixture was stirred at −78° C. for 3 h. The reaction was quenched with aq. NH₄Cl solution, and the mixture was extracted with EtOAc. The combined extracts were washed with water and brine, dried over Na₂SO₄, and concentrated. The residue was purified by silica gel chromatography (PE: EA=3:1) to give 300 mg of compound 22-7. LCMS (conditions F5): m/e=596 (M+H), $t_R$=1.26 min, 1.30 min (two resolved isomers during LC run). ¹H NMR (400 MHz, CDCl₃): δ 8.51 (s, 1H), 8.30-8.32 (m, 1H), 7.35-7.41 (m, 1H), 7.21-7.26 (m, 2H), 6.84-6.88 (m, 2H), 4.06-4.45 (m, 7H), 3.76 (s, 3H), 2.41-2.64 (m, 4H), 1.32 (s, 12H).

Step 7

To a solution of compound 22-7 (1.7 g, 2.9 mmol) in DCM (20 mL) was added 4 N HCl in dioxane (2 mL) at 0° C. The resulting mixture was stirred at 25° C. for 1 h and concentrated. The residue was diluted with aq. NaHCO₃, and the mixture was extracted with DCM. The combined extracts were dried over Na₂SO₄ and concentrated to give 1.2 g of compound 22-8. LCMS (conditions F5): m/e=492 (M+H), $t_R$=0.93 min.

Step 8

A suspension of compound 22-8 (3 g, 6.1 mmol) and CuCl (0.92 g, 9.2 mmol) in EtOH (100 mL) was stirred at 80° C. for 6 h, and then the reaction mixture was filtered. The filtrate was concentrated to afford 2.4 g of compound 22-9. LCMS (conditions F5): m/e=492 (M+H), $t_R$=1.01 min.

Step 9

To a solution of compound 22-9 (0.7 g, 1.4 mmol) and DIEA (0.36 g, 2.8 mmol) in MeOH (10 mL) at 0° C. was added Boc₂O (0.46 g, 2 mmol). The resulting mixture was stirred at RT for 6 h and concentrated. The residue was subjected to silica gel chromatography (PE: EA=5:1) to afford two separated isomeric samples, compound 22-10a (0.5 g) and compound 22-10b (0.2 g). LCMS (conditions F5): m/e=592 (M+H), $t_R$=1.22 min; same result for both isomeric samples.

Step 10

A solution of compound 22-10a (0.5 g, 0.85 mmol) and Pd/C (100 mg) in EtOH (10 mL) was stirred at rt under $H_2$ atmosphere (25 psi) for 4 h. The mixture was filtered, and the filtrate was concentrated to give 0.42 g of compound 22-11a. LCMS (conditions F5): m/e=562 (M+H), $t_R$=1.01 min.

Compound 22-11b (0.4 g) was synthesized similarly from compound 22-10b. LCMS (conditions F5): m/e=562 (M+H), $t_R$=1.02 min.

Step 11

To a solution of compound 22-11a (0.1 g, 0.18 mmol), 5-fluoropicolinic acid (28 mg, 0.2 mmol) and DIEA (45 mg, 0.36 mmol) in THF (5 mL) was added T3P (81 mg, 0.26 mmol, 50% in EtOAc) at 0° C. under $N_2$. The resulting solution was stirred at 0° C. for 30 min followed by an additional 16 h at RT. Water was added to the reaction, and the mixture was stirred at RT for 10 min. The aqueous layer was separated and extracted with EtOAc. The organic extracts were washed with brine, dried over $Na_2SO_4$, filtered and concentrated. The residue was purified by silica gel chromatography (PE: EA=3:1) to give 70 mg of compound 22-12a. LCMS (conditions F5): m/e=685 (M+H), $t_R$=1.23 min. Compound 22-12b (70 mg) was synthesized similarly from compound 22-11b. LCMS (conditions F5): m/e=685 (M+H), $t_R$=1.32 min.

Step 12

To a solution of compound 22-12a (70 mg, 0.1 mmol) in DCM (5 mL) was added TFA (0.5 mL) at 0° C. The solution was stirred at RT for 4 h, then concentrated. The residue was purified by prep RP-HPLC (column 150×30 mm, 5 μm; mobile phases A=water with 0.075% v/v TFA, B=MeCN; gradient 4-34% B, 14 min, 35 mL/min) to give Example 76a (isomeric sample 1). LCMS (conditions F3): $t_R$=2.04 min, m/e=465 (M+H). $^1$H NMR (400 MHz, $CD_3OD$): δ 8.60 (s, 1H), 8.26-8.29 (m, 1H), 7.90-7.93 (m, 1H), 7.78-7.84 (m, 2H), 7.19-7.24 (m, 1H), 4.62 (s, 1H), 4.11-4.24 (m, 2H), 2.80-2.85 (m, 1H), 2.56-2.66 (m, 2H), 2.33-2.38 (m, 1H), 2.08-2.10 (m, 1H), 1.97-2.00 (m, 4H).

Example 76b (isomeric sample 2), was synthesized similarly from compound 22-12b. LCMS (conditions F3): $t_R$=2.05 min, m/e=465 (M+H). $^1$H NMR (400 MHz, $CD_3OD$): δ 8.61 (s, 1H), 8.27-8.31 (m, 1H), 8.13-8.153 (m, 1H), 7.90-7.94 (m, 1H), 7.80-7.85 (m, 2H), 7.27-7.33 (m, 1H), 4.67 (t, J=3.2 Hz, 1H), 4.18 (d, J=15.6 Hz, 1H), 4.02 (d, J=15.6 Hz, 1H), 2.76-2.87 (m, 2H), 2.55-2.64 (m, 1H), 2.36-2.40 (m, 1H), 2.16 (s, 3H), 1.99-2.11 (m, 2H).

Data for the Examples made in Methods 21 and 22 are summarized in Table 15.

TABLE 15

| Example no. | Example | Expected M + H | Observed M + H | $t_R$ (min) | LCMS method | BACE1 $K_i$ (nM) |
|---|---|---|---|---|---|---|
| 74 | | 451 | 451 | 2.21 | F2 | 21.8 |
| 75 | | 451 | 451 | 2.24 | F2 | 12.5 |
| 76a (isomeric sample 1) | | 465 | 465 | 2.04 | F3 | 9.3 |

TABLE 15-continued

| Example no. | Example | Expected M + H | Observed M + H | $t_R$ (min) | LCMS method | BACE1 $K_i$ (nM) |
|---|---|---|---|---|---|---|
| 76b (isomeric sample 2) | | 465 | 465 | 2.05 | F3 | 104.4 |

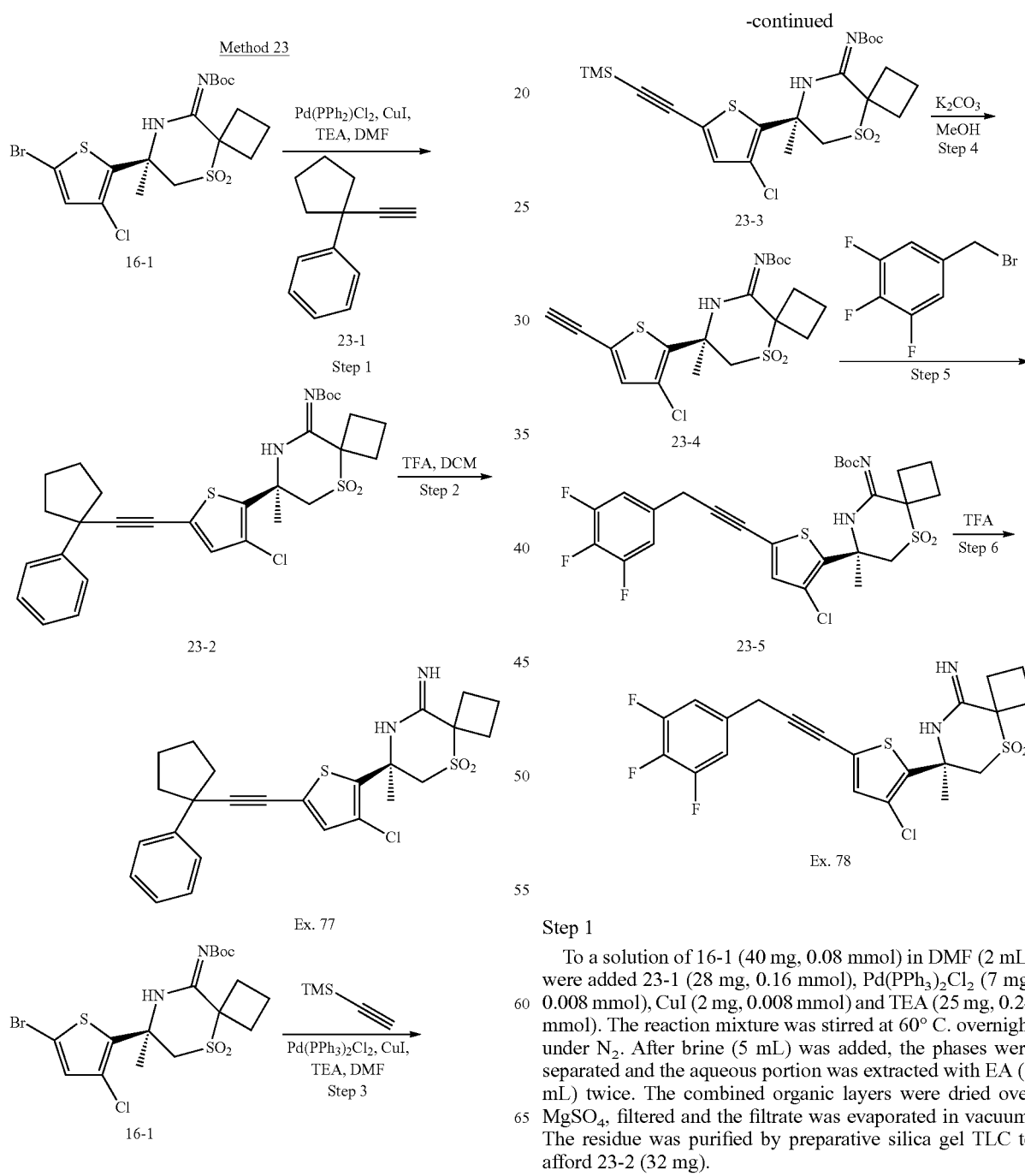

Step 1

To a solution of 16-1 (40 mg, 0.08 mmol) in DMF (2 mL) were added 23-1 (28 mg, 0.16 mmol), Pd(PPh$_3$)$_2$Cl$_2$ (7 mg, 0.008 mmol), CuI (2 mg, 0.008 mmol) and TEA (25 mg, 0.24 mmol). The reaction mixture was stirred at 60° C. overnight under N$_2$. After brine (5 mL) was added, the phases were separated and the aqueous portion was extracted with EA (5 mL) twice. The combined organic layers were dried over MgSO$_4$, filtered and the filtrate was evaporated in vacuum. The residue was purified by preparative silica gel TLC to afford 23-2 (32 mg).

Step 2

A solution of 23-2 (32 mg, 0.55 mmol) in TFA (1 mL) and DCM (2 mL) was stirred at room temperature for 3 h. The mixture was concentrated and purified by preparative RP-HPLC (column C18 250×21.2 mm, 4 μm; mobile phases A=water with 0.1% v/v TFA, B=MeCN; gradient 42-72% B, 0-10 min; 100% B, 10.5-12.5 min; 5% B, β-15 min, 35 mL/min) to afford Example 77 (10.6 mg). $^1$H NMR (CDCl$_3$, 400 MHz) δ 11.41 (br s, 1H), 8.20 (br s, 1H), 7.40-7.42 (m, 2H), 7.24-7.28 (m, 2H), 7.15-7.17 (m, 1H), 6.87 (s, 1H), 3.93 (d, J=15.2 Hz, 1H), 3.42 (d, J=15.2 Hz, 1H), 2.93-3.00 (m, 2H), 2.61-2.86 (m, 4H), 2.20-2.28 (m, 4H), 2.01 (s, 3H), 1.89-1.98 (m, 2H), 1.76-1.80 (m, 2H). LCMS (conditions F4): $t_R$=2.20 min, m/e=487 (M+H).

Step 3

To a solution of 16-1 (500 mg, 1.257 mmol) in DMF (10 mL) were added ethynyl-trimethyl-silane (185 mg, 1.89 mmol), Pd(PPh$_3$)$_2$Cl$_2$ (88 mg, 0.126 mmol), TEA (382 mg, 3.77 mmol) and CuI (24 mg, 0.126 mmol), the mixture was stirred at 80° C. for 3 h. After brine (50 mL) was added, the phases were separated and the aqueous layer was extracted with EA (50 mL) twice. The combined organic layers were washed with brine and dried over MgSO$_4$, filtered, and the filtrate was evaporated. The residue was purified by prep silica gel TLC to afford compound 23-3 (310 mg).

Step 4

To a solution of 23-3 (310 mg, 0.602 mmol) in MeOH (5 mL) was added K$_2$CO$_3$ (249 mg, 1.806 mmol), and the mixture was stirred at room temperature for 3 h. The mixture was concentrated under reduced pressure. Water (20 mL) was added and the mixture was extracted with EA. The combined organic layers were washed with brine and dried over MgSO$_4$, filtered and the filtrate was evaporated to afford 23-4 without further purification. (230 mg)

Step 5

To a solution of 23-4 (30 mg, 0.068 mmol) in acetone (1 mL) were added 3,4,5-trifluorobenzylbromide (15 mg, 0.068 mmol) and K$_2$CO$_3$ (19 mg, 0.136 mmol). The mixture was stirred at 100° C. for 3 h and then concentrated under reduced pressure. Water (5 mL) was added and the mixture was extracted with EA. The combined organic layers were washed with brine, dried over MgSO$_4$, filtered, and the filtrate was concentrated under reduced pressure. The residue was purified by preparative RP-HPLC (column C18 250×21.2 mm, 4 μm; mobile phases A=water with 0.1% v/v TFA, B=MeCN; gradient 42-72% B, 0-10 min; 100% B, 10.5-12.5 min; 5% B, β-15 min, 35 mL/min) to afford compound 23-5 (22 mg).

Step 6

To a solution of 23-5 (22 mg, 0.037 mmol) in DCM (2 mL) was added TFA (1 mL), and the mixture was stirred at room temperature for 2 h. The mixture was concentrated and the residue was purified by preparative RP-HPLC (column C18 250×21.2 mm, 4 μm; mobile phases A=water with 0.1% v/v TFA, B=MeCN; gradient 44-74% B, 0-10 min; 100% B, 10.5-12.5 min; 5% B, β-15 min, 35 mL/min) to afford Example 78 (5 mg). LCMS (conditions F3): $t_R$=2.97, m/e=487 (M+H).

Following the procedures described in Method 23 steps 1 and 2, Examples 77 to 77d in Table 16 were synthesized from 16-1 using the appropriate alkynes in step 2. Example 78 was synthesized as described in steps 3-6.

TABLE 16

| Example no. | Example | Expected M + H | Observed M + H | $t_R$ (min) | LCMS method | BACE1 $K_i$ (nM) |
|---|---|---|---|---|---|---|
| 77 | 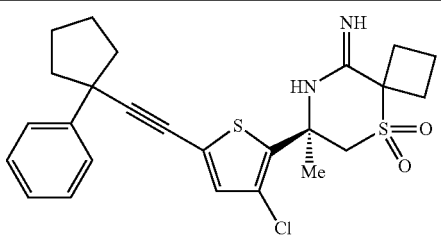 | 487 | 487 | 2.20 | F4 | 2552 |
| 77a | 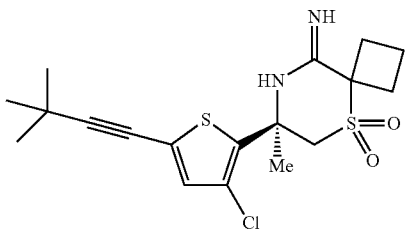 [SMILES: CC(C)(C)C#Cc1cc(Cl)c([C@]2(C)CS(=O)(=O)C3(CCC3)C(=N)N2)s1] | 399 | 399 | 2.29 | F3 | 165.4 |
| 77b | 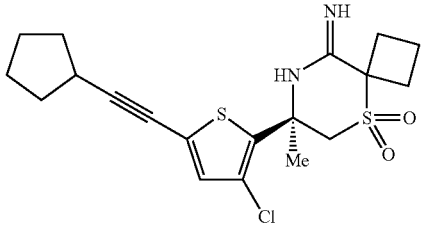 [SMILES: C[C@@]1(c2sc(C#CC3CCCC3)cc2Cl)CS(=O)(=O)C2(CCC2)C(=N)N1] | 411 | 411 | 2.36 | F3 | 109.9 |

TABLE 16-continued

| Example no. | Example | Expected M + H | Observed M + H | $t_R$ (min) | LCMS method | BACE1 $K_i$ (nM) |
|---|---|---|---|---|---|---|
| 77c | (structure) | 464 | 464 | 2.97 | F1 | 104.7 |
| 77d | (structure) | 442 | 442 | 2.52 | F1 | 2362 |
| 78 | (structure) | 487 | 487 | 2.97 | F3 | 17% Inh. at 10 μM |

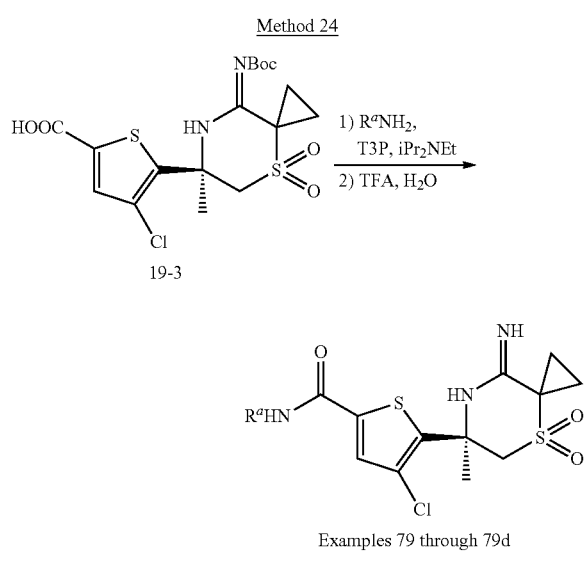

Examples 79 through 79d

Parallel preparation of Examples 79 through 79d: A set of 2-dram vials were each charged with an individual requisite amine ($R^aNH_2$, 0.069 mmol). To each vial was added a solution of 19-3 (26 mg, 0.058 mmol) and $iPr_2NEt$ (0.025 mL, 0.15 mmol) in $CH_2Cl_2$ (1 mL) followed by T3P (50% wt in EtOAc, 0.055 mL, 0.092 mmol). The resultant mixtures were stirred at RT overnight. After that time, additional T3P (50% wt in EtOAc, 0.055 mL, 0.092 mmol) and $iPr_2NEt$ (0.025 mL, 0.15 mmol) were added to each vial. The mixtures were stirred at RT for an additional 24 hours. To each vial was then added water (0.050 mL) and TFA (0.50 mL). The mixtures were stirred at RT for 2 hours. The mixtures were then concentrated in vacuo (max temp=40° C.). Each crude product was re-dissolved in 1 mL of DMSO and filtered. The crude products were purified by mass triggered HPLC (Waters XBridge C18 column, 5 μm, 19×100 mm, gradient ranges from 10-15% initial to 50-55% final MeCN (0.1% $NH_4OH$) in water (0.1% $NH_4OH$) 50 mL/min, 8 min run time) to afford Examples 79 through 79d.

TABLE 17
| Example no. | Example | Expected M+H | Observed M+H | $t_R$ (min) | LCMS method | BACE1 $K_i$ (nM) |
|---|---|---|---|---|---|---|
| 79 | | 453 | 453 | 0.95 | E | 88 |
| 79a | | 455 | 455 | 0.90 | E | 74 |
| 79b | | 459 | 459 | 0.93 | E | 17 |
| 79c | | 443 | 443 | 0.90 | E | 227 |
| 79d | | 439 | 439 | 0.86 | E | 30 |
Method 25
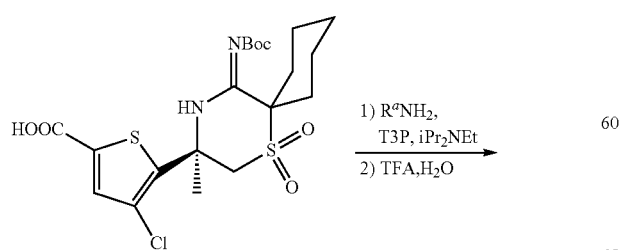
17-3
-continued
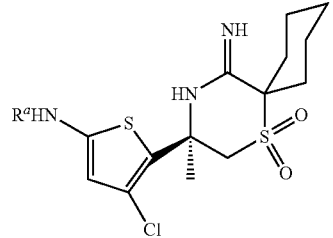
Examples 80 through 80m Parallel preparation of Examples 80 through 80m: A set of 2-dram vials were each charged with an individual requisite amine (R$^a$NH$_2$, 0.073 mmol) To each vial was added a solution of 17-3 (30 mg, 0.061 mmol) and iPr$_2$NEt (0.026 mL, 0.15 mmol) in CH$_2$Cl$_2$ (1 mL) followed by T3P (50% wt in EtOAc, 0.055 mL, 0.092 mmol). The resultant mixtures were stirred at RT overnight. To each vial was then added water (0.050 mL) and TFA (0.50 mL). The mixtures were stirred at RT for 2 hours. The mixtures were then concentrated in vacuo (max temp=40° C.). Each crude product was re-dissolved in 1 mL of DMSO and filtered. The crude products were purified by mass triggered HPLC (Waters XBridge C18 column, 5 μm, 19×100 mm, gradient ranges from 15-35% initial to 55-75% final MeCN (0.1% NH$_{40}$H) in water (0.1% NH$_{40}$H) 50 mL/min, 8 min run time) to afford Examples 80 through 80m.

TABLE 18

| Example no. | Example | Expected M + H | Observed M + H | $t_R$ (min) | LCMS method | BACE1 $K_i$ (nM) |
|---|---|---|---|---|---|---|
| 80 | | 471 | 471.08 | 0.81 | E | 249 |
| 80a | | 488 | 488.06 | 0.86 | E | 144 |
| 80b | | 520 | 520.12 | 0.86 | E | 41 |
| 80c | | 482 | 482.1 | 0.74 | E | 4154 |
| 80d | | 439 | 498.1 | 0.99 | E | 5116 |

TABLE 18-continued

| Example no. | Example | Expected M + H | Observed M + H | $t_R$ (min) | LCMS method | BACE1 $K_i$ (nM) |
|---|---|---|---|---|---|---|
| 80e | | 498 | 498.1 | 0.99 | E | 588 |
| 80f | | 505 | 505.11 | 0.93 | E | 851 |
| 80g | | 481 | 481.11 | 0.88 | E | 2156 |
| 80h | | 482 | 482.1 | 0.79 | E | 32% Inh. at 10 μM |
| 80i | | 520 | 520.1 | 1.06 | E | 6048 |

TABLE 18-continued

| Example no. | Example | Expected M + H | Observed M + H | $t_R$ (min) | LCMS method | BACE1 $K_i$ (nM) |
|---|---|---|---|---|---|---|
| 80j | | 470 | 470.1 | 0.82 | E | 2009 |
| 80k | | 487 | 487.06 | 0.84 | E | 121 |
| 80l | | 497 | 497.1 | 1.03 | E | 207 |
| 80m | | 495 | 495.12 | 1.07 | E | 717 |

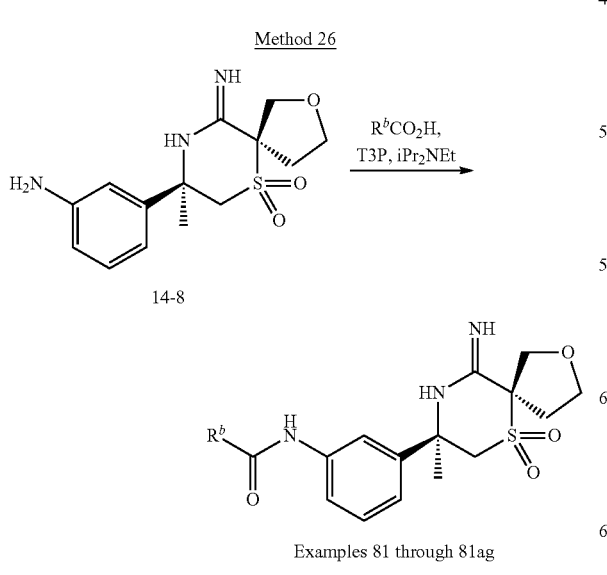

Parallel preparation of Examples 81 through 81ag. A set of 2-dram vials were each charged with an individual requisite carboxylic acid ($R^bCO_2H$, 0.092 mmol) To each vial was added a solution of 14-8 (25 mg, 0.076 mmol) and iPr$_2$NEt (0.030 mL, 0.23 mmol) in CH$_2$Cl$_2$ (1 mL) followed by T3P (50% wt in EtOAc, 0.055 mL, 0.093 mmol). The resultant mixtures were stirred at RT overnight. To each vial was then added water (0.050 mL). The mixtures were then concentrated in vacuo (max temp=40° C.). Each crude product was re-dissolved in 1 mL of DMSO and filtered. The crude products for Ex. 81 through 81r were purified by mass triggered HPLC (Waters XBridge C18 column, 5 μm, 19×100 mm, gradient ranges from 10-15% initial to 35-55% final MeCN (0.1% NH$_{40}$H) in water (0.1% NH$_{40}$H) 50 mL/min, 8 min run time) to afford Examples 81 through 81m. Examples 81n through 81r were re-purified by mass triggered HPLC using the following conditions: Waters Sunfire C18 column, 5 μm, 19×100 mm, gradient elution range of 5% initial to 25-50% final MeCN (0.1% formic acid) in water (0.1% formic acid) 50 mL/min, 8 min run time. Examples 81s through 81ag were purified by mass triggered HPLC using the following conditions: Waters Sunfire C18 column, 5 μm, 19×100 mm, gradient elution range of 10-27% initial to 20-62% final MeCN (0.1% formic acid) in water (0.1% formic acid) 25 mL/min, 8 min run time.

TABLE 19

| Example no. | Example | Expected M + H | Observed M + H | $t_R$ (min) | LCMS method | BACE1 $K_i$ (nM) |
|---|---|---|---|---|---|---|
| 81 | | 396 | 396 | 0.69 | E | 5166 |
| 81a | | 414 | 414 | 0.70 | E | 4148 |
| 81b | | 423 | 423 | 0.67 | E | 300 |
| 81c | | 423 | 423 | 0.64 | E | 180 |
| 81d | | 412 | 412 | 0.61 | E | 488 |
| 81e | | 410 | 410 | 0.72 | E | 998 |

TABLE 19-continued
| Example no. | Example | Expected M + H | Observed M + H | $t_R$ (min) | LCMS method | BACE1 $K_i$ (nM) |
| --- | --- | --- | --- | --- | --- | --- |
| 81f | 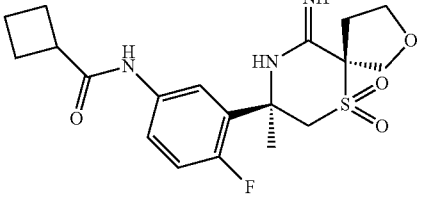 | 410 | 410 | 0.72 | E | 2080 |
| 81g | 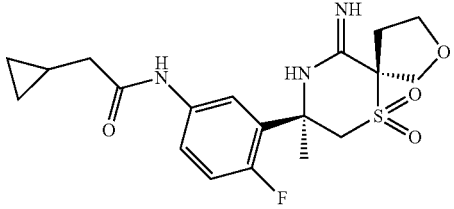 [SMILES: C[C@@]1(c2cc(NC(=O)CC3CC3)ccc2F)CS(=O)(=O)[C@]2(CCOC2)C(=N)N1] | 410 | 410 | 0.71 | E | 2960 |
| 81h | 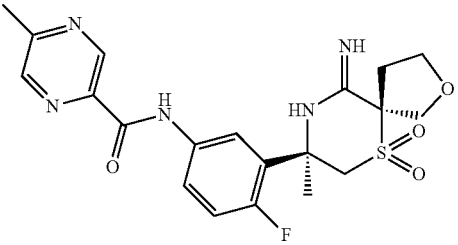 [SMILES: Cc1cnc(C(=O)Nc2ccc(F)c([C@]3(C)CS(=O)(=O)[C@]4(CCOC4)C(=N)N3)c2)cn1] | 448 | 448 | 0.71 | E | 108 |
| 81i | 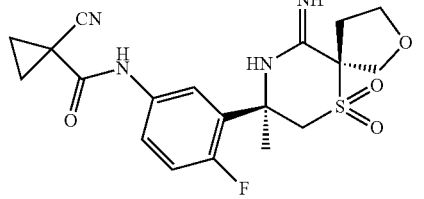 | 421 | 421 | 0.70 | E | 741 |
| 81j | 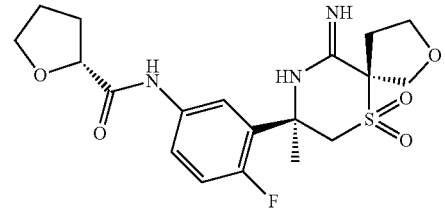 [SMILES: C[C@@]1(c2cc(NC(=O)[C@H]3CCCO3)ccc2F)CS(=O)(=O)[C@]2(CCOC2)C(=N)N1] | 426 | 426 | 0.67 | E | 1402 |
| 81k | 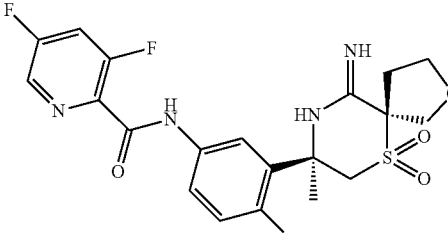 | 469 | 469 | 0.76 | E | 26 |

TABLE 19-continued
| Example no. | Example | Expected M + H | Observed M + H | $t_R$ (min) | LCMS method | BACE1 $K_i$ (nM) |
|---|---|---|---|---|---|---|
| 81l | 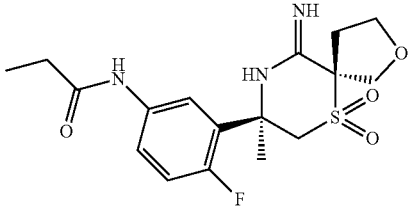 [SMILES: CCC(=O)Nc1ccc(F)c([C@]2(C)CS(=O)(=O)[C@]3(CCOC3)C(=N)N2)c1] | 384 | 384 | 0.63 | E | 949 |
| 81m | 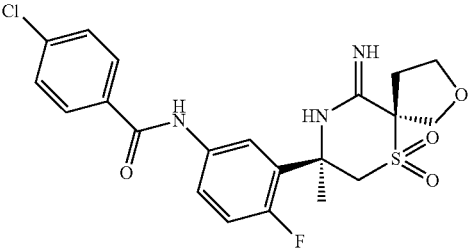 [SMILES: C[C@@]1(c2cc(NC(=O)c3ccc(Cl)cc3)ccc2F)CS(=O)(=O)[C@]2(CCOC2)C(=N)N1] | 466 | 466 | 0.87 | E | 82 |
| 81n | 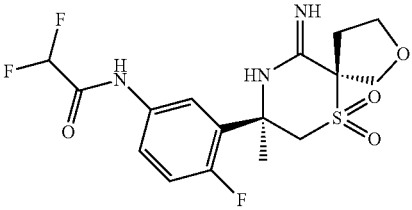 [SMILES: C[C@@]1(c2cc(NC(=O)C(F)F)ccc2F)CS(=O)(=O)[C@]2(CCOC2)C(=N)N1] | 406 | 406 | 0.67 | E | 639 |
| 81o | 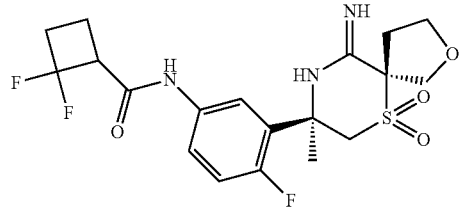 [SMILES: C[C@@]1(c2cc(NC(=O)C3CCC3(F)F)ccc2F)CS(=O)(=O)[C@]2(CCOC2)C(=N)N1] | 446 | 446 | 0.75 | E | 3709 |
| 81p | 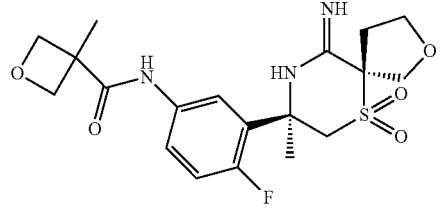 [SMILES: CC1(C(=O)Nc2ccc(F)c([C@]3(C)CS(=O)(=O)[C@]4(CCOC4)C(=N)N3)c2)COC1] | 426 | 426 | 0.62 | E | 4185 |
| 81q | 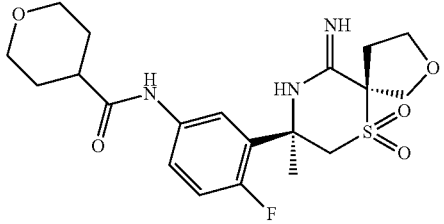 [SMILES: C[C@@]1(c2cc(NC(=O)C3CCOCC3)ccc2F)CS(=O)(=O)[C@]2(CCOC2)C(=N)N1] | 440 | 440 | 0.63 | E | 15% Inh. at 10 μM |

TABLE 19-continued
| Example no. | Example | Expected M + H | Observed M + H | $t_R$ (min) | LCMS method | BACE1 $K_i$ (nM) |
|---|---|---|---|---|---|---|
| 81r | 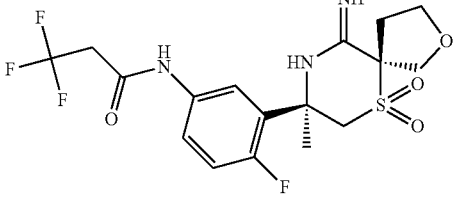 | 438 | 438 | 0.73 | E | 3169 |
| 81s | 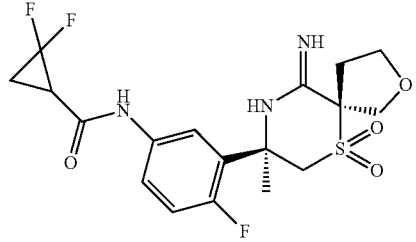 [SMILES: C[C@@]1(c2cc(NC(=O)C3CC3(F)F)ccc2F)CS(=O)(=O)[C@]2(CCOC2)C(=N)N1] | 432 | 432 | 0.72 | E | 1247 |
| 81t | 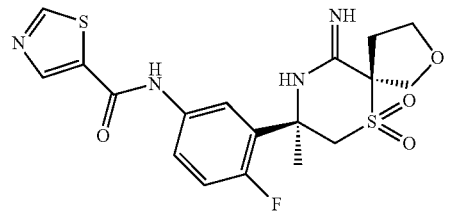 [SMILES: C[C@@]1(c2cc(NC(=O)c3cncs3)ccc2F)CS(=O)(=O)[C@]2(CCOC2)C(=N)N1] | 439 | 439 | 0.69 | E | 1945 |
| 81u | 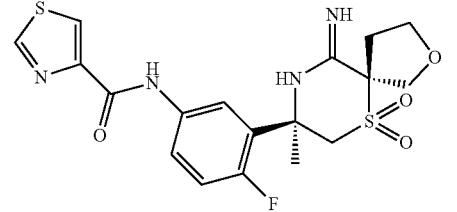 [SMILES: C[C@@]1(c2cc(NC(=O)c3cscn3)ccc2F)CS(=O)(=O)[C@]2(CCOC2)C(=N)N1] | 439 | 439 | 0.73 | E | 433 |
| 81v | 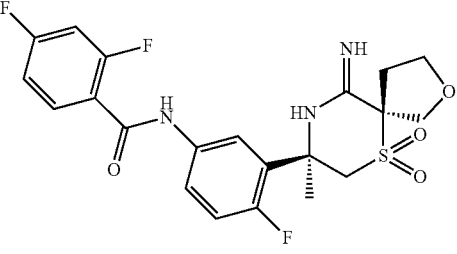 [SMILES: C[C@@]1(c2cc(NC(=O)c3ccc(F)cc3F)ccc2F)CS(=O)(=O)[C@]2(CCOC2)C(=N)N1] | 468 | 468 | 0.86 | E | 58% Inh. at 10 μM |
| 81w | 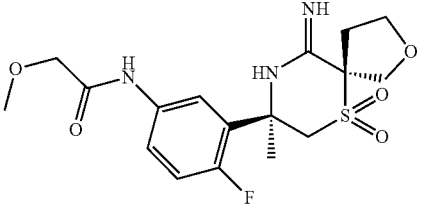 [SMILES: COCC(=O)Nc1ccc(F)c([C@]2(C)CS(=O)(=O)[C@]3(CCOC3)C(=N)N2)c1] | 400 | 400 | 0.66 | E | 429 |

TABLE 19-continued
| Example no. | Example | Expected M + H | Observed M + H | $t_R$ (min) | LCMS method | BACE1 $K_i$ (nM) |
|---|---|---|---|---|---|---|
| 81x | 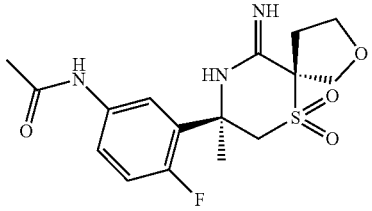 [SMILES: CC(=O)Nc1ccc(F)c([C@]2(C)CS(=O)(=O)[C@]3(CCOC3)C(=N)N2)c1] | 370 | 370 | 0.63 | E | 1522 |
| 81y | 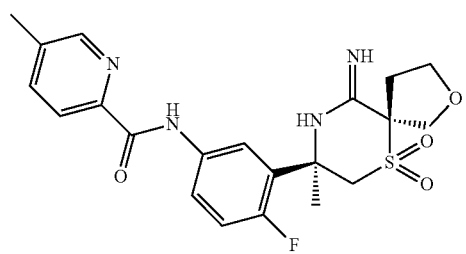 [SMILES: Cc1ccc(C(=O)Nc2ccc(F)c([C@]3(C)CS(=O)(=O)[C@]4(CCOC4)C(=N)N3)c2)nc1] | 447 | 447 | 0.87 | E | 41 |
| 81z | 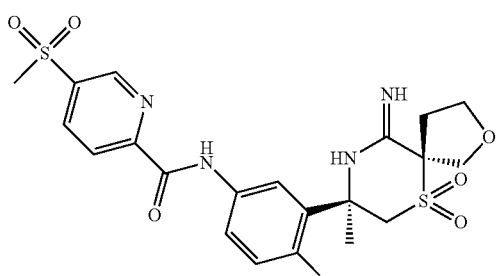 | 511 | 511 | 0.76 | E | 3166 |
| 81aa | 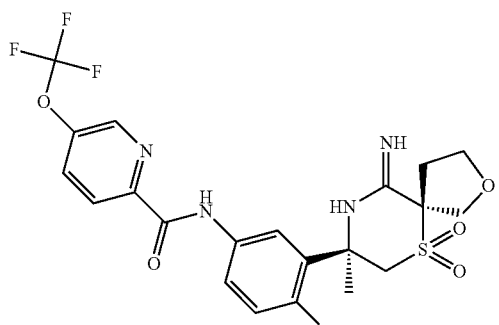 | 517 | 517 | 0.96 | E | 304 |
| 81ab | 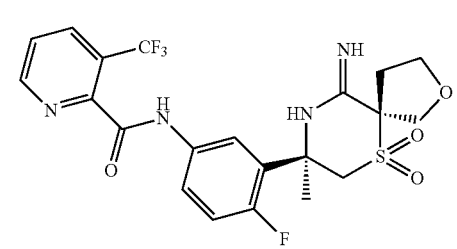 [SMILES: C[C@@]1(c2cc(NC(=O)c3ncccc3C(F)(F)F)ccc2F)CS(=O)(=O)[C@]2(CCOC2)C(=N)N1] | 501 | 501 | 0.85 | E | 146 |

TABLE 19-continued
| Example no. | Example | Expected M + H | Observed M + H | $t_R$ (min) | LCMS method | BACE1 $K_i$ (nM) |
|---|---|---|---|---|---|---|
| 81ac | 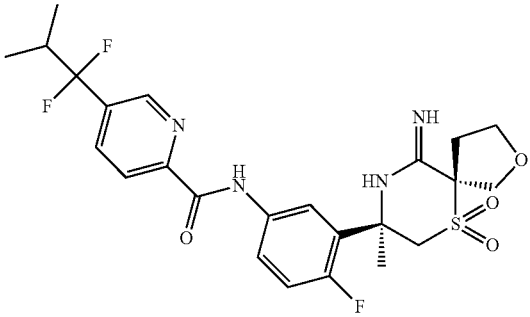 [SMILES: CC(C)C(F)(F)c1ccc(C(=O)Nc2ccc(F)c([C@]3(C)CS(=O)(=O)[C@]4(CCOC4)C(=N)N3)c2)nc1] | 525 | 525 | 1.02 | E | 35% Inh. at 10 μM |
| 81ad | 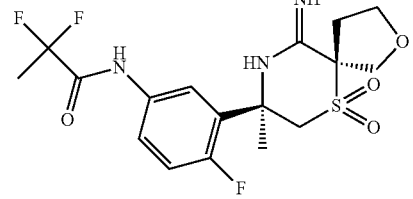 | 420 | 420 | 0.77 | E | 313 |
| 81ae | 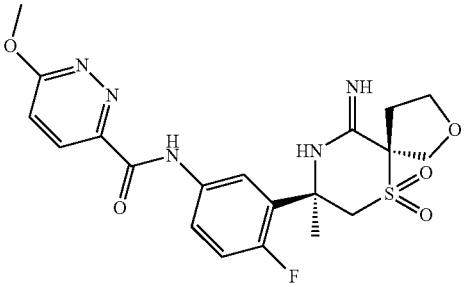 [SMILES: COc1ccc(C(=O)Nc2ccc(F)c([C@]3(C)CS(=O)(=O)[C@]4(CCOC4)C(=N)N3)c2)nn1] | 464 | 464 | 0.79 | E | 904 |
| 81af | 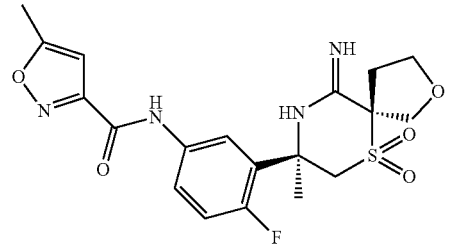 [SMILES: Cc1cc(C(=O)Nc2ccc(F)c([C@]3(C)CS(=O)(=O)[C@]4(CCOC4)C(=N)N3)c2)no1] | 437 | 437 | 0.74 | E | 1334 |
| 81ag | 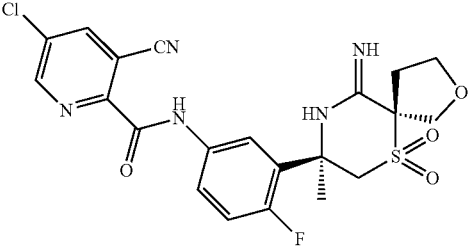 [SMILES: C[C@@]1(c2cc(NC(=O)c3ncc(Cl)cc3C#N)ccc2F)CS(=O)(=O)[C@]2(CCOC2)C(=N)N1] | 492 | 492 | 0.78 | E | 5.7 |

Method 27

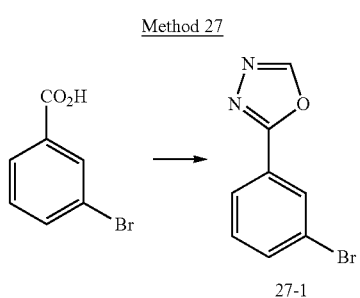 [SMILES: O=C(O)c1cccc(Br)c1 ; Brc1cccc(-c2nnco2)c1]

To 3-bromobenzoic acid (10.0 g, 49.7 mol) in EtOAc (166 mL) was added formic acid hydrazide (2.99 g, 49.7 mmol), TEA (20.8 mL, 149 mmol), and 1-propanephosphonic acid cyclic anhydride (50% solution in DMF, 74 mL, 124 mmol). The mixture was warmed to 80° C. and stirred for 12 h. After cooling, the mixture was added to water and then extracted with EtOAc. The combined organic layers were washed with water and brine, dried ($MgSO_4$), filtered, and concentrated in vacuo. The residue was purified by silica gel chromatography (0 to 30% EtOAc/hex) to provide 27-1 (8.33 g).

Method 27A

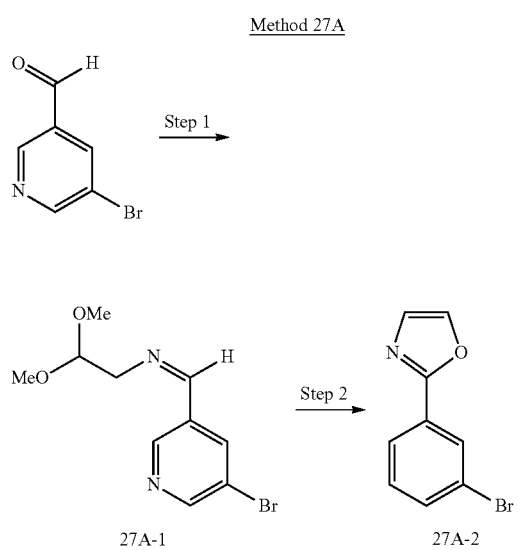 [SMILES: O=Cc1cncc(Br)c1 ; COC(C/N=C\c1cncc(Br)c1)OC ; Brc1cccc(-c2ncco2)c1]

Step 1:

To 5-bromonicotinaldehyde (1.5 g, 8.1 mmol) in toluene (80 mL) was added 2,2-dimethoxyethanamine (1.1 mL, 10 mmol). The mixture was warmed to reflux and water was removed using a Dean-Stark apparatus. After 2.5 h, the reaction was cooled and poured into EtOAc. The mixture was washed with water and brine, dried ($MgSO_4$), filtered, and concentrated in vacuo to provide 27A-1 (2.1 g).

Step 2:

To the imine 27A-1 prepared in step 1 (5.5 g, 20 mmol) cooled to 0° C. was added concentrated sulfuric acid (40 mL, 750 mmol) followed by phosphorous pentoxide (3.7 g, 26 mmol). The mixture was then warmed to 100° C. and stirred for 30 minutes. The cooled reaction mixture was poured onto ice and the pH was adjusted to ~pH 8 using concentrated $NH_4OH$. The resultant mixture was extracted with DCM. The combined organic layers were washed with water and brine, dried ($MgSO_4$), filtered, and concentrated in vacuo. The residue was purified by silica gel chromatography (0 to 30% EtOAc/hex) over 30 minutes to provide 27A-2 (2.3 g).

Method 28

To bromide 27-1 (5.0 g, 22.2 mmol) in DMSO (74 mL) was added bis(pinacolato)diboron (6.21 g, 24.4 mmol), and potassium acetate (6.54 g, 66.7 mmol). After nitrogen was bubbled through the reaction mixture for 5 minutes, [1,1'-bis(diphenylphosphino)ferrocene]-dichloropalladium(II) (0.813 g, 1.1 mmol) was added. Nitrogen was bubbled through the reaction mixture for another 5 minutes. The reaction mixture was then warmed to 80° C. and stirred for 16 h. After cooling, the mixture was diluted with water and EtOAc. The aqueous layer was separated and extracted twice with EtOAc. The combined organic layers were washed with water and brine, dried ($MgSO_4$), filtered, and concentrated in vacuo. The residue was purified by silica gel chromatography (0 to 40% EtOAc/hex) to provide boronate ester 28-1 (5.5 g).

Bromide 27A-2 in was converted to boronate ester 28-2 using conditions analogous to those described in Method 28

| Bromide | Boronate Ester |
|---|---|
| 27A-2 | 28-2 |

In addition to the examples listed above, compounds of the invention include those in Table A below:

TABLE A
| Compound | Expected M + H | Observed M + H | $t_R$ (min) | LCMS conditions | BACE1 inhibition | BACE2 inhibition |
|---|---|---|---|---|---|---|
| 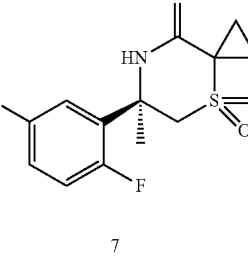 6 | 328 | 328 | 1.70 | A | | |
| 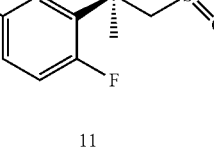 7 | 298 | 298 | 0.55 | A | $K_i$ = 4900 nM | $K_i$ = 1864 nM |
| 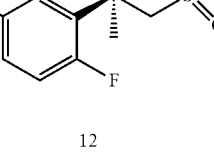 11 | 342 | 342 | 1.80 | A | $K_i$ = 3630 nM | $K_i$ = 3205 nM |
| 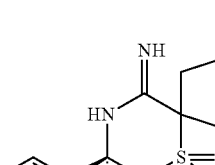 12 | 312 | 312 | 0.87 | A | 54% Inh. at 10 μM | $K_i$ = 3967 nM |
| 16 | 356 | 356 | 1.83 | A | 44% Inh. at 1 μM | $K_i$ = 734 nM |

TABLE A-continued

| Compound | Expected M + H | Observed M + H | $t_R$ (min) | LCMS conditions | BACE1 inhibition | BACE2 inhibition |
|---|---|---|---|---|---|---|
| 17 | 326 | 326 | 1.45 | A | $K_i$ = 4126 nM | $K_i$ = 1421 nM |
| 21 | 370 | 370 | 1.94 | A | | |
| 22 | 340 | 340 | 1.69 | A | 49% Inh. at 10 μM | $K_i$ = 2802 nM |
| 26 | 372 | 372 | 1.75 | A | | |
| 27 | 342 | 342 | 0.91 | A | $K_i$ = 7015 nM | $K_i$ = 3584 nM |

TABLE A-continued
| Compound | Expected M + H | Observed M + H | $t_R$ (min) | LCMS conditions | BACE1 inhibition | BACE2 inhibition |
|---|---|---|---|---|---|---|
| 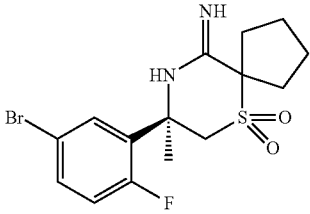<br>31 | 391 | 391 | 1.94 | A | 42% Inh. at 1 μM | $K_i$ = 935 nM |
| 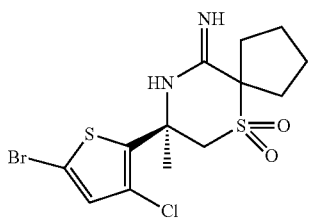<br>35 | 413 | 413 | 1.99 | A | $K_i$ = 447 nM | $K_i$ = 134 nM |
| 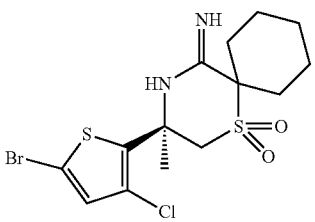<br>38 | 427 | 427 | 1.81 | A | $K_i$ = 2611 nM | $K_i$ = 715 nM |
| 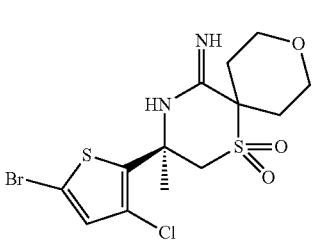<br>41 | 429 | 429 | 1.69 | A | $K_i$ = 2367 nM | $K_i$ = 1087 nM |
| 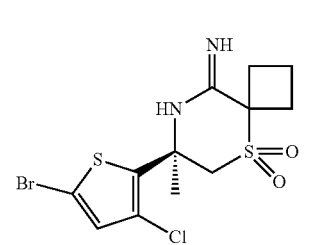<br>44 | 399 | 399 | 1.96 | A | $K_i$ = 1566 nM | $K_i$ = 531 nM |

TABLE A-continued

| Compound | Expected M + H | Observed M + H | $t_R$ (min) | LCMS conditions | BACE1 inhibition | BACE2 inhibition |
|---|---|---|---|---|---|---|
| 14-4 | 358 | 358 | 1.46 | A | $K_i$ = 6692 nM | $K_i$ = 2078 nM |
| 14-5 | 328 | 328 | 0.71 | A | 45% Inh. @ 10 µM | $K_i$ = 5106 nM |
| 14-7 | 358 | 358 | 1.23 | A | $K_i$ = 6120 nM | $K_i$ = 2669 nM |
| 14-8 | 328 | 328 | 0.60 | A | 38% Inh. at 10 µM | $K_i$ = 3818 nM |
| 15-3 | 385 | 385 | 1.40 | A | $K_i$ = 912 nM | $K_i$ = 465 nM |

LCMS Conditions

Conditions A:

Column: Agilent Zorbax SB-C18 (3.0×50 mm) 1.8 micron; Mobile phase: A: 0.05% Trifluoroacetic acid in water, B: 0.05% Trifluoroacetic acid in acetonitrile; Gradient: 90:10 (A:B) for 0.3 min, 90:10 to 5:95 (A:B) over 1.2 min, 5:95 (A:B) for 1.2 min, Flow rate: 1.0 mL/min; UV detection: 254 and 220 nm; Mass spectrometer: Agilent 6140 quadrupole.

Conditions B:
Column: Agilent Zorbax SB-C18 (3.0×50 mm) 1.8 micron; Column temp 50° C.; Mobile phase: A: 0.1% Trifluoroacetic acid in water, B: 0.1% Trifluoroacetic acid in acetonitrile; Gradient: 90:10 to 5:95 (A:B) over 1.5 min, 5:95 (A:B) for 1.2 min; Flow rate: 1.0 mL/min; UV detection: 254 and 220 nm; Mass spectrometer: Agilent 6140 quadrupole.

Conditions C:
Column: Agilent Zorbax SB-C18 (3.0×50 mm) 1.8 micron; Column temp 50° C.; Mobile phase: A: 0.05% Trifluoroacetic acid/0.5% Acetic acid in water; B: 0.05% Trifluoroacetic acid/0.5% Acetic acid in acetonitrile; Gradient: 90:10 to 5:95 (A:B) over 1.5 min, 5:95 (A:B) for 1.2 min; Flow rate: 1.0 mL/min; UV detection: 254 and 220 nm; Mass spectrometer: Agilent 6140 quadrupole.

Conditions D:
System: Waters Acquity UPLC/MS, Electrospray positive ion mode; Column: Waters Acquity UPLC BEH C18, 2.1×50 mm, 1.7 micron; Mobile Phase: A: H2O/0.05% TFA, B: ACN/0.05% TFA; Gradient: 0-1.8 min, 5-99% B; Flow Rate: 0.8 mL/min; UV: 254 nm Conditions E:
System: Waters Acquity UPLC/MS, Electrospray positive ion mode; Column: Waters Acquity UPLC BEH C18, 2.1×50 mm, 1.7 micron; Gradient elution 5:95 to 100:0 MeCN (0.1% $NH_{4OH}$): water (0.1% $NH_{4OH}$) over 1.4 min 0.8 mL/min; UV: 220 nm Conditions F1:
Column: Agilent TC-C18 (2.1×50 mm) 5 μm; Mobile phase: A: 0.0375% Trifluoroacetic acid in water, B: 0.01875% Trifluoroacetic acid in acetonitrile; Gradient: 100:0 (A:B) for 0.4 min, 100:0 to 20:80 (A:B) over 3 min, 20:80 to 0:100 (A:B) over 0.6 min; Flow rate: 0.6 mL/min; UV detection: 254 and 220 nm; Mass spectrometer: Agilent 6110 quadrupole.

Conditions F2:
Column: Agilent TC-C18 (2.1×50 mm) 5 μm; Mobile phase: A: 0.0375% Trifluoroacetic acid in water, B: 0.01875% Trifluoroacetic acid in acetonitrile; Gradient: 99:1 (A:B) for 0.4 min, 99:1 to 10:90 (A:B) over 3 min, 10:90 to 0:100 (A:B) over 0.6 min; Flow rate: 0.8 mL/min; UV detection: 254 and 220 nm; Mass spectrometer: Agilent 6110 quadrupole Conditions F3:
Column: Agilent TC-C18 (2.1×50 mm) 5 μm; Mobile phase: A: 0.0375% Trifluoroacetic acid in water, B: 0.01875% Trifluoroacetic acid in acetonitrile; Gradient: 90:10 (A:B) for 0.4 min, 90:10 to 0:100 (A:B) over 3 min, 0:100 (A:B) for 0.6 min; Flow rate: 0.8 mL/min; UV detection: 254 and 220 nm; Mass spectrometer: Agilent 6110 quadrupole.

Conditions F4:
Column: Xbridge RP 18 (2.1×50 mm) 5 μm; Mobile phase: A: 0.05% NH3 in water, B: 100% acetonitrile; Gradient: 95:5 (A:B) for 0.4 min, 95:5 to 10:90 (A:B) over 3 min, 10:90 to 0:100 (A:B) over 0.6 min; Flow rate: 0.8 mL/min; UV detection: 254 and 220 nm; Mass spectrometer: Agilent 6110 quadrupole Conditions F5:
Column: Xtimate C18 (2.1×30 mm) 3 μm; Mobile phase: A: 0.0375% Trifluoroacetic acid in water, B: 0.01875% Trifluoroacetic acid in acetonitrile; Gradient: 90:10 to 20:80 (A:B) over 0.9 min, 20:80 (A:B) for 0.6 min, 90:10 (A:B) for 0.5 min; Flow rate: 1.2 mL/min; UV detection: 254 and 220 nm; Mass spectrometer: Agilent 6110 quadrupole Assays
Protocols that used to determine the recited potency values for the compounds of the invention are described below.

BACE1 HTRF FRET Assay
Reagents
$Na^+$-Acetate pH 5.0; 1% Brij-35; Glycerol; Dimethyl Sulfoxide (DMSO); Recombinant human soluble BACE1 catalytic domain (>95% pure); APP Swedish mutant peptide substrate (QSY7-APP$^{swe}$-Eu): QSY7-EISEVNLDAEFC-Europium-amide.

A homogeneous time-resolved FRET assay can be used to determine $IC_{50}$ values for inhibitors of the soluble human BACE1 catalytic domain. This assay monitors the increase of 620 nm fluorescence that resulted from BACE1 cleavage of an APPswedish APP$^{swe}$ mutant peptide FRET substrate (QSY7-EISEVNLDAEFC-Europium-amide). This substrate contains an N-terminal QSY7 moiety that serves as a quencher of the C-terminal Europium fluorophore (620 nm Em). In the absence of enzyme activity, 620 nm fluorescence is low in the assay and increased linearly over 3 hours in the presence of uninhibited BACE1 enzyme Inhibition of BACE1 cleavage of the QSY7-APP$^{swe}$-Eu substrate by inhibitors is manifested as a suppression of 620 nm fluorescence.

Varying concentrations of inhibitors at 3× the final desired concentration in a volume of 10 ul are preincubated with purified human BACE1 catalytic domain (3 nM in 10 μl) for 30 minutes at 30° C. in reaction buffer containing 20 mM Na-Acetate pH 5.0, 10% glycerol, 0.1% Brij-35 and 7.5% DSMO. Reactions are initiated by addition of 10 μl of 600 nM QSY7-APP$^{swe}$-Eu substrate (200 nM final) to give a final reaction volume of 30 μl in a 384 well Nunc HTRF plate. The reactions are incubated at 30° C. for 1.5 hours. The 620 nm fluorescence is then read on a Rubystar HTRF plate reader (BMG Labtechnologies) using a 50 millisecond delay followed by a 400 millisecond acquisition time window Inhibitor $IC_{50}$ values are derived from non-linear regression analysis of concentration response curves. $K_i$ values are then calculated from $IC_{50}$ values using the Cheng-Prusoff equation using a previously determined μm value of 8 μM for the QSY7-APP$^{swe}$-Eu substrate at BACE1.

BACE-2 Assay
Inhibitor $IC_{50s}$ at purified human autoBACE-2 are determined in a time-resolved endpoint proteolysis assay that measures hydrolysis of the QSY7-EISEVNLDAEFC-Eu-amide FRET peptide substrate (BACE-HTRF assay). BACE-mediated hydrolysis of this peptide results in an increase in relative fluorescence (RFU) at 620 nm after excitation with 320 nm light Inhibitor compounds, prepared at 3× the desired final concentration in 1× BACE assay buffer (20 mM sodium acetate pH 5.0, 10% glycerol, 0.1% Brij-35) supplemented with 7.5% DMSO are pre-incubated with an equal volume of autoBACE-2 enzyme diluted in 1× BACE assay buffer (final enzyme concentration 1 nM) in black 384-well NUNC plates for 30 minutes at 30° C. The assay is initiated by addition of an equal volume of the QSY7-EISEVNLDAEFC-Eu-amide substrate (200 nM final concentration, $K_m$=8 μM for 4 μM for autoBACE-2) prepared in 1× BACE assay buffer supplemented with 7.5% DMSO and incubated for 90 minutes at 30° C. DMSO is present at 5% final concentration in the assay. Following laser excitation of sample wells at 320 nm, the fluorescence signal at 620 nm is collected for 400 ms following a 50 μs delay on a RUBYstar HTRF plate reader (BMG Labtechnologies). Raw RFU data is normalized to maximum (1.0 nM BACE/DMSO) and minimum (no enzyme/DMSO) RFU values. $IC_{50s}$ are determined by nonlinear regression analysis (sigmoidal dose response, variable slope) of percent inhibition data with minimum and maximum values set to 0 and 100 percent respectively. Similar $IC_{50s}$ are obtained when using raw RFU data. The $K_i$ values are calculated from the $IC_{50}$ using the Cheng-Prusoff equation.

With the exception of example 78, all of the example compounds shown in the tables that were tested for BACE2 exhibited BACE2 $K_i$ values of less than about 5.7 µM. With the exception of Examples 36, 38, 39, 39a, 39b, 47, 51, 56, 60, 62i, 62m, 63i, 63j, and 77d, all of the example compounds shown in the tables that were tested have a BACE2 $K_i$ value of less than 100 nM. Examples 27, 29, 32, 34, 43°, 46, 47a, 49, 50, 52, 54, 61a, 62d, 62j, 63, 63e, 63g, 65, 65a, 7, 76b, 77, 77b, and 79c, have a BACE2 $K_i$ value of less than about 50 nM. Examples 62e, 2, 10, 11, 16, 19, 20, 24, 26, 28, 35, 45, 57, 59, 61, 62, 62f, 62n, 62a, 62k, 63n, 63a, 63h, 63d, 77a, 78, 79a, 79, and 79d, have a BACE2 $K_i$ value of less than about 20 nM. Example compounds of the invention having a BACE2 $K_i$ value of less than about 5 nM are shown in the table below.

| Example | BACE2 $K_i$ (nM) |
| --- | --- |
| 1 | 0.4 |
| 3 | 0.9 |
| 4 | 0.5 |
| 5 | 1.9 |
| 6 | 1.9 |
| 8 | 4.2 |
| 9 | 2.5 |
| 12 | 0.3 |
| 13 | 0.3 |
| 14 | 2.1 |
| 15 | 0.6 |
| 17 | 1.5 |
| 18 | 0.8 |
| 21 | 1.3 |
| 22 | 4.3 |
| 23 | 3.1 |
| 25 | 4.4 |
| 30 | 2.1 |
| 31 | 1.2 |
| 33 | 1.6 |
| 35a | 1.4 |
| 42 | 3.4 |
| 44 | 2.0 |
| 48 | 2.0 |
| 58 | 1.0 |
| 62b | 4.3 |
| 62h | 2.8 |
| 62l | 2.2 |
| 62c | 1.8 |
| 62g | 0.9 |
| 63b | 2.7 |
| 63f | 1.5 |
| 63c | 1.3 |
| 64 | 1.0 |
| 74 | 3.8 |
| 75 | 1.7 |
| 76a | 2.4 |
| 79b | 4 |

We claim:

1. A compound, or a pharmaceutically acceptable salt thereof, said compound having the structural Formula (I):

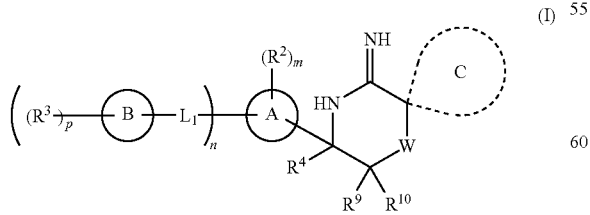

or a tautomer thereof, or a pharmaceutically acceptable salt of said tautomer, said tautomer thereof having the structural Formula (I'):

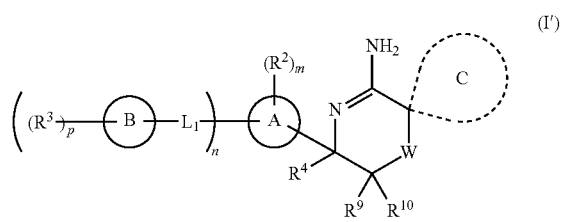

wherein:

W is selected from the group consisting of S, S(O), and $S(O)_2$;

ring C is selected from the group consisting of:

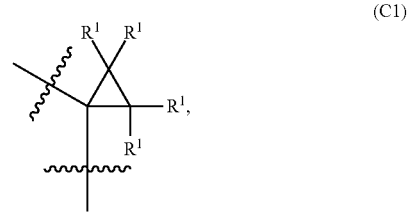

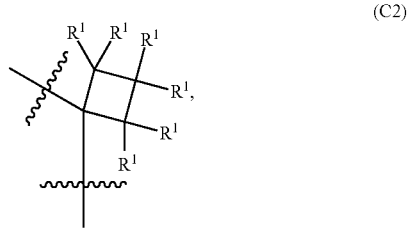

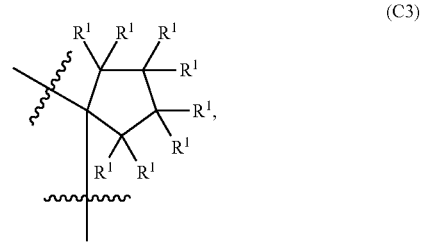

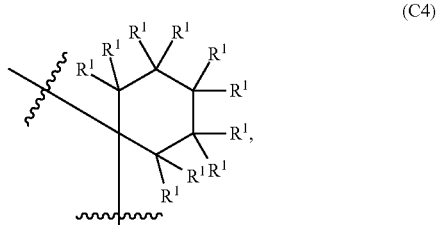

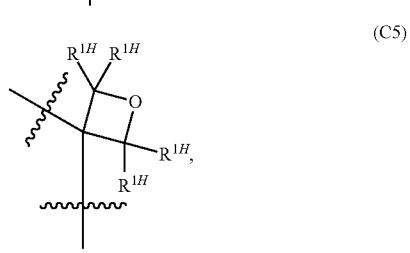

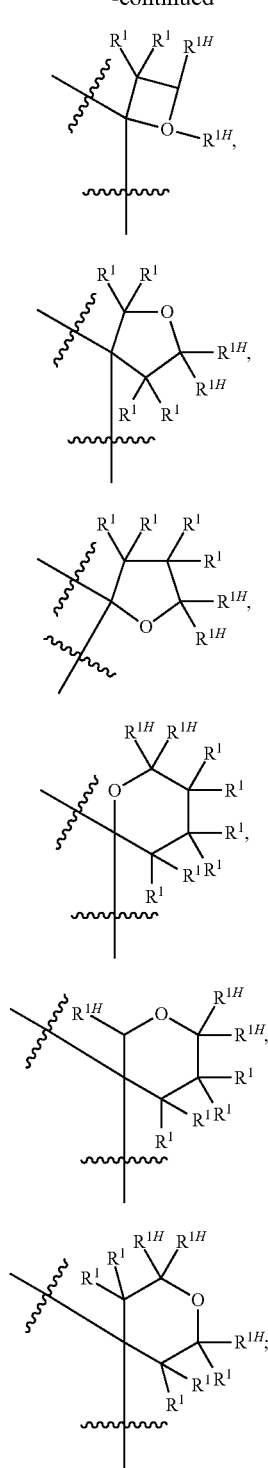

ring A is selected from the group consisting of aryl, monocyclic heteroaryl, monocyclic cycloalkyl, monocyclic cycloalkenyl, monocyclic heterocycloalkyl, monocyclic heterocycloalkenyl, and a multicyclic group;

ring B (when present) is independently selected from the group consisting of aryl, monocyclic heteroaryl, monocyclic cycloalkyl, monocyclic cycloalkenyl, monocyclic heterocycloalkyl, monocyclic heterocycloalkenyl, and a multicyclic group;

-$L_1$- (when present) independently represents a bond or a divalent moiety selected from the group consisting of -alkyl-, -haloalkyl-, -heteroalkyl-, -alkenyl-, -alkynyl-, —N($R^6$)—, —O—, —NHC(O)—, —C(O)NH—, NHS(O)$_2$—, —S(O)$_2$NH—, —O—CH$_2$—, —CH$_2$—O—, —NHCH$_2$—, —CH$_2$NH—, and —CH(CF$_3$)NH—, —NHCH(CF$_3$)—;

m, n, and p are each independently selected integers, wherein:
m is 0 or more;
n is 0 or 1; and
p is 0 or more,
wherein the maximum value of m is the maximum number of available substitutable hydrogen atoms on ring A, and
wherein the maximum value of p is the maximum number of available substitutable hydrogen atoms on ring B;

each $R^1$ (when present) is independently selected from the group consisting of: H, halogen, —OH, alkyl, alkoxy, -alkyl-OH, haloalkyl, haloalkoxy, heteroalkyl, haloheteroalkyl, cycloalkyl, -alkyl-cycloalkyl, —O-cycloalkyl, —O-alkyl-cycloalkyl, heterocycloalkyl, -alkyl-heterocycloalkyl, —O-heterocycloalkyl, and —O-alkyl-heterocycloalkyl,
wherein said cycloalkyl, -alkyl-cycloalkyl, —O-cycloalkyl, —O-alkyl-cycloalkyl, heterocycloalkyl, -alkyl-heterocycloalkyl, —O-heterocycloalkyl, and —O-alkyl-heterocycloalkyl is optionally substituted with halogen, alkyl, alkoxy, haloalkyl, haloalkoxy, heteroalkyl, haloheteroalkyl;

each $R^{1H}$ is independently selected from the group consisting of: H, alkyl, -alkyl-OH, haloalkyl, heteroalkyl, haloheteroalkyl, cycloalkyl, -alkyl-cycloalkyl, heterocycloalkyl, -alkyl-heterocycloalkyl,
wherein said cycloalkyl, -alkyl-cycloalkyl, heterocycloalkyl, and -alkyl-heterocycloalkyl is optionally substituted with halogen, alkyl, alkoxy, haloalkyl, haloalkoxy, heteroalkyl, haloheteroalkyl;

each $R^2$ (when present) is independently selected from the group consisting of: halogen, —OH, —CN, —SF$_5$, —OSF$_5$, —NO$_2$, —Si($R^5$)$_3$, —P(O)(O$R^5$)$_2$, —P(O)(O$R^5$)($R^5$), —N($R^6$)$_2$, —N$R^7$C(O)$R^6$, —N$R^7$S(O)$_2R^6$, —N$R^7$S(O)$_2$N($R^6$)$_2$, —N$R^7$C(O)N($R^6$)$_2$, —N$R^7$C(O)O$R^6$, —C(O)$R^6$, —C(O)$_2R^6$, —C(O)N($R^6$)$_2$, —S(O)$R^6$, —S(O)$_2R^6$, —S(O)$_2$N($R^6$)$_2$, —O$R^6$, —S$R^6$, alkyl, haloalkyl, heteroalkyl, alkenyl, alkynyl, cycloalkyl, -alkyl-cycloalkyl, aryl, -alkyl-aryl, heteroaryl, -alkyl-heteroaryl, heterocycloalkyl, and -alkyl-heterocycloalkyl,
wherein said alkyl, haloalkyl, heteroalkyl, alkenyl, alkynyl, cycloalkyl, -alkyl-cycloalkyl, aryl, -alkyl-aryl, heteroaryl, -alkyl-heteroaryl, heterocycloalkyl, and -alkyl-heterocycloalkyl of $R^2$ are each optionally unsubstituted or substituted with one or more groups independently selected from $R^8$;

each $R^3$ (when present) is independently selected from the group consisting of: halogen, —OH, —CN, —SF$_5$, —OSF$_5$, —NO$_2$, —Si($R^5$)$_3$, —P(O)(O$R^5$)$_2$, —P(O)(O$R^5$)($R^5$), —N($R^6$)$_2$, —N$R^7$C(O)$R^6$, —N$R^7$S(O)$_2R^6$, —N$R^7$S(O)$_2$N($R^6$)$_2$, —N$R^7$C(O)N($R^6$)$_2$, —N$R^7$C(O)O$R^6$, —C(O)$R^6$, —C(O)$_2R^6$, —C(O)N($R^6$)$_2$, —S(O)$R^6$, —S(O)$_2R^6$, —S(O)$_2$N($R^6$)$_2$, —O$R^6$, —S$R^6$, alkyl, haloalkyl, heteroalkyl, alkenyl, alkynyl, cycloalkyl, -alkyl-cycloalkyl, aryl, -alkyl-aryl, heteroaryl, -alkyl-heteroaryl, heterocycloalkyl, and -alkyl-heterocycloalkyl,
wherein said alkyl, haloalkyl, heteroalkyl, alkenyl, alkynyl, cycloalkyl, -alkyl-cycloalkyl, aryl, -alkyl-aryl, heteroaryl, -alkyl-heteroaryl, and heterocycloalkyl of $R^3$ are each optionally unsubstituted or substituted with one or more groups independently selected from $R^8$;

$R^4$ is selected from the group consisting of H, alkyl, haloalkyl, heteroalkyl, alkenyl, alkynyl, aryl, -alkyl-aryl, heteroaryl, -alkyl-heteroaryl, cycloalkyl, -alkyl-cycloalkyl, cycloalkenyl, -alkyl-cycloalkenyl, heterocycloalkyl, -alkyl-heterocycloalkyl, heterocycloalkenyl, and -alkyl-heterocycloalkenyl, wherein each of said alkyl, haloalkyl, heteroalkyl, aryl, -alkyl-aryl, heteroaryl, -alkyl-heteroaryl, cycloalkyl, -alkyl-cycloalkyl, cycloalkenyl, -alkyl-cycloalkenyl, heterocycloalkyl, -alkyl-heterocycloalkyl, heterocycloalkenyl, and -alkyl-heterocycloalkenyl of $R^4$ is unsubstituted or substituted with one or more independently selected $R^{11}$ groups;

each $R^5$ (when present) is independently selected from the group consisting of alkyl, heteroalkyl, haloalkyl, cycloalkyl, -alkyl-cycloalkyl, aryl, -alkyl-aryl, heteroaryl, and -alkyl-heteroaryl, wherein each said aryl, -alkyl-aryl, heteroaryl, and -alkyl-heteroaryl of $R^5$ is unsubstituted or substituted with one or more groups independently selected from halogen, alkyl, cycloalkyl, heteroalkyl, haloalkyl, alkoxy, —O-heteroalkyl, and haloalkoxy;

each $R^6$ (when present) is independently selected from the group consisting of H, alkyl, -alkyl-OH, alkenyl, alkynyl, heteroalkyl, -heteroalkyl-OH, haloalkyl, -haloalkyl-OH, cycloalkyl, lower alkyl-substituted cycloalkyl, lower alkyl-substituted -alkyl-cycloalkyl, heterocycloalkyl, -alkyl-heterocycloalkyl, aryl, -alkyl-aryl, heteroaryl, and -alkyl-heteroaryl, wherein each said heterocycloalkyl, -alkyl-heterocycloalkyl, aryl, -alkyl-aryl, heteroaryl, and said -alkyl-heteroaryl of $R^6$ is unsubstituted or substituted with one or more groups independently selected from halogen, —CN, alkyl, cycloalkyl, heteroalkyl, haloalkyl, alkoxy, —O-heteroalkyl, and haloalkoxy;

each $R^7$ (when present) is independently selected from the group consisting of H, alkyl, heteroalkyl, haloalkyl, cycloalkyl, -alkyl-cycloalkyl, aryl, -alkyl-aryl, heteroaryl, and -alkyl-heteroaryl, wherein each said aryl, -alkyl-aryl, heteroaryl, and -alkyl-heteroaryl of $R^7$ is unsubstituted or substituted with one or more groups independently selected from halogen, alkyl, cycloalkyl, heteroalkyl, haloalkyl, alkoxy, —O-heteroalkyl, and haloalkoxy;

each $R^8$ (when present) is independently selected from the group consisting of halogen, —OH, —CN, —$SF_5$, —$OSF_5$, alkyl, alkoxy, haloalkyl, haloalkoxy, cycloalkyl, -alkyl-cycloalkyl, —O-cycloalkyl, —O-alkyl-cycloalkyl, heteroalkyl, —O-heteroalkyl, and -alkyl-OH;

$R^9$ and $R^{10}$ are each independently selected from the group consisting of H, halogen, —CN, —$P(O)(OR^5)_2$, —$P(O)(OR^5)(R^5)$, —$NR^7C(O)R^6$, —$NR^7S(O)_2R^6$, —$NR^7C(O)N(R^6)_2$, —$NR^7C(O)OR^6$, —$C(O)R^6$, —$C(O)_2R^6$, —$C(O)N(R^6)_2$, —$S(O)R^6$, —$S(O)_2R^6$, —$S(O)_2N(R^6)_2$, —$OR^6$, —$SR^6$, alkyl, haloalkyl, heteroalkyl, alkenyl and alkynyl, wherein each of said alkyl, haloalkyl, heteroalkyl, alkenyl and alkynyl of $R^9$ and $R^{10}$ is unsubstituted or substituted with one or more independently selected $R^{12}$ groups;

each $R^{11}$ (when present) is independently selected from the group consisting of halogen, —OH, —CN, —$SF_5$, —$OSF_5$, —$P(O)(OR^5)_2$, —$P(O)(OR^5)(R^5)$, —$N(R^6)_2$, —$NR^7C(O)R^6$, —$NR^7S(O)_2R^6$, —$NR^7S(O)_2N(R^6)_2$, —$NR^7C(O)N(R^6)_2$, —$NR^7C(O)OR^6$, —$C(O)R^6$, —$C(O)_2R^6$, —$C(O)N(R^6)_2$, —$S(O)R^6$, —$S(O)_2R^6$, —$S(O)_2N(R^6)_2$, —$OR^6$, —$SR^6$, alkyl, haloalkyl, haloalkoxy, heteroalkyl, -alkyl-OH, cycloalkyl, -alkyl-cycloalkyl;

each $R^{12}$ (when present) is independently selected from the group consisting of halogen, —OH, —CN, —$SF_5$, —$OSF_5$, —$P(O)(OR^{13})_2$, —$P(O)(OR^{13})(R^{13})$, —$N(R^{14})_2$, —$NR^{14}C(O)R^{14}$, —$NR^{14}S(O)_2R^{14}$, —$NR^{14}S(O)_2N(R^{14})_2$, —$NR^{14}C(O)N(R^{14})_2$, —$NR$—$C(O)R^{14}$, —$C(O)_2R^{14}$, —$C(O)N(R^{14})_2$, —$S(O)R^{14}$, —$S(O)_2R^{14}$, —$S(O)_2N(R^{14})_2$, —$OR^{14}$, —$SR^{14}$, alkyl, haloalkyl, haloalkoxy, heteroalkyl, -alkyl-OH;

each $R^{13}$ (when present) is independently selected from the group consisting of alkyl, -alkyl-OH, alkenyl, alkynyl, heteroalkyl, -heteroalkyl-OH, haloalkyl, -haloalkyl-OH; and each $R^{14}$ (when present) is independently selected from the group consisting of H, alkyl, -alkyl-OH, alkenyl, alkynyl, heteroalkyl, -heteroalkyl-OH, haloalkyl, -haloalkyl-OH.

2. The compound of claim 1, or the tautomer thereof, or the pharmaceutically acceptable salt of said compound or said tautomer, wherein:
W is $S(O)_2$.

3. The compound of claim 2, or the tautomer thereof, or the pharmaceutically acceptable salt of said compound or said tautomer, wherein:
$R^1$ and $R^{1H}$ (when present) are each independently selected from the group consisting of H and OH.

4. The compound of claim 3, or the tautomer thereof, or the pharmaceutically acceptable salt of said compound or said tautomer, wherein:
$R^4$ is selected from the group consisting of lower alkyl and lower haloalkyl.

5. The compound of claim 4, or the tautomer thereof, or the pharmaceutically acceptable salt of said compound or said tautomer, wherein:
one of $R^9$ and $R^{10}$ is H and the other is selected from the group consisting of H, halogen, lower alkyl, lower haloalkyl, and lower alkyl ether.

6. The compound of claim 1, or the tautomer thereof, or the pharmaceutically acceptable salt of said compound or said tautomer, wherein:
$R^9$ and $R^{10}$ are each H.

7. The compound of claim 6, or the tautomer thereof, or the pharmaceutically acceptable salt of said compound or said tautomer, wherein:
n is 1 and the moiety has the form:

-$L_1$- is selected from the group consisting of -alkynyl-, —NHC(O)— and —C(O)NH—;

ring A is selected from the group consisting of phenyl, pyridyl, pyrazinyl, furanyl, thienyl, pyrimidinyl, pyridazinyl, thiazolyl, oxazolyl, imidazolyl, pyrazolyl, quinazolinyl, benzofuranyl, benzimidazolyl, benzoxazolyl, benzothiazolyl, benzothienyl, naphthyl, quinolyl, isoquinolyl, indazolyl, indolyl, thienopyridyl, and thienopyrazolyl;

m is 0, 1, 2, or 3;

each $R^2$ (when present) is independently selected from the group consisting of halogen, —CN, —SF$_5$, —OSF$_5$, —NO$_2$, —NH$_2$, —N(alkyl)$_2$, —NH(alkyl), —NHC(O)R$^6$, —NHS(O)$_2$R$^6$, —NHC(O)N(R$^6$)$_2$, —NHC(O)OR$^6$, —C(O)R$^6$, —C(O)$_2$R$^6$, —C(O)N(R$^6$)$_2$, —S(O)R$^6$, —S(O)$_2$R$^6$, —S(O)$_2$N(R$^6$)$_2$, —OR$^6$, —SR$^6$, lower alkyl, lower haloalkyl, lower heteroalkyl, lower alkenyl, lower alkynyl, phenyl, benzyl, lower cycloalkyl, —CH$_2$-(lower cycloalkyl), monocyclic heteroaryl, and —CH$_2$-(monocyclic heteroaryl), wherein said phenyl, benzyl, lower cycloalkyl, —CH$_2$-(lower cycloalkyl), monocyclic heteroaryl, and —CH$_2$-(monocyclic heteroaryl) of $R^2$ is unsubstituted or substituted with one or more groups independently selected from the group consisting of halogen, alkyl, heteroalkyl, haloalkyl, alkoxy, —O-cyclopropyl, —O-heteroalkyl, haloalkoxy, —CN, —SF$_5$, and —OSF$_5$;

ring B is selected from the group consisting of benzimidazolyl, benzofuranyl, benzoisothiazole, benzoisoxazole, benzothiazole, benzothiophenyl, benzoxazole, furanyl, cyclobutyl, cyclohexyl, cyclopentyl, cyclopropyl, imidazopyridyl, imidazothiazoyl, imidazothiadiazolyl, imidazolyl, indazolyl, indolyl, isothiazoyl, isoxazolopyridyl, isoxazolyl, morpholinoyl, oxadiazolyl, oxazolyl, oxetanyl, phenyl, pyrazinyl, pyrazolyl, pyridazinyl, pyridyl, pyrimidinyl, pyrrolyl, pyrrolopyridinyl, pyrrolopyrimidinyl, pyrazolopyridinyl, tetrahydrofuranyl, tetrahydropyranyl, thiadiazolyl, thiazolyl, thienyl, triazolyl;

p is 0, 1, 2, or 3; and each $R^3$ (when present) is independently selected from the group consisting of halogen, —CN, —SF$_5$, —OSF$_5$, —NO$_2$, —NH$_2$, —N(alkyl)$_2$, —NH(alkyl), —NHC(O)R$^6$, —NHS(O)$_2$R$^6$, —NHC(O)N(R$^6$)$_2$, —NHC(O)OR$^6$, —C(O)R$^6$, —C(O)$_2$R$^6$, —C(O)N(R$^6$)$_2$, —S(O)R$^6$, —S(O)$_2$R$^6$, —S(O)$_2$N(R$^6$)$_2$, —OR$^6$, —SR$^6$, lower alkyl, lower haloalkyl, lower heteroalkyl, lower alkenyl, lower alkynyl, phenyl, benzyl, lower cycloalkyl, —CH$_2$-(lower cycloalkyl), monocyclic heteroaryl, and —CH$_2$-(monocyclic heteroaryl), wherein said phenyl, benzyl, lower cycloalkyl, —CH$_2$-(lower cycloalkyl), monocyclic heteroaryl, and —CH$_2$-(monocyclic heteroaryl) of $R^3$ is unsubstituted or substituted with one or more groups independently selected from the group consisting of halogen, alkyl, heteroalkyl, haloalkyl, alkoxy, —O-cyclopropyl, —O-heteroalkyl, haloalkoxy, —CN, —SF$_5$, and —OSF$_5$.

8. The compound of claim 6, or the tautomer thereof, or the pharmaceutically acceptable salt of said compound or said tautomer, wherein:

n is 1;

-L$_i$- is a bond;

ring A is selected from the group consisting of phenyl, pyridyl, pyrazinyl, furanyl, thienyl, pyrimidinyl, pyridazinyl, thiazolyl, oxazolyl, imidazolyl, pyrazolyl, quinazolinyl, benzofuranyl, benzimidazolyl, benzoxazolyl, benzothiazolyl, benzothienyl, naphthyl, quinolyl, isoquinolyl, indazolyl, indolyl, thienopyridyl, and thienopyrazolyl;

m is 0 or more;

each $R^2$ group (when present) is independently selected from the group consisting of halogen, —CN, —SF$_5$, —NHCH$_3$, —N(CH$_3$)$_2$, —OCH$_3$, —OCH$_2$CH$_3$, —O-cyclopropyl, —S(CH$_3$), methyl, ethyl, propyl, cyclopropyl, —CH$_2$-cyclopropyl, —C≡C—CH$_3$, CF$_3$, —CHF$_2$, —C(O)OH, —C(O)OCH$_3$, —C(O)OCH$_2$CH$_3$, —OCF$_3$, and —OCHF$_2$;

ring B is selected from the group consisting of phenyl, cyclopropyl, cyclobutyl, cyclopentyl, cyclohexyl, pyridyl, pyrimidinyl, pyrrolyl, oxazolyl, isoxazolyl, pyrazinyl, thienyl, pyrazolyl, furanyl, thiazolyl, triazolyl, thiadiazolyl, oxadiazolyl, pyridazinyl, isothiazolyl, indolyl, pyrrolopyridinyl, pyrrolopyrimidinyl, morpholinoyl, benzofuranyl, oxetanyl, tetrahydrafuranyl, and tetrahydropyranyl;

p is 1; and $R^3$ is selected from the group consisting of cycloalkyl, -alkyl-cycloalkyl, aryl, -alkyl-aryl, heteroaryl, -alkyl-heteroaryl, heterocycloalkyl, and -alkyl-heterocycloalkyl, wherein said cycloalkyl, -alkyl-cycloalkyl, aryl, -alkyl-aryl, heteroaryl, -alkyl-heteroaryl, heterocycloalkyl, -alkyl-heterocycloalkyl of $R^3$ are each optionally unsubstituted or substituted with one or more groups independently selected from $R^8$.

9. The compound of claim 6, or the tautomer thereof, or the pharmaceutically acceptable salt of said compound or said tautomer, wherein:

n is 0;

ring A is selected from the group consisting of phenyl, pyridyl, pyrazinyl, furanyl, thienyl, pyrimidinyl, pyridazinyl, thiazolyl, and oxazolyl;

m is 0 to 5; and each $R^2$ (when present) is independently selected from the group consisting of halogen, —OH, —CN, —SF$_5$, —OSF$_5$, —NO$_2$, —N(R$^6$)$_2$, —NR$^7$C(O)R$^6$, —NR$^7$S(O)$_2$R$^6$, —NR$^7$C(O)N(R$^6$)$_2$, —NR$^7$C(O)OR$^6$, —C(O)R$^6$, —C(O)$_2$R$^6$, —C(O)N(R$^6$)$_2$, —S(O)R$^6$, —S(O)$_2$R$^6$, —S(O)$_2$N(R$^6$)$_2$, —OR$^6$, —SR$^6$, lower alkyl, -(lower alkyl)-OH, lower haloalkyl, lower heteroalkyl, lower alkenyl, lower alkynyl, lower alkynyl substituted with 1 to 3 independently selected $R^8$ groups, phenyl, benzyl, lower cycloalkyl, —CH$_2$-(lower cycloalkyl), monocyclic heteroaryl, and —CH$_2$-(monocyclic heteroaryl), wherein said phenyl, benzyl, lower cycloalkyl, —CH$_2$-(lower cycloalkyl), monocyclic heteroaryl, and —CH$_2$-(monocyclic heteroaryl) of $R^2$ is unsubstituted or substituted with one or more groups independently selected from the group consisting of halogen, alkyl, heteroalkyl, haloalkyl, alkoxy, —O-cyclopropyl, —O-heteroalkyl, haloalkoxy, —CN, —SF$_5$, and —OSF$_5$.

10. The compound of claim 1, or the tautomer thereof, or the pharmaceutically acceptable salt of said compound or said tautomer, said compound selected from the group consisting of:

| Ex: | Compound |
|---|---|
| 1 |  |

| Ex: | Compound |
|---|---|
| 2 | 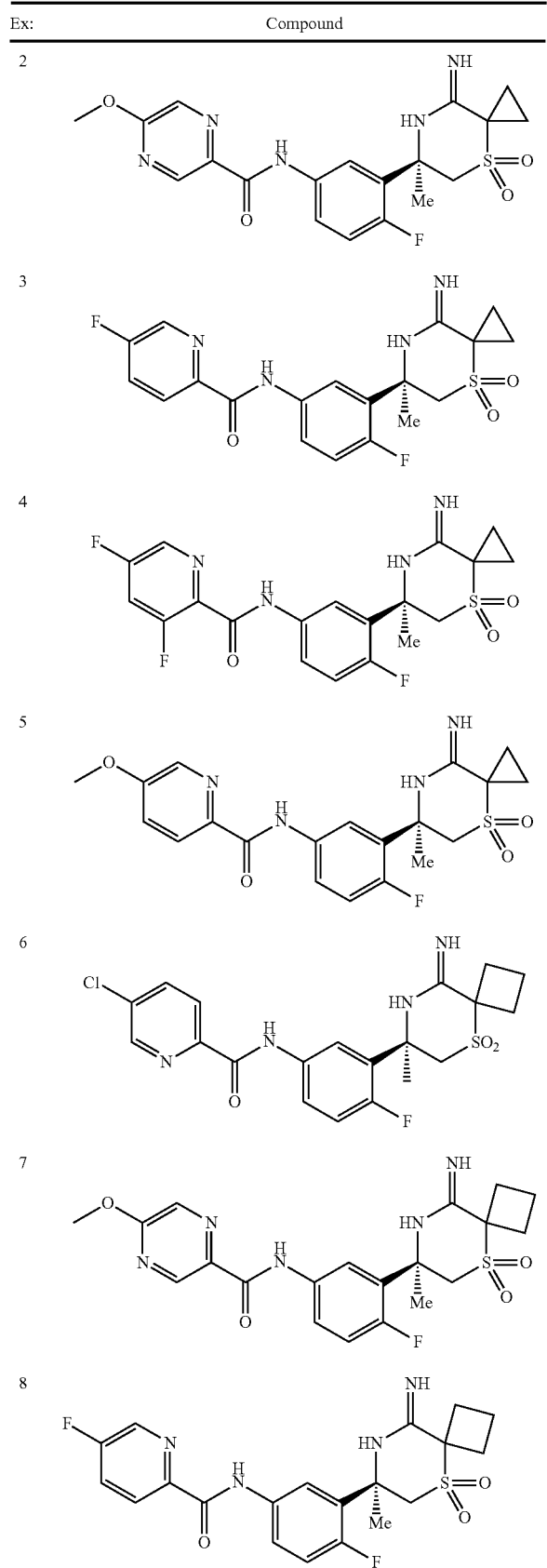 |
| 3 | |
| 4 | |
| 5 | |
| 6 | |
| 7 | |
| 8 | |
| Ex: | Compound |
|---|---|
| 9 | 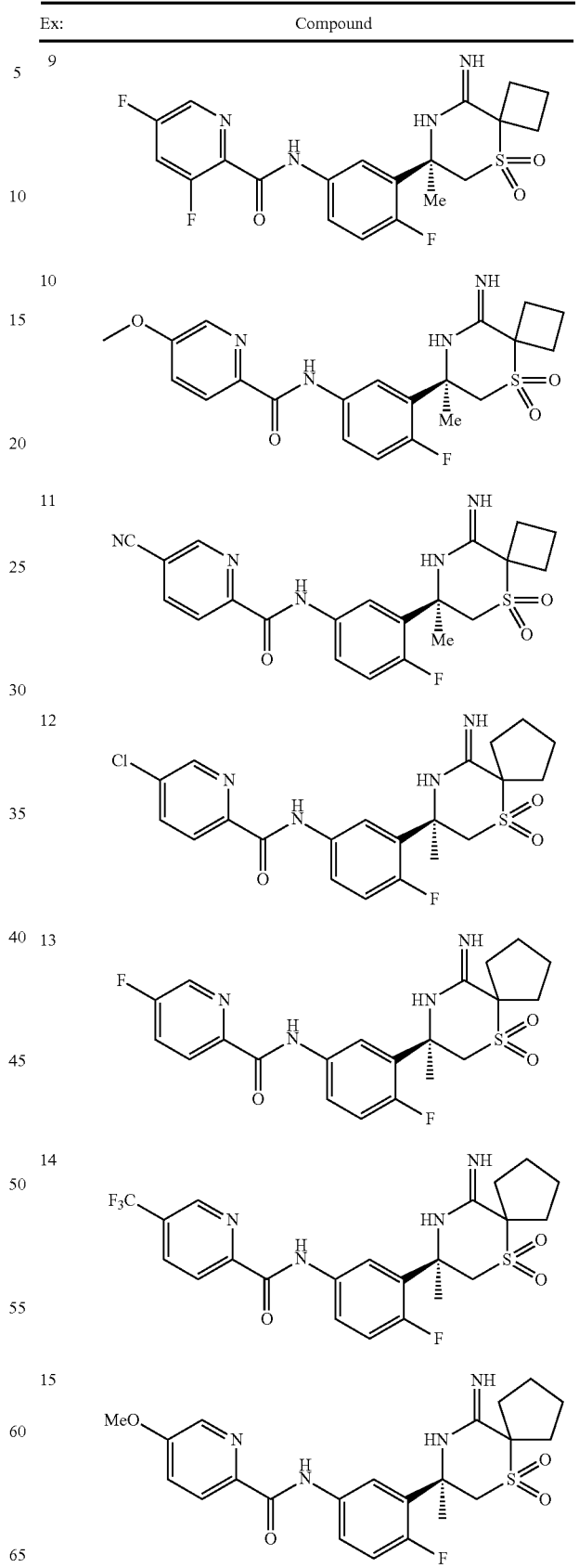 |
| 10 | |
| 11 | |
| 12 | |
| 13 | |
| 14 | |
| 15 | |

| Ex: | Compound |
|---|---|
| 16 | (5-(trifluoromethyl)pyrazine-2-carboxamide derivative with cyclopentane-spiro sulfone, methyl, fluorophenyl) |
| 17 | (5-methoxypyrazine-2-carboxamide derivative with cyclopentane-spiro sulfone) |
| 18 | (3,5-dichloropyridine-2-carboxamide derivative with cyclopentane-spiro sulfone) |
| 19 | (imidazo[2,1-b][1,3,4]thiadiazole-6-carboxamide derivative with cyclopentane-spiro SO₂) |
| 20 | (imidazo[2,1-b]thiazole-6-carboxamide derivative with cyclopentane-spiro SO₂) |
| 21 | (5-methyl-1,2,4-oxadiazole-3-carboxamide derivative with cyclopentane-spiro SO₂) |
| 22 | (1-(difluoromethyl)-1H-pyrazole-3-carboxamide derivative with cyclopentane-spiro SO₂) |
| 23 | (1,2,5-thiadiazole-3-carboxamide derivative with cyclopentane-spiro SO₂) |
| 24 | (5-chloropyridine-2-carboxamide derivative with cyclohexane-spiro SO₂) |
| 25 | (5-fluoropyridine-2-carboxamide derivative with cyclohexane-spiro SO₂, Me) |
| 26 | (5-methoxypyridine-2-carboxamide derivative with cyclohexane-spiro SO₂, Me) |
| 27 | (5-methoxypyrazine-2-carboxamide derivative with cyclohexane-spiro SO₂, Me) |
| 28 | (5-cyanopyridine-2-carboxamide derivative with cyclohexane-spiro SO₂) |
| 29 | (5-(trifluoromethyl)pyridine-2-carboxamide derivative with cyclohexane-spiro SO₂) |

| Ex: | Compound |
|---|---|
| 30 | (5-fluoropyridin-2-yl)carboxamide-N-[3-(4-imino-1,1-dioxo-2-oxa-9-thia-5-azaspiro core), 4-fluorophenyl, methyl] |
| 31 | 3,5-dichloropyridine-2-carboxamide analog |
| 32 | 5-methoxypyrazine-2-carboxamide analog |
| 33 | 5-chloropyridine-2-carboxamide analog |
| 34 | 5-(trifluoromethyl)pyridine-2-carboxamide analog |
| 35 | 5-methoxypyridine-2-carboxamide analog |
| 35a | 5-chloro-3-fluoropyridine-2-carboxamide analog |
| 35b | 5-methoxypyrazine-2-carboxamide with oxetane-spiro analog |
| 36 | 3-cyanophenyl with cyclopentane-spiro-SO2 analog |
| 37 | 5-chloropyridin-3-yl with cyclopentane-spiro-SO2 analog |
| 38 | 5-cyanopyridin-3-yl with cyclopentane-spiro-SO2 analog |
| 39 | 7-methoxy-N-Boc-indol-2-yl with cyclopentane-spiro-SO2 analog |
| 39a | 4-phenyl-1,2,3-triazol-1-yl with cyclobutane-spiro-SO2 analog |

| Ex: | Compound |
|---|---|
| 39b | 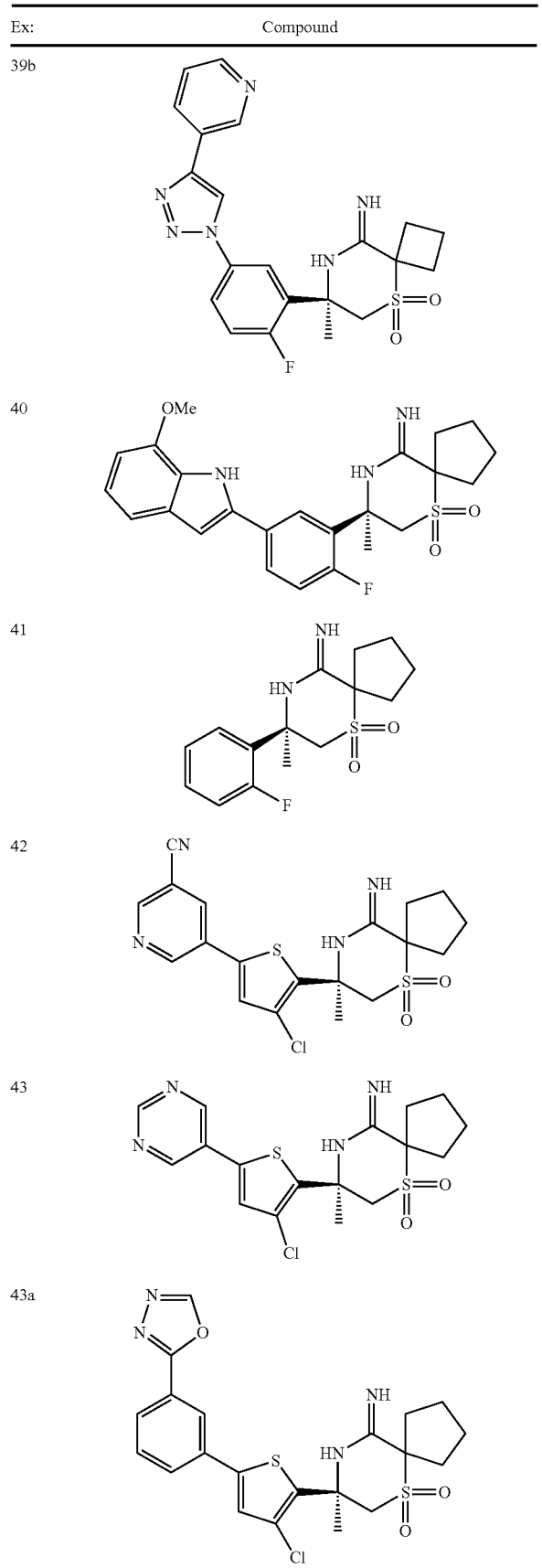 |
| 40 | |
| 41 | |
| 42 | |
| 43 | |
| 43a | |
| Ex: | Compound |
|---|---|
| 44 | 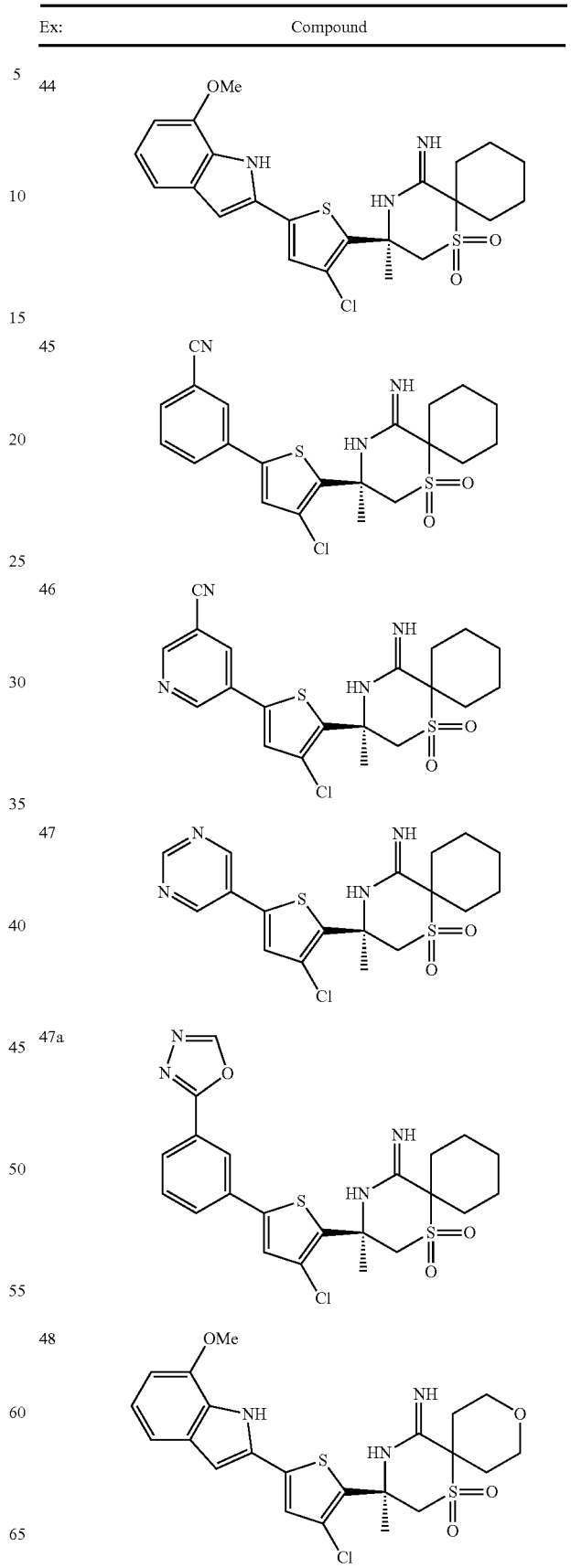 |
| 45 | |
| 46 | |
| 47 | |
| 47a | |
| 48 | |

| Ex: | Compound |
|---|---|
| 49 | 3-cyanophenyl-thiophene(Cl)-spiro tetrahydropyran sulfone imine |
| 50 | 5-cyanopyridin-3-yl-thiophene(Cl)-spiro tetrahydropyran sulfone imine |
| 51 | pyrimidin-5-yl-thiophene(Cl)-spiro tetrahydropyran sulfone imine |
| 52 | 3-(trifluoromethyl)phenyl-thiophene(Cl)-spiro tetrahydropyran sulfone imine |
| 53 | 5-methoxypyridin-3-yl-thiophene(Cl)-spiro tetrahydropyran sulfone imine |
| 54 | 5-(trifluoromethyl)pyridin-3-yl-thiophene(Cl)-spiro tetrahydropyran sulfone imine |
| 55 | 5-fluoropyridin-3-yl-thiophene(Cl)-spiro tetrahydropyran sulfone imine |
| 56 | 3-(pyrrolidin-1-yl)phenyl-thiophene(Cl)-spiro tetrahydropyran sulfone imine |
| 57 | 3-cyano-5-methoxyphenyl-thiophene(Cl)-spiro tetrahydropyran sulfone imine |
| 57a | 3-(1,3,4-oxadiazol-2-yl)phenyl-thiophene(Cl)-spiro tetrahydropyran sulfone imine |
| 58 | 7-methoxy-1H-indol-2-yl-thiophene(Cl)-spiro cyclobutane sulfone imine |
| 59 | 5-cyanopyridin-3-yl-thiophene(Cl)-spiro cyclobutane sulfone imine |

| Ex: | Compound |
|---|---|
| 60 | (structure) |
| 61 | (structure) |
| 61a | (structure) |
| 62 | (structure) |
| 62a | (structure) |
| 62b | (structure) |

| Ex: | Compound |
|---|---|
| 62c | (structure) |
| 62d | (structure) |
| 62e | (structure) |
| 62f | (structure) |
| 62g | (structure) |
| 62h | (structure) |

| Ex: | Compound |
|---|---|
| 62i | (structure) |
| 62j | (structure) |
| 62k | (structure) |
| 62l | (structure) |
| 62m | (structure) |

| Ex: | Compound |
|---|---|
| 62n | (structure) |
| 63 | (structure) |
| 63a | (structure) |
| 63b | (structure) |
| 63c | (structure) |
| 63d | (structure) |

-continued

| Ex: | Compound |
|---|---|
| 63e | (5-cyanopyridin-3-yl thiophene with chloro, methyl stereocenter, spiro tetrahydrofuran sulfone imine) |
| 63f | (7-methoxyindol-2-yl thiophene with chloro, methyl stereocenter, spiro tetrahydrofuran sulfone imine) |
| 63g | (3-(1,3,4-oxadiazol-2-yl)phenyl thiophene with chloro, methyl stereocenter, spiro tetrahydrofuran sulfone imine) |
| 63h | (5-(oxazol-2-yl)pyridin-3-yl thiophene with chloro, methyl stereocenter, spiro tetrahydrofuran sulfone imine) |
| 63i | (5-ethylpyridin-3-yl thiophene with chloro, methyl stereocenter, spiro tetrahydrofuran sulfone imine) |

-continued

| Ex: | Compound |
|---|---|
| 63j | (5-morpholinopyridin-3-yl thiophene with chloro, methyl stereocenter, spiro tetrahydrofuran sulfone imine) |
| 63k | (2-phenylpyridin-4-yl thiophene with chloro, methyl stereocenter, spiro tetrahydrofuran sulfone imine) |
| 63l | (2-(furan-3-yl)pyridin-4-yl thiophene with chloro, methyl stereocenter, spiro tetrahydrofuran sulfone imine) |
| 63m | (2-(thiophen-2-yl)pyridin-4-yl thiophene with chloro, methyl stereocenter, spiro tetrahydrofuran sulfone imine) |
| 63n | (2-(thiophen-3-yl)pyridin-4-yl thiophene with chloro, methyl stereocenter, spiro tetrahydrofuran sulfone imine) |

| Ex: | Compound |
|---|---|
| 64 | (7-methoxy-1H-indol-2-yl connected to chlorothiophene bearing methyl-substituted spirocyclopropyl iminothiomorpholine dioxide) |
| 65 | (5-cyanopyridin-3-yl connected to chlorothiophene bearing methyl-substituted spirocyclopropyl iminothiomorpholine dioxide) |
| 65a | (1,3,4-oxadiazol-2-yl-phenyl connected to chlorothiophene bearing methyl-substituted spirocyclopropyl iminothiomorpholine dioxide) |
| 66 | (6-methylpyridin-2-yl amide linked to chlorothiophene bearing methyl-substituted spirocyclobutyl iminothiomorpholine dioxide) |
| 67 | (6-methoxypyridin-2-yl amide linked to chlorothiophene bearing methyl-substituted spirocyclobutyl iminothiomorpholine dioxide) |
| 68 | (6-ethylpyridin-2-yl amide linked to chlorothiophene bearing methyl-substituted spirocyclobutyl iminothiomorpholine dioxide) |

| Ex: | Compound |
|---|---|
| 69 | (6-chloropyridin-2-yl amide linked to chlorothiophene bearing methyl-substituted spirocyclobutyl iminothiomorpholine dioxide) |
| 70 | (6-fluoropyridin-2-yl amide linked to chlorothiophene bearing methyl-substituted spirocyclobutyl iminothiomorpholine dioxide) |
| 71 | (6-trifluoromethylpyridin-2-yl amide linked to chlorothiophene bearing methyl-substituted spirocyclobutyl iminothiomorpholine dioxide) |
| 72 | (5-chloro-3-fluoropyridin-2-yl amide linked to fluorophenyl bearing methyl-substituted spirotetrahydrofuran iminothiomorpholine dioxide) |
| 73 | (6-chloroisoxazolo[4,5-b]pyridin-3-ylamino linked to fluorophenyl bearing methyl-substituted spirotetrahydrofuran iminothiomorpholine dioxide) |
| 74 | (5-fluoropyridin-2-yl amide linked to fluorophenyl bearing methyl-substituted 3-hydroxyspirocyclobutyl iminothiomorpholine dioxide) |
| 75 | (5-fluoropyridin-2-yl amide linked to fluorophenyl bearing methyl-substituted 3-hydroxyspirocyclobutyl iminothiomorpholine dioxide, other diastereomer) |

| Ex: | Compound |
|---|---|
| 76a | 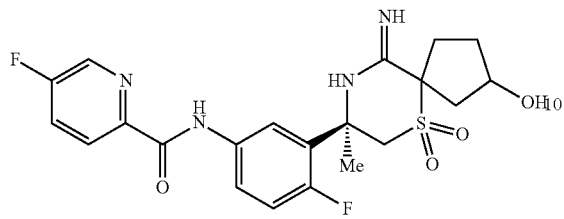 |
| 76b | 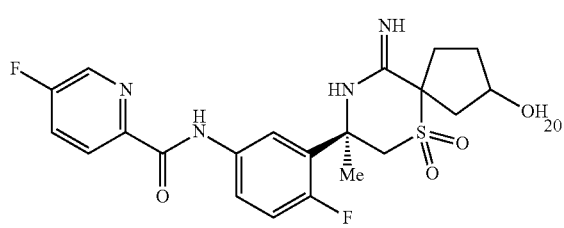 |
| 77 | 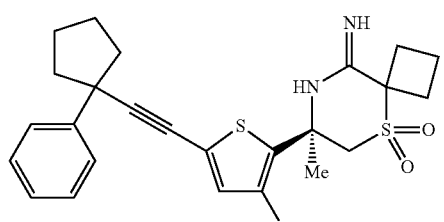 |
| 77a | 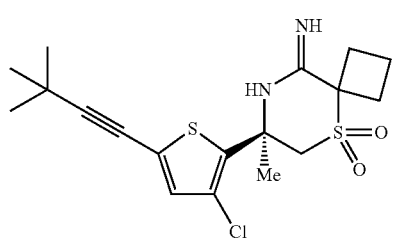 [SMILES: CC(C)(C)C#Cc1cc(Cl)c([C@]2(C)CS(=O)(=O)C3(CCC3)C(=N)N2)s1] |
| 77b | 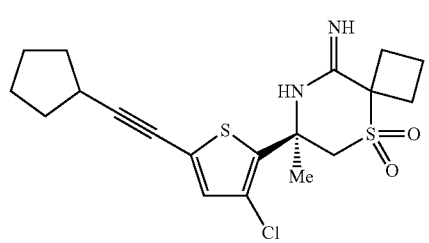 [SMILES: C[C@@]1(c2sc(C#CC3CCCC3)cc2Cl)CS(=O)(=O)C2(CCC2)C(=N)N1] |
| 77c | 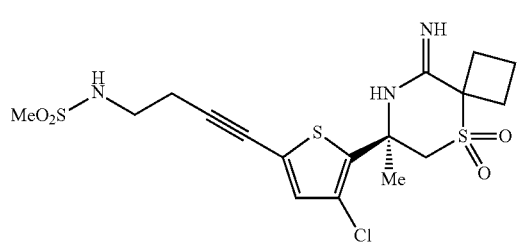 [SMILES: C[C@@]1(c2sc(C#CCCNS(C)(=O)=O)cc2Cl)CS(=O)(=O)C2(CCC2)C(=N)N1] |
| Ex: | Compound |
|---|---|
| 77d | 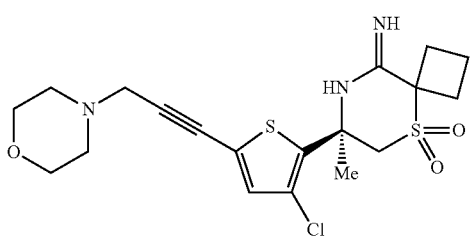 [SMILES: C[C@@]1(c2sc(C#CCN3CCOCC3)cc2Cl)CS(=O)(=O)C2(CCC2)C(=N)N1] |
| 78 | 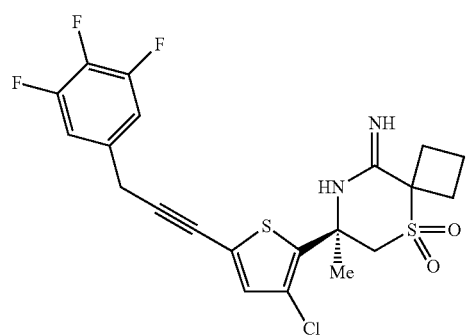 [SMILES: C[C@@]1(c2sc(C#CCc3cc(F)c(F)c(F)c3)cc2Cl)CS(=O)(=O)C2(CCC2)C(=N)N1] |
| 79 | 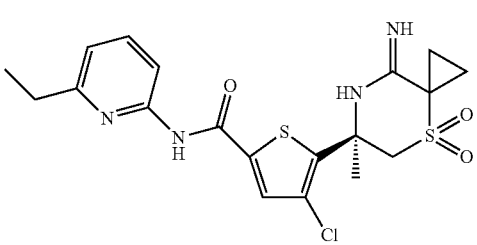 [SMILES: CCc1cccc(NC(=O)c2cc(Cl)c([C@]3(C)CS(=O)(=O)C4(CC4)C(=N)N3)s2)n1] |
| 79a | 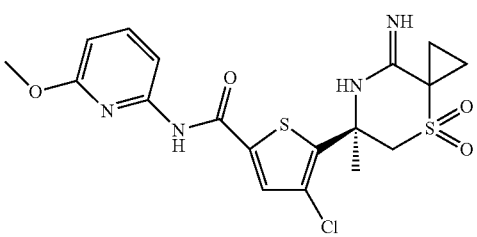 [SMILES: COc1cccc(NC(=O)c2cc(Cl)c([C@]3(C)CS(=O)(=O)C4(CC4)C(=N)N3)s2)n1] |
| 79b | 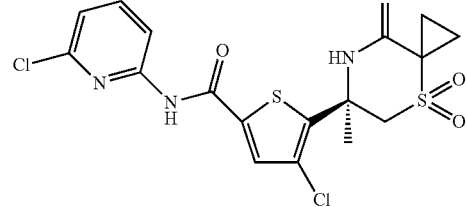 |
| 79c | 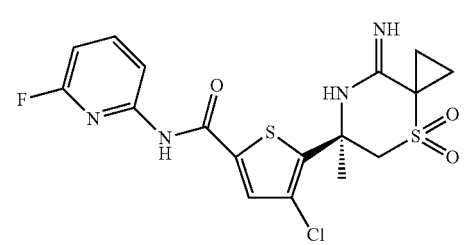 [SMILES: C[C@@]1(c2sc(C(=O)Nc3cccc(F)n3)cc2Cl)CS(=O)(=O)C2(CC2)C(=N)N1] |

| Ex: | Compound |
|---|---|
| 79d | 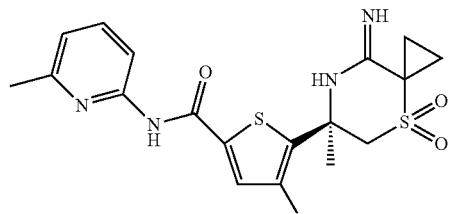 |
| 80 | 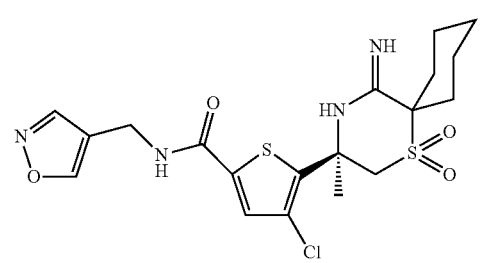 [SMILES: C[C@@]1(c2sc(C(=O)NCc3cnoc3)cc2Cl)CS(=O)(=O)C2(CCCCC2)C(=N)N1] |
| 80a | 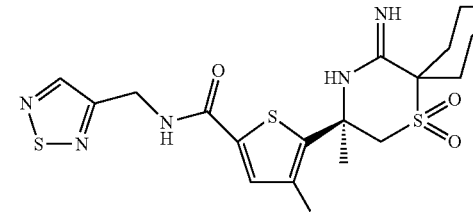 |
| 80b | 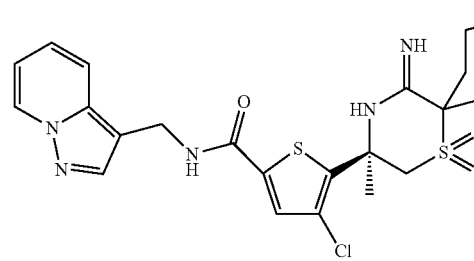 |
| 80c | 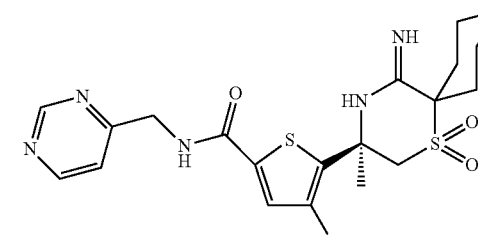 |
| 80d | 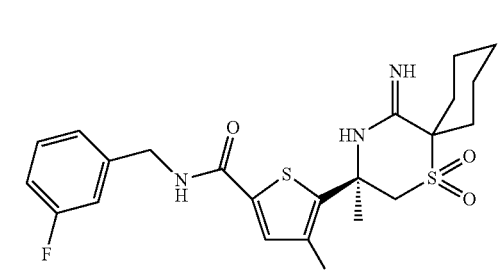 |
| 80e | 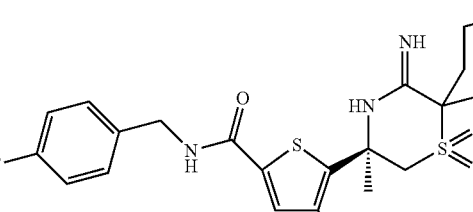 |
| 80f | 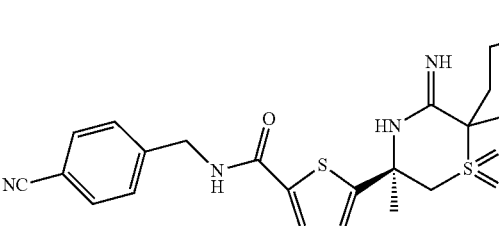 |
| 80g | 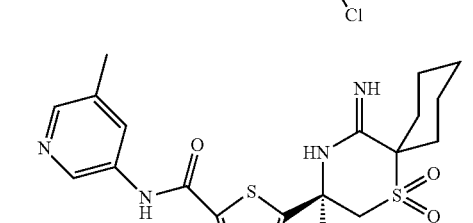 |
| 80h | 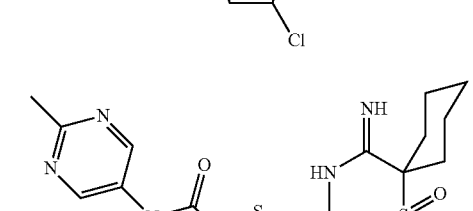 |
| 80i | 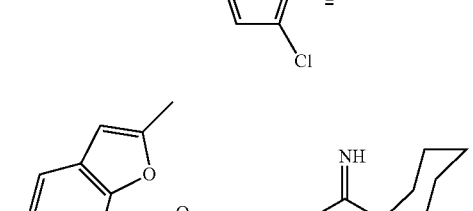 |
| 80j | 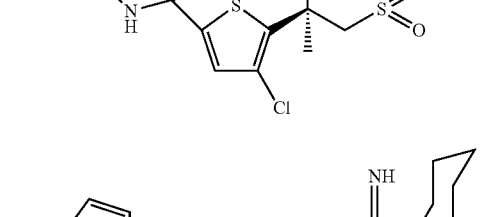 |

| Ex: | Compound |
|---|---|
| 80k | (structure) |
| 80l | (structure) |
| 80m | (structure) |
| 81 | (structure) |
| 81a | (structure) |
| 81b | (structure) |
| 81c | (structure) |
| 81d | (structure) |
| 81e | (structure) |
| 81f | (structure) |
| 81g | (structure) |
| 81h | (structure) |
| 81i | (structure) |

| Ex: | Compound |
|---|---|
| 81j | (tetrahydrofuran-2-yl)carbonyl amide derivative |
| 81k | 3,5-difluoropyridine-2-carboxamide derivative |
| 81l | propanamide derivative |
| 81m | 4-chlorobenzamide derivative |
| 81n | 2,2-difluoroacetamide derivative |
| 81o | 2,2-difluorocyclobutanecarboxamide derivative |
| 81p | 3-methyloxetane-3-carboxamide derivative |
| 81q | tetrahydro-2H-pyran-4-carboxamide derivative |
| 81r | 3,3,3-trifluoropropanamide derivative |
| 81s | 2,2-difluorocyclopropanecarboxamide derivative |
| 81t | isothiazole-5-carboxamide derivative |
| 81u | thiazole-4-carboxamide derivative |

| Ex: | Compound |
|---|---|
| 81v | 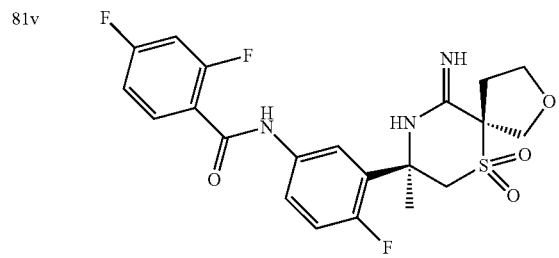 |
| 81w | 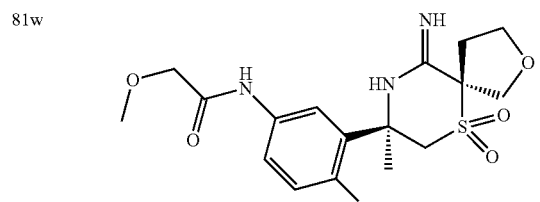 |
| 81x | 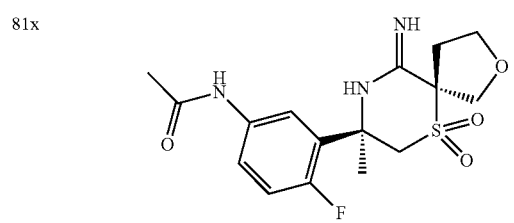 |
| 81y | 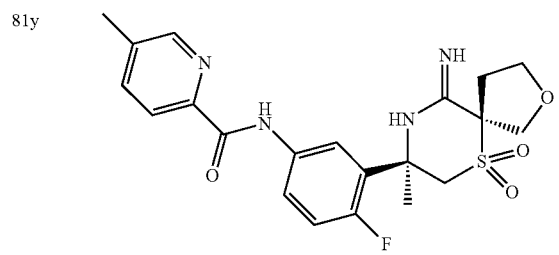 |
| 81z | 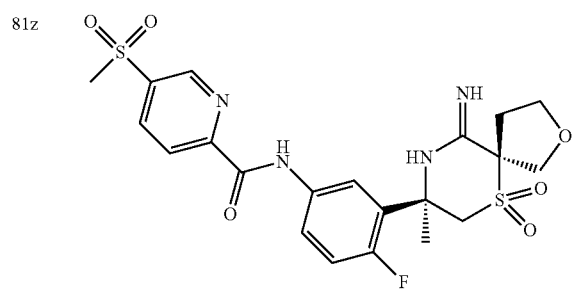 |
| 81aa | 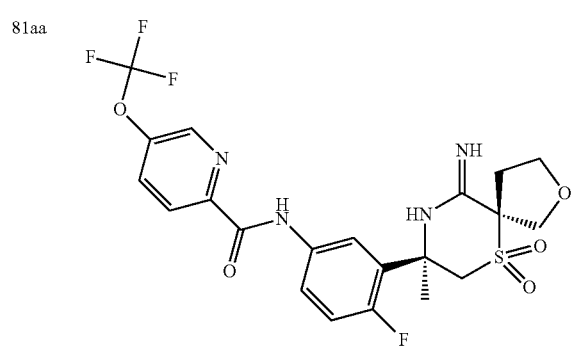 |
| Ex: | Compound |
|---|---|
| 81ab | 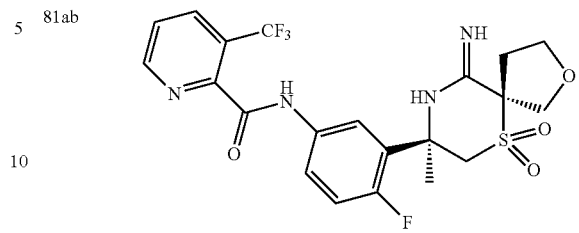 |
| 81ac | 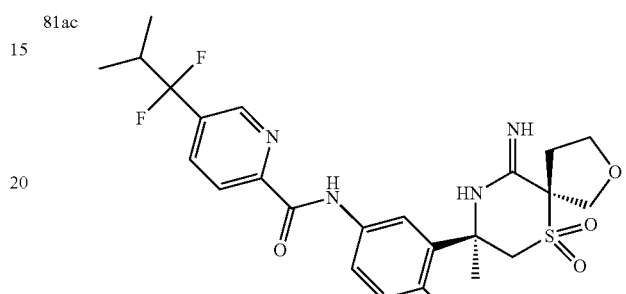 |
| 81ad | 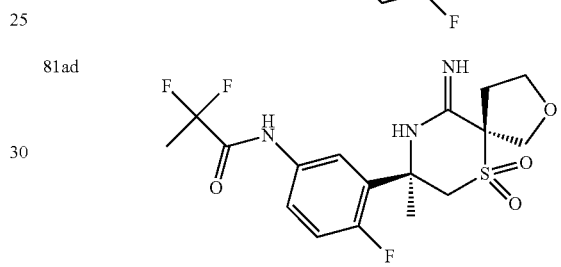 |
| 81ae | 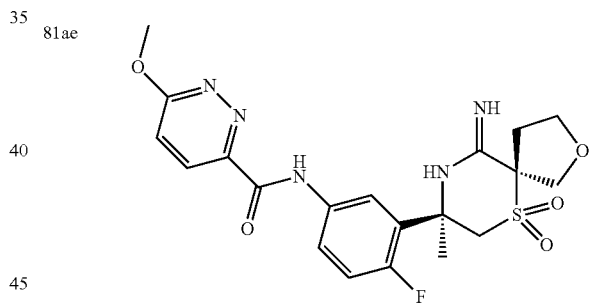 |
| 81af | 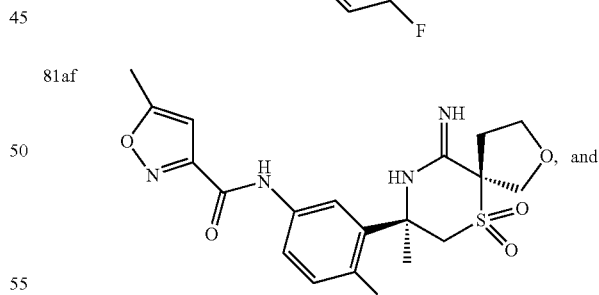, and |
| 81ag | 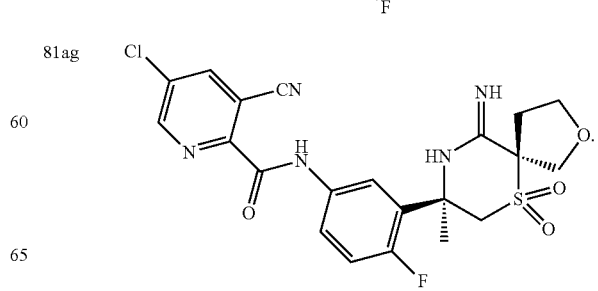 |

| Ex: | Compound | |
|---|---|---|
| | 11. The compound of claim 1, or the tautomer thereof, or the pharmaceutically acceptable salt of said compound or said tautomer, said compound selected from the group consisting of: | |
| Compound | |
|---|---|
| 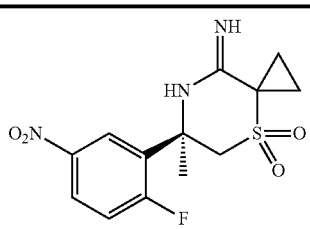 | 6 |
| 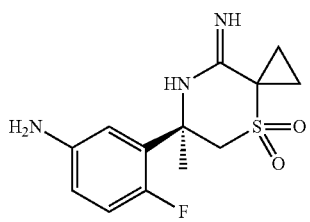 [SMILES: C[C@@]1(c2cc([N+](=O)[O-])ccc2F)CS(=O)(=O)C2(CC2)C(=N)N1] | 7 |
| 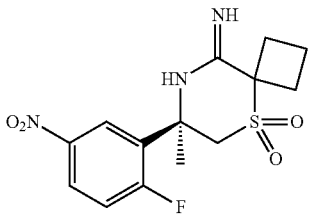 [SMILES: C[C@@]1(c2cc([N+](=O)[O-])ccc2F)CS(=O)(=O)C2(CCC2)C(=N)N1] | 11 |
| 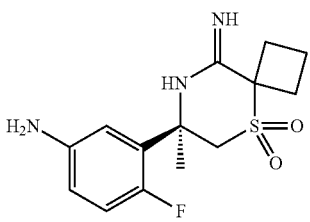 | 12 |
| 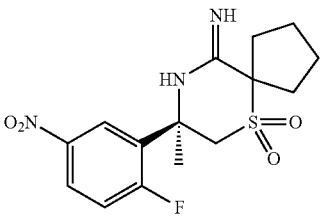 | 16 |
| 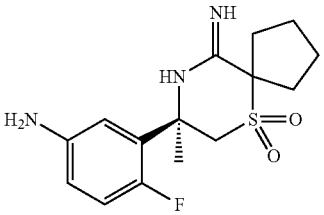 [SMILES: C[C@@]1(c2cc([N+](=O)[O-])ccc2F)CS(=O)(=O)C2(CCCC2)C(=N)N1] | 17 |
| Compound | |
|---|---|
| 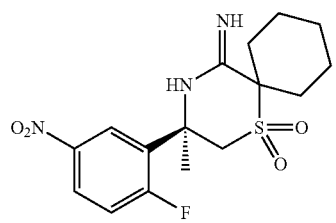 [SMILES: C[C@@]1(c2cc([N+](=O)[O-])ccc2F)CS(=O)(=O)C2(CCCCC2)C(=N)N1] | 21 |
| 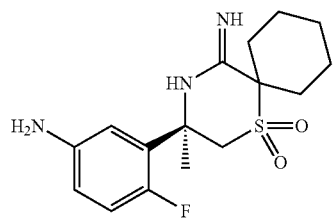 | 22 |
| 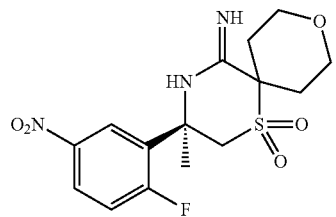 [SMILES: C[C@@]1(c2cc([N+](=O)[O-])ccc2F)CS(=O)(=O)C2(CCOCC2)C(=N)N1] | 26 |
| 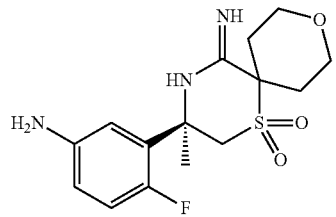 | 27 |
| 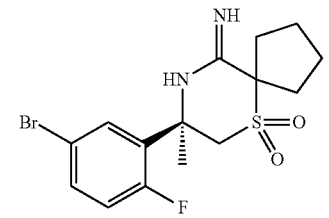 [SMILES: C[C@@]1(c2cc(Br)ccc2F)CS(=O)(=O)C2(CCCC2)C(=N)N1] | 31 |
| 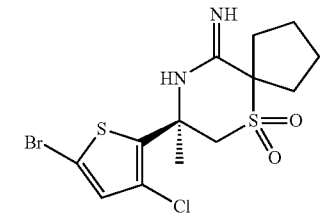 [SMILES: C[C@@]1(c2sc(Br)cc2Cl)CS(=O)(=O)C2(CCCC2)C(=N)N1] | 35 |
| 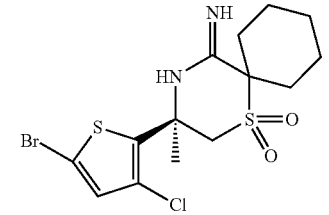 [SMILES: C[C@@]1(c2sc(Br)cc2Cl)CS(=O)(=O)C2(CCCCC2)C(=N)N1] | 38 |

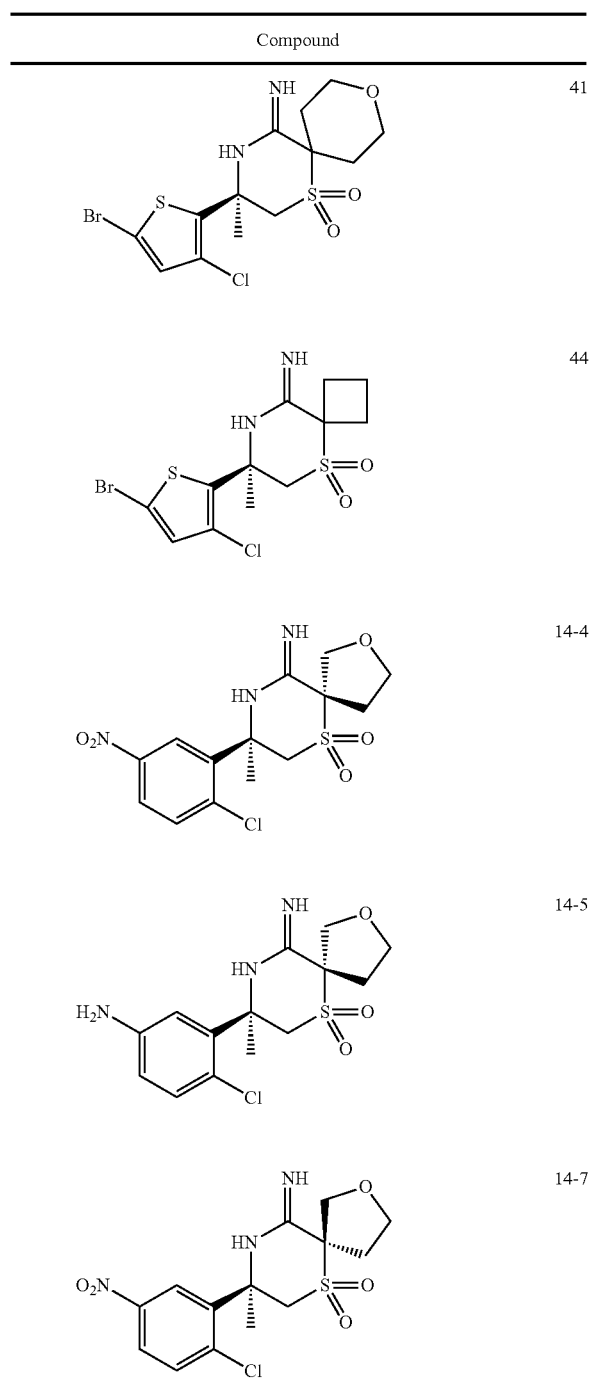

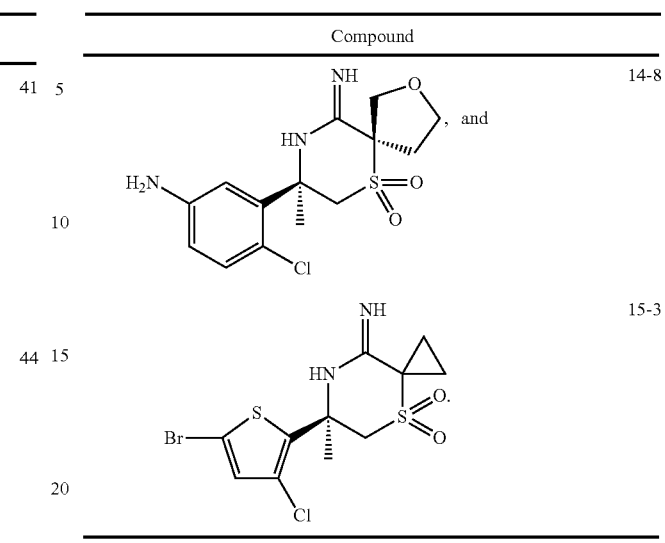

12. A pharmaceutical composition comprising a compound according to claim 1, or a tautomer thereof, or a pharmaceutically acceptable salt of said compound or said tautomer, and a pharmaceutically acceptable carrier or diluent.

13. A method of treating Alzheimer's disease, Down's syndrome, Parkinson's disease, stroke, microgliosis, brain inflammation, pre-senile dementia, senile dementia, progressive supranuclear palsy, cortical basal degeneration, olfactory impairment associated with Alzheimer's disease, olfactory impairment associated with Parkinson's disease, olfactory impairment associated with Down's syndrome, β-amyloid angiopathy, cerebral amyloid angiopathy, hereditary cerebral hemorrhage, mild cognitive impairment, glaucoma, amyloidosis, type II diabetes, diabetes-associated amyloidogenesis, hemodialysis complications, scrapie, bovine spongiform encephalitis, traumatic brain injury, or Creutzfeld-Jakob disease, said method comprising administering a compound of claim 1, or a tautomer thereof, or a pharmaceutically acceptable salt thereof, to a patient in need of such treatment.

14. A method of treating Alzheimer's disease, Down's syndrome, pre-senile dementia, senile dementia, olfactory impairment associated with Alzheimer's disease, olfactory impairment associated with Down's syndrome, β-amyloid angiopathy, cerebral amyloid angiopathy, mild cognitive impairment, type II diabetes, or traumatic brain injury, said method comprising administering a compound of claim 1, or a tautomer thereof, or a pharmaceutically acceptable salt thereof, to a patient in need of such treatment.

15. A method of treating Alzheimer's disease comprising administering a compound of claim 1, or a tautomer thereof, or a pharmaceutically acceptable salt thereof, to a patient in need of such treatment.

* * * * *